United States Patent
Ai et al.

(10) Patent No.: US 11,040,987 B2
(45) Date of Patent: Jun. 22, 2021

(54) PENAM DERIVATIVES FOR TREATING BACTERIAL INFECTIONS

(71) Applicant: TenNor Therapeutics Limited, Suzhou (CN)

(72) Inventors: Huibing Ai, Suzhou (CN); Jun Ding, Suzhou (CN); Shijie He, Suzhou (CN); Yu Liu, Suzhou (CN); Dawei Wan, Suzhou (CN); Huan Wang, Suzhou (CN); Ying Yuan, Kalamazoo, MI (US); Qian Zhang, Suzhou (CN); Zhijun Zhuang, Suzhou (CN); Zhenkun Ma, Westfield, NJ (US)

(73) Assignee: TENNOR THERAPEUTICS LIMITED, Suzhou (CN)

( * ) Notice: Subject to any disclaimer, the term of this patent is extended or adjusted under 35 U.S.C. 154(b) by 0 days.

(21) Appl. No.: 17/001,764

(22) Filed: Aug. 25, 2020

(65) Prior Publication Data

US 2021/0070774 A1    Mar. 11, 2021

Related U.S. Application Data

(60) Provisional application No. 62/898,598, filed on Sep. 11, 2019.

(51) Int. Cl.
   *C07D 499/87*    (2006.01)
   *A61K 45/06*    (2006.01)
   (Continued)

(52) U.S. Cl.
   CPC ............ *C07D 499/87* (2013.01); *A61K 31/43* (2013.01); *A61K 31/431* (2013.01);
   (Continued)

(58) Field of Classification Search
   CPC ................................................... C07D 499/87
   See application file for complete search history.

(56) References Cited

U.S. PATENT DOCUMENTS 4,668,514 A * 5/1987 Micetich ............... A61K 31/43
                                                        424/114
4,861,768 A * 8/1989 Torii .................... C07D 499/00
                                                        514/195
(Continued)

FOREIGN PATENT DOCUMENTS

WO     97/06172     2/1997
WO     02/22613     3/2002
(Continued)

OTHER PUBLICATIONS

Notification of the International Search Report and Written Opinion of the International Searching Authority—China National Intellectual Property Administration—dated Dec. 16, 2020 for International Application No. PCT/IB2020/000686, 9 pages.
(Continued)

*Primary Examiner* — Brian J Davis
(74) *Attorney, Agent, or Firm* — Jackson Walker LLP

(57) ABSTRACT

Novel iron chelating group conjugated penam derivatives described herein show antibacterial activity, and could be used as antibacterial agents or beta-lactamase inhibitors (BLIs) which are of value for application in combination with other antibacterial agents.

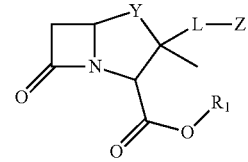

14 Claims, 18 Drawing Sheets

(51) Int. Cl.

| | | |
|---|---|---|
| *A61K 31/43* | (2006.01) | |
| *A61K 31/431* | (2006.01) | |
| *C07D 519/06* | (2006.01) | |
| *A61P 31/04* | (2006.01) | |
| *A61K 31/506* | (2006.01) | |
| *A61K 31/497* | (2006.01) | |
| *A61K 31/4439* | (2006.01) | |
| *A61K 31/454* | (2006.01) | |
| *A61K 31/496* | (2006.01) | |
| *A61K 31/455* | (2006.01) | |

(52) U.S. Cl.
CPC ........ *A61K 31/4439* (2013.01); *A61K 31/454* (2013.01); *A61K 31/455* (2013.01); *A61K 31/496* (2013.01); *A61K 31/497* (2013.01); *A61K 31/506* (2013.01); *A61K 45/06* (2013.01); *A61P 31/04* (2018.01); *C07D 519/06* (2013.01)

(56) References Cited

U.S. PATENT DOCUMENTS 5,686,441 A * 11/1997 Maiti ................. A61P 31/04
514/195
2004/0132707 A1    7/2004  Heinisch et al.

FOREIGN PATENT DOCUMENTS

| WO | 2012/070071 | 5/2012 |
|---|---|---|
| WO | 2018/014823 | 1/2018 |

OTHER PUBLICATIONS

Beharry, et al., "Evaluation of penicillin-based inhibitors of the class A and B β-lactamases from Bacillus anthracis", Biochemical and Biophysical Research Communications, 313, (2004), pp. 541-545.

Pattanaik, et al., "Strategic Design of an Effective β-Lactamase Inhibitor: LN-1-255, A 6-Alkylidene-2'-Substituted Penicillin Sulfone", Journal of Biological Chemistry, 2009, 284; pp. 945-953.

\* cited by examiner

PENAM DERIVATIVES FOR TREATING BACTERIAL INFECTIONS

This application claims priority to U.S. Provisional Patent Application No. 62/898,598, filed Sep. 11, 2019, entitled "Penam Derivatives for Treating Bacterial Infections," the entire contents of which are hereby incorporated by reference.

BACKGROUND

This disclosure pertains to penam compounds, which have antimicrobial activity or β-lactamase inhibitory activity, and pharmaceutical compositions comprising the same.

Penicillin antibiotics are one of first class of modern medications to be effective against many bacterial infections. The commercially available β-lactam antibiotics are still widely used today, though many types of bacteria have developed resistance following their extensive uses. Antibiotic resistance presents a serious threat to human health (Neu, H. C. 1992. *Science*, 257(5073), 1064-1073; Bassetti, M. et al. 2017. *Intensive care medicine*, 43(10), 1464-1475). The increased drug resistance in Gram-negative pathogens has becoming a major global challenge. In 2017, WHO published a list of 12 priority pathogens representing the greatest threat to human health for which new antibiotics are urgently needed. Among them three carbapanem-resistant Gram negative bacteria (*Acinetobacter baumannii*, *Pseudomonas aeruginosa* and Enterobacteriaceae) are prioritized as critical pathogens.

SUMMARY

The present disclosure relates generally to iron chelating group conjugated penam derivatives which are of value for use as antimicrobial compounds or as beta-lactamase inhibitors (BLIs) to enhance or restore the effectiveness of beta-lactam class antibacterial agents.

Inactivation of the β-lactam antibiotics by β-lactamases is one of the most widespread drug resistant mechanism among Gram-negative bacterial pathogens. Thousands of different β-lactamases have been identified globally. Based on the amino acid sequences, the β-lactamases are categorized into four classes (Ambler classification), of which A. C and D are serine hydrolases and B encompasses metallo-β-lactamases.

Development of β-lactamase inhibitors to restore antibacterial activity of β-lactams has been a successful strategy in compacting antibiotic resistance. FIG. 1 shows a group of representative β-lactam ring containing β-lactamases inhibitors. Three β-lactam ring containing β-lactamases inhibitors clavulanic acid (1), sulbactam (2), and tazobactam (3) are currently being used clinically for the treatment of bacterial infections. A series of 6-alkenyl penam compounds, including those containing an iron chelating group, such as compounds (4, LN-I-255), (5) and (6) have been reported to have β-lactamases inhibitory activity (Buynak, J. D. et al. 1999. *Bioorganic & medicinal chemistry letters*, 9(14), 1997-2002; U.S. Pat. No. 8,299,051 Issued Oct. 30, 2012). Another iron chelating group containing compound (7) was also reported, which contains a hydroxyl pyridone moiety as iron chelator (Setti, E. L. et al. 1995. *The Journal of antibiotics*, 48(11), 1320-1329).

Low outer membrane permeability is a major contributor to antibiotic resistance in Gram-negative bacterial (Tsai, Y. K. et al. 2011. *Antimicrobial agents and chemotherapy*, 55(4), 1485-1493). One of the approaches to increase drug permeability is to exploit the iron uptake pathway of Gram-negative bacterial by conjugating an iron chelating group mimicking a siderophore to an antibiotic (Mollmann, U. et al. 2009. *Biometals*, 22(4), 615-624). Siderophores are small, high-affinity iron-chelating compounds secreted by microorganisms such as bacteria and fungi and able to bring iron through specific receptors into bacterial cells to support growth. (Neilands, J. B. 1995. *Journal of Biological Chemistry*, 270(45), 26723-26726).

Conjugation of an iron chelating moiety to an antibiotic proves to be a promising approach to improve the activity of antibiotics, particularly for the β-lactam antibiotics which are active in periplasmic space in Gram-negative bacteria. BAL30072 (8) is a siderophore (a hydroxy pyridone moiety) conjugated monobactam in development with activity against multidrug resistant (MDR) gram-negative bacteria (Page, M. G. et al. 2010. *Antimicrobial agents and chemotherapy*, 54(6), 2291-2302). Cefiderocol (9) is an iron chelating group (a catechol moiety) conjugated cephalosporin in late stage of clinical trials. Cefiderocol showed potent antibacterial activity against *Pseudomonas aeruginosa* and *Acinetobacter baumannii*, including carbapenem-resistant strains (Ito, A. et al. 2016. *Antimicrobial agents and chemotherapy*, 60(12), 7396-7401; Portsmouth, S. et al. 2018. *The Lancet Infectious Diseases*, 18(12), 1319-1328).

Sulbactam was originally developed as a β-lactamases inhibitor. Recently this compound has been used in treating *Acinetobacter baumannii* infections, particularly for those caused by multidrug-resistant strains. However, resistant to sulbactam in *Acinetobacter baumannii* are common, particularly among carbapenem-resistant clinical isolates (Karageorgopoulos, D. E. et al. 2008. *The Lancet infectious diseases*, 8(12), 751-762).

Accordingly, the present disclosure relates to iron chelating group conjugated penam derivatives. The compounds show antibacterial activity, or could be used as beta-lactamase inhibitors (BLIs) which are of value for application in combination with antibiotics. The details of one or more embodiments of the invention are set forth in the description. Other features, objects and advantages of the invention will be apparent from the following description including claims.

DETAILED DESCRIPTION OF PREFERRED EMBODIMENTS

Figure 1:
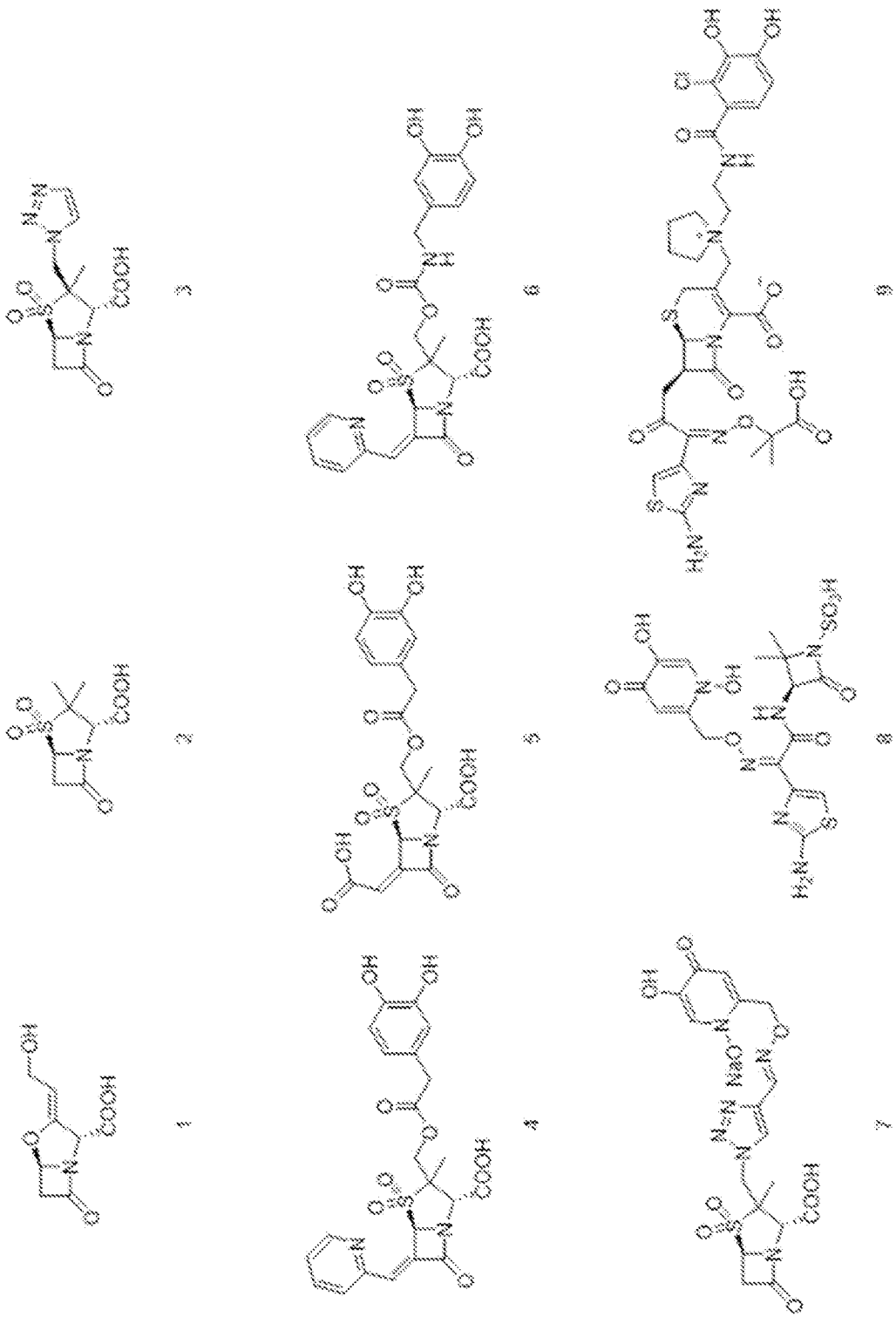
FIG. 1 shows representative β-lactamase inhibitors.

The present disclosure relates to penam derivatives and their uses as antimicrobial compounds or beta-lactamase inhibitors (BLIs).

Preferred embodiments disclosed herein include a series of penam derivatives represented by general formula I:

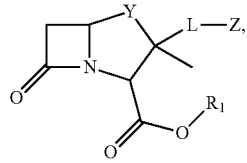

or a stereoisomer, pharmaceutically acceptable salt, solvate, prodrug, deuterium-exchanged compound thereof;

wherein $R_1$ is a hydrogen, a pharmaceutically acceptable salt forming agent, or an ester residue such as a carboxylic protecting group and the like. The esters include those esters which are readily metabolized or hydrolyzable in the body to form a carboxylate.

Y is independently a group selected from —S—, —SO—, and —SO$_2$—;

L is a linker group selected from one or a combination of two to five of the following groups:
1) ($C_1$-$C_8$)alkylene,
2) ($C_3$-$C_8$)cycloalkylene,
3) arylene,
4) heteroarylene,
5) ($C_3$-$C_8$)heterocycloalkylene containing one to three heteroatoms, and optionally unsaturated,
6) —C(=O)—,
7) —O—,
8) —S(O)$_n$—, wherein n is number 0, 1, or 2,
9) —N($R_2$)—,
10) —C($R_3$)=C($R_4$)—,
11) —C≡N—, wherein $R_2$, $R_3$ and $R_4$ are selected from hydrogen, ($C_1$-$C_8$)alkyl, ($C_3$-$C_8$)cycloalkyl, ($C_1$-$C_8$)alkyloxyl, aryl, heteroaryl, or ($C_3$-$C_8$)heterocycloalkyl; $R_3$ and $R_4$ may join together to form a bond. The carbon or nitrogen atoms of the linker group is optionally substituted by one to three substituents;

Z is an iron chelating moiety bearing at least two hydroxyl groups selected from

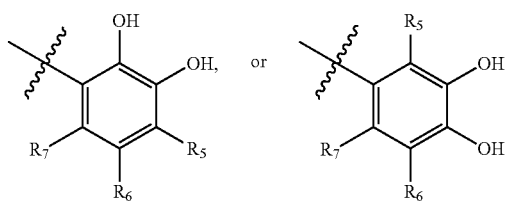

wherein $R_5$, $R_6$ and $R_7$ are independently a group selected from hydrogen, hydroxyl, halogen, nitrile, nitro, amino, $CF_3$, $OCF_3$, alkyl, alkylamino, alkoxy, aryl, heteroaryl; two of the three substituents of $R_5$, $R_6$ and $R_7$ may optionally join together to form a 5-8 membered ring that are optionally substituted.

In additional preferred embodiments of the penam derivatives having general formula I shown above, Y is —SO$_2$—.

In additional preferred embodiments of the penam derivatives having general formula I shown above, L is selected from:
—CH=N—N($R_2$)—X—,
—CH$_2$OC(O)—N($R_2$)—X—,
—CH=N—O—X—,
—CH$_2$OC(O)—X—,
—CH$_2$N($R_2$)—X—,

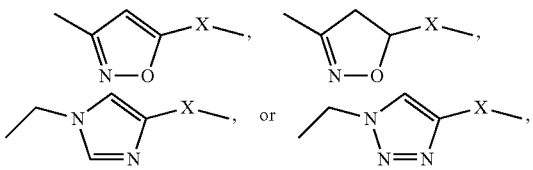

wherein X is selected from a combination of 1-5 groups selected from:
i) ($C_1$-$C_8$)alkylene,
ii) ($C_3$-$C_8$)cycloalkylene,
iii) ($C_3$-$C_8$)heterocycloalkylene,
iv) arylene,
v) heteroarylene,
vi) —O—,
vii) —N($R_2$)—, and
viii) —C(O)—, where $R_2$ is as defined above.

In additional preferred embodiments of the penam derivatives having general formula I shown above, Z is selected from:

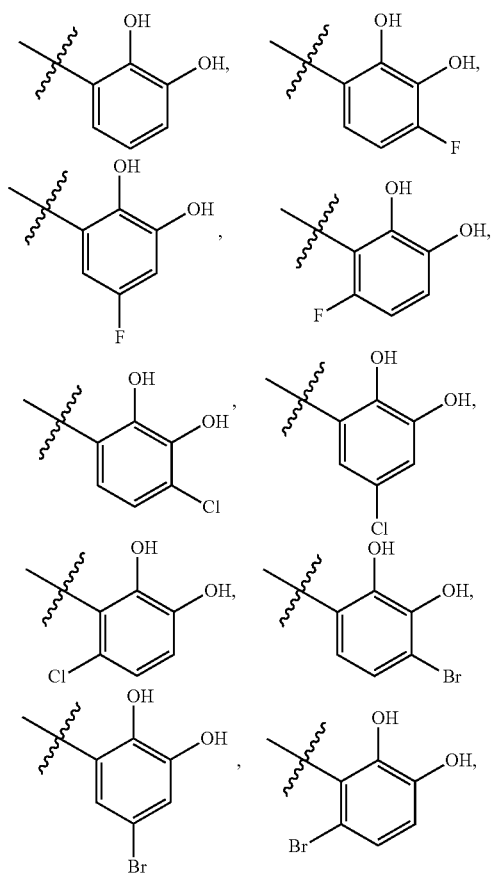

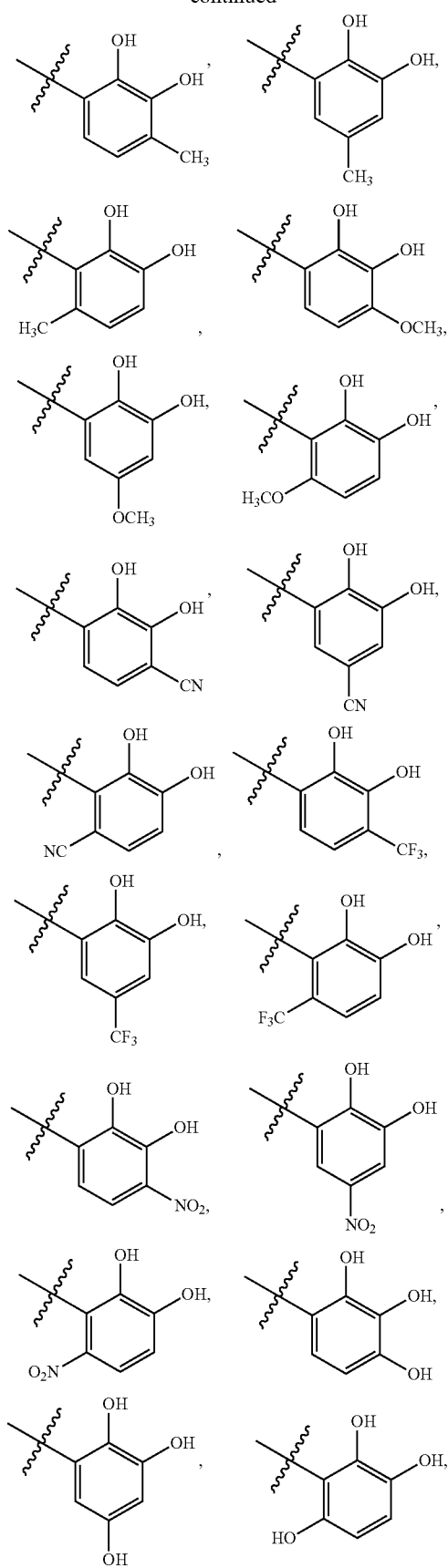
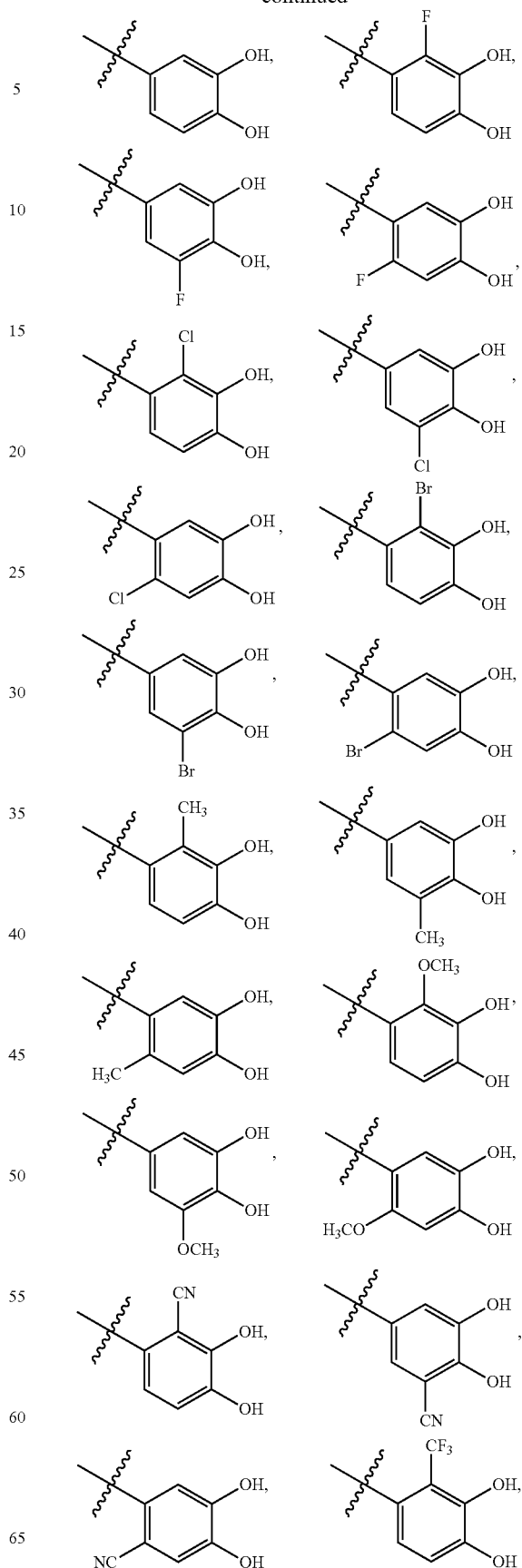

-continued

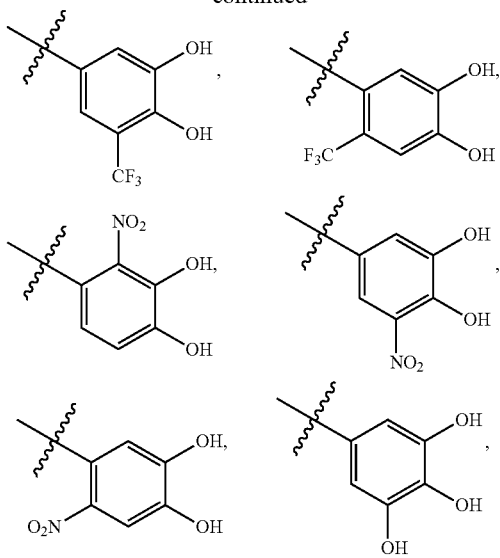

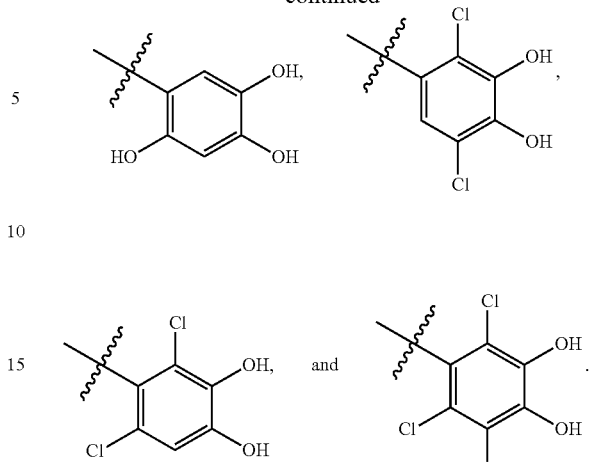

Additional preferred embodiments of the penam derivatives are identified in Table 1 below.

TABLE 1

| | Name |
|---|---|
| 1. | (2S,3R,5R)-3-((E)-(2-(2-chloro-4,5-dihydroxybenzoyl)hydrazono)methyl)-3-methyl-7-oxo-4-thia-1-azabicyclo[3.2.0]heptane-2-carboxylic acid 4,4-dioxide [See Example 1] |
| 2. | (2S,3R,5R)-3-methyl-7-oxo-3-((E)-(2-(2,3,4-trihydroxybenzoyl)hydrazono)methyl)-4-thia-1-azabicyclo[3.2.0]heptane-2-carboxylic acid 4,4-dioxide [See Example 2] |
| 3. | (2S,3R,5R)-3-((E)-(2-(2-chloro-3,4-dihydroxybenzoyl)-2-methylhydrazono)methyl)-3-methyl-7-oxo-4-thia-1-azabicyclo[3.2.0]heptane-2-carboxylic acid 4,4-dioxide [See Example 3] |
| 4. | (2S,3R,5R)-3-((E)-(2-(2,5-dichloro-3,4-dihydroxybenzoyl)hydrazono)methyl)-3-methyl-7-oxo-4-thia-1-azabicyclo[3.2.0]heptane-2-carboxylic acid 4,4-dioxide [See Example 4] |
| 5. | (2S,3R,5R)-3-((E)-(2-(3,4-dihydroxybenzoyl)hydrazono)methyl)-3-methyl-7-oxo-4-thia-1-azabicyclo[3.2.0]heptane-2-carboxylic acid 4,4-dioxide [See Example 5] |
| 6. | (2S,3R,5R)-3-methyl-7-oxo-3-((E)-(2-(3,4,5-trihydroxybenzoyl)hydrazono)methyl)-4-thia-1-azabicyclo[3.2.0]heptane-2-carboxylic acid 4,4-dioxide [See Example 6] |
| 7. | (2S,3R,5R)-3-((E)-(2-(3,4-dihydroxybenzoyl)-2-methylhydrazono)methyl)-3-methyl-7-oxo-4-thia-1-azabicyclo[3.2.0]heptane-2-carboxylic acid 4,4-dioxide [See Example 7] |
| 8. | (2S,3R,5R)-3-((E)-(2-(2-bromo-3,4-dihydroxybenzoyl)hydrazono)methyl)-3-methyl-7-oxo-4-thia-1-azabicyclo[3.2.0]heptane-2-carboxylic acid 4,4-dioxide [See Example 10] |
| 9. | (2S,3R,5R)-3-methyl-7-oxo-3-((E)-(2-(2,3,6-trichloro-4,5-dihydroxybenzoyl)hydrazono)methyl)-4-thia-1-azabicyclo[3.2.0]heptane-2-carboxylic acid 4,4-dioxide [See Example 11] |
| 10. | (2S,3R,5R)-3-((E)-(2-(2,6-dichloro-3,4-dihydroxybenzoyl)hydrazono)methyl)-3-methyl-7-oxo-4-thia-1-azabicyclo[3.2.0]heptane-2-carboxylic acid 4,4-dioxide [See Example 14] |
| 11. | (2S,3R,5R)-3-((E)-(2-(2-fluoro-3,4-dihydroxybenzoyl)hydrazono)methyl)-3-methyl-7-oxo-4-thia-1-azabicyclo[3.2.0]heptane-2-carboxylic acid 4,4-dioxide [See Example 15] |
| 12. | (2S,3R,5R)-3-((E)-(2-(3,4-dihydroxy-2-methylbenzoyl)hydrazono)methyl)-3-methyl-7-oxo-4-thia-1-azabicyclo[3.2.0]heptane-2-carboxylic acid 4,4-dioxide [See Example 16] |
| 13. | (2S,3R,5R)-3-((E)-(2-(2-(3,4-dihydroxyphenyl)acetyl)hydrazono)methyl)-3-methyl-7-oxo-4-thia-1-azabicyclo[3.2.0]heptane-2-carboxylic acid 4,4-dioxide [See Example 20] |
| 14. | (2S,3R,5R)-3-((E)-(2-((R)-2-((tert-butoxycarbonyl)amino)-3-(3,4-dihydroxyphenyl)propanoyl)hydrazono)methyl)-3-methyl-7-oxo-4-thia-1-azabicyclo[3.2.0]heptane-2-carboxylic acid 4,4-dioxide [See Example 21] |
| 15. | (2S,3R,5R)-3-((E)-(2-(3-chloro-4,5-dihydroxybenzoyl)hydrazono)methyl)-3-methyl-7-oxo-4-thia-1-azabicyclo[3.2.0]heptane-2-carboxylic acid 4,4-dioxide [See Example 22] |
| 16. | (2S,3R,5R)-3-((E)-(2-(2-chloro-3,4-dihydroxybenzoyl)hydrazono)methyl)-3-methyl-7-oxo-4-thia-1-azabicyclo[3.2.0]heptane-2-carboxylic acid 4,4-dioxide [See Example 23] |

TABLE 1-continued

| | Name |
|---|---|
| 17. | (2S,3R,5R)-3-((E)-(2-(3-(3,4-dihydroxyphenyl)propanoyl)hydrazono)methyl)-3-methyl-7-oxo-4-thia-1-azabicyclo[3.2.0]heptane-2-carboxylic acid 4,4-dioxide [See Example 25] |
| 18. | (2S,3R,5R)-3-((E)-(2-(2,5-dihydroxy-3,6-dimethylbenzoyl)hydrazono)methyl)-3-methyl-7-oxo-4-thia-1-azabicyclo[3.2.0]heptane-2-carboxylic acid 4,4-dioxide [See Example 27] |
| 19. | (2S,3R,5R)-3-((E)-(2-(2,3-dihydroxybenzoyl)hydrazono)methyl)-3-methyl-7-oxo-4-thia-1-azabicyclo[3.2.0]heptane-2-carboxylic acid 4,4-dioxide [See Example 28] |
| 20. | (2S,3R,5R)-3-((E)-(2-(1-(2-chloro-3,4-dihydroxybenzoyl)pyrrolidine-3-carbonyl)hydrazono)methyl)-3-methyl-7-oxo-4-thia-1-azabicyclo[3.2.0]heptane-2-carboxylic acid 4,4-dioxide [See Example 38] |
| 21. | (2S,3R,5R)-3-((E)-(2-(1-(2-chloro-3,4-dihydroxybenzoyl)azetidine-3-carbonyl)hydrazono)methyl)-3-methyl-7-oxo-4-thia-1-azabicyclo[3.2.0]heptane-2-carboxylic acid 4,4-dioxide [See Example 39] |
| 22. | (2S,3R,5R)-3-((E)-(2-(1-(2-chloro-3,4-dihydroxybenzoyl)pyrrolidine-2-carbonyl)hydrazono)methyl)-3-methyl-7-oxo-4-thia-1-azabicyclo[3.2.0]heptane-2-carboxylic acid 4,4-dioxide [See Example 40] |
| 23. | (2S,3R,5R)-34(E)-(2-(5-(3,4-dihydroxybenzamido)picolinoyl)hydrazono)methyl)-3-methyl-7-oxo-4-thia-1-azabicyclo[3.2.0]heptane-2-carboxylic acid 4,4-dioxide [See Example 41] |
| 24. | (2S,3R,5R)-3-((E)-(2-(1-(2-chloro-3,4-dihydroxybenzoyl)piperidine-4-carbonyl)hydrazono)methyl)-3-methyl-7-oxo-4-thia-1-azabicyclo[3.2.0]heptane-2-carboxylic acid 4,4-dioxide [See Example 42] |
| 25. | (2S,3R,5R)-3-((E)-(2-(2-(2-chloro-3,4-dihydroxybenzamido)-3-hydroxypropanoyl)hydrazono)methyl)-3-methyl-7-oxo-4-thia-1-azabicyclo[3.2.0]heptane-2-carboxylic acid 4,4-dioxide [See Example 43] |
| 26. | (2S,3R,5R)-3-((E)-(2-(2-(2-chloro-3,4-dihydroxybenzamido)-3-phenylpropanoyl)hydrazono)methyl)-3-methyl-7-oxo-4-thia-1-azabicyclo[3.2.0]heptane-2-carboxylic acid 4,4-dioxide [See Example 44] |
| 27. | (2S,3R,5R)-3-((E)-(2-(4-((2-chloro-3,4-dihydroxybenzamido)methyl)benzoyl)hydrazono)methyl)-3-methyl-7-oxo-4-thia-1-azabicyclo[3.2.0]heptane-2-carboxylic acid 4,4-dioxide [See Example 45 |
| 28. | (2S,3R,5R)-3-((E)-(2-(4-((3,4-dihydroxybenzamido)methyl)benzoyl)hydrazono)methyl)-3-methyl-7-oxo-4-thia-1-azabicyclo[3.2.0]heptane-2-carboxylic acid 4,4-dioxide [See Example 46] |
| 29. | ((2S,3R,5R)-3-((E)-(2-(2-(3,4-dihydroxybenzamido)-3-methylbutanoyl)hydrazono)methyl)-3-methyl-7-oxo-4-thia-1-azabicyclo[3.2.0]heptane-2-carboxylic acid 4,4-dioxide [See Example 47] |
| 30. | (2S,3R,5R)-3-((E)-(2-(2-(2-chloro-3,4-dihydroxybenzamido)-3-methylbutanoyl)hydrazono)methyl)-3-methyl-7-oxo-4-thia-1-azabicyclo[3.2.0]heptane-2-carboxylic acid 4,4-dioxide [See Example 48] |
| 31. | (2S,3R,5R)-3-((E)-(2-(1-(2-chloro-3,4-dihydroxybenzoyl)piperidine-3-carbonyl)hydrazono)methyl)-3-methyl-7-oxo-4-thia-1-azabicyclo[3.2.0]heptane-2-carboxylic acid 4,4-dioxide [See Example 49] |
| 32. | (2S,3R,5R)-3-((E)-(2-(2-(3,4-dihydroxybenzamido)-3-hydroxypropanoyl)hydrazono)methyl)-3-methyl-7-oxo-4-thia-1-azabicyclo[3.2.0]heptane-2-carboxylic acid 4,4-dioxide [See Example 50] |
| 33. | (2S,3R,5R)-3-((E)-(2-(2-(3,4-dihydroxybenzamido)-3-phenylpropanoyl)hydrazono)methyl)-3-methyl-7-oxo-4-thia-1-azabicyclo[3.2.0]heptane-2-carboxylic acid 4,4-dioxide [See Example 51] |
| 34. | (2S,3R,5R)-3-((E)-(2-(1-(3,4-dihydroxybenzamido)cyclopropanecarbonyl)hydrazono)methyl)-3-methyl-7-oxo-4-thia-1-azabicyclo[3.2.0]heptane-2-carboxylic acid 4,4-dioxide [See Example 52] |
| 35. | (2S,3R,5R)-3-((E)-(2-(1-(2-chloro-3,4-dihydroxybenzamido)cyclopropanecarbonyl)hydrazono)methyl)-3-methyl-7-oxo-4-thia-1-azabicyclo[3.2.0]heptane-2-carboxylic acid 4,4-dioxide [See Example 53] |
| 36. | (2S,3R,5R)-3-((E)-(2-(4-((3,4-dihydroxybenzoyl)oxy)benzoyl)hydrazono)methyl)-3-methyl-7-oxo-4-thia-1-azabicyclo[3.2.0]heptane-2-carboxylic acid 4,4-dioxide [See Example 54] |
| 37. | (2S,3R,5R)-3-((E)-(2-(2-((tert-butoxycarbonyl)amino)-3-((2-chloro-3,4-dihydroxybenzoyl)oxy)propanoyl)hydrazono)methyl)-3-methyl-7-oxo-4-thia-1-azabicyclo[3.2.0]heptane-2-carboxylic acid 4,4-dioxide [See Example 55] |
| 38. | (2S,3R,5R)-3-((E)-(2-(3',4'-dihydroxy-]1,1'-biphenyl]-4-carbonyl)hydrazono)methyl)-3-methyl-7-oxo-4-thia-1-azabicyclo[3.2.0]heptane-2-carboxylic acid 4,4-dioxide [See Example 56] |
| 39. | (2S,3R,5R)-3-((E)-(2-(4-((2-chloro-3,4-dihydroxybenzoyl)oxy)benzoyl)hydrazono)methyl)-3-methyl-7-oxo-4-thia-1-azabicyclo[3.2.0]heptane-2-carboxylic acid 4,4-dioxide [See Example 57] |
| 40. | (2S,3R,5R)-3-((E)-(2-(5-(2-chloro-3,4-dihydroxybenzamido)picolinoyl)hydrazono)methyl)-3-methyl-7-oxo-4-thia-1-azabicyclo[3.2.0]heptane-2-carboxylic acid 4,4-dioxide [See Example 58] |
| 41. | (2S,3R,5R)-3-((E)-(2-(2-(2-chloro-3,4-dihydroxybenzamido)acetyl)hydrazono)methyl)-3-methyl-7-oxo-4-thia-1-azabicyclo[3.2.0]heptane-2-carboxylic acid 4,4-dioxide [See Example 59] |

TABLE 1-continued

| | Name |
|---|---|
| 42. | (2S,3R,5R)-3-((E)-(2-(3-(2-chloro-3,4-dihydroxybenzamido)propanoyl)hydrazono)methyl)-3-methyl-7-oxo-4-thia-1-azabicyclo[3.2.0]heptane-2-carboxylic acid 4,4-dioxide [See Example 60] |
| 43. | (2S,3R,5R)-3-((E)-(2-(6-(2-chloro-3,4-dihydroxybenzamido)hexanoyl)hydrazono)methyl)-3-methyl-7-oxo-4-thia-1-azabicyclo[3.2.0]heptane-2-carboxylic acid 4,4-dioxide [See Example 61] |
| 44. | (2S,3R,5R)-3-((E)-(2-((S)-2-(2-chloro-3,4-dihydroxybenzamido)propanoyl)hydrazono)methyl)-3-methyl-7-oxo-4-thia-1-azabicyclo[3.2.0]heptane-2-carboxylic acid 4,4-dioxide [See Example 62] |
| 45. | (2S,3R,5R)-3-((E)-(2-(4-(2-chloro-3,4-dihydroxybenzamido)butanoyl)hydrazono)methyl)-3-methyl-7-oxo-4-thia-1-azabicyclo[3.2.0]heptane-2-carboxylic acid 4,4-dioxide [See Example 63] |
| 46. | (2S,3R,5R)-3-((E)-(2-(2-(3,4-dihydroxybenzamido)acetyl)hydrazono)methyl)-3-methyl-7-oxo-4-thia-1-azabicyclo[3.2.0]heptane-2-carboxylic acid 4,4-dioxide [See Example 64] |
| 47. | (2S,3R,5R)-3-((E)-(2-((S)-2-(3,4-dihydroxybenzamido)propanoyl)hydrazono)methyl)-3-methyl-7-oxo-4-thia-1-azabicyclo[3.2.0]heptane-2-carboxylic acid 4,4-dioxide [See Example 65] |
| 48. | (2S,3R,5R)-3-((E)-(2-(4-(3,4-dihydroxybenzamido)butanoyl)hydrazono)methyl)-3-methyl-7-oxo-4-thia-1-azabicyclo[3.2.0]heptane-2-carboxylic acid 4,4-dioxide [See Example 66] |
| 49. | (2S,3R,5R)-3-((E)-(2-(3-(3,4-dihydroxybenzamido)propanoyl)hydrazono)methyl)-3-methyl-7-oxo-4-thia-1-azabicyclo[3.2.0]heptane-2-carboxylic acid 4,4-dioxide [See Example 67] |
| 50. | (2S,3R,5R)-3-((E)-(2-(6-(3,4-dihydroxybenzamido)hexanoyl)hydrazono)methyl)-3-methyl-7-oxo-4-thia-1-azabicyclo[3.2.0]heptane-2-carboxylic acid 4,4-dioxide [See Example 68] |
| 51. | (2S,3R,5R)-3-(((2-(3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide [See Example 69] |
| 52. | (2S,3R,5R)-3-(((2-(2-chloro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide [See Example 70] |
| 53. | (2S,3R,5R)-3-(((2-(2-(3,4-dihydroxyphenyl)-2-oxoethyl)hydrazinecarbonyl)oxy)methyl)-3-methyl-7-oxo-4-thia-1-azabicyclo[3.2.0]heptane-2-carboxylic acid 4,4-dioxide [See Example 71] |
| 54. | (2S,3R,5R)-3-(((2-(2,3-dihydroxybenzoyl)hydrazinecarbonyl)oxy)methyl)-3-methyl-7-oxo-4-thia-1-azabicyclo[3.2.0]heptane-2-carboxylic acid 4,4-dioxide [See Example 72] |
| 55. | (2S,3R,5R)-3-methyl-7-oxo-3-(((2-(3,4,5-trihydroxybenzoyl)hydrazinecarbonyl)oxy)methyl)-4-thia-1-azabicyclo[3.2.0]heptane-2-carboxylic acid 4,4-dioxide [See Example 73] |
| 56. | (2S,3R,5R)-3-(((2-(3,4-dihydroxybenzoyl)-1-methylhydrazinecarbonyl)oxy)methyl)-3-methyl-7-oxo-4-thia-1-azabicyclo[3.2.0]heptane-2-carboxylic acid 4,4-dioxide [See Example 76] |
| 57. | (2S,3R,5R)-3-(((2-(2-chloro-4,5-dihydroxybenzoyl)hydrazinecarbonyl)oxy)methyl)-3-methyl-7-oxo-4-thia-1-azabicyclo[3.2.0]heptane-2-carboxylic acid 4,4-dioxide [See Example 77] |
| 58. | (2S,3R,5R)-3-(((2-(2-chloro-3,4-dihydroxybenzoyl)-1-methylhydrazinecarbonyl)oxy)methyl)-3-methyl-7-oxo-4-thia-1-azabicyclo[3.2.0]heptane-2-carboxylic acid 4,4-dioxide [See Example 80] |
| 59. | (2S,3R,5R)-3-(((2-(3,4-dihydroxybenzoyl)-2-methylhydrazinecarbonyl)oxy)methyl)-3-methyl-7-oxo-4-thia-1-azabicyclo[3.2.0]heptane-2-carboxylic acid 4,4-dioxide [See Example 81] |
| 60. | (2S,3R,5R)-3-methyl-7-oxo-3-(((2-(2,3,4-trihydroxybenzoyl)hydrazinecarbonyl)oxy)methyl)-4-thia-1-azabicyclo[3.2.0]heptane-2-carboxylic acid 4,4-dioxide [See Example 82] |
| 61. | (2S,3R,5R)-3-(((2-(2,6-dichloro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide [See Example 83] |
| 62 | (2S,3R,5R)-3-(((2-(2,5-dichloro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide [See Example 84] |
| 63. | (2S,3R,5R)-3-(((2-(2-fluoro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide [See Example 85] |
| 64. | (2S,3R,5R)-3-(((2-(3-(3,4-dihydroxyphenyl)-3-oxopropyl)hydrazinecarbonyl)oxy)methyl)-3-methyl-7-oxo-4-thia-1-azabicyclo[3.2.0]heptane-2-carboxylic acid 4,4-dioxide [See Example 86] |
| 65. | (2S,3R,5R)-3-(((2-(2-chloro-4,5-dihydroxybenzoyl)hydrazinecarbonyl)oxy)methyl)-3-methyl-7-oxo-4-thia-1-azabicyclo[3.2.0]heptane-2-carboxylic acid 4,4-dioxide [See Example 87] |
| 66. | (2S,3R,5R)-3-((((E)-2-(3,4-dihydroxybenzylidene)hydrazinecarbonyl)oxy)methyl)-3-methyl-7-oxo-4-thia-1-azabicyclo[3.2.0]heptane-2-carboxylic acid 4,4-dioxide [See Example 88] |
| 67. | (2S,3R,5R)-3-(((2-(3-chloro-4,5-dihydroxybenzoyl)hydrazinecarbonyl)oxy)methyl)-3-methyl-7-oxo-4-thia-1-azabicyclo[3.2.0]heptane-2-carboxylic acid 4,4-dioxide [See Example 89] |

TABLE 1-continued

| | Name |
|---|---|
| 68. | (2S,3R,5R)-3-(((2-(2-(3,4-dihydroxybenzamido)acetyl)hydrazinecarbonyl)oxy)methyl)-3-methyl-7-oxo-4-thia-1-azabicyclo[3.2.0]heptane-2-carboxylic acid 4,4-dioxide [See Example 91] |
| 69. | (2S,3R,5R)-3-(((3-(3,4-dihydroxybenzamido)pyrrolidine-1-carbonyl)oxy)methyl)-3-methyl-7-oxo-4-thia-1-azabicyclo[3.2.0]heptane-2-carboxylic acid 4,4-dioxide [See Example 92] |
| 70. | (2S,3R,5R)-3-(((4-(3,4-dihydroxybenzoyl)piperazine-1-carbonyl)oxy)methyl)-3-methyl-7-oxo-4-thia-1-azabicyclo[3.2.0]heptane-2-carboxylic acid 4,4-dioxide [See Example 93] |
| 71. | (2S,3R,5R)-3-(((2-(2-(2-chloro-3,4-dihydroxybenzamido)acetyl)hydrazinecarbonyl)oxy)methyl)-3-methyl-7-oxo-4-thia-1-azabicyclo[3.2.0]heptane-2-carboxylic acid 4,4-dioxide [See Example 94] |
| 72. | (2S,3R,5R)-3-(((((2-(2-chloro-3,4-dihydroxybenzamido)ethyl)carbamoyl)oxy)methyl)-3-methyl-7-oxo-4-thia-1-azabicyclo[3.2.0]heptane-2-carboxylic acid 4,4-dioxide [See Example 95] |
| 73. | (2S,3R,5R)-3-(((4-(3,4-dihydroxybenzamido)piperidine-1-carbonyl)oxy)methyl)-3-methyl-7-oxo-4-thia-1-azabicyclo[3.2.0]heptane-2-carboxylic acid 4,4-dioxide [See Example 96] |
| 74. | (2S,3R,5R)-3-((((1-(3,4-dihydroxybenzoyl)pyrrolidin-3-yl)carbamoyl)oxy)methyl)-3-methyl-7-oxo-4-thia-1-azabicyclo[3.2.0]heptane-2-carboxylic acid 4,4-dioxide [See Example 97] |
| 75. | (2S,3R,5R)-3-(((3-(3,4-dihydroxybenzamido)azetidine-1-carbonyl)oxy)methyl)-3-methyl-7-oxo-4-thia-1-azabicyclo[3.2.0]heptane-2-carboxylic acid 4,4-dioxide [See Example 98] |
| 76. | (2S,3R,5R)-3-(5-(2-(2-chloro-3,4-dihydroxyphenyl)-2-oxoethyl)isoxazol-3-yl)-3-methyl-7-oxo-4-thia-1-azabicyclo[3.2.0]heptane-2-carboxylic acid 4,4-dioxide [See Example 99] |
| 77. | (2S,3R,5R)-3-(5-(2-(3,4-dihydroxyphenyl)-2-oxoethyl)isoxazol-3-yl)-3-methyl-7-oxo-4-thia-1-azabicyclo[3.2.0]heptane-2-carboxylic acid 4,4-dioxide [See Example 100] |
| 78. | (2S,3R,5R)-3-(5-(2-chloro-3,4-dihydroxyphenyl)isoxazol-3-yl)-3-methyl-7-oxo-4-thia-1-azabicyclo[3.2.0]heptane-2-carboxylic acid 4,4-dioxide [See Example 108] |
| 79. | (2S,3R,5R)-3-(5-(2-(2,5-dichloro-3,4-dihydroxyphenyl)-2-oxoethyl)isoxazol-3-yl)-3-methyl-7-oxo-4-thia-1-azabicyclo[3.2.0]heptane-2-carboxylic acid 4,4-dioxide [See Example 102] |
| 80. | (2S,3R,5R)-3-(5-(3,4-dihydroxyphenyl)isoxazol-3-yl)-3-methyl-7-oxo-4-thia-1-azabicyclo[3.2.0]heptane-2-carboxylic acid 4,4-dioxide [See Example 103] |
| 81. | (2S,3R,5R)-3-(5-(2-((2-chloro-3,4-dihydroxybenzoyl)oxy)ethyl)isoxazol-3-yl)-3-methyl-7-oxo-4-thia-1-azabicyclo[3.2.0]heptane-2-carboxylic acid 4,4-dioxide [See Example 104] |
| 82. | (2S,3R,5R)-3-(5-(2,5-dichloro-3,4-dihydroxyphenyl)isoxazol-3-yl)-3-methyl-7-oxo-4-thia-1-azabicyclo[3.2.0]heptane-2-carboxylic acid 4,4-dioxide [See Example 105] |
| 83. | (2S,3R,5R)-3-(5-(2-((3,4-dihydroxybenzoyl)oxy)ethyl)isoxazol-3-yl)-3-methyl-7-oxo-4-thia-1-azabicyclo[3.2.0]heptane-2-carboxylic acid 4,4-dioxide [See Example 106] |
| 84. | (2S,3R,5R)-3-(5-(2-((2-chloro-3,4-dihydroxybenzoyl)oxy)ethyl)-4,5-dihydroisoxazol-3-yl)-3-methyl-7-oxo-4-thia-1-azabicyclo[3.2.0]heptane-2-carboxylic acid 4,4-dioxide [See Example 107] |
| 85. | (2S,3R,5R)-3-(5-(2-chloro-3,4-dihydroxyphenyl)-4,5-dihydroisoxazol-3-yl)-3-methyl-7-oxo-4-thia-1-azabicyclo[3.2.0]heptane-2-carboxylic acid 4,4-dioxide [See Example 108] |
| 86. | (2S,3R,5R)-3-(5-((2,5-dichloro-3,4-dihydroxybenzamido)methyl)-4,5-dihydroisoxazol-3-yl)-3-methyl-7-oxo-4-thia-1-azabicyclo[3.2.0]heptane-2-carboxylic acid 4,4-dioxide [See Example 109] |
| 87. | (2S,3R,5R)-3-(5-(2-((3,4-dihydroxybenzoyl)oxy)ethyl)-4,5-dihydroisoxazol-3-yl)-3-methyl-7-oxo-4-thia-1-azabicyclo[3.2.0]heptane-2-carboxylic acid 4,4-dioxide [See Example 110] |
| 88. | (2S,3R,5R)-3-(5-((2-chloro-3,4-dihydroxybenzamido)methyl)-4,5-dihydroisoxazol-3-yl)-3-methyl-7-oxo-4-thia-1-azabicyclo[3.2.0]heptane-2-carboxylic acid 4,4-dioxide [See Example 111] |
| 89. | (2S,3R,5R)-3-(5-(3,4-dihydroxybenzoyl)isoxazol-3-yl)-3-methyl-7-oxo-4-thia-1-azabicyclo[3.2.0]heptane-2-carboxylic acid 4,4-dioxide [See Example 112] |
| 90. | (2S,3R,5R)-3-(((3,4-dihydroxybenzoyl)oxy)methyl)-3-methyl-7-oxo-4-thia-1-azabicyclo[3.2.0]heptane-2-carboxylic acid 4,4-dioxide [See Example 113] |
| 91. | (2S,3R,5R)-3-(((2-chloro-3,4-dihydroxybenzoyl)oxy)methyl)-3-methyl-7-oxo-4-thia-1-azabicyclo[3.2.0]heptane-2-carboxylic acid 4,4-dioxide [See Example 114] |
| 92. | (2S,3S,5R)-3-(((3,4-dihydroxyphenyl)amino)methyl)-3-methyl-7-oxo-4-thia-1-azabicyclo[3.2.0]heptane-2-carboxylic acid 4,4-dioxide [See Example 117] |
| 93. | (2S,3R,5R)-3-((E)-((2-(2-chloro-3,4-dihydroxybenzamido)ethoxy)imino)methyl)-3-methyl-7-oxo-4-thia-1-azabicyclo[3.2.0]heptane-2-carboxylic acid 4,4-dioxide [See Example 118] |

TABLE 1-continued

| | Name |
|---|---|
| 94. | (2S,3R,5R)-3-((E)-((4-(2-chloro-3,4-dihydroxybenzamido)phenoxy)imino)methyl)-3-methyl-7-oxo-4-thia-1-azabicyclo[3.2.0]heptane-2-carboxylic acid 4,4-dioxide [See Example 119] |
| 95. | (2S,3R,5R)-3-(5-(2-chloro-3,4-dihydroxybenzoyl)isoxazol-3-yl)-3-methyl-7-oxo-4-thia-1-azabicyclo[3.2.0]heptane-2-carboxylic acid 4,4-dioxide [See Example 120] |
| 96. | (2S,3R,5R)-3-((E)-(2-(2-bromo-4,5-dihydroxybenzoyl)hydrazono)methyl)-3-methyl-7-oxo-4-thia-1-azabicyclo[3.2.0]heptane-2-carboxylic acid 4,4-dioxide [See Example 121] |
| 97. | (2S,3R,5R)-3-((E)-(2-(3-(3,4-dihydroxyphenyl)-5-methylisoxazole-4-carbonyl)hydrazono)methyl)-3-methyl-7-oxo-4-thia-1-azabicyclo[3.2.0]heptane-2-carboxylic acid 4,4-dioxide [See Example 122] |
| 98. | (2S,3R,5R)-3-((E)-(2-(3-(2-chloro-3,4-dihydroxyphenyl)isoxazole-5-carbonyl)hydrazono)methyl)-3-methyl-7-oxo-4-thia-1-azabicyclo[3.2.0]heptane-2-carboxylic acid 4,4-dioxide [See Example 123] |
| 99. | (2S,3R,5R)-34(E)-(2-(3-(3,4-dihydroxyphenyl)isoxazole-5-carbonyl)hydrazono)methyl)-3-methyl-7-oxo-4-thia-1-azabicyclo[3.2.0]heptane-2-carboxylic acid 4,4-dioxide [See Example 124] |
| 100. | (2S,3R,5R)-3-((E)-(2-((4S,5R)-2-(2,3-dihydroxyphenyl)-5-methyl-4,5-dihydrooxazole-4-carbonyl)hydrazono)methyl)-3-methyl-7-oxo-4-thia-1-azabicyclo[3.2.0]heptane-2-carboxylic acid 4,4-dioxide [See Example 125] |
| 101. | (2S,3R,5R)-3-((E)-(2-((4S,5R)-2-(3,4-dihydroxyphenyl)-5-methyl-4,5-dihydrooxazole-4-carbonyl)hydrazono)methyl)-3-methyl-7-oxo-4-thia-1-azabicyclo[3.2.0]heptane-2-carboxylic acid 4,4-dioxide [See Example 126] |
| 102. | (2S,3R,5R)-3-(((2-(3-(2,3-dihydroxyphenyl)isoxazole-5-carbonyl)hydrazinecarbonyl)oxy)methyl)-3-methyl-7-oxo-4-thia-1-azabicyclo[3.2.0]heptane-2-carboxylic acid 4,4-dioxide [See Example 127] |
| 103. | (2S,3R,5R)-3-(((2-(3-(2,3-dihydroxyphenyl)-4,5-dihydroisoxazole-5-carbonyl)hydrazinecarbonyl)oxy)methyl)-3-methyl-7-oxo-4-thia-1-azabicyclo[3.2.0]heptane-2-carboxylic acid 4,4-dioxide [See Example 128] |
| 104. | (2S,3R,5R)-3-(((4-(2-chloro-3,4-dihydroxybenzoyl)piperazine-1-carbonyl)oxy)methyl)-3-methyl-7-oxo-4-thia-1-azabicyclo[3.2.0]heptane-2-carboxylic acid 4,4-dioxide [See Example 129] |
| 105. | (2S,3R,5R)-3-(((3-(2-chloro-3,4-dihydroxybenzamido)azetidine-1-carbonyl)oxy)methyl)-3-methyl-7-oxo-4-thia-1-azabicyclo[3.2.0]heptane-2-carboxylic acid 4,4-dioxide [See Example 130] |
| 106. | (2S,3R,5R)-3-(((2-(3-(2-chloro-3,4-dihydroxyphenyl)-4,5-dihydroisoxazole-5-carbonyl)hydrazine-1-carbonyl)oxy)methyl)-3-methyl-7-oxo-4-thia-1-azabicyclo[3.2.0]heptane-2-carboxylic acid 4,4-dioxide [See Example 131] |
| 107. | (2S,3R,5R)-3-(((2-(3-(2-chloro-3,4-dihydroxyphenyl)-4,5-dihydroisoxazole-5-carbonyl)hydrazinecarbonyl)oxy)methyl)-3-methyl-7-oxo-4-thia-1-azabicyclo[3.2.0]heptane-2-carboxylic acid 4,4-dioxide [See Example 132] |
| 108. | (2S,3R,5R)-3-(((2-((4S,5R)-2-(2,3-dihydroxyphenyl)-5-methyl-4,5-dihydrooxazole-4-carbonyl)hydrazinecarbonyl)oxy)methyl)-3-methyl-7-oxo-4-thia-1-azabicyclo[3.2.0]heptane-2-carboxylic acid 4,4-dioxide [See Example 133] |
| 109. | (2S,3R,5R)-3-((((3,4-dihydroxyphenethyl)carbamoyl)oxy)methyl)-3-methyl-7-oxo-4-thia-1-azabicyclo[3.2.0]heptane-2-carboxylic acid 4,4-dioxide [See Example 134] |
| 110. | (2S,3R,5R)-3-(5-(3,4-dihydroxybenzoyl)isoxazol-3-yl)-3-methyl-7-oxo-4-thia-1-azabicyclo[3.2.0]heptane-2-carboxylic acid 4,4-dioxide [See Example 135] |
| 111. | (2S,3S,5R)-3-((4-((E)-(2-(2-chloro-3,4-dihydroxybenzoyl)hydrazono)methyl)-1H-imidazol-1-yl)methyl)-3-methyl-7-oxo-4-thia-1-azabicyclo[3.2.0]heptane-2-2-carboxylic acid 4,4-dioxide [See Example 136] |
| 112. | (2S,3R,5R)-3-((E)-(((1-(2-chloro-3,4-dihydroxybenzoyl)piperidin-4-yl)oxy)imino)methyl)-3-methyl-7-oxo-4-thia-1-azabicyclo[3.2.0]heptane-2-carboxylic acid 4,4-dioxide [See Example 137] |
| 113. | (2S,3R,5R)-3-((E)-(((1-(2-chloro-3,4-dihydroxybenzoyl)azetidin-3-yl)oxy)imino)methyl)-3-methyl-7-oxo-4-thia-1-azabicyclo[3.2.0]heptane-2-carboxylic acid 4,4-dioxide [See Example 138] |

As used herein, the terms and phrases have the meanings and definitions known in the art. Some of the more commonly used phrases are described in more detail below.

The carbon atom content of various hydrocarbon-containing moieties is indicated by a prefix designating the minimum and maximum number of carbon atoms in the moiety, i.e., the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "alkyl," as used herein, refers to a monovalent radical of saturated, straight or branched chain hydrocarbon group. Examples of alkyl groups include methyl, ethyl, propyl, iso-propyl, n-butyl, iso-butyl, tert-butyl, neo-pentyl, and n-hexyl. The alkyl groups of this invention are optionally substituted. The preferred alkyl group of this invention has one to eight carbons. The alkyl groups of this invention could be optionally substituted.

The term "alkenyl," as used herein, refers to a monovalent radical of unsaturated, straight or branched chain hydrocarbon group with at least one C=C double bond. Examples of alkenyl group include allyl or propenyl, butenyl, isobutenyl, pentenyl and the likes. The alkenyl groups of this invention are optionally substituted.

The term "alkynyl," as used herein, refers to a monovalent radical of unsaturated, straight or branched chain hydrocarbon group with at least one CC triple bond. Examples of alkynyl group include propargyl, butynyl, isobutynyl, pentynyl and the likes. The alkynyl groups of this invention are optionally substituted.

The term "alkylene," "alkenylene" or "alkynylene" as used herein, refers to bivalent radicals of alkyl, alkenyl, or alkynyl group as defined above. Examples of alkylene groups include methylene, ethylene, propylene, iso-propylene, n-butylene, isobutylene, n-hexylene and the like. Examples of alkenylene groups include ethenylene, propenylene and the like. Examples of alkynylene groups include ethynylene, propynylene and the like. The "alkylene," "alkenylene" or "alkynylene" groups of this invention are optionally substituted.

The term "alkylamino," as used herein, refers to an amino group (—NH$_2$), wherein one hydrogen atom is replaced by an alkyl group. Examples of alkylamino include methylamino, ethylamino, propylamino, and isopropylamino.

The term "alkoxy," as used herein, refers to an alkyl group, as previously defined, attached to an oxygen atom. Examples of alkoxy include methoxy, ethoxy, propoxy, iso-propoxy, n-butoxy, tert-butoxy, neo-pentoxy and n-hexyloxy. The alkoxy groups of this invention are optionally substituted.

The term "aryl" as used herein refers to a monovalent radical of carbocyclic aromatic group including phenyl, naphthyl, and anthracenyl. The aryl groups of this invention are optionally substituted.

The term "arylene" as used herein refers to bivalent radical of aryl group as defined above, which are optionally substituted, such as phenylene.

The term "cycloalkyl," as used herein, refers to a monovalent radical of saturated carbocyclic group having three to eight carbons such as cyclopropyl, cyclobutyl, cyclopentyl, cyclohexyl, cycloheptyl and cyclooctyl. The cycloalkyl groups of this invention are optionally substituted.

The term "cycloalkylene," as used herein, refers to bivalent radical of saturated carbocyclic groups having three to eight carbons. The cycloalkylene groups of this invention are optionally substituted.

The term "halogen," or "halide" as used herein, refers to fluorine, chlorine, bromine and iodine atoms and the term "halo" refers to —F, —Cl, —Br, and —I as substituent.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. Heteroaryl groups of this invention include those derived from furan, imidazole, isothiazole, isoxazole, oxazole, pyrazine, pyrazole, pyridazine, pyridine, pyrimidine, pyrrole, quinoline, thiazole, 1,3,4-thiadiazole, triazole, and tetrazole. The heteroaryl groups of this invention are optionally substituted.

The term "heteroarylene," as used herein, refers to a bivalent cyclic aromatic group having five or six ring atoms wherein at least one ring atom is selected from the group consisting of oxygen, sulfur, and nitrogen, and the remaining ring atoms are carbon. The heteroarylene groups are optionally substituted.

The term "heteroatom," as used herein, refers to an oxygen, nitrogen or sulfur atom.

The term "heterocycloalkyl" as used herein, refers to a non-aromatic five-, six-, seven- or eight-membered ring or a bi- or tricyclic group having one or more heteroatoms independently selected from oxygen, sulfur and nitrogen wherein each 5-membered ring has zero to one double bonds and each six-membered ring has zero to 2 double bonds. The nitrogen and sulfur heteroatoms are optionally be oxidized, the nitrogen heteroatom can optionally be quaternized, and any of the above heterocyclic rings can be fused to an aryl or heteroaryl ring. Representative heterocycloalkyls include, but are not limited to: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, morpholinyl, isothiazolidinyl, and tetrahydrofuranyl. The heterocycloalkyl groups of this invention are optionally substituted with one, two, or three substituents independently selected from —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH— alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -cycloheteroalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "heterocycloalkylene" as used herein, refers to a bivalent heterocycloalkyl group as defined above. The heterocycloalkylene groups of this invention can be optionally substituted.

The term "hydroxyl" as used herein, refers to —OH.

The term "substituted," as used herein, refers to having one or more substituents covalently attached.

The term "prodrugs" as used herein, refers to the prodrugs of the compounds of the current invention which are suitable for use in humans and animals with acceptable toxicity, irritation, allergic response, and the like, commensurate with a reasonable benefit to risk ratio, and effective for their intended use. The term "prodrugs" as used herein, represents compounds which can be transformed in vivo to parent compounds of defined above.

The term "salt" as used herein, refers to those salts which are suitable for use in humans and animals with acceptable toxicity, irritation, allergic response, etc., and are commensurate with a reasonable benefit to risk ratio. Pharmaceutically acceptable salts are well known in the art. The salts can be prepared by reacting the compounds of the invention with an acid or base (pharmaceutically acceptable salt forming agent), or be prepared in situ during the last step of isolation. Examples of pharmaceutically acceptable salts are salts of an acid group formed with inorganic bases such as sodium hydroxide, sodium carbonate, sodium phosphate, etc. Examples of pharmaceutically acceptable salts are salts of an amino group formed with inorganic acid such as hydrochloric acid, hydroboromic acid, phosphoric acid, and sulfuric acid or with organic acid such as acetic acid, oxalic acid, maleic acid, tartaric acid, citric acid, succinic acid or malonic acid. Other metal salts include lithium, potassium, calcium and magnesium. Additional pharmaceutically acceptable salts include ammonium cations formed with counterions such as halide, hydroxide, carboxylate, sulfate, phosphate, nitrate, loweralkyl sulfonate, and aryl sulfonate.

The term "solvate" as used herein, refers to a compound disclosed herein which is associated with solvent in the molecular form, i.e., in which the solvent is coordinatively bound, and may be represented, for example, by the formula R•(solvent), where R is a compound disclosed herein. A given compound may form more than one solvate including, for example, monosolvates (R•solvent)) or polysolvates (R•n(solvent)) wherein n is an integer greater than 1) including, for example, disolvates (R•2 (solvent)), trisolvates (12-3 (solvent)), and the like, or hemisolvates, such as, for example, R•n/2 (solvent), R•n/3 (solvent), R•n/4 (solvent) and the like, wherein n is an integer. Solvents herein include mixed solvents, for example, methanol/water, and as such, the solvates may incorporate one or more solvents within the solvate.

The term "deuterium-exchanged compound," as used herein, refers to a compound with one or more hydrogen atoms contained therein replaced with deuterium atoms. The deuterated compounds can be made by either chemically in reactions using deuterated oxide or biologically by growing organisms such as bacteria in a deuterium oxide containing medium or plants wherein the water source is replaced by deuterium oxide.

The term "pharmaceutically acceptable salt forming agent," as used herein, refers to an acid or base which could react with the compounds of the invention to form the pharmaceutically acceptable salts. Examples of bases are inorganic bases such as sodium hydroxide, sodium carbonate, or sodium phosphate, and organic bases such as pyridine, triethylamine, or N,N-Diisopropylmethylamine. Examples of acids are inorganic acids such as hydrochloric acid, hydroboromic acid, phosphoric acid, or sulfuric acid and organic acids such as acetic acid, oxalic acid, maleic acid, tartaric acid, citric acid, succinic acid or malonic acid.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use.

"A pharmaceutically acceptable carrier" as used in the specification and claims includes both one and more than one such carrier.

"Treating" or "treatment" of a disease includes: preventing the disease, i.e. causing the clinical symptoms of the disease not to develop in a mammal that may be exposed to or predisposed to the disease but does not yet experience or display symptoms of the disease, inhibiting the disease, i.e., arresting or reducing the development of the disease or its clinical symptoms, or relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Figure 2:
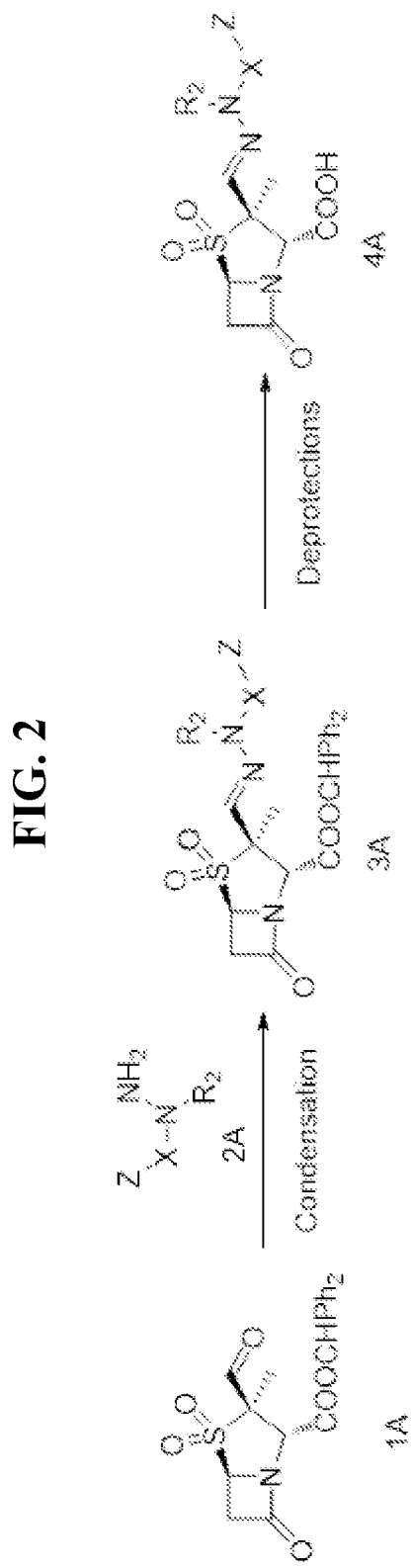
FIG. 2 shows Scheme A, a synthetic scheme for preparation of representative compounds in accordance with preferred embodiments disclosed herein.
Figure 3:
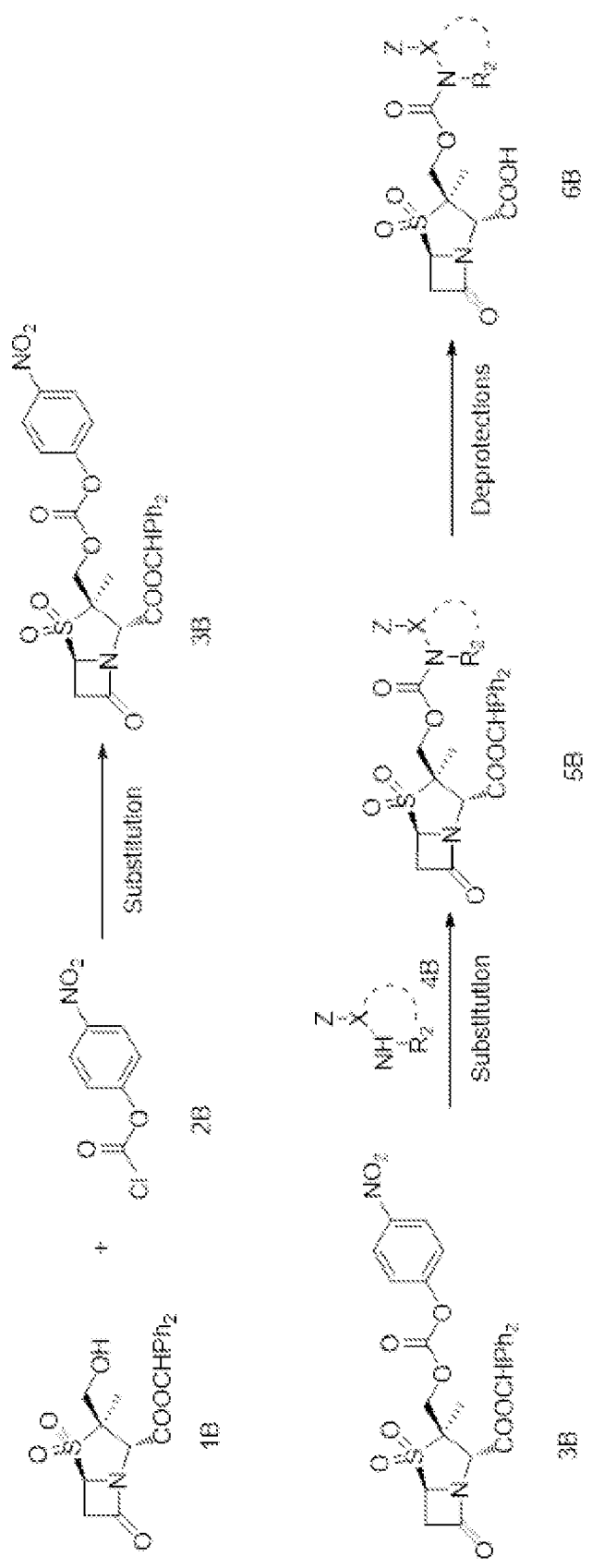
FIG. 3 shows Scheme B, a synthetic scheme for preparation of representative compounds in accordance with preferred embodiments disclosed herein.
Figure 4:
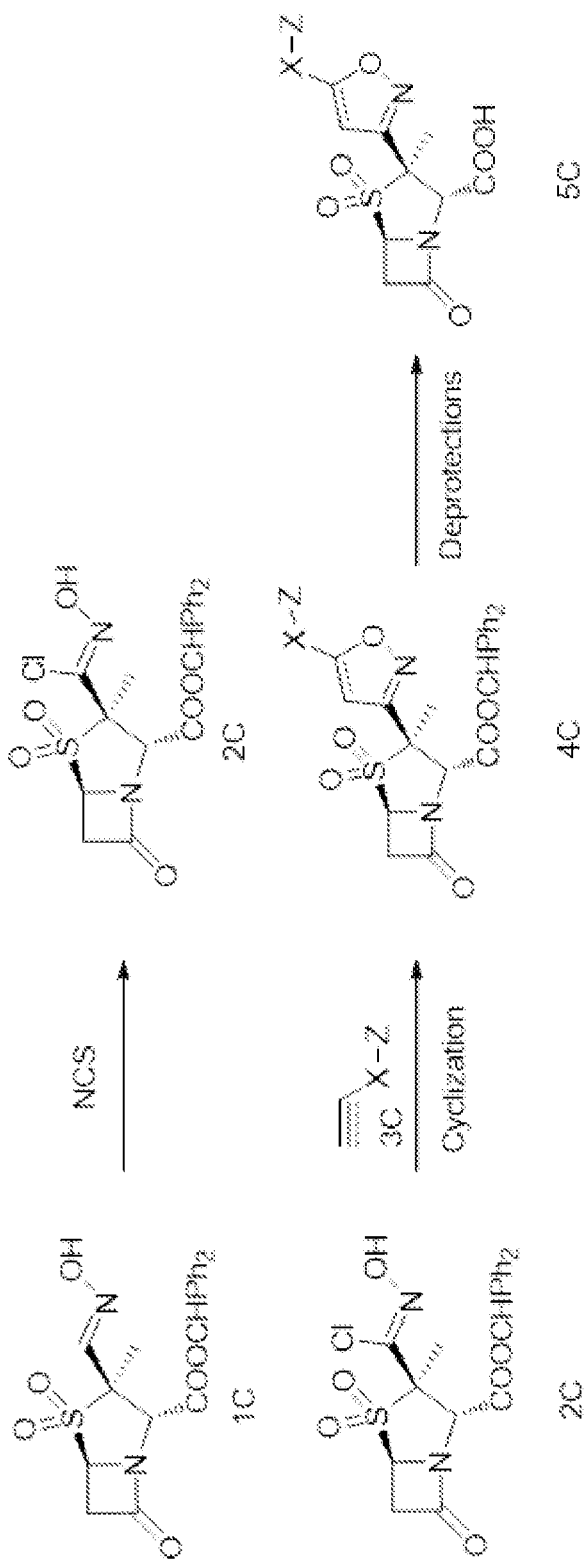
FIG. 4 shows Scheme C, a synthetic scheme for preparation of representative compounds in accordance with preferred embodiments disclosed herein.

The compounds of the preferred embodiments described herein can be better understood in connection with their synthetic schemes. The synthetic procedures in Scheme A to C, shown in FIGS. 2-4, are for illustration purpose and are not intended to limit the scope of the invention. It will be apparent to one skilled in the art that the compounds of the current invention could be prepared by a variety of synthetic routes, including but not limited to substitution of appropriate reagents, solvents or catalysts, change of reaction sequence, and variation of protecting groups.

Scheme A, shown in FIG. 2, shows a preparation of preferred embodiments of the penam derivative compounds of formula I as described herein. (2S,3R,5R)-benzhydryl 3-formyl-3-methyl-7-oxo-4-thia-1-azabicyclo[3.2.0]heptane-2-carboxylate-4,4-dioxide (1A, synthesis reported in U.S. Pat. No. 5,686,441) is an important aldehyde as starting material, by reacting (1A) with different iron chelating moiety bearing hydrazide or substituted hydrazide (2A) through condensation reaction could offer compounds (3A). A series of the compounds of formula I (4A) could be synthesized by deprotection of protecting groups of (3A).

Scheme B, shown in FIG. 3, illustrates a preparation of other sets of preferred embodiments of penam derivative compounds of formula I disclosed herein. (2S,3R,5R)-benzhydryl-3-methyl-3-((((4-nitrophenoxy)carbonyl)oxy)methyl)-7-oxo-4-thia-1-azabicyclo[3.2.0]heptane-2-carboxylate 4,4-dioxide (3B) is prepared by reacting (1B) (known compound reported in Hyodo, A. et al. 1996. *The Journal of Antibiotics,* 49(9), 944-946) with 4-nitrophenyl carbonochloridate (2B) through a substitution reaction. Compounds (3B) is an important intermediate bearing a leaving group for next step (the synthesis of 3B-like compounds could be found from U.S. Pat. 2010/9954 A1; U.S. Pat. No. 8,299,051 B2; U.S. Pat. 2013/79318 A1; U.S. Pat. No. 8,575,144 B2), by reacting (3B) with several types of nucleophilic compounds (4B) through substitution reaction could offer compounds (5B). Compounds (4B) is selected from iron chelating moiety bearing hydrazide or substituted hydrazide; iron chelating moiety bearing primary amine, secondary amine or cyclic amine. A series of the compounds of formula I (6B) could be synthesized by deprotection of protecting groups of (5B).

Scheme C, shown in FIG. 4, illustrates a preparation of yet other sets of preferred embodiments of penam derivative compounds of formula I as disclosed herein. Reacting (2S,3R,5R)-benzhydryl-3-((E)-(hydroxyimino)methyl)-3-methyl-7-oxo-4-thia-1-azabicyclo[3.2.0]heptane-2-carboxylate 4,4-dioxide (1C) (known compound reported in Phillips, O. A. et al. 2005. *Bioorganic & medicinal chemistry*, 13(8), 2847-2858) with NCS offers (2S,3R,5R)-benzhydryl-3-((Z)-chloro(hydroxyimino)methyl)-3-methyl-7-oxo-4-thia-1-azabicyclo[3.2.0]heptane-2-carboxylate 4,4-dioxide (2C). Cyclization reaction between (2C) and (3C) offers intermediate compounds (4C). (3C) is iron chelating moiety bearing alkene or alkyne. A series of the compounds of formula I (5C) could be synthesized by deprotection of protecting groups of (4C).

Preferred embodiments described herein also include a pharmaceutical composition comprising a pharmaceutically effective amount of a penam derivative compound of formula I in combination with a pharmaceutically acceptable carrier optionally in combination with other antibacterial agents.

Preferred embodiments described herein also include a method of treating or preventing a microbial infection in a subject in need of such treatment by administering the pharmaceutical composition of Formula I.

Preferred embodiments of the pharmaceutical composition of the present invention comprise a therapeutically effective amount of a penam derivative compound described herein formulated with one or more pharmaceutically acceptable carriers. For example, injectable preparations or sterile injectable solution; compositions for rectal or vaginal administrations; liquid or solid dosage forms for oral administration; dosage forms for topical or transdermal administration; powders and sprays.

According to the methods of treatment using the penam derivative compounds described herein, bacterial infections are treated or prevented in a patient such as a human or animal by administrating to the patient a therapeutically effective amount of a compound of the current invention, in such amounts and for such time as is necessary to achieve the desired therapeutic effects.

Preferred embodiments of the compounds of the current invention are penam derivatives of formula I identified above. In one aspect, compounds of the current invention contain several asymmetric and geometric centers. In some cases, one or more of the asymmetric and geometric centers can be converted to their opposite configurations. These stereoisomers are within the scope of the present invention. The examples are intended for illustration purposes only and are not intended to limit the scope of this invention.

Abbreviation as used herein have the meanings known by one skilled in the art. Specially, Ac represents acetyl group, Boc represents t-butoxycarbonyl group, Bn represents benzyl group, Cbz represents benzyloxycarbonyl group, DCM represents dichloromethane, DMAP represents 4-N,N-dimethylaminopyridine, DMF represents N,N-dimethylformamide, DMSO represents dimethyl sulfoxide, EDCI represents 1-(3-Dimethylaminopropyl)-3-ethylcarbodiimide Hydrochloride, Et represents ethyl group, EtOAc represents ethyl acetate, EtOH represents ethanol, HOBT represents 1-Hydroxybenzotriazole, Me represents methyl group, NCS represents for N-chlorosuccinimide, NMM represents N-methylmorpholine, OMe represents methoxyl group, PE represents petroleum ether, PMB represents para-methoxyl benzyl, Ph represents phenyl group, Pr represents propyl group, TEA represents triethylamine, TFA represents trifluoroacetic acid, THF represents tetrahedrofuran. The following abbreviations are also used: millimole (mmol), milliliter (mL), milligram (mg), microliter (μL), microgram (m).

EXAMPLES

The following examples describe how to prepare the various compounds and/or perform the various processes of the invention, and are to be construed as merely illustrative, and not limitations of the preceding disclosure in any way whatsoever. Those skilled in the art will recognize appropriate variations from the procedures both as to reagents and as to reaction conditions and techniques.

Example 1

(2S,3R,5R)-3-((E)-(2-(2-chloro-4,5-dihydroxybenzoyl)hydrazono)methyl)-3-methyl-7-oxo-4-thia-1-azabicyclo[3.2.0]heptane-2-carboxylic acid 4,4-dioxide

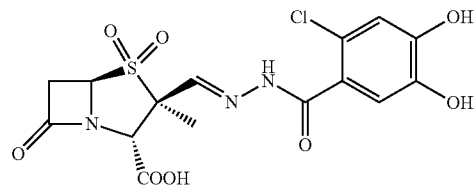 [SMILES: C[C@]1(/C=N/NC(=O)c2cc(O)c(O)cc2Cl)[C@H](C(=O)O)N2C(=O)C[C@H]2S1(=O)=O]

Figure 5:
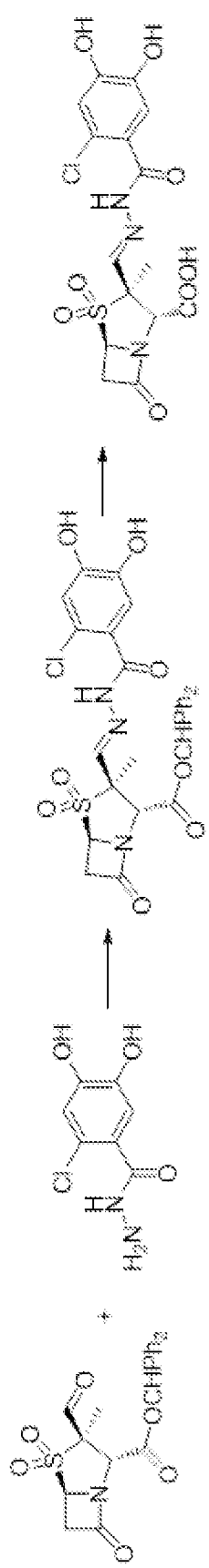
FIGS. 5-19 show synthetic schemes for the preparation of representative compounds in accordance with preferred embodiments disclosed herein.

FIG. 5 shows a synthetic scheme for the preparation of this compound. Step 1: (2S,3R,5R)-benzhydryl 3-((E)-(2-(2-chloro-4,5-dihydroxybenzoyl)hydrazono)methyl)-3-methyl-7-oxo-4-thia-1-azabicyclo[3.2.0]heptane-2-carboxylate 4,4-dioxide. To a solution of (3R,5R)-benzhydryl 3-formyl-3-methyl-7-oxo-4-thia-1-azabicyclo[3.2.0]heptane-2-carboxylate 4,4-dioxide (1.7 g, 4.1 mmol) in DCM (10 mL) and EtOH (10 mL) was added 2-chloro-4,5-dihydroxybenzohydrazide (0.87 g, 4.3 mmol). The mixture was stirred at rt for 6 h. Then the solvent was evaporated in vacuo, the residue was purified with flash chromatography (DCM:MeOH=20:1) to afforded the title product as white solid (1.0 g, yield 41%). LC-MS (ESI): m/z=598 (M+H)⁺.

Step 2: (2S,3R,5R)-3-((E)-(2-(2-chloro-4,5-dihydroxybenzoyl)hydrazono)methyl)-3-methyl-7-oxo-4-thia-1-azabicyclo[3.2.0]heptane-2-carboxylic acid 4,4-dioxide. A solution of (2S,3R,5R)-benzhydryl 3-((E)-(2-(2-chloro-4,5-dihydroxybenzoyl)hydrazono)methyl)-3-methyl-7-oxo-4-thia-1-azabicyclo[3.2.0]heptane-2-carboxylate 4,4-dioxide (1.0 g, 1.7 mmol) in m-cresol (5 mL) was stirred at 50° C. for 5 h. The solution was poured into PE (10 mL). The solid obtained after filtration was purified by column chromatography (silica gel, DCM:MeOH=20:1) to afford white solid (400 mg, yield 56%). ¹H NMR (400 MHz, DMSO-d6) δ12.10 (s, H), 10.20 (s, 1H), 9.41 (s, 1H), 7.79 (s, 1H), 7.12 (s, 1H), 6.94 (d, 1H), 6.83 (d, 1H), 6.62 (s, 1H), 5.30 (d, 1H), 5.01 (s, 1H), 3.74 (t, 3H), 3.31 (m, 1H), 2.20 (s, 1H), 1.62 (s, 3H). LC-MS (ESI): m/z=432 (M+H)⁺.

Example 2

(2S,3R,5R)-3-methyl-7-oxo-3-((E)-(2-(2,3,4-trihydroxybenzoyl)hydrazono)methyl)-4-thia-1-azabicyclo[3.2.0]heptane-2-carboxylic acid 4,4-dioxide

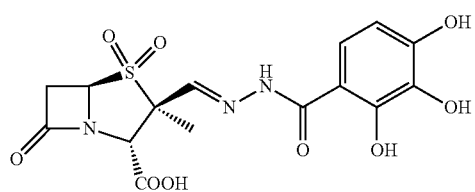 [SMILES: C[C@]1(/C=N/NC(=O)c2ccc(O)c(O)c2O)[C@H](C(=O)O)N2C(=O)C[C@H]2S1(=O)=O]

The title compound was prepared using the similar procedure as described in Example 1 except 2,3,4-trihydroxybenzohydrazide was used in place of 2-chloro-4,5-dihydroxybenzohydrazide. $^1$H NMR (400 MHz, DMSO-d6) δ 13.84 (br, 1H), 12.08 (s, 1H), 12.05 (s, 1H), 9.79 (s, 1H), 8.61 (s, 1H), 7.92 (s, 1H), 7.31 (d, 1H), 6.39 (d, 1H), 5.28 (d, 1H), 4.90 (s, 1H), 3.72 (dd, 1H), 3.26 (dd, 1H), 1.61 (s, 3H). LC-MS (ESI): m/z=414 (M+H)$^+$.

Example 3

(2S,3R,5R)-3-((E)-(2-(2-chloro-3,4-dihydroxybenzoyl)-2-methylhydrazono)methyl)-3-methyl-7-oxo-4-thia-1-azabicyclo[3.2.0]heptane-2-carboxylic acid 4,4-dioxide

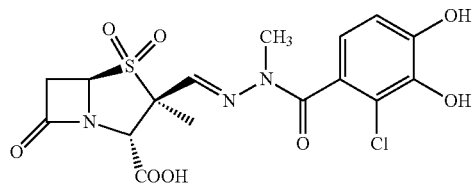 [SMILES: CN(/N=C/[C@@]1(C)[C@H](C(=O)O)N2C(=O)C[C@H]2S1(=O)=O)C(=O)c1ccc(O)c(O)c1Cl]

The title compound was prepared using the similar procedure as described in Example 1 except 2-chloro-3,4-dihydroxy-N-methylbenzohydrazide was used in place of 2-chloro-4,5-dihydroxybenzohydrazide.

$^1$H NMR (400 MHz, DMSO-d6) δ 13.81 (br, 1H), 9.98 (s, 1H), 9.19 (s, 1H), 7.44 (s, 1H), 6.75 (d, 1H), 6.61 (d, 1H), 5.16 (d, 1H), 4.68 (d, 1H), 4.57 (s, 1H), 4.54 (d, 1H), 3.61 (dd, 1H), 3.31 (s, 3H), 3.26 (dd, 1H), 1.61 (s, 3H). LC-MS (ESI): m/z=446 (M+H)$^+$.

Example 4

(2S,3R,5R)-3-((E)-(2-(2,5-dichloro-3,4-dihydroxybenzoyl)hydrazono)methyl)-3-methyl-7-oxo-4-thia-1-azabicyclo[3.2.0]heptane-2-carboxylic acid 4,4-dioxide

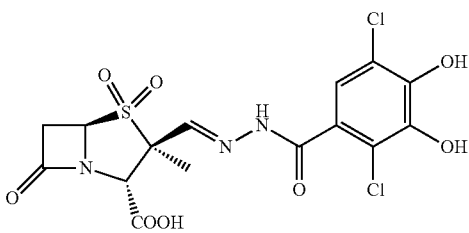 [SMILES: C[C@]1(/C=N/NC(=O)c2cc(Cl)c(O)c(O)c2Cl)[C@H](C(=O)O)N2C(=O)C[C@H]2S1(=O)=O]

The title compound was prepared using the similar procedure as described in EXAMPLE 1 except 2,5-dichloro-3,4-dihydroxybenzohydrazide was used in place of 2-chloro-4,5-dihydroxybenzohydrazide. $^1$H NMR (400 MHz, DMSO-d6) δ 13.88 (br, 1H), 12.13 (s, 1H), 10.08 (br, 2H), 7.74 (s, 1H), 7.15 (s, 1H), 5.29 (d, 1H), 4.90 (s, 1H), 3.78 (dd, 1H), 3.26 (dd, 1H), 1.61 (s, 3H). LC-MS (ESI): m/z=466 (M+H)$^+$.

Example 5

(2S,3R,5R)-3-((E)-(2-(3,4-dihydroxybenzoyl)hydrazono)methyl)-3-methyl-7-oxo-4-thia-1-azabicyclo[3.2.0]heptane-2-carboxylic acid 4,4-dioxide

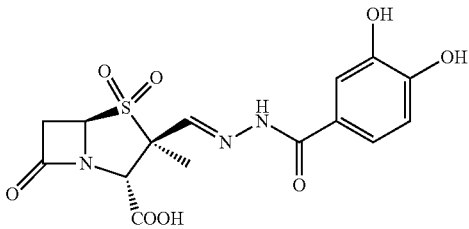 [SMILES: C[C@]1(/C=N/NC(=O)c2ccc(O)c(O)c2)[C@H](C(=O)O)N2C(=O)C[C@H]2S1(=O)=O]

The title compound was prepared using the similar procedure as described in EXAMPLE 1 except 3,4-dihydroxybenzohydrazide was used in place of 2-chloro-4,5-dihydroxybenzohydrazide.

$^1$H NMR (400 MHz, DMSO-d6): δ 13.84 (br, 1H), 11.92 (s, 1H), 9.69 (s, 1H), 9.27 (s, 1H), 7.90 (s, 1H), 7.34 (s, 1H), 7.29 (d, 1H), 6.82 (d, 1H), 5.28 (d, 1H), 4.90 (s, 1H), 3.72 (dd, 1H), 3.26 (dd, 1H), 1.61 (s, 3H). LC-MS (ESI): m/z=398 (M+H)$^+$.

Example 6

(2S,3R,5R)-3-methyl-7-oxo-3-((E)-(2-(3,4,5-trihydroxybenzoyl)hydrazono)methyl)-4-thia-1-azabicyclo[3.2.0]heptane-2-carboxylic acid 4,4-dioxide

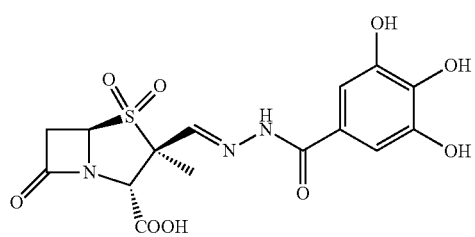 [SMILES: C[C@]1(/C=N/NC(=O)c2cc(O)c(O)c(O)c2)[C@H](C(=O)O)N2C(=O)C[C@H]2S1(=O)=O]

The title compound was prepared using the similar procedure as described in EXAMPLE 1 except 3,4,5-trihydroxybenzohydrazide was used in place of 2-chloro-4,5-dihydroxybenzohydrazide.

$^1$H NMR (400 MHz, DMSO-d6) δ 13.79 (br, 1H), 11.90 (s, 1H), 9.21 (s, 2H), 7.88 (s, 1H), 6.90 (s, 2H), 5.28 (d, 1H), 4.90 (s, 1H), 3.72 (dd, 1H), 3.26 (dd, 1H), 1.61 (s, 3H). LC-MS (ESI): m/z=414 (M+H)$^+$.

Example 7

(2S,3R,5R)-3-((E)-(2-(3,4-dihydroxybenzoyl)-2-methylhydrazono)methyl)-3-methyl-7-oxo-4-thia-1-azabicyclo[3.2.0]heptane-2-carboxylic acid 4,4-dioxide

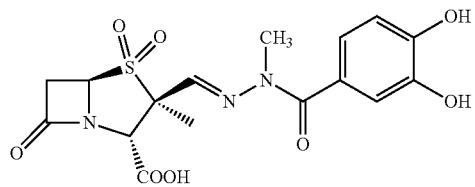 [SMILES: CN(/N=C/[C@@]1(C)[C@H](C(=O)O)N2C(=O)C[C@H]2S1(=O)=O)C(=O)c1ccc(O)c(O)c1]

The title compound was prepared using the similar procedure as described in EXAMPLE 1 except 3,4-dihydroxy-N-methylbenzohydrazide was used in place of 2-chloro-4,5-dihydroxybenzohydrazide.

$^1$H NMR (400 MHz, DMSO-d6) δ 13.83 (br, 1H), 9.54 (s, 1H), 9.11 (s, 1H), 7.42 (s, 1H), 7.13 (s, 1H), 7.05 (d, 1H), 6.71 (d, 1H), 5.16 (d, 1H), 4.68 (d, 1H), 4.57 (s, 1H), 4.54 (d, 1H), 3.61 (dd, 1H), 3.34 (s, 3H), 3.26 (dd, 1H), 1.61 (s, 3H). LC-MS (ESI): m/z=412 (M+H)$^+$.

Example 8

(2S,3R,5R)-3-((E)-(2-(2-hydroxy-3-methylbenzoyl)hydrazono)methyl)-3-methyl-7-oxo-4-thia-1-azabicyclo[3.2.0]heptane-2-carboxylic acid 4,4-dioxide

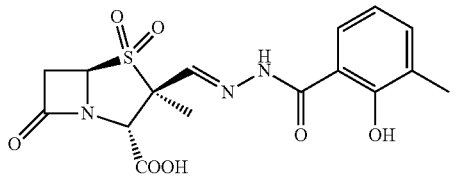 [SMILES: Cc1cccc(C(=O)N/N=C/[C@@]2(C)[C@H](C(=O)O)N3C(=O)C[C@H]3S2(=O)=O)c1O]

The title compound was prepared using the similar procedure as described in EXAMPLE 1 except 2-hydroxy-3-methylbenzohydrazide was used in place of 2-chloro-4,5-dihydroxybenzohydrazide. $^1$H NMR (400 MHz, DMSO-d6) δ 13.84 (br, 1H), 12.38 (s, 1H), 12.32 (s, 1H), 7.98 (s, 1H), 7.78 (d, 1H), 7.39 (d, 1H), 8.86 (t, 1H), 5.29 (d, 1H), 4.90 (s, 1H), 3.78 (dd, 1H), 3.26 (dd, 1H), 2.18 (s, 3H), 1.61 (s, 3H). LC-MS (ESI): m/z=396 (M+H)$^+$.

Example 9

(2S,3R,5R)-3-((E)-(2-(2-hydroxybenzoyl)hydrazono)methyl)-3-methyl-7-oxo-4-thia-1-azabicyclo[3.2.0]heptane-2-carboxylic acid 4,4-dioxide

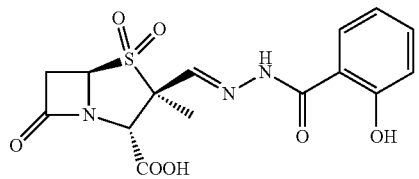 [SMILES: C[C@]1(/C=N/NC(=O)c2ccccc2O)[C@H](C(=O)O)N2C(=O)C[C@H]2S1(=O)=O]

The title compound was prepared using the similar procedure as described in EXAMPLE 1 except 2-hydroxybenzohydrazide was used in place of 2-chloro-4,5-dihydroxybenzohydrazide. $^1$H NMR (400 MHz, DMSO-d6) δ 13.84 (br, 1H), 12.09 (s, 1H), 11.52 (s, 1H), 7.97 (s, 1H), 7.83 (d, 1H), 7.48 (t, 1H), 6.97 (dd, 2H), 5.29 (d, 1H), 4.90 (s, 1H), 3.78 (dd, 1H), 3.26 (dd, 1H), 1.61 (s, 3H). LC-MS (ESI): m/z=382 (M+H)$^+$.

Example 10

(2S,3R,5R)-3-((E)-(2-(2-bromo-3,4-dihydroxybenzoyl)hydrazono)methyl)-3-methyl-7-oxo-4-thia-1-azabicyclo[3.2.0]heptane-2-carboxylic acid 4,4-dioxide

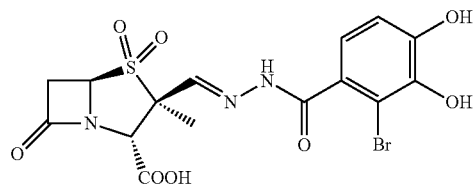 [SMILES: C[C@]1(/C=N/NC(=O)c2ccc(O)c(O)c2Br)[C@H](C(=O)O)N2C(=O)C[C@H]2S1(=O)=O]

The title compound was prepared using the similar procedure as described in EXAMPLE 1 except 2-bromo-3,4-dihydroxybenzohydrazide was used in place of 2-chloro-4,5-dihydroxybenzohydrazide. $^1$H NMR (400 MHz, DMSO-d6) δ 13.82 (br, 1H), 11.97 (s, 1H), 10.21 (s, 1H), 9.38 (s, 1H), 7.72 (s, 1H), 6.81 (d, 2H), 5.29 (d, 1H), 4.90 (s, 1H), 3.78 (dd, 1H), 3.26 (dd, 1H), 1.61 (s, 3H). LC-MS (ESI): m/z=476 (M+H)$^+$.

Example 11

(2S,3R,5R)-3-methyl-7-oxo-3-((E)-(2-(2,3,6-trichloro-4,5-dihydroxybenzoyl)hydrazono)methyl)-4-thia-1-azabicyclo[3.2.0]heptane-2-carboxylic acid 4,4-dioxide

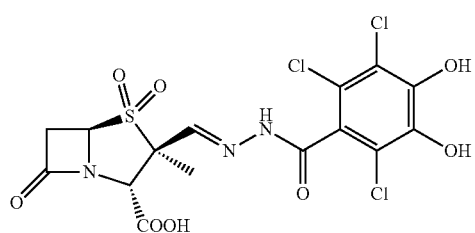 [SMILES: C[C@]1(/C=N/NC(=O)c2c(Cl)c(O)c(O)c(Cl)c2Cl)[C@H](C(=O)O)N2C(=O)C[C@H]2S1(=O)=O]

The title compound was prepared using the similar procedure as described in EXAMPLE 1 except 2,3,6-trichloro-4,5-dihydroxybenzohydrazide was used in place of 2-chloro-4,5-dihydroxybenzohydrazide. $^1$H NMR (400 MHz, DMSO-d6) δ 13.91 (br, 1H), 12.37 (s, 1H), 7.71 (s, 1H), 5.14 (d, 1H), 5.00 (s, 1H), 3.78 (dd, 1H), 3.26 (dd, 1H), 1.61 (s, 3H). LC-MS (ESI): m/z=500 (M+H)$^+$.

Example 12

(2S,3R,5R)-3-((E)-(2-isonicotinoylhydrazono)methyl)-3-methyl-7-oxo-4-thia-1-azabicyclo[3.2.0]heptane-2-carboxylic acid 4,4-dioxide

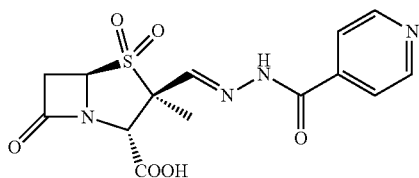 [SMILES: C[C@]1(/C=N/NC(=O)c2ccncc2)[C@H](C(=O)O)N2C(=O)C[C@H]2S1(=O)=O]

The title compound was prepared using the similar procedure as described in EXAMPLE 1 except isonicotinohydrazide was used in place of 2-chloro-4,5-dihydroxybenzohydrazide. $^1$H NMR (400 MHz, DMSO-d6) δ 13.76 (br, 1H), 12.42 (s, 1H), 8.79 (d, 2H), 7.98 (s, 1H), 7.80 (d, 2H), 5.23 (d, 1H), 4.89 (s, 1H), 3.73 (dd, 1H), 3.32 (dd, 1H), 1.63 (s, 3H). LC-MS (ESI): m/z=367 (M+H)$^+$.

Example 13

(2S,3R,5R)-3-methyl-3-((E)-(2-nicotinoylhydrazono)methyl)-7-oxo-4-thia-1-azabicyclo[3.2.0]heptane-2-carboxylic acid 4,4-dioxide

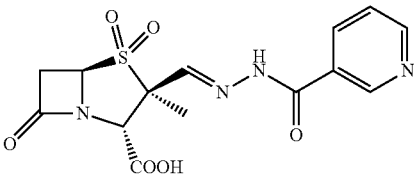 [SMILES: C[C@]1(/C=N/NC(=O)c2cccnc2)[C@H](C(=O)O)N2C(=O)C[C@H]2S1(=O)=O]

The title compound was prepared using the similar procedure as described in EXAMPLE 1 except nicotinohydrazide was used in place of 2-chloro-4,5-dihydroxybenzohydrazide. $^1$H NMR (400 MHz, DMSO-d6) δ 13.76 (br, 1H), 8.33 (d, 2H), 7.62 (s, 1H), 7.22 (br, 1H), 7.02 (t, 1H), 6.55 (s, 1H), 5.23 (d, 1H), 4.89 (s, 1H), 3.73 (dd, 1H), 3.32 (dd, 1H), 1.63 (s, 3H). LC-MS (ESI): m/z=367 (M+H)$^+$.

Example 14

(2S,3R,5R)-3-((E)-(2-(2,6-dichloro-3,4-dihydroxybenzoyl)hydrazono)methyl)-3-methyl-7-oxo-4-thia-1-azabicyclo[3.2.0]heptane-2-carboxylic acid 4,4-dioxide

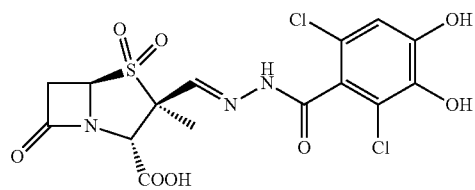 [SMILES: C[C@]1(/C=N/NC(=O)c2c(Cl)cc(O)c(O)c2Cl)[C@H](C(=O)O)N2C(=O)C[C@H]2S1(=O)=O]

The title compound was prepared using the similar procedure as described in EXAMPLE 1 except 2,6-dichloro-3,4-dihydroxybenzohydrazide was used in place of 2-chloro-4,5-dihydroxybenzohydrazide. $^1$H NMR (400 MHz, DMSO-d6) δ 14.00 (br, 1H), 12.15 (s, 1H), 10.40 (s, 1H), 10.13 (s, 1H), 7.72 (s, 1H), 6.88 (s, 1H), 5.29 (d, 1H), 4.90 (s, 1H), 3.78 (dd, 1H), 3.26 (dd, 1H), 1.61 (s, 3H). LC-MS (ESI): m/z=466 (M+H)$^+$.

Example 15

(2S,3R,5R)-3-((E)-(2-(2-fluoro-3,4-dihydroxybenzoyl)hydrazono)methyl)-3-methyl-7-oxo-4-thia-1-azabicyclo[3.2.0]heptane-2-carboxylic acid 4,4-dioxide

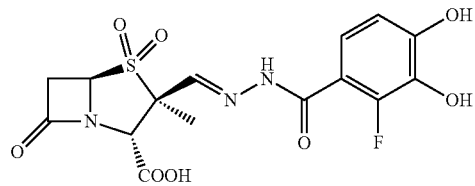 [SMILES: C[C@]1(/C=N/NC(=O)c2ccc(O)c(O)c2F)[C@H](C(=O)O)N2C(=O)C[C@H]2S1(=O)=O]

The title compound was prepared using the similar procedure as described in EXAMPLE 1 except 2-fluoro-3,4-dihydroxybenzohydrazide was used in place of 2-chloro-4,5-dihydroxybenzohydrazide. $^1$H NMR (400 MHz, DMSO-d6) δ 13.89 (br, 1H), 11.88 (s, 1H), 10.12 (s, 1H), 9.33 (s, 1H), 7.81 (s, 1H), 6.98 (s, 1H), 6.88 (d, 1H), 5.29 (d, 1H), 4.90 (s, 1H), 3.78 (dd, 1H), 3.26 (dd, 1H), 1.61 (s, 3H). LC-MS (ESI): m/z=416 (M+H)$^+$.

Example 16

(2S,3R,5R)-3-((E)-(2-(3,4-dihydroxy-2-methylbenzoyl)hydrazono)methyl)-3-methyl-7-oxo-4-thia-1-azabicyclo[3.2.0]heptane-2-carboxylic acid 4,4-dioxide

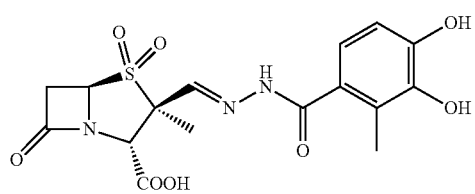 [SMILES: Cc1c(C(=O)N/N=C/[C@@]2(C)[C@H](C(=O)O)N3C(=O)C[C@H]3S2(=O)=O)ccc(O)c1O]

The title compound was prepared using the similar procedure as described in EXAMPLE 1 except 3,4-dihydroxy-2-methylbenzohydrazide was used in place of 2-chloro-4,5-dihydroxybenzohydrazide. $^1$H NMR (400 MHz, DMSO-d6) δ 13.69 (br, 1H), 11.83 (s, 1H), 9.73 (s, 1H), 8.44 (s, 1H), 7.78 (s, 1H), 6.78 (d, 1H), 6.67 (dd, 1H), 5.28 (s, 1H), 4.85 (s, 1H), 3.78 (dd, 1H), 3.26 (dd, 1H), 2.17 (s, 3H), 1.61 (s, 3H). LC-MS (ESI): m/z=412 (M+H)$^+$.

Example 17

(2S,3R,5R)-3-methyl-7-oxo-3-((E)-(2-picolinoylhydrazono)methyl)-4-thia-1-azabicyclo[3.2.0]heptane-2-carboxylic acid 4,4-dioxide

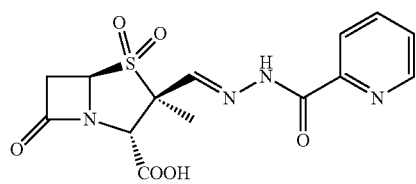 [SMILES: C[C@]1(/C=N/NC(=O)c2ccccn2)[C@H](C(=O)O)N2C(=O)C[C@H]2S1(=O)=O]

The title compound was prepared using the similar procedure as described in EXAMPLE 1 except picolinohydrazide was used in place of 2-chloro-4,5-dihydroxybenzohydrazide. $^1$H NMR (400 MHz, DMSO-d6) δ 13.79 (br, 1H), 12.51 (s, 1H), 8.71 (d, 1H), 8.16 (s, 1H), 8.11 (d, 1H), 8.06 (t, 1H), 7.69 (t, 1H), 5.23 (d, 1H), 4.89 (s, 1H), 3.73 (dd, 1H), 3.32 (dd, 1H), 1.63 (s, 3H). LC-MS (ESI): m/z=367 (M+H)$^+$.

Example 18

(2S,3R,5R)-3-methyl-7-oxo-3-((E)-(2-(pyrimidine-5-carbonyl)hydrazono)methyl)-4-thia-1-azabicyclo[3.2.0]heptane-2-carboxylic acid 4,4-dioxide

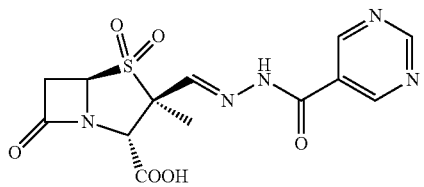 [SMILES: C[C@]1(/C=N/NC(=O)c2cncnc2)[C@H](C(=O)O)N2C(=O)C[C@H]2S1(=O)=O]

The title compound was prepared using the similar procedure as described in Example 1, except pyrimidine-5-carbohydrazide was used in place of 2-chloro-4,5-dihydroxybenzohydrazide. $^1$H NMR (400 MHz, DMSO-d6) δ 13.75 (br, 1H), 9.35 (s, 1H), 9.09 (d, 1H), 8.12 (s, 1H), 8.07 (d, 1H), 5.23 (d, 1H), 4.89 (s, 1H), 3.73 (dd, 1H), 3.32 (dd, 1H), 1.63 (s, 3H). LC-MS (ESI): m/z=368 (M+H)$^+$.

Example 19

(2S,3R,5R)-3-methyl-7-oxo-3-((E)-(2-(pyrazine-2-carbonyl)hydrazono)methyl)-4-thia-1-azabicyclo[3.2.0]heptane-2-carboxylic acid 4,4-dioxide

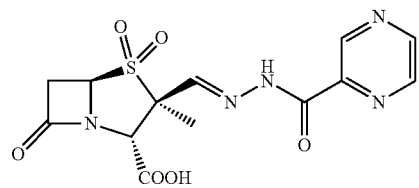 [SMILES: C[C@]1(/C=N/NC(=O)c2cnccn2)[C@H](C(=O)O)N2C(=O)C[C@H]2S1(=O)=O]

The title compound was prepared using the similar procedure as described in EXAMPLE 1 except pyrazine-2-carbohydrazide was used in place of 2-chloro-4,5-dihydroxybenzohydrazide. $^1$H NMR (400 MHz, DMSO-d6) δ 13.83 (br, 1H), 9.22 (d, 1H), 8.91 (d, 1H), 8.78 (s, 1H), 8.12 (s, 1H), 5.23 (d, 1H), 4.89 (s, 1H), 3.67 (dd, 1H), 3.31 (dd, 1H), 1.61 (s, 3H). LC-MS (ESI): m/z=368 (M+H)$^+$.

Example 20

(2S,3R,5R)-3-((E)-(2-(2-(3,4-dihydroxyphenyl)acetyl)hydrazono)methyl)-3-methyl-7-oxo-4-thia-1-azabicyclo[3.2.0]heptane-2-carboxylic acid 4,4-dioxide

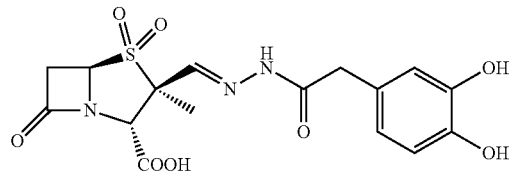 [SMILES: C[C@]1(/C=N/NC(=O)Cc2ccc(O)c(O)c2)[C@H](C(=O)O)N2C(=O)C[C@H]2S1(=O)=O]

The title compound was prepared using the similar procedure as described in EXAMPLE 1 except 2-(3,4-dihydroxy-2-methylphenyl)acetohydrazide was used in place of 2-chloro-4,5-dihydroxybenzohydrazide. ¹H NMR (400 MHz, DMSO-d6) δ 13.73 (br, 1H), 11.81 (s, 1H), 8.87 (s, 1H), 8.74 (s, 1H), 7.70 (s, 1H), 6.68 (d, 1H), 6.61 (dd, 1H), 6.51 (dd, 1H), 5.28 (d, 1H), 4.90 (s, 1H), 3.72 (d, 1H), 3.61 (dd, 1H), 3.31 (d, 1H), 3.26 (dd, 1H), 1.61 (s, 3H). LC-MS (ESI): m/z=412 (M+H)⁺.

Example 21

(2S,3R,5R)-3-((E)-(2-((R)-2-((tert-butoxycarbonyl)amino)-3-(3,4-dihydroxyphenyl)propanoyl)hydrazono)methyl)-3-methyl-7-oxo-4-thia-1-azabicyclo[3.2.0]heptane-2-carboxylic acid 4,4-dioxide

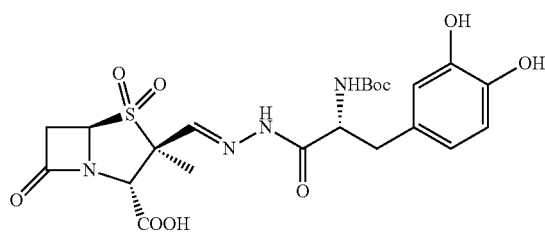 [SMILES: CC(C)(C)OC(=O)N[C@H](Cc1ccc(O)c(O)c1)C(=O)N/N=C/[C@@]1(C)[C@H](C(=O)O)N2C(=O)C[C@H]2S1(=O)=O]

The title compound was prepared using the similar procedure as described in EXAMPLE 1 except (R)-tert-butyl (3-(3,4-dihydroxy-2-methylphenyl)-1-hydrazinyl-1-oxopropan-2-yl)carbamate was used in place of 2-chloro-4,5-dihydroxybenzohydrazide. ¹H NMR (400 MHz, DMSO-d6) δ 13.75 (br, 1H), 11.62 (s, 1H), 8.68 (br, 2H), 7.73 (s, 1H), 7.64 (s, 1H), 7.06 (d, 1H), 6.51 (d, 1H), 5.28 (d, 1H), 4.90 (s, 1H), 3.72 (d, 1H), 3.61 (dd, 1H), 3.26 (dd, 1H), 4.80 (m, 1H), 3.71 (br, 1H), 2.74 (m, 1H), 2.59 (d, 1H), 1.61 (s, 3H), 1.10 (s, 9H). LC-MS (ESI): m/z=541 (M+H)⁺.

Example 22

(2S,3R,5R)-3-((E)-(2-(3-chloro-4,5-dihydroxybenzoyl)hydrazono)methyl)-3-methyl-7-oxo-4-thia-1-azabicyclo[3.2.0]heptane-2-carboxylic acid 4,4-dioxide

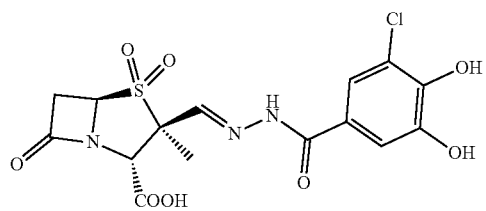 [SMILES: C[C@]1(/C=N/NC(=O)c2cc(O)c(O)c(Cl)c2)[C@H](C(=O)O)N2C(=O)C[C@H]2S1(=O)=O]

The title compound was prepared using the similar procedure as described in EXAMPLE 1 except 3-chloro-4,5-dihydroxybenzohydrazide was used in place of 2-chloro-4,5-dihydroxybenzohydrazide. ¹H NMR (400 MHz, DMSO-d6) δ 12.11 (s, H), 10.20 (s, 1H), 9.41 (s, 1H), 7.83 (s, 1H), 7.10 (s, 1H), 6.92 (d, 1H), 6.82 (d, 1H), 6.64 (s, 1H), 5.28 (d, 1H), 5.01 (s, 1H), 3.73 (t, 3H), 3.33 (m, 1H), 2.20 (s, 1H), 1.62 (s, 3H). LC-MS (ESI): m/z=432 (M+H)⁺.

Example 23

(2S,3R,5R)-3-((E)-(2-(2-chloro-3,4-dihydroxybenzoyl)hydrazono)methyl)-3-methyl-7-oxo-4-thia-1-azabicyclo[3.2.0]heptane-2-carboxylic acid 4,4-dioxide

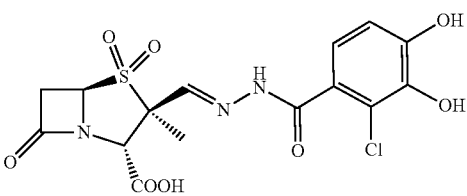 [SMILES: C[C@]1(/C=N/NC(=O)c2ccc(O)c(O)c2Cl)[C@H](C(=O)O)N2C(=O)C[C@H]2S1(=O)=O]

The title compound was prepared using the similar procedure as described in EXAMPLE 1 except 2-chloro-3,4-dihydroxybenzohydrazide was used in place of 2-chloro-4,5-dihydroxybenzohydrazide. ¹H NMR (400 MHz, DMSO-d6) δ 12.12 (s, H), 10.21 (s, 1H), 9.43 (s, 1H), 7.84 (s, 1H), 7.13 (d, 1H), 6.89 (d, 1H), 6.60 (s, 1H), 5.33 (d, 1H), 5.04 (s, 1H), 3.75 (t, 1H), 3.36 (m, 1H), 2.23 (s, 1H), 1.64 (s, 3H). LC-MS (ESI): m/z=432 (M+H)⁺.

Example 24

(2S,3R,5R)-3-((E)-(2-(3,6-difluoropicolinoyl)hydrazono)methyl)-3-methyl-7-oxo-4-thia-1-azabicyclo[3.2.0]heptane-2-carboxylic acid 4,4-dioxide

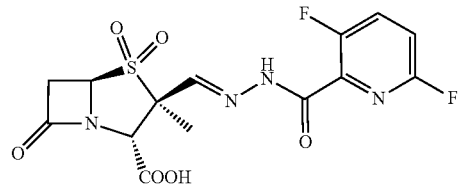 [SMILES: C[C@]1(/C=N/NC(=O)c2nc(F)ccc2F)[C@H](C(=O)O)N2C(=O)C[C@H]2S1(=O)=O]

The title compound was prepared using the similar procedure as described in Example 1 except 3,6-difluoropicolinohydrazide was used in place of 2-chloro-4,5-dihydroxybenzohydrazide. ¹H NMR (400 MHz, DMSO-d6) δ 13.87 (br, 1H), 12.42 (s, 1H), 8.17 (m, 1H), 8.01 (s, 1H), 7.58 (d, 1H), 7.28 (m, 1H), 5.23 (d, 1H), 4.89 (s, 1H), 3.71 (dd, 1H), 3.33 (dd, 1H), 1.63 (s, 3H). LC-MS (ESI): m/z=368 (M+H)⁺.

Example 25

(2S,3R,5R)-3-((E)-(2-(3-(3,4-dihydroxyphenyl)propanoyl)hydrazono)methyl)-3-methyl-7-oxo-4-thia-1-azabicyclo[3.2.0]heptane-2-carboxylic acid 4,4-dioxide

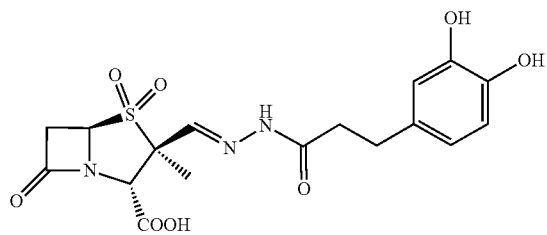 [SMILES: C[C@]1(/C=N/NC(=O)CCc2ccc(O)c(O)c2)[C@H](C(=O)O)N2C(=O)C[C@H]2S1(=O)=O]

The title compound was prepared using the similar procedure as described in EXAMPLE 1 except 3-(3,4-dihydroxy-2-methylphenyl)propanehydrazide was used in place of 2-chloro-4,5-dihydroxybenzohydrazide. $^1$H NMR (400 MHz, DMSO-d6) δ 13.76 (br, 1H), 11.65 (s, 1H), 8.65 (br, 2H), 7.67 (s, 1H), 6.65 (d, 1H), 6.62 (s, 1H), 6.48 (d, 1H), 5.28 (d, 1H), 4.90 (s, 1H), 3.72 (d, 1H), 3.31 (dd, 1H), 2.70 (m, 3H), 2.42 (m, 1H), 1.61 (s, 3H). LC-MS (ESI): m/z=426 (M+H)$^+$.

Example 26

(2S,3R,5R)-3-((E)-(2-(2-(benzo[d][1,3]dioxol-5-yl)acetyl)hydrazono)methyl)-3-methyl-7-oxo-4-thia-1-azabicyclo[3.2.0]heptane-2-carboxylic acid 4,4-dioxide

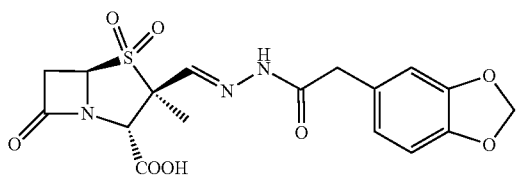 [SMILES: C[C@]1(/C=N/NC(=O)Cc2ccc3c(c2)OCO3)[C@H](C(=O)O)N2C(=O)C[C@H]2S1(=O)=O]

The title compound was prepared using the similar procedure as described in EXAMPLE 1 except 2-(benzo[d][1,3]dioxol-5-yl)acetohydrazide was used in place of 2-chloro-4,5-dihydroxybenzohydrazide. $^1$H NMR (400 MHz, DMSO-d6) δ 13.76 (br, 1H), 9.92 (s, 1H), 9.35 (s, 1H), 6.67 (s, 1H), 6.63 (d, 1H), 6.84 (s, 1H), 5.97 (s, 2H), 5.13 (d, 1H), 4.87 (s, 1H), 3.88 (dd, 1H), 3.35 (s, 2H), 3.26 (dd, 1H), 3.21 (dd, 1H), 1.61 (s, 3H). LC-MS (ESI): m/z=424 (M+H)$^+$.

Example 27

(2S,3R,5R)-3-((E)-(2-(2,5-dihydroxy-3,6-dimethylbenzoyl)hydrazono)methyl)-3-methyl-7-oxo-4-thia-1-azabicyclo[3.2.0]heptane-2-carboxylic acid 4,4-dioxide

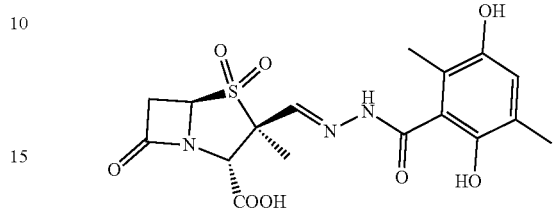

The title compound was prepared using the similar procedure as described in EXAMPLE 1 except 2,5-dihydroxy-3,6-dimethylbenzohydrazide was used in place of 2-chloro-4,5-dihydroxybenzohydrazide. $^1$H NMR (400 MHz, DMSO-d6) δ 9.64 (s, 1H), 8.98 (s, 1H), 7.50 (s, 1H), 6.97 (s, 1H), 6.68 (s, 1H), 5.24 (s, 1H), 4.70 (t, 1H), 3.46 (m, 1H), 3.32 (s, 1H), 3.21 (m, 1H), 2.36 (s, 3H), 2.31 (s, 3H), 1.53 (s, 3H). LC-MS (ESI): m/z=426 (M+H)$^+$.

Example 28

(2S,3R,5R)-3-((E)-(2-(2,3-dihydroxybenzoyl)hydrazono)methyl)-3-methyl-7-oxo-4-thia-1-azabicyclo[3.2.0]heptane-2-carboxylic acid 4,4-dioxide

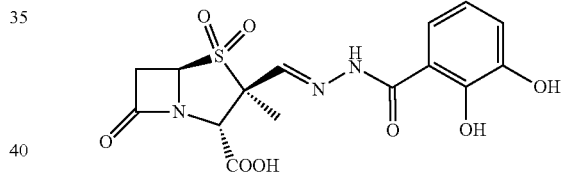

The title compound was prepared using the similar procedure as described in EXAMPLE 1 except 2,3-dihydroxybenzohydrazide was used in place of 2-chloro-4,5-dihydroxybenzohydrazide. $^1$H NMR (400 MHz, DMSO-d6) δ 12.12 (s, H), 10.22 (s, 1H), 9.42 (s, 1H), 7.84 (s, 1H), 7.33 (t, 1H), 7.11 (d, 1H), 6.89 (d, 1H), 6.60 (s, 1H), 5.30 (d, 1H), 5.01 (s, 1H), 3.74 (t, 1H), 3.35 (m, 1H), 1.65 (s, 3H). LC-MS (ESI): m/z=398 (M+H)$^+$.

Example 29

(2S,3R,5R)-3-((E)-(2-(4-hydroxybenzoyl)hydrazono)methyl)-3-methyl-7-oxo-4-thia-1-azabicyclo[3.2.0]heptane-2-carboxylic acid 4,4-dioxide

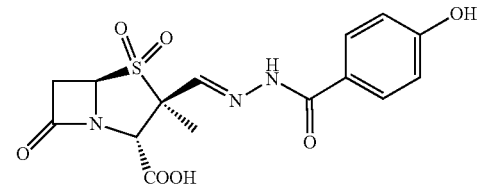 [SMILES: C[C@]1(/C=N/NC(=O)c2ccc(O)cc2)[C@H](C(=O)O)N2C(=O)C[C@H]2S1(=O)=O]

The title compound was prepared using the similar procedure as described in EXAMPLE 1 except 4-hydroxybenzohydrazide was used in place of 2-chloro-4,5-dihydroxybenzohydrazide. $^1$H NMR (400 MHz, DMSO-d6) δ 12.12 (s, H), 10.20 (s, 1H), 9.40 (s, 1H), 7.83 (m, 2H), 7.11 (s, 1H), 6.91 (m, 2H), 6.60 (m, 1H), 5.33 (d, 1H), 5.02 (s, 1H), 3.74 (t, 1H), 3.34 (m, 1H), 1.65 (s, 3H). LC-MS (ESI): m/z=382 (M+H)$^+$.

Example 30

(2S,3R,5R)-3-((E)-(2-(2-chloro-3,4-dimethoxybenzoyl)hydrazono)methyl)-3-methyl-7-oxo-4-thia-1-azabicyclo[3.2.0]heptane-2-carboxylic acid 4,4-dioxide

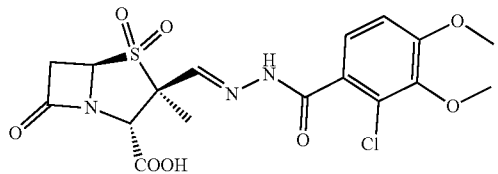 [SMILES: COc1ccc(C(=O)N/N=C/[C@@]2(C)[C@H](C(=O)O)N3C(=O)C[C@H]3S2(=O)=O)c(Cl)c1OC]

The title compound was prepared using the similar procedure as described in EXAMPLE 1 except 2-chloro-3,4-dimethoxybenzohydrazide was used in place of 2-chloro-4,5-dihydroxybenzohydrazide. $^1$H NMR (400 MHz, DMSO-d6) δ 12.12 (s, H), 7.82 (s, 1H), 7.43 (s, 1H), 7.13 (m, 2H), 5.32 (s, 1H), 4.81 (s, 1H), 3.89 (s, 3H), 3.85 (s, 3H), 3.74 (m, 1H), 3.34 (m, 1H), 1.64 (s, 3H). LC-MS (ESI): m/z=460 (M+H)$^+$.

Example 31

(2S,3R,5R)-3-methyl-3-((E)-(2-(4-methylbenzoyl)hydrazono)methyl)-7-oxo-4-thia-1-azabicyclo[3.2.0]heptane-2-carboxylic acid 4,4-dioxide

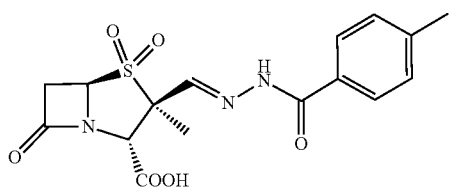 [SMILES: Cc1ccc(C(=O)N/N=C/[C@@]2(C)[C@H](C(=O)O)N3C(=O)C[C@H]3S2(=O)=O)cc1]

The title compound was prepared using the similar procedure as described in EXAMPLE 1 except 4-methylbenzohydrazide was used in place of 2-chloro-4,5-dihydroxybenzohydrazide. $^1$H NMR (400 MHz, DMSO-d6) δ 12.13 (s, 1H), 7.94 (s, 1H), 7.81 (d, 2H), 7.34 (d, 2H), 5.31 (d, 1H), 4.91 (s, 1H), 3.76 (dd, 1H), 3.34 (d, 2H), 2.38 (s, 3H), 1.63 (s, 3H). LC-MS (ESI): m/z=380 (M+H)$^+$.

Example 32

(2S,3R,5R)-3-methyl-7-oxo-3-((E)-(2-(4-(trifluoromethyl)benzoyl)hydrazono)methyl)-4-thia-1-azabicyclo[3.2.0]heptane-2-carboxylic acid 4,4-dioxide

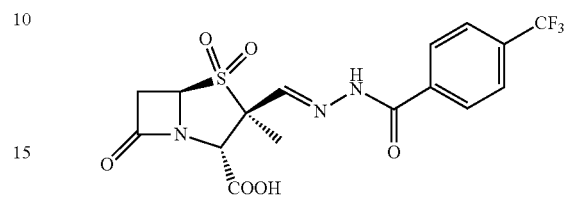

The title compound was prepared using the similar procedure as described in EXAMPLE 1 except 4-(trifluoromethyl)benzohydrazide was used in place of 2-chloro-4,5-dihydroxybenzohydrazide. $^1$H NMR (400 MHz, DMSO-d6) δ 12.40 (s, 1H), 8.11 (d, 2H), 7.96 (s, 1H), 7.93 (d, 2H), 5.32 (d, 1H), 4.97 (s, 1H), 3.76 (dd, 1H), 3.34 (d, 2H), 1.64 (s, 3H). LC-MS (ESI): m/z=434 (M+H)$^+$.

Example 33

(2S,3R,5R)-3-((E)-(2-(4-fluorobenzoyl)hydrazono)methyl)-3-methyl-7-oxo-4-thia-1-azabicyclo[3.2.0]heptane-2-carboxylic acid 4,4-dioxide

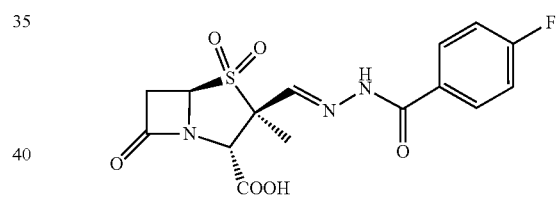

The title compound was prepared using the similar procedure as described in EXAMPLE 1 except 4-fluorobenzohydrazide was used in place of 2-chloro-4,5-dihydroxybenzohydrazide. $^1$H NMR (400 MHz, DMSO-d6) δ 12.2 (s, 1H), 7.97 (t, 3H), 7.38 (m, 2H), 5.3 (d, 1H), 4.92 (s, 1H), 3.91 (dd, 1H), 3.33 (d, 2H), 1.63 (s, 3H). LC-MS (ESI): m/z=384 (M+H)$^+$.

Example 34

(2S,3R,5R)-3-((E)-(2-benzoylhydrazono)methyl)-3-methyl-7-oxo-4-thia-1-azabicyclo[3.2.0]heptane-2-carboxylic acid 4,4-dioxide

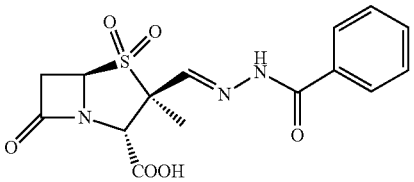 [SMILES: C[C@]1(/C=N/NC(=O)c2ccccc2)[C@H](C(=O)O)N2C(=O)C[C@H]2S1(=O)=O]

The title compound was prepared using the similar procedure as described in EXAMPLE 1 except benzohydrazide was used in place of 2-chloro-4,5-dihydroxybenzohydrazide.

¹H NMR (400 MHz, DMSO-d6) δ 12.22 (s, 1H), 7.95 (s, 1H), 7.90 (d, 2H), 7.61 (d, 1H), 7.55 (m, 2H), 5.32 (d, 1H), 4.94 (s, 1H), 3.77 (dd, 1H), 3.34 (d, 2H), 1.64 (s, 3H). LC-MS (ESI): m/z=366 (M+H)⁺.

Example 35

(2S,3R,5R)-3-((E)-(2-(4-methoxybenzoyl)hydrazono)methyl)-3-methyl-7-oxo-4-thia-1-azabicyclo[3.2.0]heptane-2-carboxylic acid 4,4-dioxide

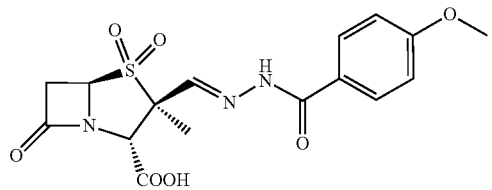 [SMILES: COc1ccc(C(=O)N/N=C/[C@@]2(C)[C@H](C(=O)O)N3C(=O)C[C@H]3S2(=O)=O)cc1]

The title compound was prepared using the similar procedure as described in EXAMPLE 1 except 4-methoxybenzohydrazide was used in place of 2-chloro-4,5-dihydroxybenzohydrazide. ¹H NMR (400 MHz, DMSO-d6) δ 12.07 (s, 1H), 7.93 (m, 3H), 7.06 (d, 2H), 5.31 (d, 1H), 4.91 (s, 1H), 3.83 (s 3H), 3.76 (dd, 1H), 3.34 (d, 2H), 1.62 (s, 3H). LC-MS (ESI): m/z=396 (M+H)⁺.

Example 36

(2S,3R,5R)-3-((E)-(2-(4-chlorobenzoyl)hydrazono)methyl)-3-methyl-7-oxo-4-thia-1-azabicyclo[3.2.0]heptane-2-carboxylic acid 4,4-dioxide

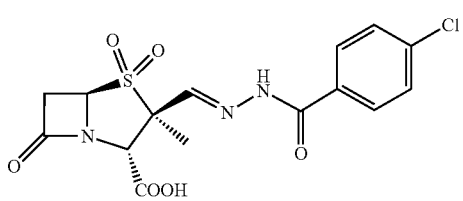 [SMILES: C[C@]1(/C=N/NC(=O)c2ccc(Cl)cc2)[C@H](C(=O)O)N2C(=O)C[C@H]2S1(=O)=O]

The title compound was prepared using the similar procedure as described in EXAMPLE 1 except 4-chlorobenzohydrazide was used in place of 2-chloro-4,5-dihydroxybenzohydrazide. ¹H NMR (400 MHz, DMSO-d6) δ 12.25 (s, 1H), 7.95 (m, 3H), 7.61 (d, 2H), 5.3 (d, 1H), 4.93 (s, 1H), 3.76 (dd, 1H), 3.33 (d, 2H), 1.63 (s, 3H). LC-MS (ESI): m/z=400 (M+H)⁺.

Example 37

(2S,3R,5R)-3-((E)-(2-(3-ethyl-7-oxo-4,7-dihydropyrazolo[1,5-a]pyrimidine-5-carbonyl)hydrazono)methyl)-3-methyl-7-oxo-4-thia-1-azabicyclo[3.2.0]heptane-2-carboxylic acid 4,4-dioxide

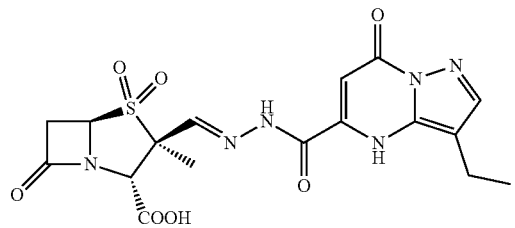 [SMILES: CCc1cnn2c(=O)cc(C(=O)N/N=C/[C@@]3(C)[C@H](C(=O)O)N4C(=O)C[C@H]4S3(=O)=O)[nH]c12]

The title compound was prepared using the similar procedure as described in EXAMPLE 1 except 3-ethyl-7-oxo-4,7-dihydropyrazolo[1,5-a]pyrimidine-5-carbohydrazide was used in place of 2-chloro-4,5-dihydroxybenzohydrazide. ¹H NMR (400 MHz, DMSO-d6) δ 13.86 (br, 1H), 12.58 (s, 1H), 7.98 (s, 1H), 7.90 (s, 1H), 6.25 (s, 1H), 5.16 (d, 1H), 4.57 (s, 1H), 3.61 (dd, 1H), 3.26 (dd, 1H), 2.69 (q, 2H), 1.64 (s, 3H), 1.20 (t, 3H). LC-MS (ESI): m/z=451 (M+H)⁺.

Example 38

(2S,3R,5R)-3-((E)-(2-(1-(2-chloro-3,4-dihydroxybenzoyl)pyrrolidine-3-carbonyl)hydrazono)methyl)-3-methyl-7-oxo-4-thia-1-azabicyclo[3.2.0]heptane-2-carboxylic acid 4,4-dioxide

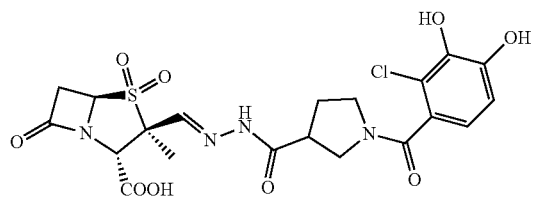 [SMILES: C[C@]1(/C=N/NC(=O)C2CCN(C(=O)c3ccc(O)c(O)c3Cl)C2)[C@H](C(=O)O)N2C(=O)C[C@H]2S1(=O)=O]

Figure 6:
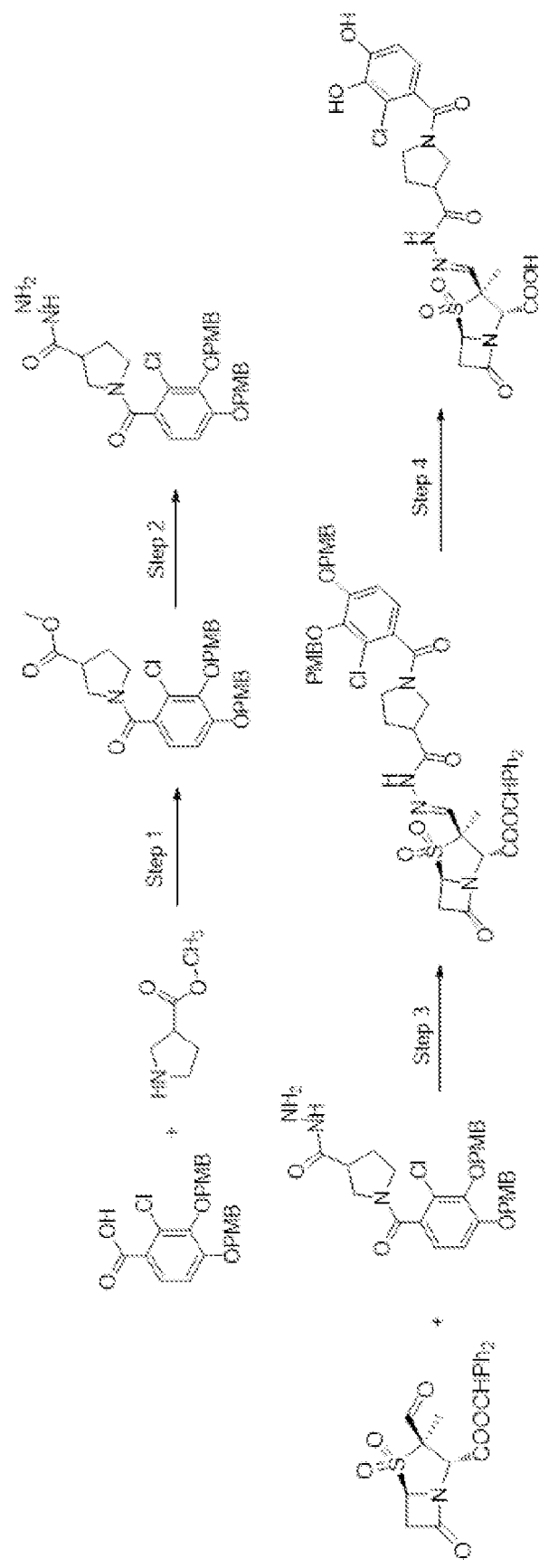

FIG. 6 shows a synthetic scheme for the preparation of this compound. Step 1. methyl 1-(2-chloro-3,4-bis((4-methoxybenzyl)oxy)benzoyl)pyrrolidine-3-carboxylate. 2-chloro-3,4-bis((4-methoxybenzyl)oxy)benzoic acid (1 g, 2.3 mmol) and methyl pyrrolidine-3-carboxylate (0.3 g, 2.3 mmol) was dissolved into 10 mL DMF in round bottom flask. EDCI (0.7 g, 4.6 mmol), HOBT (0.3 g, 2.3 mmol) and then NMM (0.7 g, 6.9 mmol) was added to the flask. The mixture was stirred at rt for 6 h. Then the solvent was poured into ice water to afford the white solid, the crude product was filtered and dried under vacuum (1.0 g, yield 81%). LC-MS (ESI): m/z=540 (M+H)⁺.

Step 2. 1-(2-chloro-3,4-bis((4-methoxybenzyl)oxy)benzoyl)pyrrolidine-3-carbohydrazide. Methyl 1-(2-chloro-3,4-bis((4-methoxybenzyl)oxy)benzoyl)pyrrolidine-3-carboxylate (1.0 g, 1.8 mmol) was dissolved in 30 mL EtOH. Hydrazine hydrate (0.5 g, 9.3 mmol) was added and the solution was refluxed for 8 hours. Then the reaction solution was cooled to rt. The white solid was filtered and dried as crude product (0.7 g, yield 76%). LC-MS (ESI): m/z=540 (M+H)⁺.

Step 3. (2S,3R,5R)-benzhydryl 3-((E)-(2-(1-(2-chloro-3,4-bis((4-methoxybenzyl)oxy)benzoyl)pyrrolidine-3-carbonyl)hydrazono)methyl)-3-methyl-7-oxo-4-thia-1-azabicyclo[3.2.0]heptane-2-carboxylate 4,4-dioxide. (2S,5R)-benzhydryl 3-formyl-3-methyl-7-oxo-4-thia-1-azabicyclo[3.2.0]heptane-2-carboxylate 4,4-dioxide (0.6 g, 1.3 mmol) and 1-(2-chloro-3,4-bis((4-methoxybenzyl)oxy)benzoyl)pyrrolidine-3-carbohydrazide (0.7 g, 1.3 mmol) was dissolved in 20 mL DMF and the solution was stirred at rt for 8 hours. Then the solvent was evaporated in vacuo, the residue was purified by silica gel (Ethyl Acetate:Petroleum Ether=1:1) to afford white solid (0.7 g, yield 51%). LC-MS (ESI): m/z=935 (M+H)+.

Step 4. (2S,3R,5R)-3-((E)-(2-(1-(2-chloro-3,4-dihydroxybenzoyl)pyrrolidine-3-carbonyl)hydrazono)methyl)-3-methyl-7-oxo-4-thia-1-azabicyclo[3.2.0]heptane-2-carboxylic acid 4,4-dioxide. (2S,5R)-benzhydryl 3-((E)-(2-(1-(2-chloro-3,4-bis((4-methoxybenzyl)oxy)benzoyl)pyrrolidine-3-carbonyl)hydrazono)methyl)-3-methyl-7-oxo-4-thia-1-azabicyclo[3.2.0]heptane-2-carboxylate 4,4-dioxide (0.7 g, 0.9 mmol) was dissolved into 30 mL of THF, Pd/C (10%, 100 mg) was added and the solution was stirred under charged hydrogen balloon for 8 hours. Filtration to remove the palladium, Then the solvent was evaporated in vacuo, the residue was purified by column chromatography (silica gel, DCM:MeOH=20:1) to afford the title compound as white solid (321 mg, yield 67%). 1H NMR (400 MHz, DMSO-d6) δ 8.31 (s, 1H), 7.50 (s, 1H), 7.17 (d, 1H), 6.66 (d, 1H), 5.43 (s, 1H), 4.70 (t, 1H), 4.46 (s, 1H), 4.27 (s, 1H), 3.89 (m, 1H), 3.71 (m, 1H), 3.64 (m, 1H), 3.55 (m, 1H), 3.46 (m, 1H), 3.21 (m, 1H), 2.95 (m, 1H), 2.19 (m, 1H), 1.6 (s, 3H), 1.91 (m, 1H). LC-MS (ESI): m/z=529 (M+H)+.

Example 39

(2S,3R,5R)-3-((E)-(2-(1-(2-chloro-3,4-dihydroxybenzoyl)azetidine-3-carbonyl)hydrazono)methyl)-3-methyl-7-oxo-4-thia-1-azabicyclo[3.2.0]heptane-2-carboxylic acid 4,4-dioxide The title compound was prepared using the similar procedure as described in Example 38 except methyl azetidine-3-carboxylate was used in place of methyl pyrrolidine-3-carboxylate. 1H NMR (400 MHz, DMSO-d6) δ 8.97 (s, 1H), 7.11 (s, 1H), 6.80 (s, 1H), 6.22 (s, 1H), 5.16 (s, 1H), 5.02 (s, 1H), 4.31 (t, 1H), 3.85-3.79 (m, 2H), 3.59-3.54 (m, 2H), 3.19 (m, 1H), 3.07 (m, 1H), 2.89 (s, 1H), 2.82 (s, 1H), 1.62 (m, 3H). LC-MS (ESI): m/z=515 (M+H)+.

Example 40

(2S,3R,5R)-3-((E)-(2-(1-(2-chloro-3,4-dihydroxybenzoyl)pyrrolidine-2-carbonyl)hydrazono)methyl)-3-methyl-7-oxo-4-thia-1-azabicyclo[3.2.0]heptane-2-carboxylic acid 4,4-dioxide

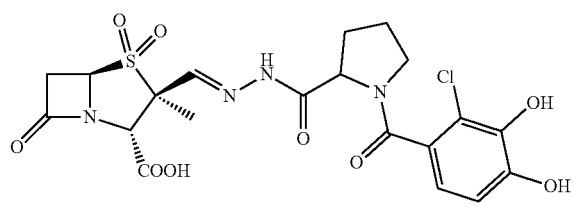 [SMILES: C[C@]1(/C=N/NC(=O)C2CCCN2C(=O)c2ccc(O)c(O)c2Cl)[C@H](C(=O)O)N2C(=O)C[C@H]2S1(=O)=O]

The title compound was prepared using the similar procedure as described in Example 38 except methyl pyrrolidine-2-carboxylate was used in place of methyl pyrrolidine-3-carboxylate. 1H NMR (400 MHz, DMSO-d6) δ 9.66 (s, 1H), 7.50 (s, 1H), 7.03 (d, 1H), 6.62 (d, 1H), 5.15 (s, 1H), 5.08 (s, 1H), 4.70 (t, 1H), 3.83 (m, 1H), 3.47 (m, 2H), 3.21 (m, 1H), 2.92 (m, 1H), 2.83 (m, 1H), 2.18 (m, 1H), 1.93 (d, 2H), 1.86 (s, 1H), 1.50 (s, 3H). LC-MS (ESI): m/z=529 (M+H)+.

Example 41

(2S,3R,5R)-3-((E)-(2-(5-(3,4-dihydroxybenzamido)picolinoyl)hydrazono)methyl)-3-methyl-7-oxo-4-thia-1-azabicyclo[3.2.0]heptane-2-carboxylic acid 4,4-dioxide

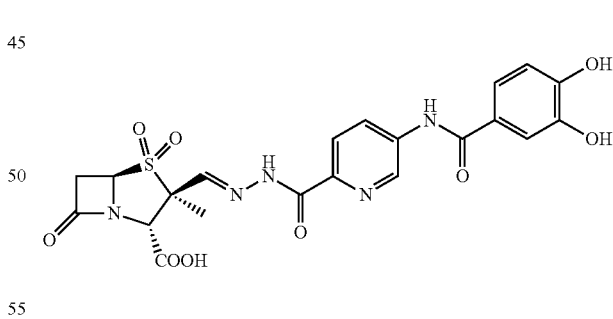

The title compound was prepared using the similar procedure as described in Example 38. 1H NMR (400 MHz, DMSO-d6) δ 13.81 (br, 1H), 12.43 (s, 1H), 10.48 (s, 1H), 9.79 (s, 1H), 9.34 (s, 1H), 9.08 (d, 1H), 8.44 (dd, 1H), 8.14 (s, 1H), 8.11 (d, 1H), 7.44 (dd, 1H), 7.42 (dd, 1H), 6.87 (d, 1H), 5.32 (d, 1H), 4.81 (s, 1H), 3.78 (dd, 1H), 3.26 (dd, 1H), 1.63 (s, 3H). LC-MS (ESI): m/z=518 (M+H)+.

Example 42

(2S,3R,5R)-3-((E)-(2-(1-(2-chloro-3,4-dihydroxy-benzoyl)piperidine-4-carbonyl)hydrazono)methyl)-3-methyl-7-oxo-4-thia-1-azabicyclo[3.2.0]heptane-2-carboxylic acid 4,4-dioxide

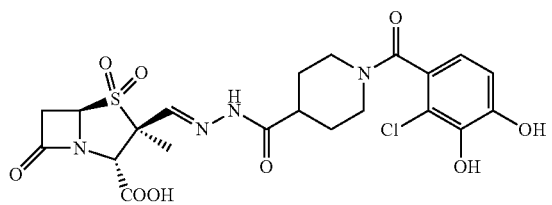 [SMILES: C[C@]1(/C=N/NC(=O)C2CCN(C(=O)c3ccc(O)c(O)c3Cl)CC2)[C@H](C(=O)O)N2C(=O)C[C@H]2S1(=O)=O]

The title compound was prepared using the similar procedure as described in Example 38 except methyl piperidine-4-carboxylate was used in place of methyl pyrrolidine-3-carboxylate. $^1$H NMR (400 MHz, DMSO) δ 8.28 (s, 1H), 7.50 (s, 1H), 7.19 (d, 1H), 6.66 (d, 1H), 5.43 (s, 1H), 4.70 (t, 1H), 4.47 (s, 1H), 4.26 (s, 1H), 3.72-3.68 (m, 2H), 3.44 (m, 4H), 3.21 (m, 4H), 2.53 (s, 1H), 2.07 (m, 2H), 1.88-1.84 (m, 2H), 1.6 (s, 3H). LC-MS (ESI): m/z=543 (M+H)$^+$.

Example 43

(2S,3R,5R)-3-((E)-(2-(2-(2-chloro-3,4-dihydroxy-benzamido)-3-hydroxypropanoyl)hydrazono)methyl)-3-methyl-7-oxo-4-thia-1-azabicyclo[3.2.0]heptane-2-carboxylic acid 4,4-dioxide

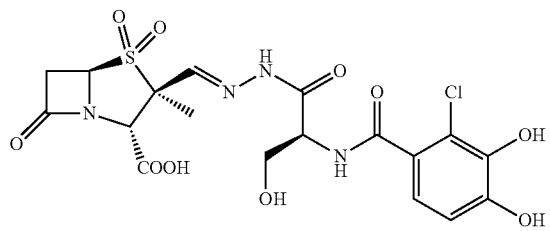 [SMILES: C[C@]1(/C=N/NC(=O)[C@H](CO)NC(=O)c2ccc(O)c(O)c2Cl)[C@H](C(=O)O)N2C(=O)C[C@H]2S1(=O)=O]

The title compound was prepared using the similar procedure as described in Example 38 except (S)-methyl 2-amino-3-hydroxypropanoate was used in place of methyl pyrrolidine-3-carboxylate. $^1$H NMR (400 MHz, DMSO-d6) δ 9.77 (s, 1H), 7.50 (s, 1H), 7.40 (s, 1H), 7.22 (d, 1H), 6.67 (d, 1H), 6.60 (s, 1H), 5.54 (s, 1H), 4.70 (t, 1H), 4.53 (s, 1H), 4.28 (m, 2H), 4.11 (m, 1H), 3.81 (m, 1H), 3.46 (m, 1H), 3.21 (m, 1H), 1.70 (s, 3H). LC-MS (ESI): m/z=519 (M+H)$^+$.

Example 44

(2S,3R,5R)-3-((E)-(2-(2-(2-chloro-3,4-dihydroxybenzamido)-3-phenylpropanoyl)hydrazono)methyl)-3-methyl-7-oxo-4-thia-1-azabicyclo[3.2.0]heptane-2-carboxylic acid 4,4-dioxide

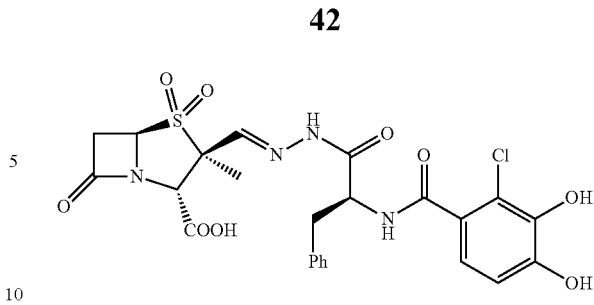

The title compound was prepared using the similar procedure as described in Example 38 except (S)-methyl 2-amino-3-phenylpropanoate was used in place of methyl pyrrolidine-3-carboxylate. $^1$H NMR (400 MHz, DMSO-d6) δ 7.01 (s, 1H), 6.84-6.76 (m, 3H), 6.76-6.65 (m, 3H), 6.62 (s, 1H), 6.13 (d, 1H), 4.97 (s, 1H), 4.62 (t, 1H), 4.21 (t, 1H), 4.09 (s, 1H), 3.76 (s, 1H), 2.97 (m, 1H), 2.72 (m, 1H), 2.67 (m, 1H), 2.45 (s, 1H), 1.59 (s, 3H). LC-MS (ESI): m/z=579 (M+H)$^+$.

Example 45

(2S,3R,5R)-3-((E)-(2-(4-((2-chloro-3,4-dihydroxy-benzamido)methyl)benzoyl)hydrazono)methyl)-3-methyl-7-oxo-4-thia-1-azabicyclo[3.2.0]heptane-2-carboxylic acid 4,4-dioxide

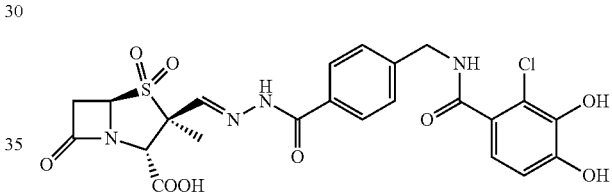

The title compound was prepared using the similar procedure as described in Example 38 except methyl 4-(aminomethyl)benzoate was used in place of methyl pyrrolidine-3-carboxylate. $^1$H NMR (400 MHz, DMSO-d6) δ 9.80 (s, 1H), 7.64 (s, 1H), 7.50 (s, 1H), 7.29-7.25 (m, 2H), 7.17 (s, 1H), 6.77 (m, 1H), 5.54 (s, 1H), 4.70 (t, 1H), 4.42 (t, 1H), 4.28 (s, 1H), 4.03 (m, 1H), 3.80 (m, 1H), 3.57 (s, 1H), 3.46 (s, 1H), 3.21 (s, 1H), 1.74 (s, 3H). LC-MS (ESI): m/z=485 (M+H)$^+$.

Example 46

(2S,3R,5R)-3-((E)-(2-(4-((3,4-dihydroxybenzamido)methyl)benzoyl)hydrazono)methyl)-3-methyl-7-oxo-4-thia-1-azabicyclo[3.2.0]heptane-2-carboxylic acid 4,4-dioxide

The title compound was prepared using the similar procedure as described in Example 38 except methyl 4-(aminomethyl)benzoate was used in place of methyl pyrrolidine- 3-carboxylate and 3,4-bis((4-methoxybenzyl)oxy)benzoic acid was used in place of 2-chloro-3,4-bis((4-methoxybenzyl)oxy)benzoic acid. ¹H NMR (400 MHz, DMSO-d6) δ 9.86 (s, 1H), 8.86 (s, 1H), 7.95-7.80 (m, 2H), 7.52-7.41 (m, 3H), 7.30 (m, 1H), 7.19 (s, 1H), 6.73 (d, 1H), 6.36 (s, 1H), 5.05 (s, 1H), 4.70 (t, 1H), 4.61 (s, 1H), 4.53 (s, 1H), 3.87 (s, 1H), 3.51-3.44 (m, 2H), 3.21 (m, 1H), 1.53 (s, 3H). LC-MS (ESI): m/z=485 (M+H)⁺.

Example 47

((2S,3R,5R)-3-((E)-(2-(2-(3,4-dihydroxybenzamido)-3-methylbutanoyl)hydrazono)methyl)-3-methyl-7-oxo-4-thia-1-azabicyclo[3.2.0]heptane-2-carboxylic acid 4,4-dioxide

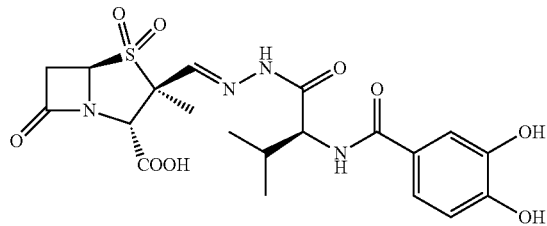 [SMILES: CC(C)[C@H](NC(=O)c1ccc(O)c(O)c1)C(=O)N/N=C/[C@@]1(C)[C@H](C(=O)O)N2C(=O)C[C@H]2S1(=O)=O]

The title compound was prepared using the similar procedure as described in Example 38 except (S)-methyl 2-amino-3-methylbutanoate was used in place of methyl pyrrolidine-3-carboxylate and 3,4-bis((4-methoxybenzyl)oxy)benzoic acid was used in place of 2-chloro-3,4-bis((4-methoxybenzyl)oxy)benzoic acid. ¹H NMR (400 MHz, DMSO-d6) δ 9.94 (s, 1H), 7.50 (s, 1H), 7.39 (s, 1H), 7.27 (d, J=12.4 Hz, 2H), 6.78 (s, 1H), 5.60 (s, 1H), 4.70 (s, 1H), 4.56 (s, 1H), 4.26 (s, 1H), 3.54 (s, 1H), 3.46 (s, 1H), 3.21 (s, 1H), 2.43 (s, 1H), 1.68 (s, 3H), 1.10 (s, 3H), 0.96 (s, 3H). LC-MS (ESI): m/z=497 (M+H)⁺.

Example 48

(2S,3R,5R)-3-((E)-(2-(2-(2-chloro-3,4-dihydroxybenzamido)-3-methylbutanoyl)hydrazono)methyl)-3-methyl-7-oxo-4-thia-1-azabicyclo[3.2.0]heptane-2-carboxylic acid 4,4-dioxide

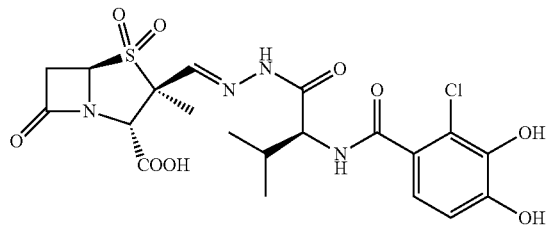 [SMILES: CC(C)[C@H](NC(=O)c1ccc(O)c(O)c1Cl)C(=O)N/N=C/[C@@]1(C)[C@H](C(=O)O)N2C(=O)C[C@H]2S1(=O)=O]

The title compound was prepared using the similar procedure as described in Example 38 except (S)-methyl 2-amino-3-methylbutanoate was used in place of methyl pyrrolidine-3-carboxylate. ¹H NMR (400 MHz, DMSO-d6) δ 9.82 (s, 1H), 8.31 (s, 1H), 7.50 (s, 1H), 7.20 (s, 1H), 7.01 (d, 1H), 6.66 (d, 1H), 5.65 (s, 1H), 4.70 (s, 1H), 4.52 (s, 1H), 4.40 (d, 1H), 4.27 (s, 1H), 3.46 (m, 1H), 3.21 (m, 1H), 2.48 (m, 1H), 1.76 (s, 3H), 1.11 (s, 3H), 0.97 (s, 3H). LC-MS (ESI): m/z=531 (M+H)⁺.

Example 49

(2S,3R,5R)-3-((E)-(2-(1-(2-chloro-3,4-dihydroxybenzoyl)piperidine-3-carbonyl)hydrazono)methyl)-3-methyl-7-oxo-4-thia-1-azabicyclo[3.2.0]heptane-2-carboxylic acid 4,4-dioxide

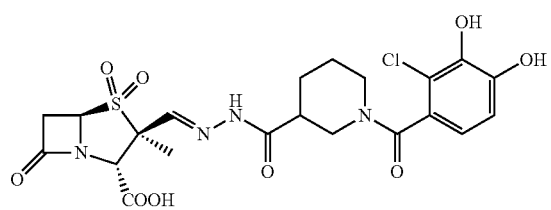 [SMILES: C[C@]1(/C=N/NC(=O)C2CCCN(C(=O)c3ccc(O)c(O)c3Cl)C2)[C@H](C(=O)O)N2C(=O)C[C@H]2S1(=O)=O]

The title compound was prepared using the similar procedure as described in Example 38 except methyl piperidine-3-carboxylate was used in place of methyl pyrrolidine-3-carboxylate. ¹H NMR (400 MHz, DMSO-d6) δ 8.76 (s, 1H), 7.50 (s, 1H), 7.16 (d, 1H), 6.64 (d, 1H), 5.90 (s, 1H), 4.70 (t, 1H), 3.98 (m, 1H), 3.93 (s, 1H), 3.55-3.44 (m, 5H), 3.21 (m, 1H), 2.50 (m, 1H), 2.12 (m, 1H), 1.95 (m, 1H), 1.88 (m, 1H), 1.82 (m, 1H), 1.61 (s, 3H). LC-MS (ESI): m/z=543 (M+H)⁺.

Example 50

(2S,3R,5R)-3-((E)-(2-(2-(3,4-dihydroxybenzamido)-3-hydroxypropanoyl)hydrazono)methyl)-3-methyl-7-oxo-4-thia-1-azabicyclo[3.2.0]heptane-2-carboxylic acid 4,4-dioxide

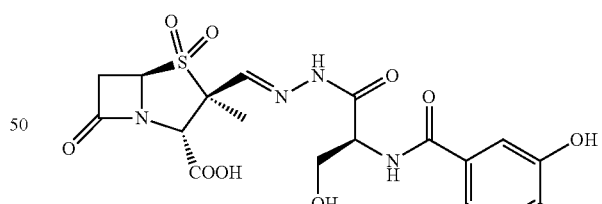

The title compound was prepared using the similar procedure as described in Example 38 except (S)-methyl 2-amino-3-phenylpropanoate was used in place of methyl pyrrolidine-3-carboxylate and 3,4-bis((4-methoxybenzyl)oxy)benzoic acid was used in place of 2-chloro-3,4-bis((4-methoxybenzyl)oxy)benzoic acid. ¹H NMR (400 MHz, DMSO-d6) δ 9.80 (s, 1H), 7.64 (s, 1H), 7.50 (s, 1H), 7.29-7.25 (m, 2H), 7.17 (s, 1H), 6.77 (m, 1H), 5.54 (s, 1H), 4.70 (t, 1H), 4.42 (t, 1H), 4.28 (s, 1H), 4.03 (m, 1H), 3.80 (m, 1H), 3.57 (s, 1H), 3.46 (s, 1H), 3.21 (s, 1H), 1.74 (s, 3H). LC-MS (ESI): m/z=485 (M+H)⁺.

Example 51

(2S,3R,5R)-3-((E)-(2-(2-(3,4-dihydroxybenzamido)-3-phenylpropanoyl)hydrazono)methyl)-3-methyl-7-oxo-4-thia-1-azabicyclo[3.2.0]heptane-2-carboxylic acid 4,4-dioxide

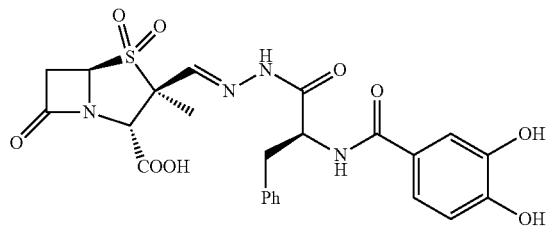 [SMILES: C[C@]1(/C=N/NC(=O)[C@H](Cc2ccccc2)NC(=O)c2ccc(O)c(O)c2)[C@H](C(=O)O)N2C(=O)C[C@H]2S1(=O)=O]

The title compound was prepared using the similar procedure as described in Example 38 except (S)-methyl 2-amino-3-phenylpropanoate was used in place of methyl pyrrolidine-3-carboxylate and 3,4-bis((4-methoxybenzyl)oxy)benzoic acid was used in place of 2-chloro-3,4-bis((4-methoxybenzyl)oxy)benzoic acid. $^1$H NMR (400 MHz, DMSO-d6) δ 9.49 (s, 1H), 7.09 (s, 1H), 6.92 (d, 1H), 6.88 (m, 4H), 6.76 (s, 1H), 6.74 (d, 2H), 6.30 (d, 1H), 5.35 (s, 1H), 5.20 (s, 1H), 4.39 (t, 1H), 4.29 (t, 1H), 3.79 (s, 1H), 3.06 (s, 1H), 3.00 (m, 1H), 2.83 (m, 2H), 2.78 (m, 1H), 2.61 (m, 1H), 1.56 (s, 3H). LC-MS (ESI): m/z=545 (M+H)$^+$.

Example 52

(2S,3R,5R)-3-((E)-(2-(1-(3,4-dihydroxybenzamido)cyclopropanecarbonyl)hydrazono)methyl)-3-methyl-7-oxo-4-thia-1-azabicyclo[3.2.0]heptane-2-carboxylic acid 4,4-dioxide

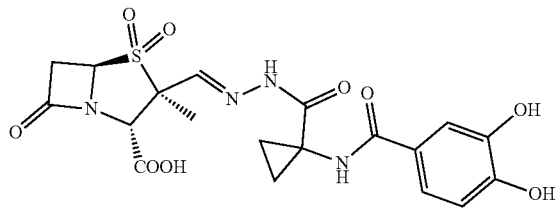 [SMILES: C[C@]1(/C=N/NC(=O)C2(NC(=O)c3ccc(O)c(O)c3)CC2)[C@H](C(=O)O)N2C(=O)C[C@H]2S1(=O)=O]

The title compound was prepared using the similar procedure as described in Example 38 except methyl 1-aminocyclopropanecarboxylate was used in place of methyl pyrrolidine-3-carboxylate and 3,4-bis((4-methoxybenzyl)oxy)benzoic acid was used in place of 2-chloro-3,4-bis((4-methoxybenzyl)oxy)benzoic acid. $^1$H NMR (400 MHz, DMSO-d6) δ 9.81 (s, 1H), 7.50 (s, 1H), 7.22 (d, 2H), 6.73 (d, 2H), 5.58 (s, 1H), 4.70 (t, 1H), 4.22 (s, 1H), 3.46 (m, 2H), 3.21 (m, 1H), 1.68 (s, 3H), 0.99-0.94 (m, 2H), 0.74-0.69 (m, 2H). LC-MS (ESI): m/z=481 (M+H)$^+$.

Example 53

(2S,3R,5R)-3-((E)-(2-(1-(2-chloro-3,4-dihydroxybenzamido)cyclopropanecarbonyl)hydrazono)methyl)-3-methyl-7-oxo-4-thia-1-azabicyclo[3.2.0]heptane-2-carboxylic acid 4,4-dioxide

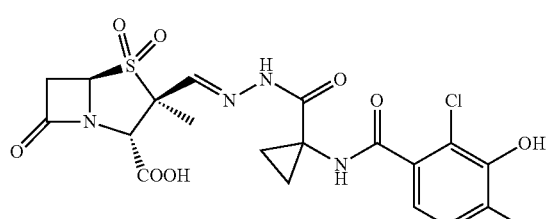

The title compound was prepared using the similar procedure as described in Example 38 except methyl 1-aminocyclopropanecarboxylate was used in place of methyl pyrrolidine-3-carboxylate. $^1$H NMR (400 MHz, DMSO-d6) δ 9.42 (s, 1H), 8.09 (s, 1H), 7.90 (s, 1H), 7.28 (s, 1H), 7.02 (d, 1H), 6.41 (d, 1H), 5.43 (s, 1H), 4.48 (t, 1H), 4.23 (s, 1H), 3.29 (s, 1H), 3.24 (m, 1H), 2.99 (m, 1H), 1.77 (s, 3H), 0.75 (m, 2H), 0.50 (m, 2H). LC-MS (ESI): m/z=515 (M+H)$^+$.

Example 54

(2S,3R,5R)-3-((E)-(2-(4-((3,4-dihydroxybenzoyl)oxy)benzoyl)hydrazono)methyl)-3-methyl-7-oxo-4-thia-1-azabicyclo[3.2.0]heptane-2-carboxylic acid 4,4-dioxide

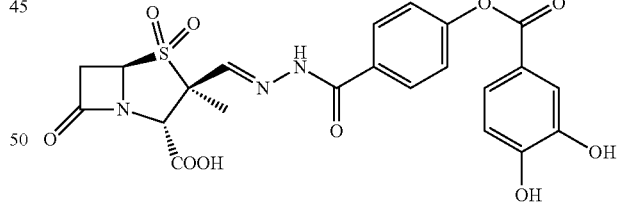

The title compound was prepared using the similar procedure as described in EXAMPLE 1 except 4-(hydrazinecarbonyl)phenyl 3,4-bis(benzyloxy)benzoate was used in place of 2-chloro-4,5-dihydroxybenzohydrazide. $^1$H NMR (400 MHz, DMSO-d6) δ 9.20 (s, 1H), 7.98-7.84 (m, 2H), 7.58-7.47 (m, 3H), 7.35-7.21 (m, 2H), 6.75 (d, 1H), 5.76 (s, 1H), 4.70 (t, 1H), 3.68 (s, 1H), 3.54 (s, 1H), 3.46 (m, 1H), 3.21 (m, 1H), 1.80 (s, 3H). LC-MS (ESI): m/z=518 (M+H)$^+$.

Example 55

(2S,3R,5R)-3-((E)-(2-(2-((tert-butoxycarbonyl)amino)-3-((2-chloro-3,4-dihydroxybenzoyl)oxy)propanoyl)hydrazono)methyl)-3-methyl-7-oxo-4-thia-1-azabicyclo[3.2.0]heptane-2-carboxylic acid 4,4-dioxide

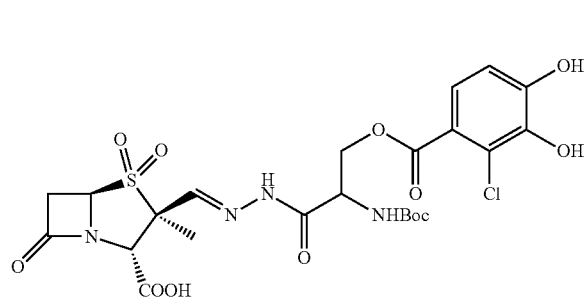 [SMILES: CC(C)(C)OC(=O)NC(COC(=O)c1ccc(O)c(O)c1Cl)C(=O)N/N=C/[C@@]1(C)[C@H](C(=O)O)N2C(=O)C[C@H]2S1(=O)=O]

The title compound was prepared using the similar procedure as described in EXAMPLE 1 except 2-((tert-butoxycarbonyl)amino)-3-hydrazinyl-3-oxopropyl 2-chloro-3,4-bis((4-methoxybenzyl)oxy)benzoate was used in place of 2-chloro-4,5-dihydroxybenzohydrazide. $^1$H NMR (400 MHz, DMSO-d6) δ 7.34 (s, 1H), 7.04 (d, 1H), 6.44 (d, 1H), 5.36 (s, 1H), 5.28 (s, 1H), 5.02 (t, 1H), 4.89 (m, 1H), 4.67 (m, 1H), 4.54 (t, 1H), 4.25 (s, 1H), 4.13 (s, 1H), 3.30 (m, 1H), 3.05 (m, 1H), 1.89 (s, 3H), 1.30 (s, 9H). LC-MS (ESI): m/z=619 (M+H)$^+$.

Example 56

(2S,3R,5R)-3-((E)-(2-(3',4'-dihydroxy-[1,1'-biphenyl]-4-carbonyl)hydrazono)methyl)-3-methyl-7-oxo-4-thia-1-azabicyclo[3.2.0]heptane-2-carboxylic acid 4,4-dioxide

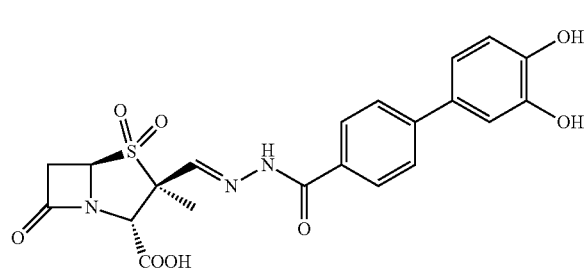 [SMILES: C[C@]1(/C=N/NC(=O)c2ccc(-c3ccc(O)c(O)c3)cc2)[C@H](C(=O)O)N2C(=O)C[C@H]2S1(=O)=O]

The title compound was prepared using the similar procedure as described in EXAMPLE 1 except 3',4'-dihydroxy-[1,1'-biphenyl]-4-carbohydrazide was used in place of 2-chloro-4,5-dihydroxybenzohydrazide.

$^1$H NMR (400 MHz, DMSO-d6) δ 12.22 (s, 1H), 9.20 (d, 2H), 8.04 (m, 3H), 7.76 (d, 2H), 7.24 (s, 1H), 7.13 (m, 1H), 6.92 (d, 1H), 6.62 (m, 1H), 5.32 (s, 1H), 4.89 (s, 1H), 3.77 (d, 1H), 3.32 (d, 3H), 1.72 (s, 3H). LC-MS: m/z=474 (M+H)$^+$.

Example 57

(2S,3R,5R)-3-((E)-(2-(4-((2-chloro-3,4-dihydroxybenzoyl)oxy)benzoyl)hydrazono)methyl)-3-methyl-7-oxo-4-thia-1-azabicyclo[3.2.0]heptane-2-carboxylic acid 4,4-dioxide

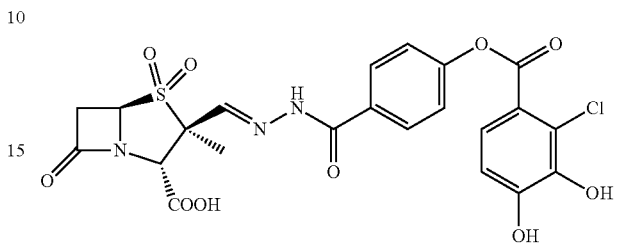

The title compound was prepared using the similar procedure as described in EXAMPLE 1 except 4-(hydrazinecarbonyl)phenyl 3,4-bis(benzyloxy)-2-chlorobenzoate was used in place of 2-chloro-4,5-dihydroxybenzohydrazide. 1H NMR (400 MHz, DMSO-d6) δ 7.70-7.56 (m, 2H), 7.20 (s, 1H), 7.17-7.02 (m, 3H), 6.32 (d, 1H), 5.11 (s, 1H), 4.40 (t, 1H), 4.07 (s, 1H), 3.88 (s, 1H), 3.16 (m, 1H), 2.91 (m, 1H), 1.66 (s, 3H). LC-MS (ESI): m/z=552 (M+H)+.

Example 58

(2S,3R,5R)-3-((E)-(2-(5-(2-chloro-3,4-dihydroxybenzamido)picolinoyl)hydrazono)methyl)-3-methyl-7-oxo-4-thia-1-azabicyclo[3.2.0]heptane-2-carboxylic acid 4,4-dioxide

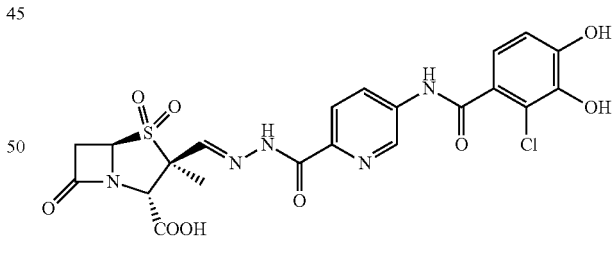

The title compound was prepared using the similar procedure as described in Example 38. 1H NMR (400 MHz, DMSO-d6): δ 13.81 (br, 1H), 12.42 (s, 1H), 10.81 (s, 1H), 10.23 (s, 1H), 9.44 (s, 1H), 9.00 (s, 1H), 8.38 (d, 1H), 8.15 (s, 1H), 8.11 (d, 1H), 6.98 (d, 1H), 6.85 (d, 1H), 5.32 (d, 1H), 4.81 (s, 1H), 3.78 (dd, 1H), 3.26 (dd, 1H), 1.63 (s, 3H). LC-MS (ESI): m/z=552 (M+H)+.

Example 59

(2S,3R,5R)-3-((E)-(2-(2-(2-chloro-3,4-dihydroxy-benzamido)acetyl)hydrazono)methyl)-3-methyl-7-oxo-4-thia-1-azabicyclo[3.2.0]heptane-2-carboxylic acid 4,4-dioxide

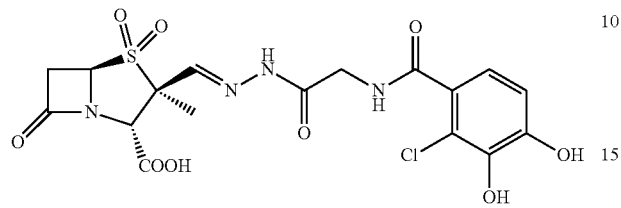

Figure 7:
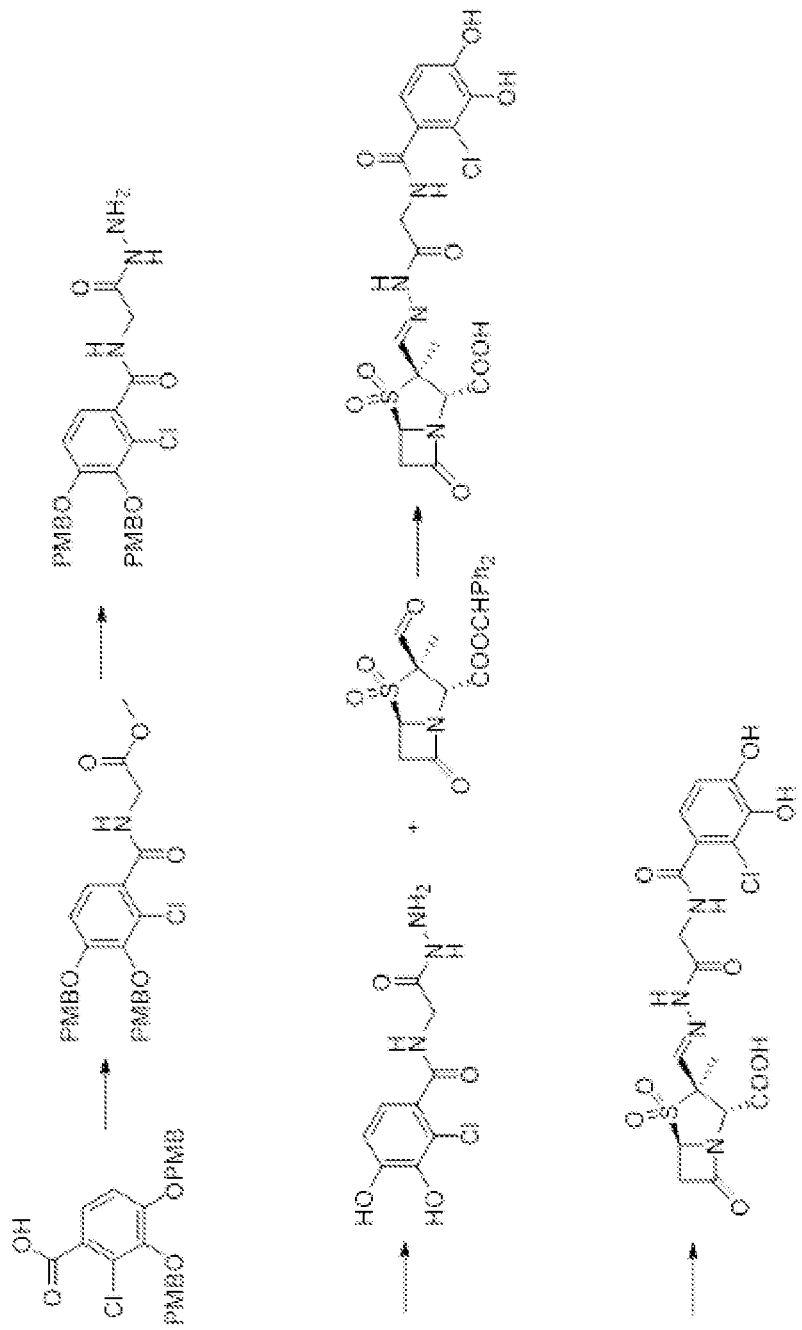
Figure 8:
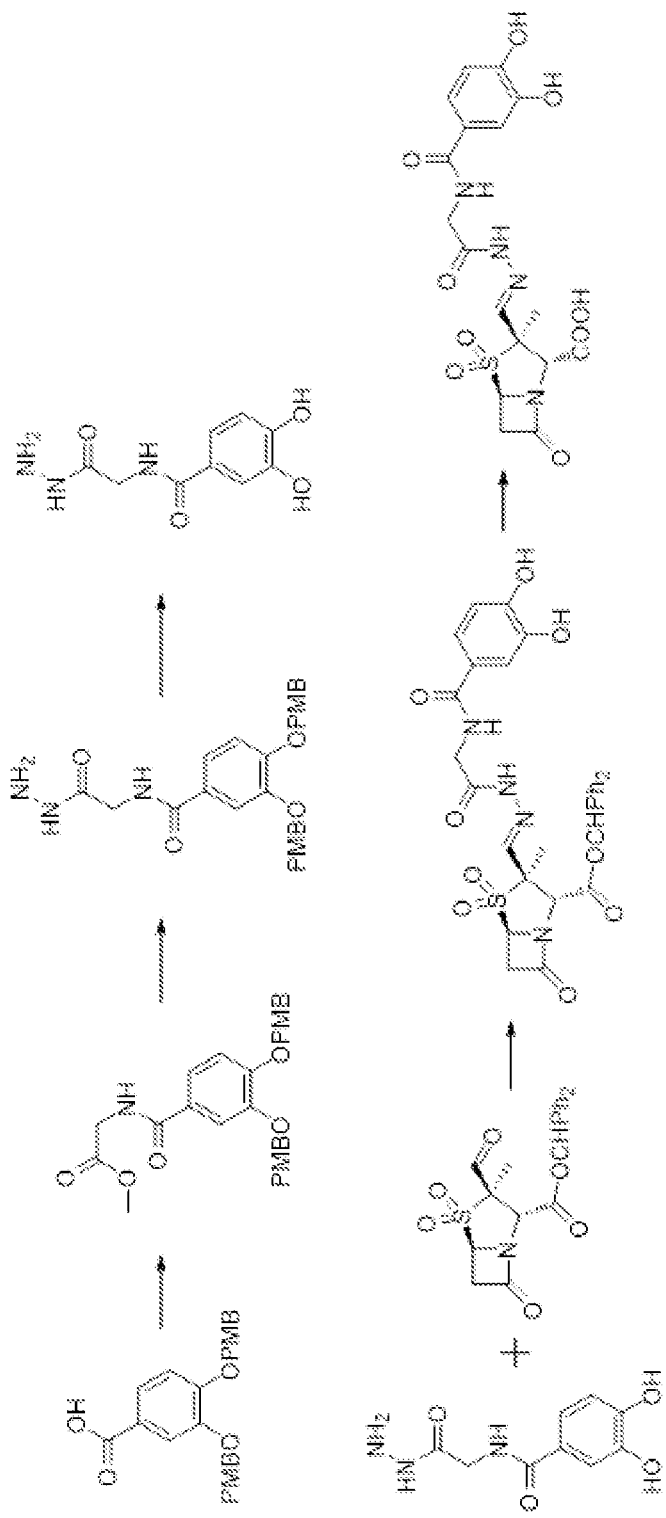

FIG. 7 shows a synthetic scheme for the preparation of this compound. Step 1: methyl 2-(2-chloro-3,4-bis((4-methoxybenzyl)oxy)benzamido)acetate. To a solution of 2-chloro-3,4-bis((4-methoxybenzyl)oxy)benzoic acid (2.2 g, 5.1 mmol) in DMF (40 mL) was added methyl 2-aminoacetate hydrochloride (0.63 g, 5.0 mmol), EDCI (1.9 g, 10 mmol), HOBT (0.7 g, 5.0 mmol) and then NMM (0.5 g, 5.0 mmol). The mixture was stirred at rt for 6 h. Then the solution was poured into ice water. The mixture was stirred for 0.5 h, filtered under reduced pressure. The filter cake was collected and dried with lyophilization to afford the title compound as a pale solid (2.3 g, yield 90%). LC-MS (ESI): m/z=500 (M+H)+.

Step 2: 2-chloro-N-(2-hydrazinyl-2-oxoethyl)-3,4-bis((4-methoxybenzyl)oxy)benzamide. To a solution of methyl 2-(2-chloro-3,4-bis((4-methoxybenzyl)oxy)benzamido)acetate (2.0 g, 4.0 mmol) in EtOH (50 mL) was added hydrazine hydrate (85% in water, 3.0 g, 51 mmol). The mixture was stirred at 80° C. for 16 h. The temperature was let cool down to rt. A lot of solid was precipitated. The mixture was filtered under reduced pressure. The filter cake was collected and dried in vacuo to afford a white solid (2 g, yield 100%). LC-MS (ESI): m/z=500 (M+H)+.

Step 3: 2-chloro-N-(2-hydrazinyl-2-oxoethyl)-3,4-dihydroxybenz amide hydrochloride. A solution of 2-chloro-N-(2-hydrazinyl-2-oxoethyl)-3,4-bis((4-methoxybenzyl)oxy) benzamide (1.0 g, 2.0 mmol) in HCl/EtOH (10 mL, 4.0 M) was stirred at rt for 5 h. The solvent was evaporated in vacuo. The crude (600 mg) was used for the next step without further purification. LC-MS: m/z=260 (M+H)+.

Step 4: (2S,3R,5R)-benzhydryl 3-((E)-(2-(2-(2-chloro-3,4-dihydroxybenzamido)acetyl)hydrazono)methyl)-3-methyl-7-oxo-4-thia-1-azabicyclo[3.2.0]heptane-2-carboxylate 4,4-dioxide. To a solution of 2-chloro-N-(2-hydrazinyl-2-oxoethyl)-3,4-dihydroxybenzamide hydrochloride (1.0 g, 3.4 mmol) in EtOH/DCM (10/10 mL) was added (2S,3R,5R)-benzhydryl 3-formyl-3-methyl-7-oxo-4-thia-1-azabicyclo[3.2.0]heptane-2-carboxylate 4,4-dioxide (1.5 g, 3.6 mmol) and pyridine (0.1 g, 1.3 mmol). The solution was stirred at rt for 3 h. The solvent was evaporated in vacuo. The residue was purified by column chromatography (silica gel, DCM:MeOH=20:1) to afford the title compound as a white solid (400 mg, yield 18%). LC-MS (ESI): m/z=655 (M+H)+.

Step 5: (2S,3R,5R)-3-((E)-(2-(2-(2-chloro-3,4-dihydroxybenzamido)acetyl)hydrazono)methyl)-3-methyl-7-oxo-4-thia-1-azabicyclo[3.2.0]heptane-2-carboxylic acid 4,4-dioxide. A solution of (2S,3R,5R)-benzhydryl 3-((E)-(2-(2-(2-chloro-3,4-dihydroxybenzamido)acetyl)hydrazono) methyl)-3-methyl-7-oxo-4-thia-1-azabicyclo[3.2.0]heptane-2-carboxylate 4,4-dioxide (400 mg, 0.6 mmol) in m-cresol (5 mL) was stirred at 50° C. for 5 h. The solution was poured into PE (10 mL). The solid obtained after filtration was purified by column chromatography (silica gel, DCM:MeOH=20:1) to afford the title compound as a white solid (90 mg, yield 30%). 1H NMR (400 MHz, DMSO-d6) δ 11.86 (s, 1H), 9.50 (s, 1H), 9.23 (s, 1H), 7.33 (s, 1H), 7.04 (d, 1H), 6.82 (d, 1H), 6.65 (m, 2H), 5.33 (s, 1H), 5.00 (s, 1H), 4.22 (d, 1H), 3.72 (d, 1H), 3.62 (s, 1H), 2.20 (s, 2H), 1.61 (s, 3H). LC-MS (ESI): m/z=489 (M+H)+.

Example 60

(2S,3R,5R)-3-((E)-(2-(3-(2-chloro-3,4-dihydroxy-benzamido)propanoyl)hydrazono)methyl)-3-methyl-7-oxo-4-thia-1-azabicyclo[3.2.0]heptane-2-carboxylic acid 4,4-dioxide

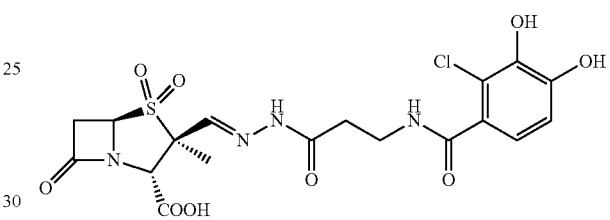

The title compound was prepared using the similar procedure as described in EXAMPLE 59 except methyl 3-aminopropanoate hydrochloride was used in place of methyl 2-aminoacetate hydrochloride. 1H NMR (400 MHz, DMSO-d6) δ 11.85 (s, 1H), 9.50 (s, 1H), 9.31 (s, 1H), 8.22 (s, 1H), 7.02 (d, 1H), 6.63 (m, 2H), 5.32 (s, 1H), 5.04 (s, 1H), 3.84 (d, 1H), 3.53 (m, 2H), 3.33 (d, 1H), 2.20 (m, 2H), 1.62 (s, 3H). LC-MS (ESI): m/z=503 (M+H)+.

Example 61

(2S,3R,5R)-3-((E)-(2-(6-(2-chloro-3,4-dihydroxy-benzamido)hexanoyl)hydrazono)methyl)-3-methyl-7-oxo-4-thia-1-azabicyclo[3.2.0]heptane-2-carboxylic acid 4,4-dioxide

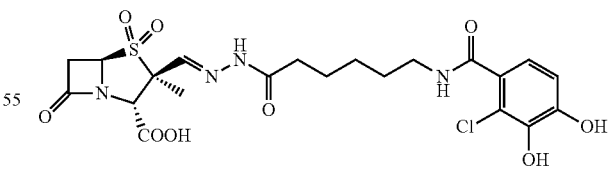

The title compound was prepared using the similar procedure as described in EXAMPLE 59 except methyl 6-aminohexanoate hydrochloride was used in place of methyl 2-aminoacetate hydrochloride. 1H NMR (400 MHz, DMSO-d6) δ 11.85 (s, 1H), 9.54 (s, 1H), 9.34 (s, 1H), 8.13 (s, 1H), 7.56 (s, 1H), 6.74 (d, 2H), 6.56 (s, 1H), 5.34 (s, 1H), 5.05 (s, 1H), 3.83 (d, 1H), 3.23 (m, 3H), 2.20 (m, 2H), 1.60 (s, 3H), 1.44 (m, 6H). LC-MS (ESI): m/z=545 (M+H)+.

Example 62

(2S,3R,5R)-3-((E)-(2-((S)-2-(2-chloro-3,4-dihydroxybenzamido)propanoyl)hydrazono)methyl)-3-methyl-7-oxo-4-thia-1-azabicyclo[3.2.0]heptane-2-carboxylic acid 4,4-dioxide

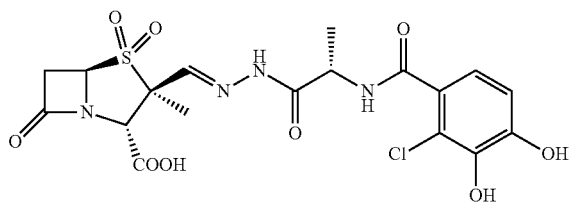 [SMILES: C[C@H](NC(=O)c1ccc(O)c(O)c1Cl)C(=O)N/N=C/[C@@]1(C)[C@H](C(=O)O)N2C(=O)C[C@H]2S1(=O)=O]

The title compound was prepared using the similar procedure as described in EXAMPLE 59 except (S)-methyl 2-aminopropanoate hydrochloride was used in place of methyl 2-aminoacetate hydrochloride. 1H NMR (400 MHz, DMSO-d6) δ 11.85 (s, 1H), 9.55 (s, 1H), 9.22 (s, 1H), 7.33 (s, 1H), 7.02 (d, 1H), 6.85 (s, 1H), 6.64 (d, 1H), 5.33 (s, 1H), 5.03 (s, 1H), 4.23 (d, 1H), 3.73 (d, 1H), 3.66 (s, 1H), 2.23 (m, 1H), 1.60 (s, 3H), 1.44 (d, 3H). LC-MS (ESI): m/z=503 (M+H)+.

Example 63

(2S,3R,5R)-3-((E)-(2-(4-(2-chloro-3,4-dihydroxybenzamido)butanoyl)hydrazono)methyl)-3-methyl-7-oxo-4-thia-1-azabicyclo[3.2.0]heptane-2-carboxylic acid 4,4-dioxide

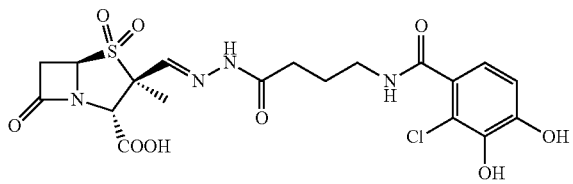 [SMILES: C[C@]1(/C=N/NC(=O)CCCNC(=O)c2ccc(O)c(O)c2Cl)[C@H](C(=O)O)N2C(=O)C[C@H]2S1(=O)=O]

The title compound was prepared using the similar procedure as described in EXAMPLE 59 except methyl 4-aminobutanoate hydrochloride was used in place of methyl 2-aminoacetate hydrochloride. 1H NMR (400 MHz, DMSO-d6) δ 11.84 (s, 1H), 9.54 (s, 1H), 9.32 (s, 1H), 8.23 (s, 1H), 7.33 (s, 1H), 6.82 (s, 1H), 6.61 (m, 2H), 5.32 (s, 1H), 5.01 (s, 1H), 3.85 (d, 1H), 3.34 (m, 1H), 2.54 (m, 2H), 2.20 (m, 2H), 1.82 (br, 2H), 1.60 (s, 3H). LC-MS (ESI): m/z=517 (M+H)+.

Example 64

(2S,3R,5R)-3-((E)-(2-(2-(3,4-dihydroxybenzamido)acetyl)hydrazono)methyl)-3-methyl-7-oxo-4-thia-1-azabicyclo[3.2.0]heptane-2-carboxylic acid 4,4-dioxide

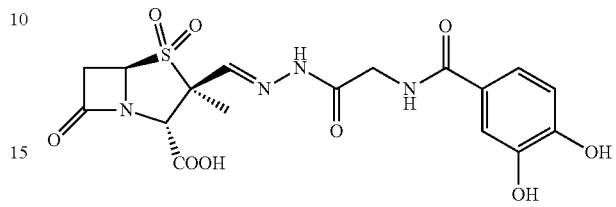

Figure 9:
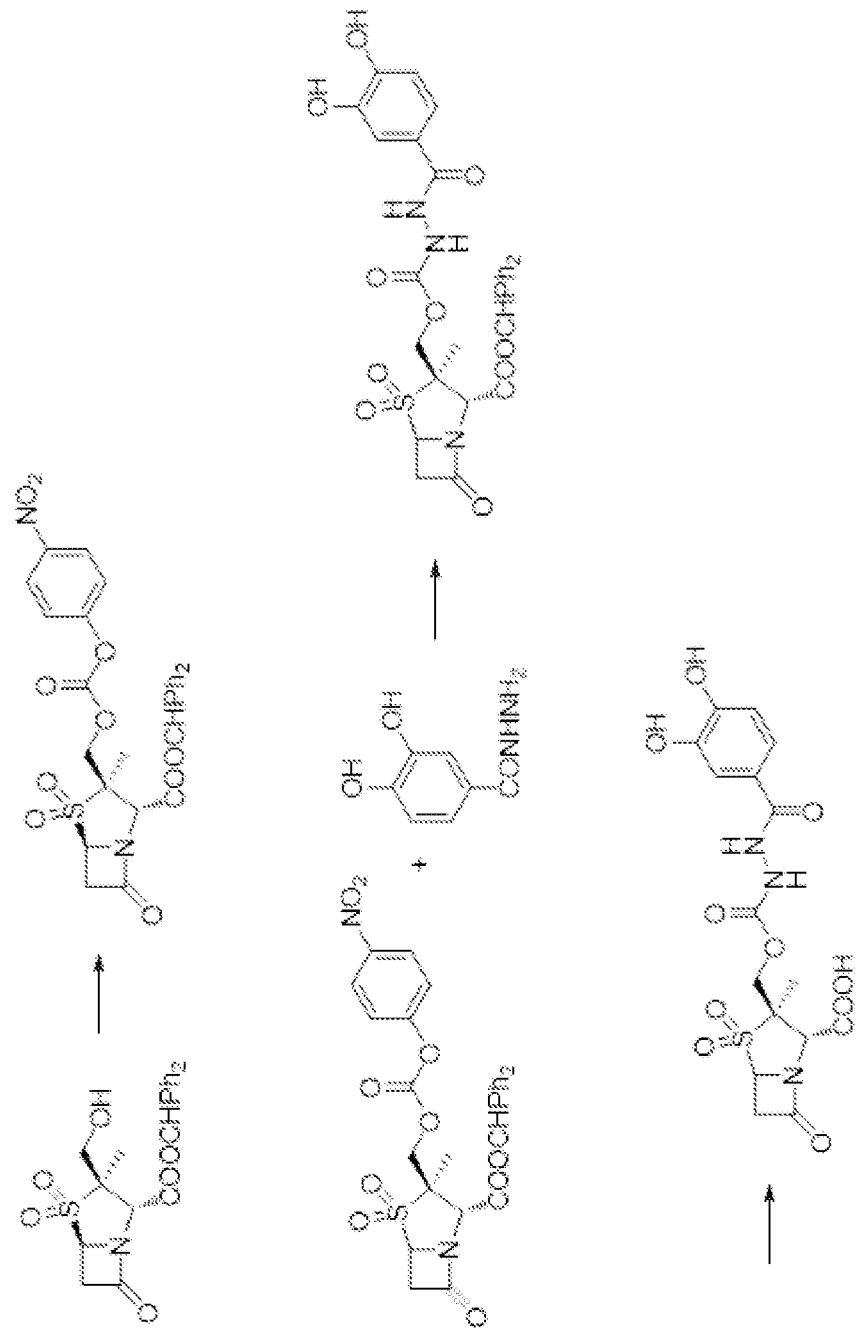

FIG. 9 shows a synthetic scheme for the preparation of this compound. Step 1: methyl 2-(3,4-bis((4-methoxybenzyl)oxy)benzamido)acetate. To a solution of 3,4-bis((4-methoxybenzyl)oxy)benzoic acid (2.0 g, 5.1 mmol) in DMF (40 mL) was added methyl 2-aminoacetate hydrochloride (0.63 g, 5.0 mmol), EDCI (1.9 g, 10 mmol), HOBT (0.7 g, 5.0 mmol) and then NMM (0.5 g, 5.0 mmol). The mixture was stirred at rt for 6 h. Then the solution was poured into ice water. The mixture was stirred for 0.5 h, filtered under reduced pressure. The filter cake was collected and dried with lyophilization to afford the title compound as a pale solid (2.3 g, yield 97%). LC-MS (ESI): m/z=466 (M+H)+.

Step 2: N-(2-hydrazinyl-2-oxoethyl)-3,4-bis((4-methoxybenzyl)oxy)benzamide. To a solution of methyl 2-(3,4-bis((4-methoxybenzyl)oxy)benzamido)acetate (2.3 g, 5.0 mmol) in EtOH (50 mL) was added hydrazine hydrate (85% in water, 3.0 g, 51 mmol). The mixture was stirred at 80° C. for 16 h. The temperature was let cool down to RT. A lot of solid was precipitated. The system was filtered under reduced pressure. The filter cake was collected and dried in vacuo to afford a white solid (2.3 g, yield 100%). LC-MS (ESI): m/z=466 (M+H)+.

Step 3: N-(2-hydrazinyl-2-oxoethyl)-3,4-dihydroxybenzamide. A solution of N-(2-hydrazinyl-2-oxoethyl)-3,4-bis((4-methoxybenzyl)oxy)benzamide (0.96 g, 2.0 mmol) in HCl/EtOH (10 mL, 4.0 M) was stirred at RT for 5 h. The solvent was evaporated in vacuo. The crude was used for the next step without further purification. (600 mg). LC-MS (ESI): m/z=226 (M+H)+.

Step 4: (2S,3R,5R)-benzhydryl 3-((E)-(2-(2-(3,4-dihydroxybenzamido)acetyl)hydrazono)methyl)-3-methyl-7-oxo-4-thia-1-azabicyclo[3.2.0]heptane-2-carboxylate 4,4-dioxide. To a solution of N-(2-hydrazinyl-2-oxoethyl)-3,4-dihydroxybenzamide (1.0 g, 3.8 mmol) in EtOH/DCM (10/10 mL) was added (2S,3R,5R)-benzhydryl 3-formyl-3-methyl-7-oxo-4-thia-1-azabicyclo[3.2.0]heptane-2-carboxylate 4,4-dioxide (1.5 g, 3.6 mmol) and pyridine (0.1 g, 1.3 mmol). The solution was stirred at RT for 3 h. The solvent was evaporated in vacuo. The residue was purified by column chromatography (silica gel, DCM:MeOH=20:1) to afford the title compound as a white solid (400 mg, yield 18%). LC-MS (ESI): m/z=621 (M+H)+.

Step 5: (2S,3R,5R)-3-((E)-(2-(2-(3,4-dihydroxybenzamido)acetyl)hydrazono)methyl)-3-methyl-7-oxo-4-thia-1-azabicyclo[3.2.0]heptane-2-carboxylic acid 4,4-dioxide. A solution of (E)-benzhydryl 3-((2-(2-(3,4-dihydroxybenzamido)acetyl)hydrazono)methyl)-3-methyl-7-oxo-4-thia-1-azabicyclo[3.2.0]heptane-2-carboxylate 4,4-dioxide (400 mg, 0.6 mmol) in m-cresol (5 mL) was stirred at 50° C. for 5 h. The solution was poured into PE (10 mL). The solid obtained after filtration was purified with silica gel-column (DCM:MeOH=20:1) to afford a white solid (90 mg, yield 30%). 1H NMR (400 MHz, DMSO-d6) δ 11.84 (s, 1H), 9.54 (d, 1H), 9.24 (d, 1H), 8.33 (s, 1H), 7.44 (s, 1H), 7.14 (d, 1H), 6.81 (s, 1H), 6.62 (m, 2H), 5.30 (s, 1H), 5.03 (s, 1H), 4.23 (d, 1H), 3.70 (d, 1H), 3.62 (s, 1H), 2.20 (s, 2H), 1.60 (s, 3H). LC-MS (ESI): m/z=455 (M+H)+.

Example 65

(2S,3R,5R)-3-((E)-(2-((S)-2-(3,4-dihydroxybenzamido)propanoyl)hydrazono)methyl)-3-methyl-7-oxo-4-thia-1-azabicyclo[3.2.0]heptane-2-carboxylic acid 4,4-dioxide

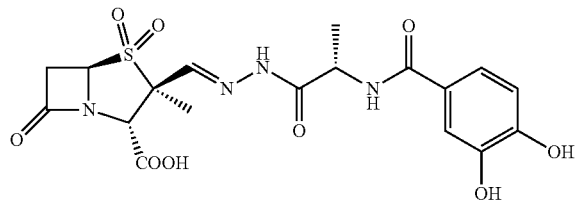 [SMILES: C[C@H](NC(=O)c1ccc(O)c(O)c1)C(=O)N/N=C/[C@@]1(C)[C@H](C(=O)O)N2C(=O)C[C@H]2S1(=O)=O]

The title compound was prepared using the similar procedure as described in EXAMPLE 64 except (S)-methyl 2-aminopropanoate hydrochloride was used in place of methyl 2-aminoacetate hydrochloride. 1H NMR (400 MHz, DMSO-d6) δ 11.78 (s, 1H), 9.45 (s, 1H), 9.24 (s, 1H), 8.25 (s, 1H), 7.33 (s, 1H), 7.03 (d, 1H), 6.82 (s, 1H), 6.64 (d, 1H), 5.34 (s, 1H), 5.01 (s, 1H), 4.23 (d, 1H), 3.73 (d, 1H), 3.63 (s, 1H), 2.20 (m, 1H), 1.60 (s, 3H), 1.44 (d, 3H). LC-MS (ESI): m/z=469 (M+H)+.

Example 66

(2S,3R,5R)-3-((E)-(2-(4-(3,4-dihydroxybenzamido)butanoyl)hydrazono)methyl)-3-methyl-7-oxo-4-thia-1-azabicyclo[3.2.0]heptane-2-carboxylic acid 4,4-dioxide

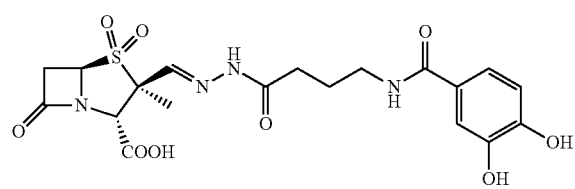 [SMILES: C[C@]1(/C=N/NC(=O)CCCNC(=O)c2ccc(O)c(O)c2)[C@H](C(=O)O)N2C(=O)C[C@H]2S1(=O)=O]

The title compound was prepared using the similar procedure as described in EXAMPLE 64 except methyl 4-aminobutanoate hydrochloride was used in place of methyl 2-aminoacetate hydrochloride.

¹H NMR (400 MHz, DMSO-d6) δ 11.80 (s, 1H), 9.51 (s, 1H), 9.32 (s, 1H), 8.21 (s, 1H), 7.64 (s, 1H), 7.35 (s, 1H), 6.86 (s, 1H), 6.65 (m, 2H), 5.33 (s, 1H), 5.07 (s, 1H), 3.84 (d, 1H), 3.34 (m, 1H), 2.50 (m, 2H), 2.20 (m, 2H), 1.82 (br, 2H), 1.61 (s, 3H). LC-MS (ESI): m/z=483 (M+H)+.

Example 67

(2S,3R,5R)-3-((E)-(2-(3-(3,4-dihydroxybenzamido)propanoyl)hydrazono)methyl)-3-methyl-7-oxo-4-thia-1-azabicyclo[3.2.0]heptane-2-carboxylic acid 4,4-dioxide

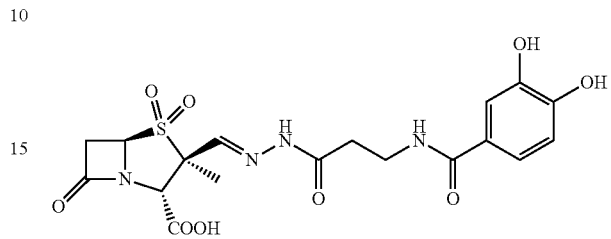

The title compound was prepared using the similar procedure as described in EXAMPLE 64 except methyl 3-aminopropanoate hydrochloride was used in place of methyl 2-aminoacetate hydrochloride.

¹H NMR (400 MHz, DMSO-d6) δ 11.82 (s, 1H), 9.51 (s, 1H), 9.32 (s, 1H), 8.23 (s, 1H), 7.54 (s, 1H), 7.03 (d, 1H), 6.85 (d, 1H), 6.67 (m, 2H), 5.35 (s, 1H), 5.03 (s, 1H), 3.82 (d, 1H), 3.52 (m, 2H), 3.34 (d, 1H), 2.21 (m, 2H), 1.60 (s, 3H). LC-MS (ESI): m/z=469 (M+H)+.

Example 68

(2S,3R,5R)-3-((E)-(2-(6-(3,4-dihydroxybenzamido)hexanoyl)hydrazono)methyl)-3-methyl-7-oxo-4-thia-1-azabicyclo[3.2.0]heptane-2-carboxylic acid 4,4-dioxide

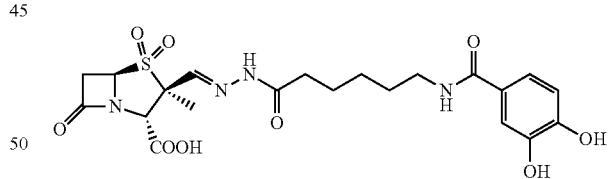

The title compound was prepared using the similar procedure as described in EXAMPLE 64 except methyl 6-aminohexanoate hydrochloride was used in place of methyl 2-aminoacetate hydrochloride. ¹H NMR (400 MHz, DMSO-d6) δ 11.82 (s, 1H), 9.54 (s, 1H), 9.32 (s, 1H), 8.22 (s, 1H), 7.63 (s, 1H), 7.33 (s, 1H), 6.85 (s, 1H), 6.62 (m, 2H), 5.35 (s, 1H), 5.07 (s, 1H), 3.82 (d, 1H), 3.24 (m, 3H), 2.22 (m, 2H), 1.60 (s, 3H), 1.43 (m, 6H). LC-MS (ESI): m/z=511 (M+H)+.

Example 69

(2S,3R,5R)-3-(((2-(3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide

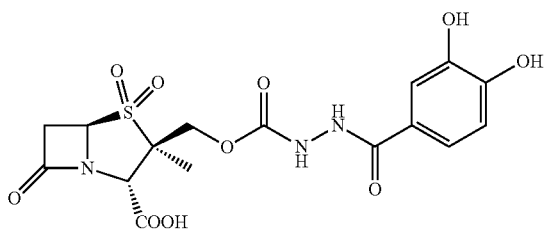 [SMILES: C[C@]1(COC(=O)NNC(=O)c2ccc(O)c(O)c2)[C@H](C(=O)O)N2C(=O)C[C@H]2S1(=O)=O]

FIG. 9 shows a synthetic scheme for the preparation of this compound. Step 1: (2S,3R,5R)-benzhydryl 3-methyl-3-((((4-nitrophenoxy)carbonyl)oxy)methyl)-7-oxo-4-thia-1-azabicyclo[3.2.0]heptane-2-carboxylate 4,4-dioxide. (2S,3R,5R)-benzhydryl 3-(hydroxymethyl)-3-methyl-7-oxo-4-thia-1-azabicyclo[3.2.0]heptane-2-carboxylate 4,4-dioxide (54 g, 0.13 mol) was dissolved in tetrahydrofuran (500 mL). The solution was cooled to 0° C., 4-nitrophenyl carbonochloridate (52.4 g, 0.26 mol) was added. Then pyridine (20 mL) and N,N-dimethylpyridin-4-amine (800 mg, 0.0065 mol) were added. The mixture was stirred 15 h. The solution was washed with water, and extracted with ethyl acetate (200 mL) twice. The organic layer was dried over $Na_2SO_4$. The solvent was evaporated in vacuo. The residue was purified by column chromatography (silica gel, DCM:hexene=3:1) to give the title compound (29.4 g, yield: 39.2%).

Step 2: (2S,3R)-benzhydryl 3-(((2-(3,4-dihydroxybenzoyl)hydrazinecarbonyl)oxy)methyl)-3-methyl-7-oxo-4-thia-1-azabicyclo[3.2.0]heptane-2-carboxylate 4,4-dioxide. To a solution of 3,4-dihydroxybenzohydrazide (0.4 g, 2.38 mmol) in DMF (5 mL) and Pyridine (1 mL) was added (2S,3R)-benzhydryl 3-methyl-3-((((4-nitrophenoxy)carbonyl)oxy)methyl)-7-oxo-4-thia-1-azabicyclo[3.2.0]heptane-2-carboxylate 4,4-dioxide (1.38 g, 2.38 mmol). The mixture was stirred at rt for 12 hours. The solution was washed with water, and extracted with ethyl acetate (100 mL). The organic layer was dried over $Na_2SO_4$. The solvent was evaporated in vacuo. The residue was purified by column chromatography (silica gel, DCM:MeOH=100:1 to 50:1) to give the title compound (350 mg, yield 24%). LC-MS (ESI): m/z=610 (M+H)$^+$.

Step 3: (2S,3R)-3-(((2-(3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide. (2S,3R)-benzhydryl 3-(((2-(3,4-dihydroxybenzoyl)hydrazinecarbonyl)oxy)methyl)-3-methyl-7-oxo-4-thia-1-azabicyclo[3.2.0]heptane-2-carboxylate 4,4-dioxide (350 mg, 0.57 mmol) was dissolved in THF (5 mL). The mixture was degassed with $N_2$ twice, Pd/C (10%, 150 mg) was added, then the flask was degassed with $H_2$ twice, and stirred at rt for 12 h. The solution was filtered, and the filtrate was concentrated. Ethyl acetate (10 mL) was added, and stirred for 30 min. The slurry was filtered and the cake was washed with MTBE (20 mL) to give the title compound (110 mg, yield 43%). $^1$H NMR (400 MHz, DMSO-d6) δ 11.88 (s, 1H), 10.53 (s, 1H), 9.63 (s, 1H), 9.33 (s, 1H), 7.28 (d, 1H), 6.96 (d, 1H), 6.72 (m, 1H), 5.75 (s, 1H), 5.16 (s, 1H), 4.68 (d, 1H), 4.51 (d, 1H), 3.66 (d, 1H), 3.26 (d, 1H), 1.51 (s, 3H). LC-MS (ESI): m/z=444 (M+H)$^+$.

Example 70

(2S,3R,5R)-3-(((2-(2-chloro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide

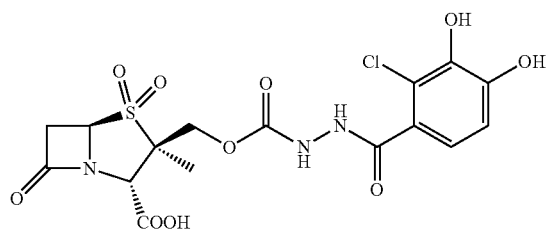 [SMILES: C[C@]1(COC(=O)NNC(=O)c2ccc(O)c(O)c2Cl)[C@H](C(=O)O)N2C(=O)C[C@H]2S1(=O)=O]

The title compound was prepared using the similar procedure as described in Example 69 except 2-chloro-3,4-dihydroxybenzohydrazide was used in place of 3,4-dihydroxybenzohydrazide. $^1$H NMR (400 MHz, DMSO-d6) δ 10.08 (s, 1H), 9.94 (s, 1H), 9.50 (s, 1H), 9.26 (s, 1H), 6.78 (dd, 2H), 5.75 (s, 1H), 5.16 (d, 1H), 4.68 (d, 1H), 4.57 (s, 1H), 4.54 (d, 1H), 3.61 (dd, 1H), 3.26 (d, 1H), 1.51 (s, 3H). LC-MS (ESI): m/z=478 (M+H)$^+$.

Example 71

(2S,3R,5R)-3-(((2-(2-(3,4-dihydroxyphenyl)acetyl)hydrazinecarbonyl)oxy)methyl)-3-methyl-7-oxo-4-thia-1-azabicyclo[3.2.0]heptane-2-carboxylic acid 4,4-dioxide

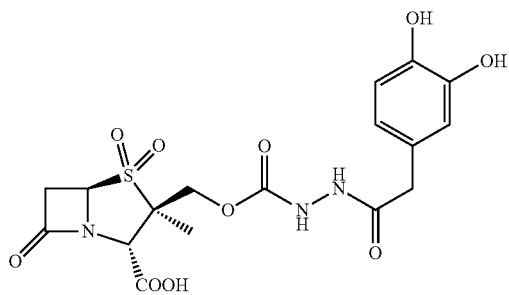 [SMILES: C[C@]1(COC(=O)NNC(=O)Cc2ccc(O)c(O)c2)[C@H](C(=O)O)N2C(=O)C[C@H]2S1(=O)=O]

The title compound was prepared using the similar procedure as described in Example 69 except 2-(3,4-dihydroxyphenyl)acetohydrazide was used in place of 3,4-dihydroxybenzohydrazide. $^1$H NMR (400 MHz, DMSO-d6): δ13.83 (br, 1H), 9.84 (s, 1H), 9.31 (s, 1H), 8.78 (s, 1H), 8.68 (d, 1H), 6.70 (s, 1H), 6.63 (d, 1H), 6.51 (d, 1H), 5.13 (d, 1H), 4.87 (s, 1H), 4.47 (s, 1H), 4.44 (d, 1H), 3.88 (dd, 1H), 3.26 (dd, 1H), 3.21 (2, 1H), 1.48 (s, 3H). LC-MS (ESI): m/z=458 (M+H)$^+$.

Example 72

(2S,3R,5R)-3-(((2-(2,3-dihydroxybenzoyl)hydrazinecarbonyl)oxy)methyl)-3-methyl-7-oxo-4-thia-1-azabicyclo[3.2.0]heptane-2-carboxylic acid 4,4-dioxide

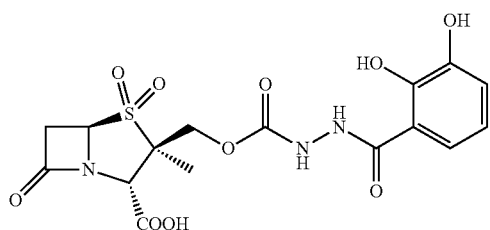 [SMILES: C[C@]1(COC(=O)NNC(=O)c2cccc(O)c2O)[C@H](C(=O)O)N2C(=O)C[C@H]2S1(=O)=O]

The title compound was prepared using the similar procedure as described in Example 69 except 2,3-dihydroxybenzohydrazide was used in place of 3,4-dihydroxybenzohydrazide. $^1$H NMR (400 MHz, DMSO-d6) δ 11.88 (s, 1H), 10.53 (s, 1H), 9.64 (s, 1H), 9.34 (s, 1H), 7.28 (d, 1H), 6.96 (d, 1H), 6.73 (t, 1H), 5.75 (s, 1H), 5.16 (d, 1H), 4.68 (d, 1H), 4.57 (s, 1H), 4.54 (d, 1H), 3.61 (dd, 1H), 3.26 (d, 1H), 1.51 (s, 3H); LC-MS (ESI): m/z=444 (M+H)$^+$.

Example 73

(2S,3R,5R)-3-methyl-7-oxo-3-(((2-(3,4,5-trihydroxybenzoyl)hydrazinecarbonyl)oxy)methyl)-4-thia-1-azabicyclo[3.2.0]heptane-2-carboxylic acid 4,4-dioxide

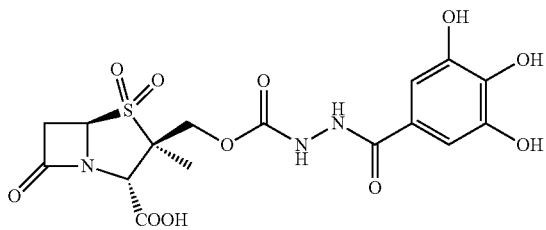 [SMILES: C[C@]1(COC(=O)NNC(=O)c2cc(O)c(O)c(O)c2)[C@H](C(=O)O)N2C(=O)C[C@H]2S1(=O)=O]

The title compound was prepared using the similar procedure as described in Example 69 except 3,4,5-trihydroxybenzohydrazide was used in place of 3,4-dihydroxybenzohydrazide. $^1$H NMR (400 MHz, DMSO-d6) δ 9.94 (s, 1H), 9.29 (s, 1H), 9.12 (br, 2H), 8.78 (br, 1H), 6.84 (s, 2H), 5.75 (s, 1H), 5.16 (d, 1H), 4.68 (d, 1H), 4.57 (s, 1H), 4.54 (d, 1H), 3.61 (dd, 1H), 3.26 (d, 1H), 1.51 (s, 3H). LC-MS (ESI): m/z=460 (M+H)$^+$.

Example 74

(2S,3R,5R)-3-(((2-(2-hydroxy-3-methylbenzoyl)hydrazinecarbonyl)oxy)methyl)-3-methyl-7-oxo-4-thia-1-azabicyclo[3.2.0]heptane-2-carboxylic acid 4,4-dioxide

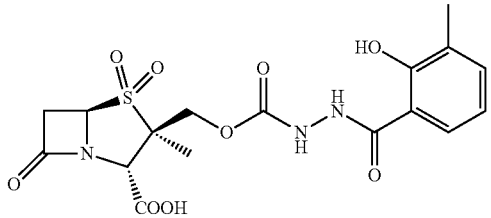 [SMILES: Cc1cccc(C(=O)NNC(=O)OC[C@@]2(C)[C@H](C(=O)O)N3C(=O)C[C@H]3S2(=O)=O)c1O]

The title compound was prepared using the similar procedure as described in Example 69 except 2-hydroxy-3-methylbenzohydrazide was used in place of 3,4-dihydroxybenzohydrazide. $^1$H NMR (400 MHz, DMSO-d6) δ12.47 (s, 1H), 10.73 (s, 1H), 9.69 (s, 1H), 7.69 (d, 1H), 7.36 (d, 1H), 6.83 (t, 1H), 5.75 (s, 1H), 5.16 (d, 1H), 4.68 (d, 1H), 4.57 (s, 1H), 4.54 (d, 1H), 3.61 (dd, 1H), 3.26 (dd, 1H), 2.18 (s, 3H), 1.51 (s, 3H); LC-MS (ESI): m/z=442 (M+H)$^+$.

Example 75

(2S,3R,5R)-3-(((2-(4-hydroxybenzoyl)hydrazinecarbonyl)oxy)methyl)-3-methyl-7-oxo-4-thia-1-azabicyclo[3.2.0]heptane-2-carboxylic acid 4,4-dioxide

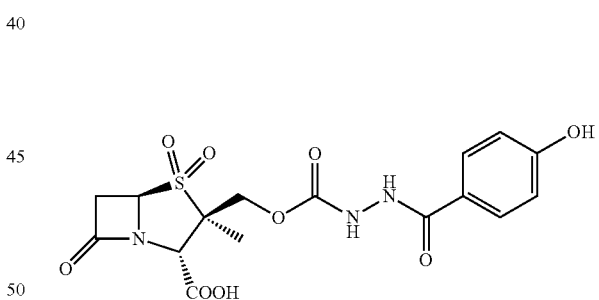

The title compound was prepared using the similar procedure as described in Example 69 except 4-hydroxybenzohydrazide was used in place of 3,4-dihydroxybenzohydrazide. $^1$H NMR (400 MHz, DMSO-d6): δ 13.81 (br, 1H), δ 13.84 (br, 1H), 10.11 (br, 2H), 9.38 (s, 1H), 7.75 (d, 2H), 6.84 (d, 1H), 6.63 (d, 1H), 6.51 (d, 1H), 5.13 (d, 1H), 4.87 (s, 1H), 4.47 (s, 1H), 4.44 (d, 1H), 3.88 (dd, 1H), 3.26 (dd, 1H), 3.21 (2, 1H), 1.48 (s, 3H). LC-MS (ESI): m/z=428 (M+H)$^+$.

Example 76

(2S,3R,5R)-3-(((2-(3,4-dihydroxybenzoyl)-1-methylhydrazinecarbonyl)oxy)methyl)-3-methyl-7-oxo-4-thia-1-azabicyclo[3.2.0]heptane-2-carboxylic acid 4,4-dioxide

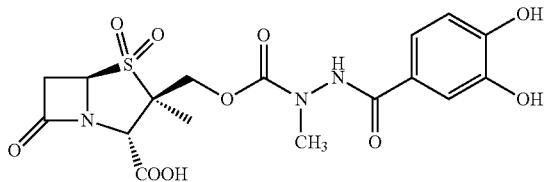 [SMILES: CN(NC(=O)c1ccc(O)c(O)c1)C(=O)OC[C@@]1(C)[C@H](C(=O)O)N2C(=O)C[C@H]2S1(=O)=O]

The title compound was prepared using the similar procedure as described in Example 69 except 3,4-dihydroxy-N'-methylbenzohydrazide was used in place of 3,4-dihydroxybenzohydrazide. $^1$H NMR (400 MHz, DMSO-d6) δ 13.82 (br, 1H), 10.51 (s, 1H), 9.64 (s, 1H), 9.27 (s, 1H), 7.28 (d, 2H), 6.79 (d, 1H), 5.16 (d, 1H), 4.68 (d, 1H), 4.57 (s, 1H), 4.54 (d, 1H), 3.61 (dd, 1H), 3.26 (dd, 1H), 3.13 (s, 3H), 1.51 (s, 3H). LC-MS (ESI): m/z=458 (M+H)$^+$.

Example 77

(2S,3R,5R)-3-(((2-(2-chloro-4,5-dihydroxybenzoyl)hydrazinecarbonyl)oxy)methyl)-3-methyl-7-oxo-4-thia-1-azabicyclo[3.2.0]heptane-2-carboxylic acid 4,4-dioxide

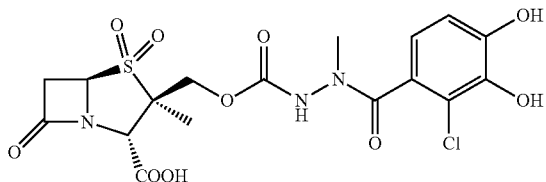 [SMILES: CN(NC(=O)OC[C@@]1(C)[C@H](C(=O)O)N2C(=O)C[C@H]2S1(=O)=O)C(=O)c1ccc(O)c(O)c1Cl]

The title compound was prepared using the similar procedure as described in Example 69 except 2-chloro-3,4-dihydroxy-N-methylbenzohydrazide was used in place of 3,4-dihydroxybenzohydrazide. $^1$H NMR (400 MHz, DMSO-d6) δ 13.84 (br, 1H), 10.08 (s, 1H), 9.86 (s, 1H), 9.61 (s, 1H), 6.65 (d, 1H), 6.55 (d, 1H), 5.16 (d, 1H), 4.68 (d, 1H), 4.57 (s, 1H), 4.54 (d, 1H), 3.61 (dd, 1H), 3.26 (dd, 1H), 3.10 (s, 3H), 1.51 (s, 3H). LC-MS (ESI): m/z=492 (M+H)$^+$.

Example 78

(2S,3R,5R)-3-(((2-(2-hydroxybenzoyl)hydrazinecarbonyl)oxy)methyl)-3-methyl-7-oxo-4-thia-1-azabicyclo[3.2.0]heptane-2-carboxylic acid 4,4-dioxide

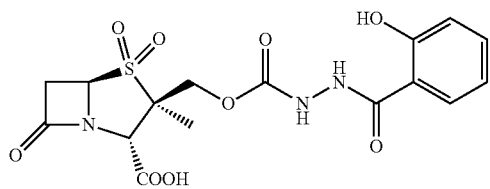 [SMILES: C[C@]1(COC(=O)NNC(=O)c2ccccc2O)[C@H](C(=O)O)N2C(=O)C[C@H]2S1(=O)=O]

The title compound was prepared using the similar procedure as described in Example 69 except 2-hydroxybenzohydrazide was used in place of 3,4-dihydroxybenzohydrazide. $^1$H NMR (400 MHz, DMSO-d6) δ 13.84 (br, 1H), 11.96 (s, 1H), 10.49 (s, 1H), 9.62 (s, 1H), 7.84 (d, 1H), 7.45 (d, 1H), 6.95 (dd, 2H), 5.75 (s, 1H), 5.16 (d, 1H), 4.68 (d, 1H), 4.57 (s, 1H), 4.54 (d, 1H), 3.61 (dd, 1H), 3.26 (dd, 1H), 1.51 (s, 3H). LC-MS (ESI): m/z=428 (M+H)$^+$.

Example 79

(2S,3R,5R)-3-(((2-(3-ethyl-7-oxo-4,7-dihydropyrazolo[1,5-a]pyrimidine-5-carbonyl)hydrazinecarbonyl)oxy)methyl)-3-methyl-7-oxo-4-thia-1-azabicyclo[3.2.0]heptane-2-carboxylic acid 4,4-dioxide

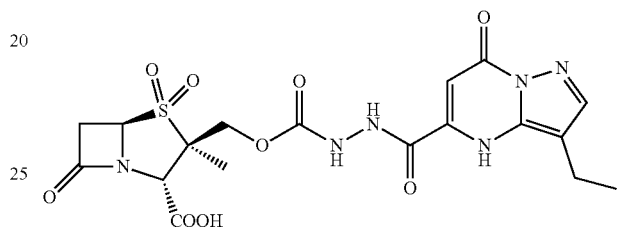

The title compound was prepared using the similar procedure as described in Example 69 except 3-ethyl-7-oxo-4,7-dihydropyrazolo[1,5-a]pyrimidine-5-carbohydrazide was used in place of 3,4-dihydroxybenzohydrazide. $^1$H NMR (400 MHz, DMSO-d6) δ 13.81 (br, 1H), 10.81 (s, 1H), 9.73 (s, 1H), 7.85 (s, 1H), 6.18 (s, 1H), 5.75 (s, 1H), 5.16 (d, 1H), 4.68 (d, 1H), 4.57 (s, 1H), 4.54 (d, 1H), 3.61 (dd, 1H), 3.26 (dd, 1H), 2.69 (q, 2H), 1.51 (s, 3H), 1.17 (t, 3H). LC-MS (ESI): m/z=497 (M+H)$^+$.

Example 80

(2S,3R,5R)-3-(((2-(2-chloro-3,4-dihydroxybenzoyl)-1-methylhydrazinecarbonyl)oxy)methyl)-3-methyl-7-oxo-4-thia-1-azabicyclo[3.2.0]heptane-2-carboxylic acid 4,4-dioxide

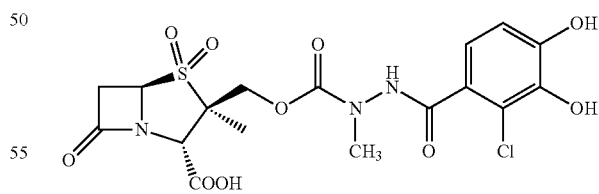

The title compound was prepared using the similar procedure as described in Example 69 except 2-chloro-3,4-dihydroxy-N'-methylbenzohydrazide was used in place of 3,4-dihydroxybenzohydrazide. $^1$H NMR (400 MHz, DMSO-d6) δ 13.82 (br, 1H), 10.48 (s, 1H), 10.19 (s, 1H), 9.37 (s, 1H), 6.98 (d, 1H), 6.72 (d, 1H), 5.16 (d, 1H), 4.68 (d, 1H), 4.57 (s, 1H), 4.54 (d, 1H), 3.61 (dd, 1H), 3.26 (dd, 1H), 3.08 (s, 3H), 1.51 (s, 3H). LC-MS (ESI): m/z=492 (M+H)$^+$.

Example 81

(2S,3R,5R)-3-(((2-(3,4-dihydroxybenzoyl)-2-methylhydrazinecarbonyl)oxy)methyl)-3-methyl-7-oxo-4-thia-1-azabicyclo[3.2.0]heptane-2-carboxylic acid 4,4-dioxide

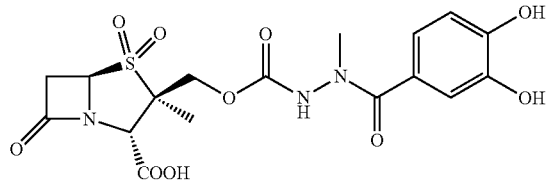 [SMILES: CN(NC(=O)OC[C@@]1(C)[C@H](C(=O)O)N2C(=O)C[C@H]2S1(=O)=O)C(=O)c1ccc(O)c(O)c1]

The title compound was prepared using the similar procedure as described in Example 69 except 3,4-dihydroxy-N-methylbenzohydrazide was used in place of 3,4-dihydroxybenzohydrazide. $^1$H NMR (400 MHz, DMSO-d6) δ 13.82 (br, 1H), 10.10 (s, 1H), 9.34 (s, 1H), 9.10 (s, 1H), 6.91 (s, 1H), 6.82 (d, 1H), 6.68 (d, 1H), 5.16 (d, 1H), 4.68 (d, 1H), 4.57 (s, 1H), 4.54 (d, 1H), 3.61 (dd, 1H), 3.26 (dd, 1H), 3.07 (s, 3H), 1.51 (s, 3H). LC-MS (ESI): m/z=458 (M+H)$^+$.

Example 82

(2S,3R,5R)-3-methyl-7-oxo-3-(((2-(2,3,4-trihydroxybenzoyl)hydrazinecarbonyl)oxy)methyl)-4-thia-1-azabicyclo[3.2.0]heptane-2-carboxylic acid 4,4-dioxide

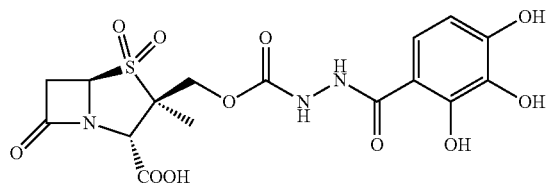 [SMILES: C[C@]1(COC(=O)NNC(=O)c2ccc(O)c(O)c2O)[C@H](C(=O)O)N2C(=O)C[C@H]2S1(=O)=O]

The title compound was prepared using the similar procedure as described in Example 69, except 2,3,4-trihydroxybenzohydrazide was used in place of 3,4-dihydroxybenzohydrazide. $^1$H NMR (400 MHz, DMSO-d6) δ 13.86 (br, 1H), 12.24 (s, 1H), 10.35 (s, 1H), 9.72 (s, 1H), 9.54 (s, 1H), 8.55 (s, 1H), 7.24 (d, 1H), 6.36 (d, 1H), 5.16 (d, 1H), 4.68 (d, 1H), 4.57 (s, 1H), 4.54 (d, 1H), 3.61 (dd, 1H), 3.26 (dd, 1H), 1.51 (s, 3H). LC-MS (ESI): m/z=460 (M+H)$^+$.

Example 83

(2S,3R,5R)-3-(((2-(2,6-dichloro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide

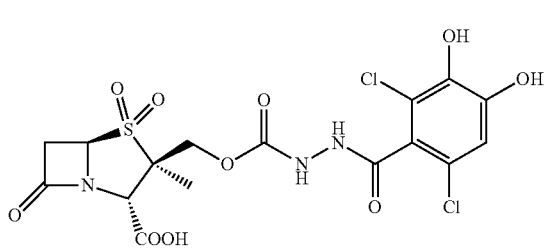 [SMILES: C[C@]1(COC(=O)NNC(=O)c2c(Cl)cc(O)c(O)c2Cl)[C@H](C(=O)O)N2C(=O)C[C@H]2S1(=O)=O]

The title compound was prepared using the similar procedure as described in Example 69 except 2-chloro-4,5-dihydroxybenzohydrazide was used in place of 3,4-dihydroxybenzohydrazide. $^1$H NMR (400 MHz, DMSO-d6) δ13.87 (br, 1H), 10.37 (s, 1H), 10.21 (s, 1H), 10.04 (s, 1H), 9.81 (s, 1H), 6.88 (s, 1H), 5.17 (d, 1H), 4.71 (s, 1H), 4.58 (s, 1H), 4.53 (d, 1H), 3.72 (dd, 1H), 3.26 (dd, 1H), 1.51 (s, 3H). LC-MS (ESI): m/z=512 (M+H)$^+$.

Example 84

(2S,3R,5R)-3-(((2-(2,5-dichloro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide

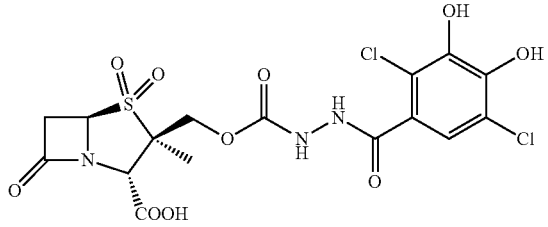 [SMILES: C[C@]1(COC(=O)NNC(=O)c2cc(Cl)c(O)c(O)c2Cl)[C@H](C(=O)O)N2C(=O)C[C@H]2S1(=O)=O]

The title compound was prepared using the similar procedure as described in Example 69 except 2,5-dichloro-3,4-dihydroxybenzohydrazide was used in place of 3,4-dihydroxybenzohydrazide. $^1$H NMR (400 MHz, DMSO-d6) δ 13.87 (br, 1H), 10.35 (s, 1H), 10.20 (s, 1H), 10.02 (s, 1H), 9.59 (s, 1H), 6.92 (s, 1H), 5.17 (d, 1H), 4.71 (s, 1H), 4.58 (s, 1H), 4.53 (d, 1H), 3.72 (dd, 1H), 3.26 (dd, 1H), 1.48 (s, 3H). LC-MS (ESI): m/z=512 (M+H)$^+$.

Example 85

(2S,3R,5R)-3-(((2-(2-fluoro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide

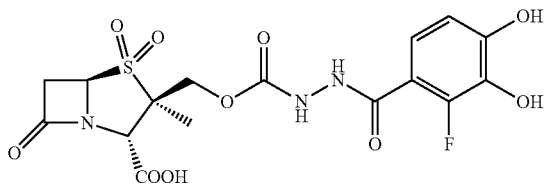 [SMILES: C[C@]1(COC(=O)NNC(=O)c2ccc(O)c(O)c2F)[C@H](C(=O)O)N2C(=O)C[C@H]2S1(=O)=O]

The title compound was prepared using the similar procedure as described in EXAMPLE 69 except 2-fluoro-3,4-dihydroxybenzohydrazide was used in place of 3,4-dihydroxybenzohydrazide. $^1$H NMR (400 MHz, DMSO-d6) δ 13.85 (br, 1H), 10.07 (s, 1H), 9.83 (s, 1H), 9.47 (s, 1H), 9.29 (s, 1H), 6.99 (t, 1H), 6.67 (d, 1H), 5.17 (d, 1H), 4.71 (s, 1H), 4.58 (s, 1H), 4.53 (d, 1H), 3.72 (dd, 1H), 3.26 (d, 1H), 1.51 (s, 3H). LC-MS (ESI): m/z=462 (M+H)$^+$.

Example 86

(2S,3R,5R)-3-(((2-(3-(3,4-dihydroxyphenyl)propanoyl)hydrazinecarbonyl)oxy)methyl)-3-methyl-7-oxo-4-thia-1-azabicyclo[3.2.0]heptane-2-carboxylic acid 4,4-dioxide

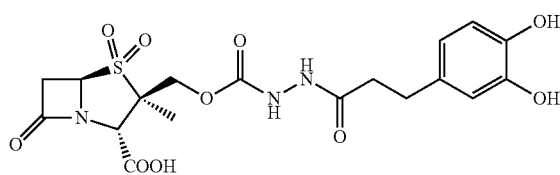 [SMILES: C[C@]1(COC(=O)NNC(=O)CCc2ccc(O)c(O)c2)[C@H](C(=O)O)N2C(=O)C[C@H]2S1(=O)=O]

The title compound was prepared using the similar procedure as described in Example 69 except 3-(3,4-dihydroxyphenyl)propanehydrazide was used in place of 3,4-dihydroxybenzohydrazide. $^1$H NMR (400 MHz, DMSO-d6) δ 13.83 (br, 1H), 9.69 (s, 1H), 9.28 (s, 1H), 8.84 (s, 1H), 8.71 (s, 1H), 6.82 (d, 1H), 6.57 (s, 1H), 6.45 (d, 1H), 5.12 (d, 1H), 4.65 (d, 1H), 4.50 (s, 1H), 4.38 (d, 1H), 3.68 (dd, 1H), 3.26 (dd, 1H), 2.64 (t, 2H), 2.31 (t, 2H), 1.48 (s, 3H). LC-MS (ESI): m/z=472 (M+H)$^+$.

Example 87

(2S,3R,5R)-3-(((2-(2-chloro-4,5-dihydroxybenzoyl)hydrazinecarbonyl)oxy)methyl)-3-methyl-7-oxo-4-thia-1-azabicyclo[3.2.0]heptane-2-carboxylic acid 4,4-dioxide

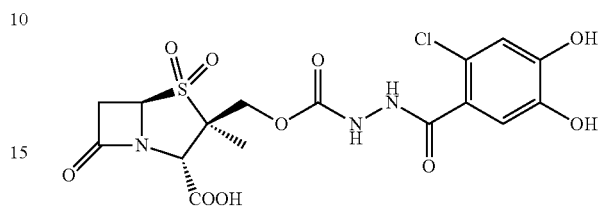

The title compound was prepared using the similar procedure as described in Example 69 except 2-chloro-4,5-dihydroxybenzohydrazide was used in place of 3,4-dihydroxybenzohydrazide. $^1$H NMR (400 MHz, DMSO-d6) δ 13.85 (br, 1H), 9.99 (s, 1H), 9.82 (s, 1H), 9.56 (s, 1H), 9.52 (s, 1H), 6.88 (s, 1H), 6.80 (s, 1H), 5.16 (d, 1H), 4.68 (d, 1H), 4.57 (s, 1H), 4.54 (d, 1H), 3.61 (dd, 1H), 3.26 (dd, 1H), 1.50 (s, 3H). LC-MS (ESI): m/z=478 (M+H)$^+$.

Example 88

(2S,3R,5R)-3-((((E)-2-(3,4-dihydroxybenzylidene)hydrazinecarbonyl)oxy)methyl)-3-methyl-7-oxo-4-thia-1-azabicyclo[3.2.0]heptane-2-carboxylic acid 4,4-dioxide

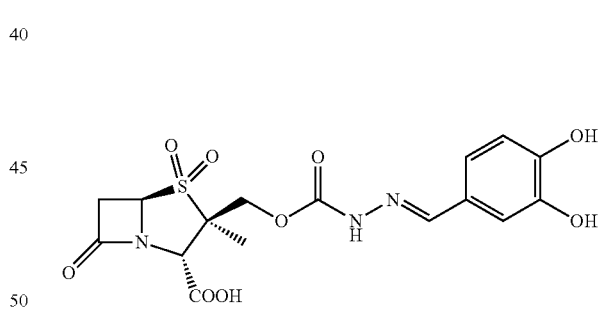

The title compound was prepared using the similar procedure as described in Example 69 except (E)-4-(hydrazonomethyl)benzene-1,2-diol was used in place of 3,4-dihydroxybenzohydrazide. $^1$H NMR (400 MHz, DMSO-d6) δ 13.84 (br, 1H), 11.11 (s, 1H), 9.33 (s, 1H), 9.22 (s, 1H), 7.92 (s, 1H), 7.12 (s, 1H), 8.84 (d, 1H), 8.75 (d, 1H), 5.17 (d, 1H), 4.71 (s, 1H), 4.58 (s, 1H), 4.53 (d, 1H), 3.72 (dd, 1H), 3.26 (dd, 1H), 1.51 (s, 3H). LC-MS (ESI): m/z=428 (M+H)$^+$.

Example 89

(2S,3R,5R)-3-(((2-(3-chloro-4,5-dihydroxybenzoyl)hydrazinecarbonyl)oxy)methyl)-3-methyl-7-oxo-4-thia-1-azabicyclo[3.2.0]heptane-2-carboxylic acid 4,4-dioxide

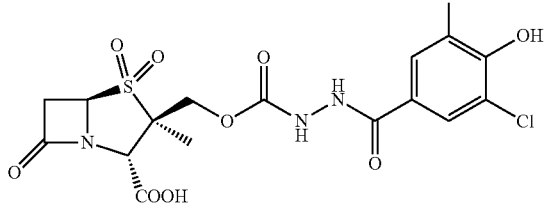

The title compound was prepared using the similar procedure as described in Example 69 except 3,4-bis(benzyloxy)-5-chlorobenzohydrazide was used in place of 3,4-dihydroxybenzohydrazide. $^1$H NMR (400 MHz, DMSO-d6) δ 7.28 (s, 1H), 7.14 (s, 1H), 7.00 (s, 1H), 5.57 (s, 1H), 4.72 (d, 1H), 4.67 (d, 2H), 4.39 (d, 2H), 4.02 (s, 1H), 3.78 (s, 1H), 3.46 (m, 1H), 3.21 (m, 1H), 1.45 (s, 3H). LC-MS (ESI): m/z=478 (M+H)$^+$.

Example 90

(2S,3R,5R)-3-(((2-(2-(benzo[d][1,3]dioxol-5-yl)acetyl)hydrazinecarbonyl)oxy)methyl)-3-methyl-7-oxo-4-thia-1-azabicyclo[3.2.0]heptane-2-carboxylic acid 4,4-dioxide

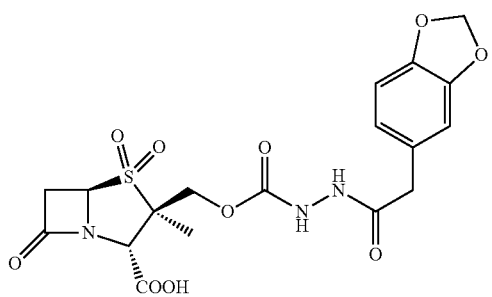 [SMILES: C[C@]1(COC(=O)NNC(=O)Cc2ccc3c(c2)OCO3)[C@H](C(=O)O)N2C(=O)C[C@H]2S1(=O)=O]

The title compound was prepared using the similar procedure as described in Example 69, except 2-(benzo[d][1,3]dioxol-5-yl)acetohydrazide was used in place of 3,4-dihydroxybenzohydrazide. $^1$H NMR (400 MHz, DMSO-d6): δ13.81 (br, 1H), 9.92 (s, 1H), 9.35 (s, 1H), 6.67 (s, 1H), 6.63 (d, 1H), 6.84 (s, 1H), 5.97 (s, 2H), 5.13 (d, 1H), 4.87 (s, 1H), 4.47 (s, 1H), 4.44 (d, 1H), 3.88 (dd, 1H), 3.35 (s, 2H), 3.26 (dd, 1H), 3.21 (dd, 1H), 1.48 (s, 3H). LC-MS (ESI): m/z=470 (M+H)$^+$.

Example 91

(2S,3R,5R)-3-(((2-(2-(3,4-dihydroxybenzamido)acetyl)hydrazinecarbonyl)oxy)methyl)-3-methyl-7-oxo-4-thia-1-azabicyclo[3.2.0]heptane-2-carboxylic acid 4,4-dioxide

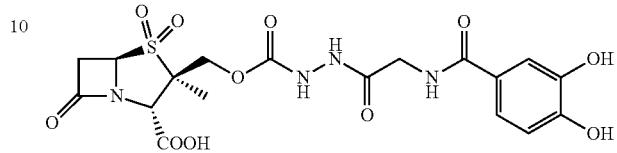

The title compound was prepared using the similar procedure as described in Example 95. $^1$H NMR (400 MHz, DMSO-d6): δ13.81 (br, 1H), 9.84 (s, 1H), 9.12 (s, 1H), 8.98 (s, 1H), 8.34 (t, 1H), 6.87 (d, 1H), 6.80 (s, 2H), 6.78 (d, 1H), 5.13 (d, 1H), 4.87 (s, 1H), 4.47 (s, 1H), 4.44 (d, 1H), 3.88 (dd, 1H), 3.67 (d, 1H), 3.26 (dd, 1H), 1.48 (s, 3H). LC-MS (ESI): m/z=501 (M+H)$^+$.

Example 92

(2S,3R,5R)-3-(((3-(3,4-dihydroxybenzamido)pyrrolidine-1-carbonyl)oxy)methyl)-3-methyl-7-oxo-4-thia-1-azabicyclo[3.2.0]heptane-2-carboxylic acid 4,4-dioxide

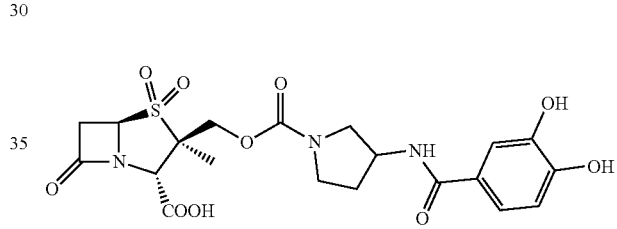

The title compound was prepared using the similar procedure as described in Example 69 except 3,4-bis(benzyloxy)-N-(pyrrolidin-3-yl)benzamide was used in place of 3,4-dihydroxybenzohydrazide. $^1$H NMR (400 MHz, DMSO-d6) δ 9.87 (s, 1H), 7.23 (d, 2H), 6.75 (d, 1H), 6.67 (s, 1H), 5.50 (s, 1H), 4.72 (s, 1H), 4.67 (d, 2H), 4.39 (d, 2H), 3.91 (d, 2H), 3.81 (d, 2H), 3.66 (d, 2H), 3.46 (m, 1H), 3.21 (m, 1H), 2.18 (m, 1H), 1.94 (m, 1H), 1.45 (s, 3H). LC-MS (ESI): m/z=498 (M+H)$^+$.

Example 93

(2S,3R,5R)-3-(((4-(3,4-dihydroxybenzoyl)piperazine-1-carbonyl)oxy)methyl)-3-methyl-7-oxo-4-thia-1-azabicyclo[3.2.0]heptane-2-carboxylic acid 4,4-dioxide

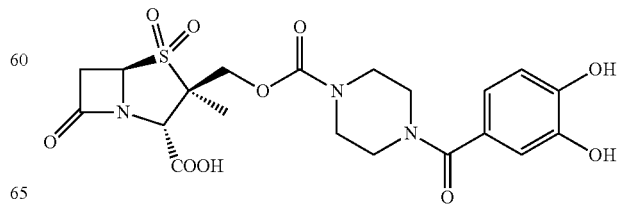

The title compound was prepared using the similar procedure as described in Example 69 except (3,4-bis(benzyloxy)phenyl)(piperazin-1-yl)methanone was used in place of 3,4-dihydroxybenzohydrazide. $^1$H NMR (400 MHz, DMSO-d6) δ 9.74 (s, 1H), 7.26 (m, 1H), 7.19 (d, 1H), 6.77 (d, 1H), 4.67 (m, 2H), 4.39 (d, 2H), 4.29 (s, 1H), 3.68-3.59 (m, 4H), 3.59-3.53 (m, 3H), 3.53-3.44 (m, 3H), 3.21 (m, 1H), 1.45 (s, 3H). LC-MS (ESI): m/z=498 (M+H)$^+$.

Example 94

(2S,3R,5R)-3-(((2-(2-(2-chloro-3,4-dihydroxybenzamido)acetyl)hydrazinecarbonyl)oxy)methyl)-3-methyl-7-oxo-4-thia-1-azabicyclo[3.2.0]heptane-2-carboxylic acid 4,4-dioxide

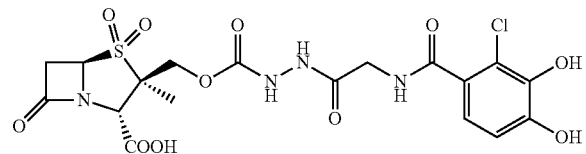 [SMILES: C[C@]1(COC(=O)NNC(=O)CNC(=O)c2ccc(O)c(O)c2Cl)[C@H](C(=O)O)N2C(=O)C[C@H]2S1(=O)=O]

The title compound was prepared using the similar procedure as described in Example 95. $^1$H NMR (400 MHz, DMSO-d6): δ13.83 (br, 1H), 9.84 (s, 1H), 9.42 (s, 1H), 9.25 (s, 1H), 8.34 (t, 1H), 6.87 (m, 3H), 5.13 (d, 1H), 4.67 (d, 1H), 4.47 (s, 1H), 4.44 (d, 1H), 3.86 (d, 2H), 3.67 (d, 1H), 3.26 (dd, 1H), 1.48 (s, 3H). LC-MS (ESI): m/z=535 (M+H)$^+$.

Example 95

(2S,3R,5R)-3-((((2-(2-chloro-3,4-dihydroxybenzamido)ethyl)carbamoyl)oxy)methyl)-3-methyl-7-oxo-4-thia-1-azabicyclo[3.2.0]heptane-2-carboxylic acid 4,4-dioxide

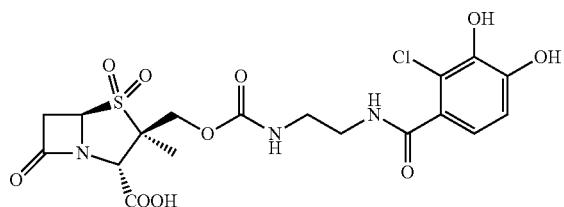 [SMILES: C[C@]1(COC(=O)NCCNC(=O)c2ccc(O)c(O)c2Cl)[C@H](C(=O)O)N2C(=O)C[C@H]2S1(=O)=O]

Figure 10:
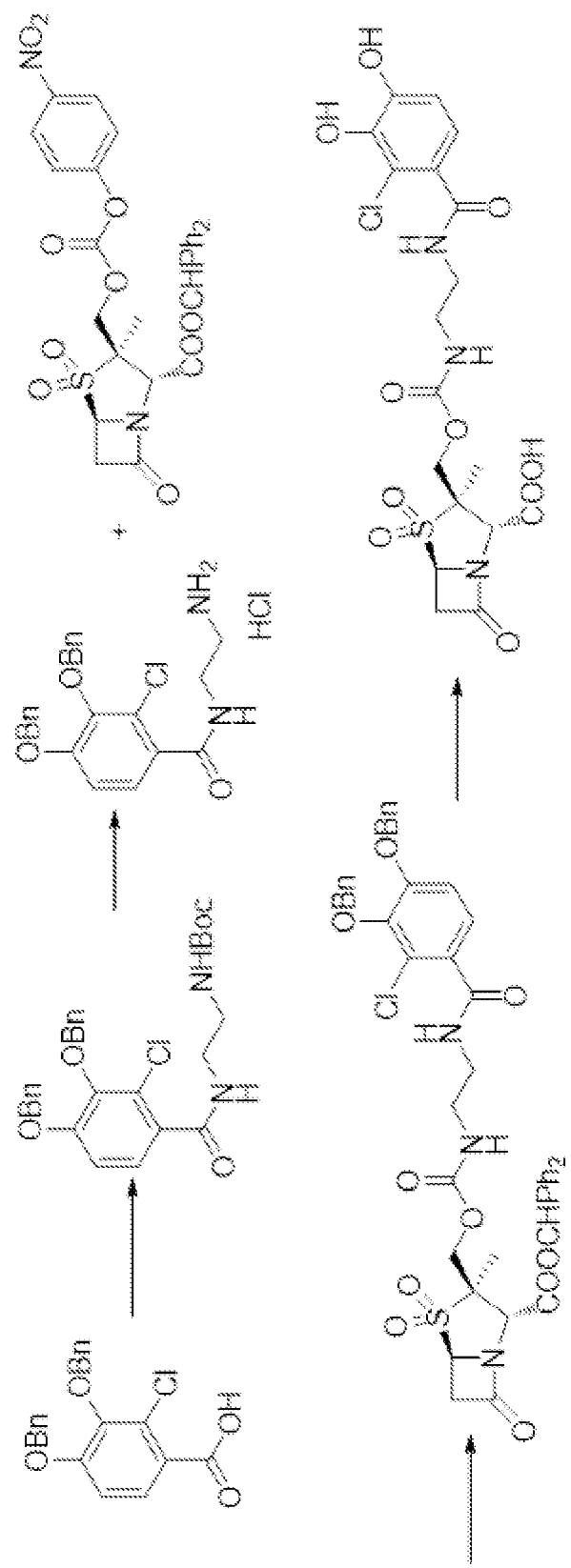

FIG. 10 shows a synthetic scheme for the preparation of this compound. Step 1: tert-butyl (2-(3,4-bis(benzyloxy)-2-chlorobenzamido)ethyl)carbamate. 3,4-bis(benzyloxy)-2-chlorobenzoic acid (1.0 g, 2.71 mmol) was dissolved in DMF (10 mL). The solution was cooled to 5° C. Then tert-butyl (2-aminoethyl)carbamate (433 mg, 2.71 mmol), 1-Hydroxybenzotriazole (439 mg, 3.25 mmol), DIPEA (0.9 mL, 5.42 mmol) and 1-(3-Dimethylaminopropyl)-3-ethylcarbodiimide hydrochloride (623 mg, 3.25 mmol) were added. The mixture was stirred at rt for 12 hours. The solution was washed with water and extracted with ethyl acetate (100 mL). The organic layer was dried over Na$_2$SO$_4$. The solvent was evaporated in vacuo to give the title compound (1.2 g, yield 86.7%). LC-MS (ESI): m/z=511 (M+H)$^+$.

Step 2: N-(2-aminoethyl)-3,4-bis(benzyloxy)-2-chlorobenz amide hydrochloride. tert-butyl (2-(3,4-bis(benzyloxy)-2-chlorobenzamido)ethyl)carbamate (1.2 g, 2.35 mmol) was dissolve in ethyl acetate (5 mL). The solution was cooled to 5° C. Then hydrogen chloride ethyl acetate solution (4 M, 10 mL) was added. The mixture was stirred for 5 hours. Then ethyl acetate was evaporated in vacuo to give N-(2-aminoethyl)-3,4-bis(benzyloxy)-2-chlorobenzamide hydrochloride (763 mg, yield 72.7%). LC-MS (ESI): m/z=411 (M+H)$^+$.

Step 3: (2S,3R,5R)-benzhydryl 3-((((2-(3,4-bis(benzyloxy)-2-chlorobenzamido)ethyl)carbamoyl)oxy)methyl)-3-methyl-7-oxo-4-thia-1-azabicyclo[3.2.0]heptane-2-carboxylate 4,4-dioxide. (2S,3R,5R)-benzhydryl 3-methyl-3-((((4-nitrophenoxy)carbonyl)oxy)methyl)-7-oxo-4-thia-1-azabicyclo[3.2.0]heptane-2-carboxylate 4,4-dioxide (980 mg, 1.69 mmol) and N-(2-aminoethyl)-3,4-bis(benzyloxy)-2-chlorobenzamide hydrochloride (760 mg, 1.69 mmol) were added into a solution of DMF (20 mL) and pyridine (1 mL). The mixture was stirred at rt for 12 hours. The solution was washed with water, and extracted with ethyl acetate (100 mL). The organic layer was dried over Na$_2$SO$_4$. The solvent was evaporated in vacuo. The residue was purified by column chromatography (silica gel, DCM:MeOH=50:1) to give the title compound (300 mg, yield 20.7%). LC-MS (ESI): m/z=852 (M+H)$^+$.

Step 4: (2S,3R,5R)-3-((((2-(2-chloro-3,4-dihydroxybenzamido)ethyl)carbamoyl)oxy)methyl)-3-methyl-7-oxo-4-thia-1-azabicyclo[3.2.0]heptane-2-carboxylic acid 4,4-dioxide. (2S,3R,5R)-benzhydryl 3-((((2-(3,4-bis(benzyloxy)-2-chlorobenzamido)ethyl)carbamoyl)oxy)methyl)-3-methyl-7-oxo-4-thia-1-azabicyclo[3.2.0]heptane-2-carboxylate 4,4-dioxide (300 mg, 0.35 mmol) was dissolved in THF (5 mL). The mixture was degassed with N$_2$ twice, Pd/C (10%, 150 mg) was added into the mixture, then the flask was degassed with H$_2$ twice, and stirred at rt for 12 hours. The solution was filtered, and the filtrate was concentrated. Ethyl acetate (10 mL) was added, and stirred for 30 min. The slurry was filtered and the cake was washed with MTBE (20 ml) to give the title compound (110 mg, yield 43%). $^1$H NMR (400 MHz, DMSO-d6) δ 13.84 (br, 1H), 9.92 (s, 1H), 9.17 (s, 1H), 8.09 (t, 1H), 6.67 (d, 1H), 6.64 (d, 1H), 5.12 (d, 1H), 4.65 (d, 1H), 4.50 (s, 1H), 4.38 (d, 1H), 3.68 (dd, 1H), 3.26 (dd, 1H), 3.24 (m, 1H), 3.15 (m, 1H), 1.48 (s, 3H). LC-MS (ESI): m/z=506 (M+H)$^+$.

Example 96

(2S,3R,5R)-3-(((4-(3,4-dihydroxybenzamido)piperidine-1-carbonyl)oxy)methyl)-3-methyl-7-oxo-4-thia-1-azabicyclo[3.2.0]heptane-2-carboxylic acid 4,4-dioxide

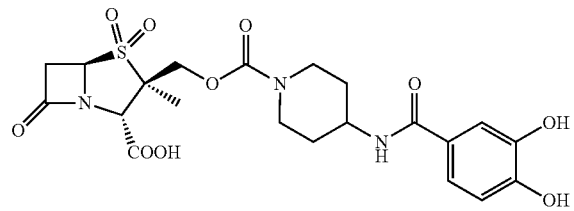 [SMILES: C[C@]1(COC(=O)N2CCC(NC(=O)c3ccc(O)c(O)c3)CC2)[C@H](C(=O)O)N2C(=O)C[C@H]2S1(=O)=O]

The title compound was prepared using the similar procedure as described in Example 69 except 3,4-bis(benzyloxy)-N-(pyrrolidin-3-yl)benzamide was used in place of 3,4-dihydroxybenzohydrazide. $^1$H NMR (400 MHz, DMSO-d6) δ 7.28 (m, 1H), 7.17 (s, 1H), 6.75 (m, 1H), 5.50 (s, 1H), 4.72 (t, 1H), 4.67 (d, 2H), 4.39 (d, 2H), 4.09 (m, 1H), 3.80 (s, 1H), 3.77-3.73 (m, 2H), 3.55-3.50 (m, 2H), 3.45 (d, 2H), 3.21 (m, 1H), 2.25-2.14 (m, 2H), 1.88-1.80 (m, 2H), 1.45 (s, 3H). LC-MS (ESI): m/z=498 (M+H)+.

Example 97

(2S,3R,5R)-3-((((1-(3,4-dihydroxybenzoyl)pyrrolidin-3-yl)carbamoyl)oxy)methyl)-3-methyl-7-oxo-4-thia-1-azabicyclo[3.2.0]heptane-2-carboxylic acid 4,4-dioxide

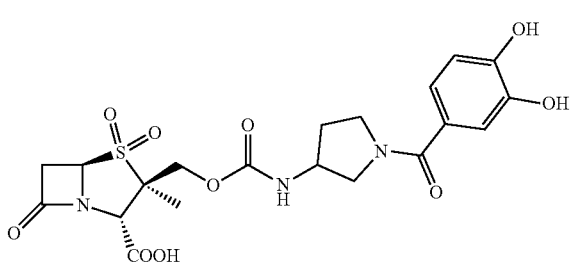 [SMILES: C[C@]1(COC(=O)NC2CCN(C(=O)c3ccc(O)c(O)c3)C2)[C@H](C(=O)O)N2C(=O)C[C@H]2S1(=O)=O]

The title compound was prepared using the similar procedure as described in Example 69 except 3,4-bis(benzyloxy)-N-(piperidin-4-yl)benzamide was used in place of 3,4-dihydroxybenzohydrazide. ¹H NMR (400 MHz, DMSO-d6) δ 9.88 (s, 1H), 7.21 (d, 2H), 6.75 (d, 1H), 4.94 (m, 1H), 4.72 (t, 1H), 4.67 (d, 2H), 4.39 (d, 2H), 4.15 (s, 1H), 3.87 (m, 1H), 3.76 (m, 1H), 3.61 (d, 2H), 3.46 (s, 1H), 3.21 (m, 1H), 2.97 (s, 1H), 2.92 (s, 1H), 2.16 (m, 1H), 1.90 (m, 1H), 1.45 (s, 3H). LC-MS (ESI): m/z=498 (M+H)+.

Example 98

(2S,3R,5R)-3-(((3-(3,4-dihydroxybenzamido)azetidine-1-carbonyl)oxy)methyl)-3-methyl-7-oxo-4-thia-1-azabicyclo[3.2.0]heptane-2-carboxylic acid 4,4-dioxide

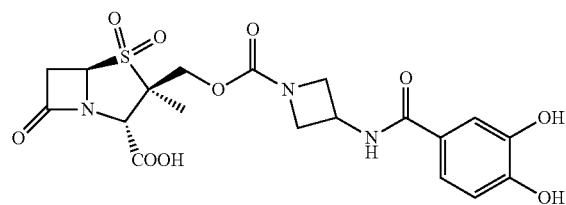 [SMILES: C[C@]1(COC(=O)N2CC(NC(=O)c3ccc(O)c(O)c3)C2)[C@H](C(=O)O)N2C(=O)C[C@H]2S1(=O)=O]

The title compound was prepared using the similar procedure as described in Example 69 except N-(azetidin-3-yl)-3,4-dihydroxybenzamide was used in place of 3,4-dihydroxybenzohydrazide. ¹H NMR (400 MHz, DMSO-d6) δ 7.23 (m, 2H), 6.77 (d, 1H), 6.25 (s, 1H), 4.70 (t, 1H), 4.64 (d, 1H), 4.39 (d, 2H), 4.32 (d, 2H), 4.24-4.20 (m, 1H), 4.02-3.93 (m, 2H), 3.56 (s, 1H), 3.46 (m, 1H), 3.21 (m, 1H), 1.45 (s, 3H). LC-MS (ESI): m/z=484 (M+H)+.

Example 99

(2S,3R,5R)-3-(5-((2-chloro-3,4-dihydroxybenzamido)methyl)isoxazol-3-yl)-3-methyl-7-oxo-4-thia-1-azabicyclo[3.2.0]heptane-2-carboxylic acid 4,4-dioxide

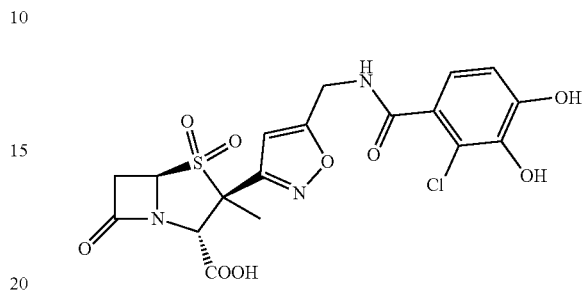

Figure 11:
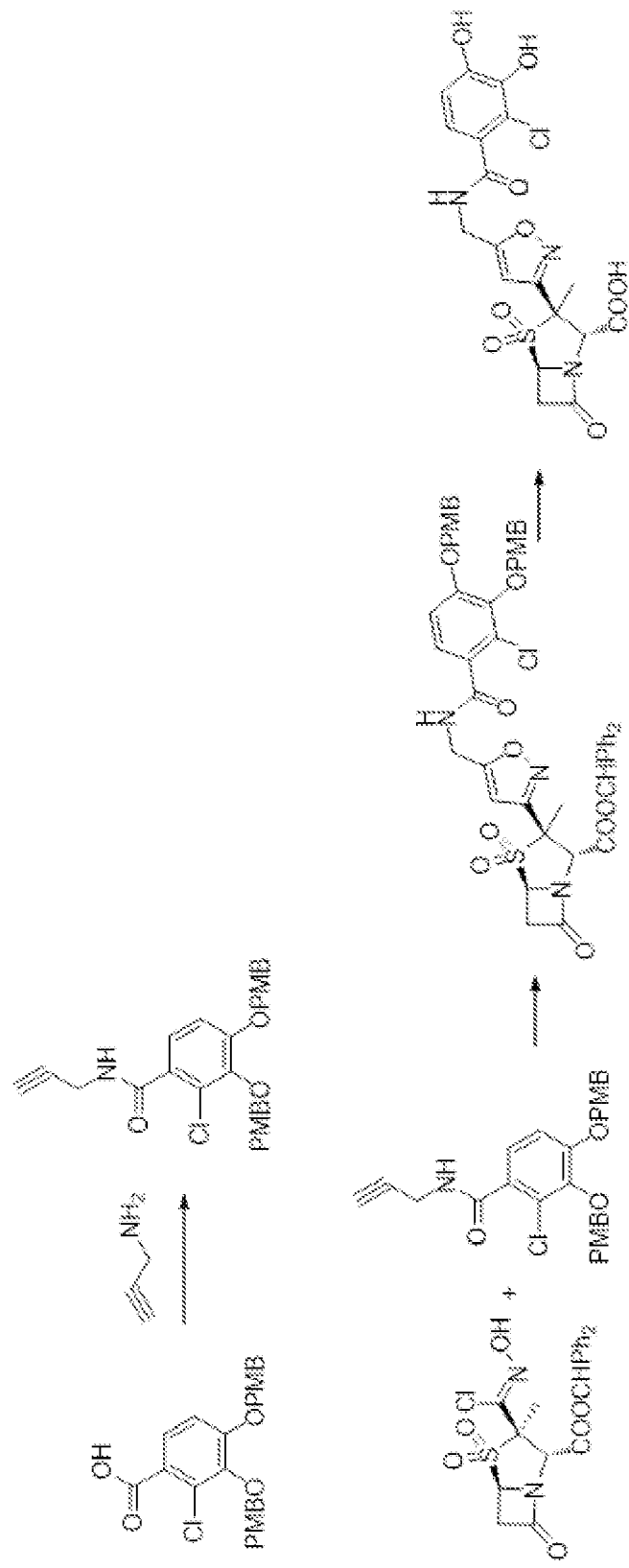

FIG. 11 shows a synthetic scheme for the preparation of this compound. Step 1: 2-chloro-3,4-bis((4-methoxybenzyl)oxy)-N-(prop-2-yn-1-yl)benzamide. To a solution of 2-chloro-3,4-bis((4-methoxybenzyl)oxy)benzoic acid (1 g, 2.3 mmol) in DMF (20 mL) was added propargylamine (0.16 g, 2.8 mmol), EDCI (0.72 g, 4.6 mmol), HOBT (0.31 g, 2.3 mmol) and then NMM (0.71 g, 6.9 mmol). The mixture was stirred at rt for 6 hours. Then the solution was poured into the ice water. The mixture was stirred for 0.5 hours, filtered under the reduced pressure. The filter cake was collected and dried to afford the title compound as a pale solid (0.91 g, yield 85%).

Step 2: (2S,3R,5R)-benzhydryl 3-(5-((2-chloro-3,4-bis((4-methoxybenzyl)oxy)benzamido)methyl)isoxazol-3-yl)-3-methyl-7-oxo-4-thia-1-azabicyclo[3.2.0]heptane-2-carboxylate 4,4-dioxide. To a solution of (2S)-benzhydryl 3-((Z)-chloro(hydroxyimino)methyl)-3-methyl-7-oxo-4-thia-1-azabicyclo[3.2.0]heptane-2-carboxylate 4,4-dioxide (500 mg, 1.07 mmol) in DMF (5 mL) was added 2-chloro-3,4-bis((4-methoxybenzyl)oxy)-N-(prop-2-yn-1-yl)benzamide (520 mg, 1.2 mmol) and 1,1,1,3,3,3-hexabutyldistannoxane (313 mg, 0.53 mmol). The solution was stirred at rt for 2 hours. The solvent was evaporated in vacuo, the residue was purified by column chromatography (silica gel, PE:EtOAc=5:1) to afford the title compound as the white solid (524 mg, yield 56%).

Step 3: (2S,3R,5R)-3-(5-((2-chloro-3,4-dihydroxybenzamido)methyl)isoxazol-3-yl)-3-methyl-7-oxo-4-thia-1-azabicyclo[3.2.0]heptane-2-carboxylic acid 4,4-dioxide. To a solution of (2S)-benzhydryl 3-(5-(2-(2-chloro-3,4-bis((4-methoxybenzyl)oxy)phenyl)-2-oxoethyl)isoxazol-3-yl)-3-methyl-7-oxo-4-thia-1-azabicyclo[3.2.0]heptane-2-carboxylate 4,4-dioxide. (175 mg, 0.20 mmol) in THF (10 mL) was added Pd/C (10%, 50 mg). The solution was stirred at rt for 12 hours. The mixture was filtered, and the filtrate was evaporated in vacuo, the residue was washed with MTBE (20 mL) to afford pale solid (74 mg, yield 79%). ¹H NMR (400 MHz, DMSO-d6) δ 7.23 (d, 1H), 6.92 (s, 1H), 6.66 (d, 1H), 6.61 (s, 1H), 4.87 (s, 1H), 4.70 (t, 1H), 4.61 (s, 1H), 4.55 (s, 1H), 4.42 (s, 1H), 4.27 (s, 1H), 3.46 (m, 1H), 3.21 (m, 1H), 1.76 (m, 3H). LC-MS (ESI): m/z=471 (M+H)+.

Example 100

(2S,3R,5R)-3-(5-((3,4-dihydroxybenzamido)methyl)isoxazol-3-yl)-3-methyl-7-oxo-4-thia-1-azabicyclo[3.2.0]heptane-2-carboxylic acid 4,4-dioxide

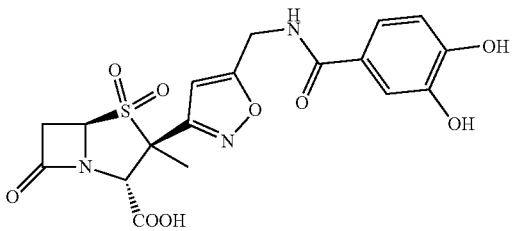 [SMILES: C[C@]1(c2cc(CNC(=O)c3ccc(O)c(O)c3)on2)[C@H](C(=O)O)N2C(=O)C[C@H]2S1(=O)=O]

The title compound was prepared using the similar procedure as described in Example 99 except 3,4-bis((4-methoxybenzyl)oxy)-N-(prop-2-yn-1-yl)benzamide was used in place of 2-chloro-3,4-bis((4-methoxybenzyl)oxy)-N-(prop-2-yn-1-yl)benzamide. $^1$H NMR (400 MHz, DMSO-d6) δ 7.06 (dd, 1H), 6.97 (d, 1H), 6.54 (s, 1H), 6.37 (s, 1H), 6.21 (s, 1H), 4.65 (s, 1H), 4.48 (t, 1H), 4.40 (s, 1H), 4.19 (s, 1H), 4.05 (s, 1H), 3.32 (s, 1H), 3.24 (m, 1H), 2.99 (m, 1H), 1.58 (s, 3H). LC-MS (ESI): m/z=452 (M+H)$^+$.

Example 101

(2S,3R,5R)-3-(5-(2-chloro-3,4-dihydroxyphenyl)isoxazol-3-yl)-3-methyl-7-oxo-4-thia-1-azabicyclo[3.2.0]heptane-2-carboxylic acid 4,4-dioxide

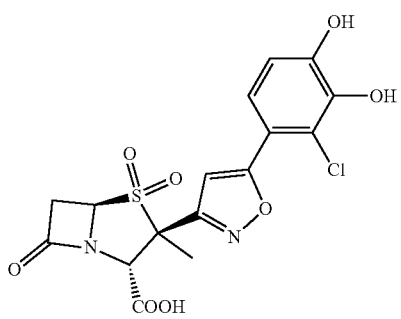 [SMILES: C[C@]1(c2cc(-c3ccc(O)c(O)c3Cl)on2)[C@H](C(=O)O)N2C(=O)C[C@H]2S1(=O)=O]

Figure 12:
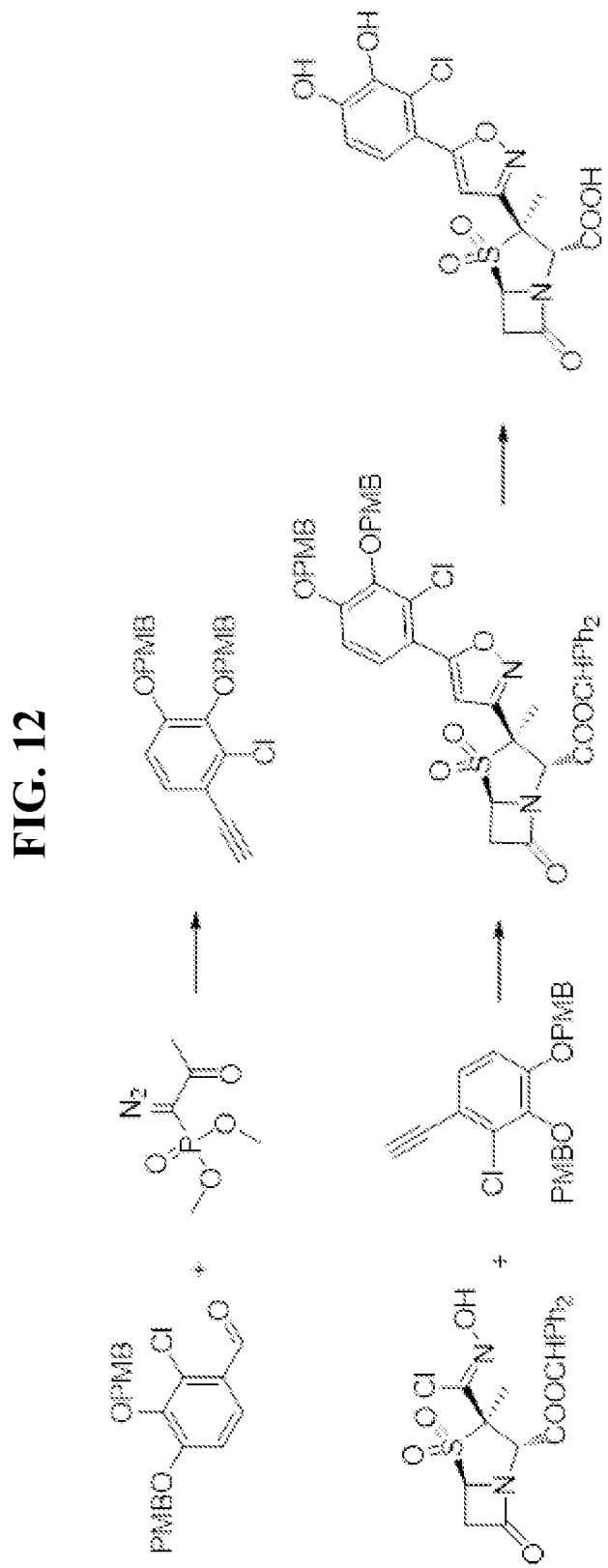

FIG. 12 shows a synthetic scheme for the preparation of this compound. Step 1: 4,4'-(((3-chloro-4-ethynyl-1,2-phenylene)bis(oxy))bis(methylene))bis(methoxybenzene). To a solution of 2-chloro-3,4-bis((4-methoxybenzyl)oxy)benzaldehyde (2.1 g, 5.1 mmol) in MeOH (10 mL) was added dimethyl (1-diazo-2-oxopropyl)phosphonate (1.2 g, 6.2 mmol). The mixture was stirred at rt for 4 h. Then the solvent was evaporated in vacuo, the residue was purified by column chromatography (silica gel, PE:EtOAc=20:1) to afford white solid (1.0 g, yield 48%).

Step 2: (2S,3R,5R)-benzhydryl 3-(5-(2-chloro-3,4-bis((4-methoxybenzyl)oxy)phenyl)isoxazol-3-yl)-3-methyl-7-oxo-4-thia-1-azabicyclo[3.2.0]heptane-2-carboxylate 4,4-dioxide. To a solution of (2S,3R,5R)-benzhydryl 3-((Z)-chloro(hydroxyimino)methyl)-3-methyl-7-oxo-4-thia-1-azabicyclo[3.2.0]heptane-2-carboxylate 4,4-dioxide (400 mg, 0.86 mmol) in DMF (5 mL) was added a mixture of 4,4'-(((3-chloro-4-ethynyl-1,2-phenylene)bis(oxy))bis(methylene))bis(methoxybenzene) (600 mg, 1.5 mmol) and 1,1,1,3,3,3-hexabutyldistannoxane (260 mg, 0.44 mmol). The solution was stirred at RT for 2 h. The solvent was evaporated in vacuo, the residue was purified by column chromatography (silica gel, PE:EtOAc=5:1) to afford white solid (130 mg, yield 18%). LC-MS: m/z=835 (M+H)$^+$ Step 3: (2S,3R,5R)-3-(5-(2-chloro-3,4-dihydroxyphenyl)isoxazol-3-yl)-3-methyl-7-oxo-4-thia-1-azabicyclo[3.2.0]heptane-2-carboxylic acid 4,4-dioxide. To a solution of (2S,3R,5R)-benzhydryl 3-(5-(2-chloro-3,4-bis((4-methoxybenzyl)oxy)phenyl)isoxazol-3-yl)-3-methyl-7-oxo-4-thia-1-azabicyclo[3.2.0]heptane-2-carboxylate 4,4-dioxide (130 mg, 0.16 mmol) in EtOAc (10 mL) was added Pd/C (10%, 50 mg). The solution was stirred at RT for 12 h. The mixture was filtered, and the filtrate was evaporated in vacuo, the residue was washed with MTBE (20 mL) to afford pale solid (20 mg, yield 29%). $^1$H NMR (400 MHz, DMSO-d6) δ 10.63 (s, H), 9.61 (s, 1H), 7.34 (d, 2H), 6.90 (d, 1H), 5.51 (s, 1H), 5.32 (s, 1H), 3.83 (m, 1H), 3.43 (d, 1H), 1.94 (s, 3H). LC-MS (ESI): m/z=429 (M+H)$^+$.

Example 102

(2S,3R,5R)-3-(5-(2-(2,5-dichloro-3,4-dihydroxyphenyl)-2-oxoethyl)isoxazol-3-yl)-3-methyl-7-oxo-4-thia-1-azabicyclo[3.2.0]heptane-2-carboxylic acid 4,4-dioxide

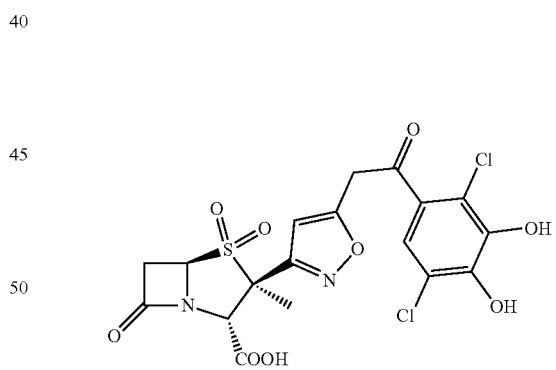

The title compound was prepared using the similar procedure as described in Example 99 except 2,5-dichloro-3,4-bis((4-methoxybenzyl)oxy)-N-(prop-2-yn-1-yl)benzamide was used in place of 2-chloro-3,4-bis((4-methoxybenzyl)oxy)-N-(prop-2-yn-1-yl)benzamide. $^1$H NMR (400 MHz, DMSO-d6) δ 7.16 (s, 1H), 6.57 (s, 1H), 4.87 (s, 1H), 4.70 (t, 1H), 4.51 (s, 1H), 4.37 (s, 1H), 4.33 (m, 2H), 3.46 (m, 1H), 3.21 (m, 1H), 1.76 (s, 3H). LC-MS (ESI): m/z=505 (M+H)$^+$.

Example 103

(2S,3R,5R)-3-(5-(3,4-dihydroxyphenyl)isoxazol-3-yl)-3-methyl-7-oxo-4-thia-1-azabicyclo[3.2.0]heptane-2-carboxylic acid 4,4-dioxide

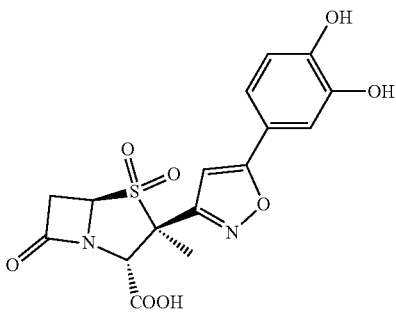 [SMILES: C[C@]1(c2cc(-c3ccc(O)c(O)c3)on2)[C@H](C(=O)O)N2C(=O)C[C@H]2S1(=O)=O]

The title compound was prepared using the similar procedure as described in EXAMPLE 101 except 4,4'-(((4-ethynyl-1,2-phenylene)bis(oxy))bis(methylene))bis(methoxybenzene) was used in place of 4,4'-(((3-chloro-4-ethynyl-1,2-phenylene)bis(oxy))bis(methylene))bis(methoxybenzene). $^1$H NMR (400 MHz, DMSO-d6) δ 10.62 (s, H), 9.62 (s, 1H), 7.32 (d, 1H), 7.11 (s, 1H), 6.89 (d, 1H), 5.78 (s, 1H), 5.45 (s, 1H), 5.30 (s, 1H), 3.83 (m, 1H), 3.43 (d, 2H), 1.90 (s, 3H). LC-MS (ESI): m/z=395 (M+H)$^+$.

Example 104

(2S,3R,5R)-3-(5-(2-((2-chloro-3,4-dihydroxybenzoyl)oxy)ethyl)isoxazol-3-yl)-3-methyl-7-oxo-4-thia-1-azabicyclo[3.2.0]heptane-2-carboxylic acid 4,4-dioxide

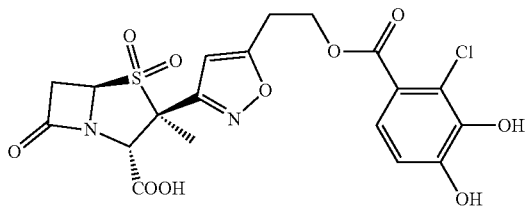 [SMILES: C[C@]1(c2cc(CCOC(=O)c3ccc(O)c(O)c3Cl)on2)[C@H](C(=O)O)N2C(=O)C[C@H]2S1(=O)=O]

Figure 13:
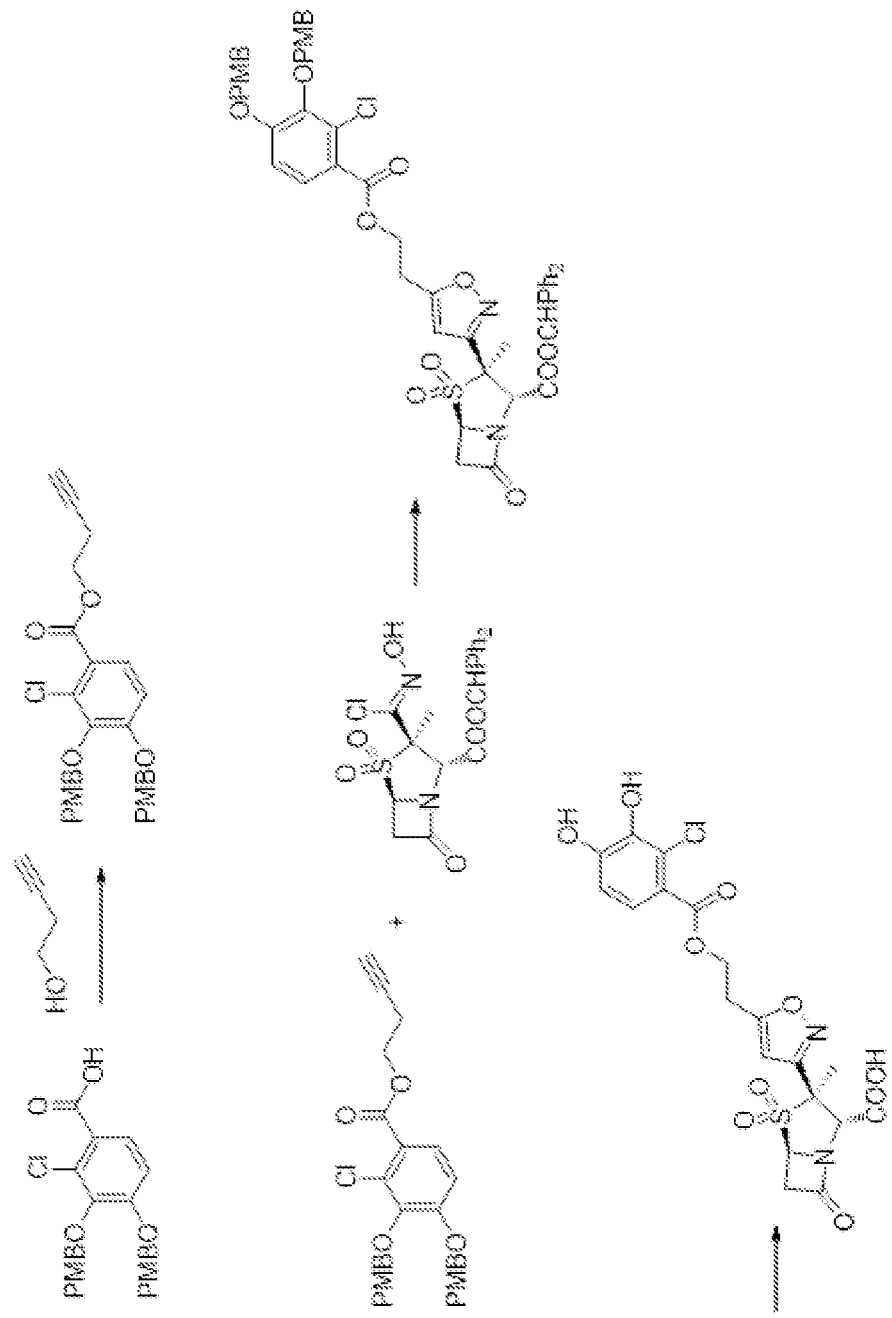

FIG. 13 shows a synthetic scheme for the preparation of this compound. Step 1: but-3-yn-1-yl 2-chloro-3,4-bis((4-methoxybenzyl)oxy)benzoate. To a solution of 2-chloro-3,4-bis((4-methoxybenzyl)oxy)benzoic acid (2.1 g, 5 mmol) in CH$_2$Cl$_2$ (20 mL) was added 1,3-dicyclohexylcarbodiimide (2.1 g, 10 mmol) and N,N-dimethylpyridin-4-amine (1.2 g, 5 mmol). The mixture was stirred at rt for 8 h. Then the solvent was evaporated in vacuo, the residue was purified by column chromatography (silica gel, PE:EtOAc=20:1) to afford white solid (1.2 g, yield 53%).

Step 2: (2S,3R,5R)-benzhydryl 3-(5-(2-((2-chloro-3,4-bis((4-methoxybenzyl)oxy)benzoyl)oxy)ethyl)isoxazol-3-yl)-3-methyl-7-oxo-4-thia-1-azabicyclo[3.2.0]heptane-2-carboxylate 4,4-dioxide. To a solution of but-3-yn-1-yl 2-chloro-3,4-bis((4-methoxybenzyl)oxy)benzoate (480 mg, 1 mmol) in Tol (10 mL) was added (2S,3R,5R)-benzhydryl 3-((Z)-chloro(hydroxyimino)methyl)-3-methyl-7-oxo-4-thia-1-azabicyclo[3.2.0]heptane-2-carboxylate 4,4-dioxide (690 mg, 1.5 mmol). The solution was stirred at RT for 3 h. The solvent was evaporated in vacuo, the residue was purified by column chromatography (silica gel, PE:EtOAc=3:1) to afford white solid (230 mg, yield 25%). LC-MS: m/z=907 (M+H)$^+$.

Step 3: (2S,3R,5R)-3-(5-(2-((2-chloro-3,4-dihydroxybenzoyl)oxy)ethyl)isoxazol-3-yl)-3-methyl-7-oxo-4-thia-1-azabicyclo[3.2.0]heptane-2-carboxylic acid 4,4-dioxide. To a solution of (2S,3R,5R)-benzhydryl 3-(5-(2-((2-chloro-3,4-bis((4-methoxybenzyl)oxy)benzoyl)oxy)ethyl)isoxazol-3-yl)-3-methyl-7-oxo-4-thia-1-azabicyclo[3.2.0]heptane-2-carboxylate 4,4-dioxide (230 mg, 0.25 mmol) in THF (10 mL) was added Pd/C (10%, 50 mg). The solution was stirred at RT for 12 h. The mixture was filtered, and the filtrate was evaporated in vacuo, the residue was washed with MTBE (20 mL) to afford pale solid (60 mg, yield 48%). $^1$H NMR (400 MHz, DMSO-d6) δ 10.62 (s, H), 9.62 (s, 1H), 7.32 (d, 1H), 7.01 (d, 1H), 5.89 (s, 1H), 5.33 (s, 1H), 5.01 (s, 1H), 4.23 (t, 2H), 3.67 (m, 1H), 3.41-3.20 (m, 3H), 1.90 (s, 3H). LC-MS (ESI): m/z=501 (M+H)$^+$.

Example 105

(2S,3R,5R)-3-(5-(2,5-dichloro-3,4-dihydroxyphenyl)isoxazol-3-yl)-3-methyl-7-oxo-4-thia-1-azabicyclo[3.2.0]heptane-2-carboxylic acid 4,4-dioxide

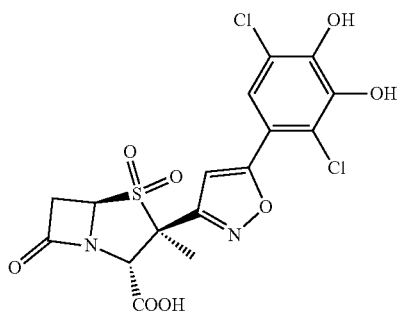 [SMILES: C[C@]1(c2cc(-c3cc(Cl)c(O)c(O)c3Cl)on2)[C@H](C(=O)O)N2C(=O)C[C@H]2S1(=O)=O]

The title compound was prepared using the similar procedure as described in EXAMPLE 101 except 4,4'-(((3,6-dichloro-4-ethynyl-1,2-phenylene)bis(oxy))bis(methylene))bis(methoxybenzene) was used in place of 4,4'-(((3-chloro-4-ethynyl-1,2-phenylene)bis(oxy))bis(methylene))bis(methoxybenzene). $^1$H NMR (400 MHz, DMSO-d6) 7.53 (s, 1H), 7.42 (s, 1H), 5.52 (s, 1H), 5.32 (s, 1H), 3.83 (m, 1H), 3.41 (d, 2H), 1.90 (s, 3H). LC-MS (ESI): m/z=463 (M+H)$^+$.

Example 106

(2S,3R,5R)-3-(5-(2-((3,4-dihydroxybenzoyl)oxy)ethyl)isoxazol-3-yl)-3-methyl-7-oxo-4-thia-1-azabicyclo[3.2.0]heptane-2-carboxylic acid 4,4-dioxide

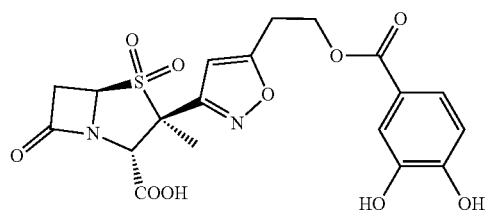 [SMILES: C[C@]1(c2cc(CCOC(=O)c3ccc(O)c(O)c3)on2)[C@H](C(=O)O)N2C(=O)C[C@H]2S1(=O)=O]

The title compound was prepared using the similar procedure as described in EXAMPLE 104 except but-3-yn-1-yl 3,4-bis((4-methoxybenzyl)oxy)benzoate was used in place of but-3-yn-1-yl 2-chloro-3,4-bis((4-methoxybenzyl)oxy)benzoate. ¹H NMR (400 MHz, DMSO-d6) δ 10.62 (s, H), 9.60 (s, 1H), 8.64 (s, 1H), 7.33 (m, 2H), 7.03 (d, 1H), 5.91 (s, 1H), 5.32 (s, 1H), 5.01 (s, 1H), 4.22 (t, 2H), 3.75 (m, 1H), 3.40-3.22 (m, 3H), 1.89 (s, 3H). LC-MS (ESI): m/z=467 (M+H)⁺.

Example 107

(2S,3R,5R)-3-(5-(2-((2-chloro-3,4-dihydroxybenzoyl)oxy)ethyl)-4,5-dihydroisoxazol-3-yl)-3-methyl-7-oxo-4-thia-1-azabicyclo[3.2.0]heptane-2-carboxylic acid 4,4-dioxide

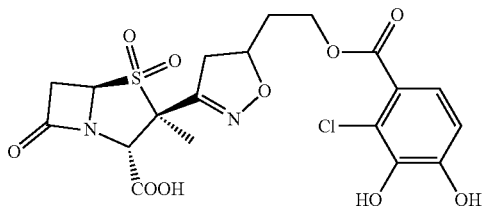 [SMILES: C[C@]1(C2=NOC(CCOC(=O)c3ccc(O)c(O)c3Cl)C2)[C@H](C(=O)O)N2C(=O)C[C@H]2S1(=O)=O]

The title compound was prepared using the similar procedure as described in EXAMPLE 104 except but-3-en-1-yl 2-chloro-3,4-bis((4-methoxybenzyl)oxy)benzoate was used in place of but-3-yn-1-yl 2-chloro-3,4-bis((4-methoxybenzyl)oxy)benzoate.

¹H NMR (400 MHz, DMSO-d6) δ10.60 (s, H), 9.56 (s, 1H), 7.33 (d, 1H), 7.03 (d, 1H), 5.32 (s, 1H), 5.02 (s, 1H), 4.23 (t, 2H), 3.71 (m, 1H), 3.43-3.24 (m, 4H), 1.91 (s, 3H), 1.63 (m, 2H). LC-MS: m/z=503 (M+H)⁺.

Example 108

(2S,3R,5R)-3-(5-(2-chloro-3,4-dihydroxyphenyl)-4,5-dihydroisoxazol-3-yl)-3-methyl-7-oxo-4-thia-1-azabicyclo[3.2.0]heptane-2-carboxylic acid 4,4-dioxide

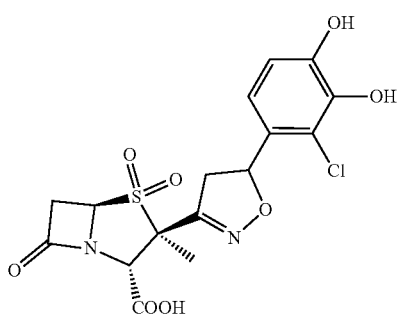

The title compound was prepared using the similar procedure as described in EXAMPLE 101 except 4,4'-(((3-chloro-4-vinyl-1,2-phenylene)bis(oxy))bis(methylene))bis(methoxybenzene) was used in place of 4,4'-(((3-chloro-4-ethynyl-1,2-phenylene)bis(oxy))bis(methylene))bis(methoxybenzene). ¹H NMR (400 MHz, DMSO-d6) δ10.65 (s, H), 9.64 (s, 1H), 7.32 (d, 1H), 6.92 (d, 1H), 5.95 (t, 1H), 5.52 (s, 1H), 5.33 (s, 1H), 3.87 (m, 1H), 3.42-3.25 (d, 3H), 1.92 (s, 3H). LC-MS (ESI): m/z=431 (M+H)⁺.

Example 109

(2S,3R,5R)-3-(5-((2,5-dichloro-3,4-dihydroxybenzamido)methyl)-4,5-dihydroisoxazol-3-yl)-3-methyl-7-oxo-4-thia-1-azabicyclo[3.2.0]heptane-2-carboxylic acid 4,4-dioxide

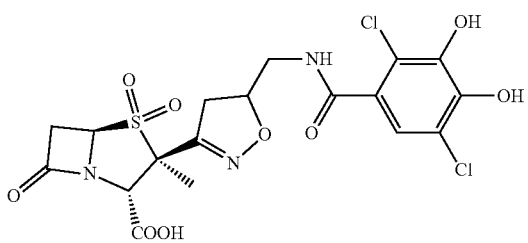 [SMILES: C[C@]1(C2=NOC(CNC(=O)c3cc(Cl)c(O)c(O)c3Cl)C2)[C@H](C(=O)O)N2C(=O)C[C@H]2S1(=O)=O]

The title compound was prepared using the similar procedure as described in EXAMPLE 101 except but-N-allyl-2,5-dichloro-3,4-bis((4-methoxybenzyl)oxy)benzamide was used in place of but-3-yn-1-yl 2-chloro-3,4-bis((4-methoxybenzyl)oxy)benzoate.

¹H NMR (400 MHz, DMSO-d6) 8.62 (s, 1H) 7.02 (s, 1H), 5.33 (s, 1H), 5.04 (s, 1H), 3.70 (m, 1H), 3.40-3.20 (m, 4H), 2.74 (m, 2H), 1.92 (s, 3H). LC-MS (ESI): m/z=522 (M+H)⁺.

Example 110

(2S,3R,5R)-3-(5-(2-((3,4-dihydroxybenzoyl)oxy)ethyl)-4,5-dihydroisoxazol-3-yl)-3-methyl-7-oxo-4-thia-1-azabicyclo[3.2.0]heptane-2-carboxylic acid 4,4-dioxide

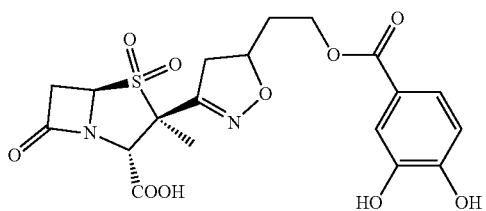 [SMILES: C[C@]1(C2=NOC(CCOC(=O)c3ccc(O)c(O)c3)C2)[C@H](C(=O)O)N2C(=O)C[C@H]2S1(=O)=O]

The title compound was prepared using the similar procedure as described in EXAMPLE 104 except but-3-en-1-yl 3,4-bis((4-methoxybenzyl)oxy)benzoate was used in place of but-3-yn-1-yl 2-chloro-3,4-bis((4-methoxybenzyl)oxy)benzoate. ¹H NMR (400 MHz, DMSO-d6) δ 10.63 (s, H), 9.62 (s, 1H), 7.23 (m, 2H), 7.01 (d, 1H), 5.31 (s, 1H), 5.01 (s, 1H), 4.22 (t, 2H), 3.72 (m, 1H), 3.42-3.24 (m, 4H), 1.93 (s, 3H), 1.60 (m, 2H). LC-MS (ESI): m/z=469 (M+H)⁺.

Example 111

(2S,3R,5R)-3-(5-((2-chloro-3,4-dihydroxybenzamido)methyl)-4,5-dihydroisoxazol-3-yl)-3-methyl-7-oxo-4-thia-1-azabicyclo[3.2.0]heptane-2-carboxylic acid 4,4-dioxide

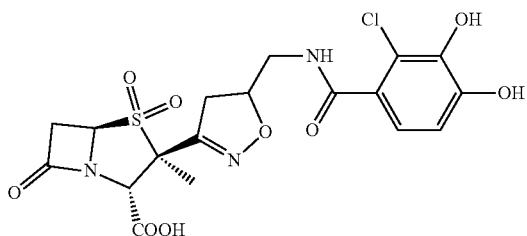 [SMILES: C[C@]1(C2=NOC(CNC(=O)c3ccc(O)c(O)c3Cl)C2)[C@H](C(=O)O)N2C(=O)C[C@H]2S1(=O)=O]

The title compound was prepared using the similar procedure as described in EXAMPLE 101 except but-N-allyl-2-chloro-3,4-bis((4-methoxybenzyl)oxy)benzamide was used in place of but-3-yn-1-yl 2-chloro-3,4-bis((4-methoxybenzyl)oxy)benzoate. $^1$H NMR (400 MHz, DMSO-d6) δ 10.64 (s, H), 9.64 (s, 1H), 8.61 (s, 1H), 7.32 (d, 1H), 7.01 (d, 1H), 5.32 (s, 1H), 5.04 (s, 1H), 3.72 (m, 1H), 3.40-3.21 (m, 4H), 2.72 (m, 2H), 1.92 (s, 3H). LC-MS (ESI): M/Z m/z=488 (M+H)$^+$.

Example 112

(2S,3R,5R)-3-(5-(3,4-dihydroxybenzoyl)isoxazol-3-yl)-3-methyl-7-oxo-4-thia-1-azabicyclo[3.2.0]heptane-2-carboxylic acid 4,4-dioxide

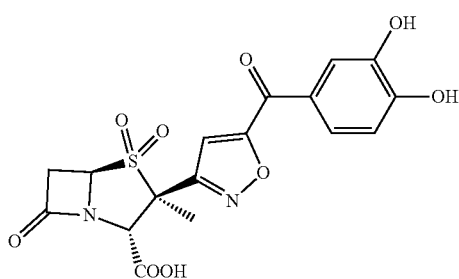 [SMILES: C[C@]1(c2cc(C(=O)c3ccc(O)c(O)c3)on2)[C@H](C(=O)O)N2C(=O)C[C@H]2S1(=O)=O]

The title compound was prepared using the similar procedure as described in EXAMPLE 101 except 1-(3,4-bis((4-methoxybenzyl)oxy)phenyl)prop-2-yn-1-one was used in place of 4,4'-(((3-chloro-4-ethynyl-1,2-phenylene)bis(oxy))bis(methylene))bis(methoxybenzene). $^1$H NMR (400 MHz, DMSO-d6) 7.73 (s, 1H), 7.45 (d, 2H), 7.02 (d, 1H), 5.52 (s, 1H), 5.33 (s, 1H), 3.83 (d, 1H), 3.72 (d, 1H), 1.90 (s, 3H). LC-MS (ESI): m/z=423 (M+H)$^+$.

Example 113

(2S,3R,5R)-3-(((3,4-dihydroxybenzoyl)oxy)methyl)-3-methyl-7-oxo-4-thia-1-azabicyclo[3.2.0]heptane-2-carboxylic acid 4,4-dioxide

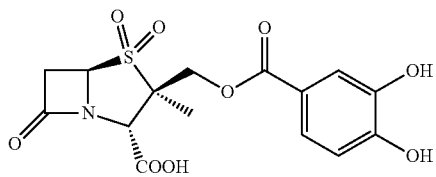 [SMILES: C[C@]1(COC(=O)c2ccc(O)c(O)c2)[C@H](C(=O)O)N2C(=O)C[C@H]2S1(=O)=O]

Figure 14:
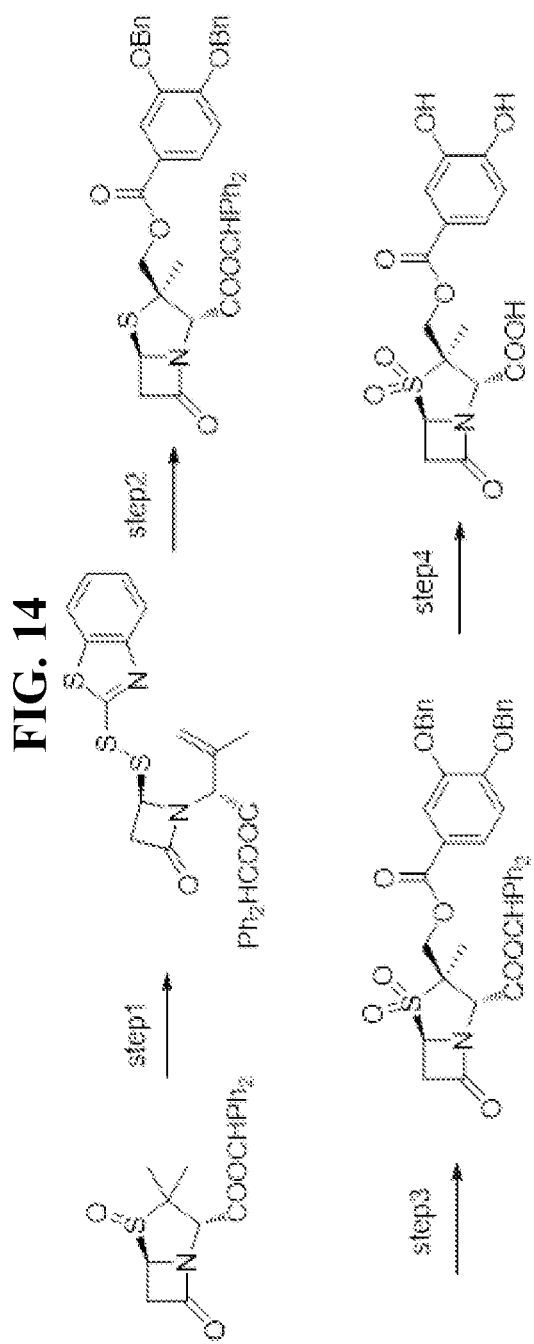

FIG. 14 shows a synthetic scheme for the preparation of this compound. Step 1. (R)-benzhydryl 2-((R)-2-(benzo[d]thiazol-2-yldisulfanyl)-4-oxoazetidin-1-yl)-3-methylbut-3-enoate. (2S,4R,5R)-benzhydryl 3,3-dimethyl-7-oxo-4-thia-1-azabicyclo[3.2.0]heptane-2-carboxylate 4-oxide (5 g, 13.0 mmol) and 2-Mercaptobenzothiazole (2.17 g, 13.0 mmol) was dissolved into 40 mL Toluene and 40 mL Cyclohexane in round bottom flask. The mixture was stirred at 100° C. for 10 h. Then the solvent was evaporated in vacuo. EtOAc (100 mL) was added and the organic layer was dried over Na$_2$SO$_4$. Then the solvent was evaporated in vacuo. LC-MS (ESI): m/z=533 (M+H)$^+$.

Step 2. (2S,3R,5R)-benzhydryl 3-(((3,4-bis(benzyloxy)benzoyl)oxy)methyl)-3-methyl-7-oxo-4-thia-1-azabicyclo[3.2.0]heptane-2-carboxylate. 3,4-bis(benzyloxy)benzoic acid (4.3 g, 13.0 mmol) and Silver acetate (4.3 g, 26.0 mmol) was dissolved into DCM (75 mL) in round bottom flask. (R)-benzhydryl 2-((R)-2-(benzo[d]thiazol-2-yldisulfanyl)-4-oxoazetidin-1-yl)-3-methylbut-3-enoate (6.9 g, 13.0 mmol) was dissolved into DCM (25 mL) then was added to the solution dropwisely. The mixture was stirred at 25° C. for 12 hours. The solvent was filtered and the mother liquor was evaporated in vacuo. The solution was washed with water and extracted with EtOAc (200 mL). The organic layer was dried over Na$_2$SO$_4$. The solvent was evaporated in vacuo. The residue was purified by column chromatography (silica gel, hexane:EtOAc=3:1) to give the title compound (2.2 g, yield 24.2%). LC-MS (ESI): m/z=700 (M+H)$^+$.

Step 3. (2S,3R,5R)-benzhydryl 3-(((3,4-bis(benzyloxy)benzoyl)oxy)methyl)-3-methyl-7-oxo-4-thia-1-azabicyclo[3.2.0]heptane-2-carboxylate 4,4-dioxide. (2S,3R,5R)-benzhydryl 3-(((3,4-bis(benzyloxy)benzoyl)oxy)methyl)-3-methyl-7-oxo-4-thia-1-azabicyclo[3.2.0]heptane-2-carboxylate (2.2 g, 3.1 mmol) was dissolved into acetic acid (15 mL), acetone (3 mL) and H$_2$O (3 mL) in round bottom flask. The mixture was stirred at 10° C. for 4 hours. EtOAc (100 mL) was added into the solvent. Then sodium metabisulfite solution was added slowly. The solution was extracted with EtOAc (100 mL). The organic layer was dried over Na$_2$SO$_4$. The solvent was evaporated in vacuo. The residue was purified by column chromatography (silica gel, hexane:EtOAc=3:1) to give the title compound (680 mg, yield 30.0%). LC-MS (ESI): m/z=732 (M+H)$^+$.

Step 4. (2S,3R,5R)-3-(((3,4-dihydroxybenzoyl)oxy)methyl)-3-methyl-7-oxo-4-thia-1-azabicyclo[3.2.0]heptane-2-carboxylic acid 4,4-dioxide (2S,3R,5R)-benzhydryl 3-(((3,4-bis(benzyloxy)benzoyl)oxy)methyl)-3-methyl-7-oxo-4-thia-1-azabicyclo[3.2.0]heptane-2-carboxylate 4,4-dioxide was dissolved in THF (30 mL), Pd/C (10%, 500 mg) was added and the solution was stirred under charged hydrogen balloon for 10 hours. Filtration to remove the palladium, Then the solvent was evaporated in vacuo, the residue was purified with silica gel (DCM:MeOH=20:1) to afford white solid (205 mg, yield 57.3%). ¹H NMR (400 MHz, DMSO-d6) δ 9.91 (s, 1H), 9.41 (s, 1H), 7.38 (md, 2H), 6.84 (d, 1H), 5.19 (d, 1H), 4.76 (d, 1H), 4.66 (m, 2H), 3.71 (dd, 1H), 3.32 (d, 2H), 1.55 (s, 3H). LC-MS (ESI): m/z=386 (M+H)⁺.

Example 114

(2S,3R,5R)-3-(((2-chloro-3,4-dihydroxybenzoyl)oxy)methyl)-3-methyl-7-oxo-4-thia-1-azabicyclo[3.2.0]heptane-2-carboxylic acid 4,4-dioxide

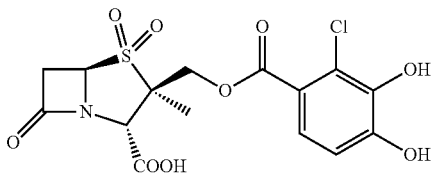 [SMILES: C[C@]1(COC(=O)c2ccc(O)c(O)c2Cl)[C@H](C(=O)O)N2C(=O)C[C@H]2S1(=O)=O]

The title compound was prepared using the similar procedure as described in EXAMPLE 113 except 3,4-bis(benzyloxy)-2-chlorobenzoic acid was used in place of 3,4-bis(benzyloxy)benzoic acid. ¹H NMR (400 MHz, DMSO-d6) δ 10.64 (s, 1H), 9.45 (s, 1H), 7.39 (d, 1H), 6.83 (d, 1H), 5.18 (d, 1H), 4.76 (d, 1H), 4.68 (t, 2H), 3.71 (dd, 1H), 3.3 (d, 2H), 1.55 (s, 3H), LC-MS (ESI): m/z=420 (M+H)⁺.

Example 115

(2S,3S,5R)-3-((3,4-dihydroxybenzamido)methyl)-3-methyl-7-oxo-4-thia-1-azabicyclo[3.2.0]heptane-2-carboxylic acid 4,4-dioxide

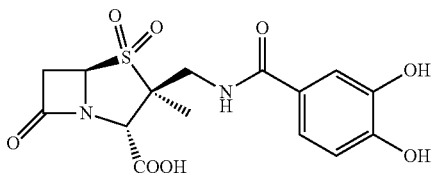 [SMILES: C[C@]1(CNC(=O)c2ccc(O)c(O)c2)[C@H](C(=O)O)N2C(=O)C[C@H]2S1(=O)=O]

Figure 15:
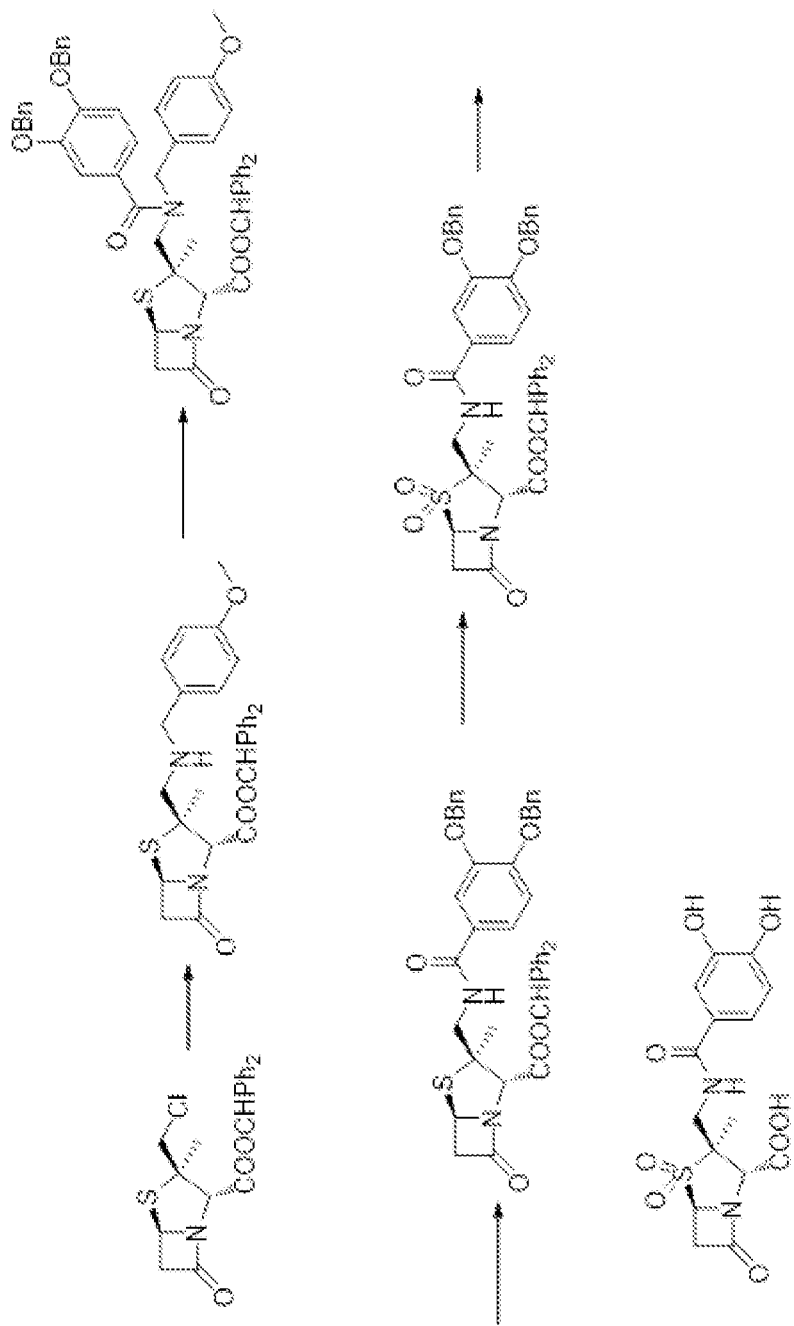

FIG. 15 shows a synthetic scheme for the preparation of this compound. Step 1. (2S,3S,5R)-benzhydryl 3-(((4-methoxybenzyl)amino)methyl)-3-methyl-7-oxo-4-thia-1-azabicyclo[3.2.0]heptane-2-carboxylate. To a solution of (2S,3R,5R)-benzhydryl 3-(chloromethyl)-3-methyl-7-oxo-4-thia-1-azabicyclo[3.2.0]heptane-2-carboxylate (10 g, 24.9 mmol) in acetonitrile (90 mL) and water (30 mL) was added 4-methoxybenzylamine (3.4 g, 24.9 mmol). Then sodium bicarbonate (4.2 g, 49.8 mmol) was added. The mixture was stirred at rt for 16 hours. The solution was washed with water and extracted with EtOAc (100 mL). The organic layer was dried over Na₂SO₄. The solvent was evaporated in vacuo. The residue was purified by column chromatography (silica gel, DCM:MeOH=100:1) to give the title compound (4.0 g, yield 32%). LC-MS (ESI): m/z=503 (M+H)⁺.

Step 2: (2S,3S,5R)-benzhydryl 3-((3,4-bis(benzyloxy)-N-(4-methoxybenzyl)benzamido)methyl)-3-methyl-7-oxo-4-thia-1-azabicyclo[3.2.0]heptane-2-carboxylate. To a solution of (2S,3S,5R)-benzhydryl 3-(((4-methoxybenzyl)amino)methyl)-3-methyl-7-oxo-4-thia-1-azabicyclo[3.2.0]heptane-2-carboxylate (4.0 g, 7.96 mmol) in dry acetonitrile (100 mL) was added triethylamine (2.06 mL, 15.92 mmol). The solution was cooled to 5° C., then 3,4-bis(benzyloxy)benzoyl chloride (4.2 g, 11.95 mmol) was added dropwise. The mixture was stirred at 5° C. for 6 hours, then warmed to rt for 16 hours. The solution was washed with water and extracted with ethyl acetate (100 mL). The organic layer was dried over Na₂SO₄. The solvent was evaporated in vacuo. The residue was purified by column chromatography (silica gel, DCM:MeOH=100:1) to give the title compound (1.2 g, yield 18.4%). LC-MS (ESI): m/z=819 (M+H)⁺.

Step 3: (2S,3S,5R)-benzhydryl 3-((3,4-bis(benzyloxy)benzamido)methyl)-3-methyl-7-oxo-4-thia-1-azabicyclo[3.2.0]heptane-2-carboxylate. (2S,3S,5R)-benzhydryl 3-((3,4-bis(benzyloxy)-N-(4-methoxybenzyl)benzamido)methyl)-3-methyl-7-oxo-4-thia-1-azabicyclo[3.2.0]heptane-2-carboxylate (1.0 g, 1.22 mmol) was dissolved in acetonitrile (10 mL). Water (10 mL) and ceric ammonium nitrate (2.0 g, 3.66 mmol) were added. The mixture was stirred for 5 hours. The solution was washed with water, and extracted with ethyl acetate (50 mL). The organic layer was dried over Na₂SO₄. The solvent was evaporated in vacuo. The residue was purified by column chromatography (silica gel, DCM:MeOH=50:1) to give the title compound (570 mg, yield 67%). LC-MS (ESI): m/z=699 (M+H)⁺.

Step 4: (2S,3S,5R)-benzhydryl 3-((3,4-bis(benzyloxy)benzamido)methyl)-3-methyl-7-oxo-4-thia-1-azabicyclo[3.2.0]heptane-2-carboxylate 4,4-dioxide. (2S,3S,5R)-benzhydryl 3-((3,4-bis(benzyloxy)benzamido)methyl)-3-methyl-7-oxo-4-thia-1-azabicyclo[3.2.0]heptane-2-carboxylate (570 mg, 0.82 mmol) was dissolved in acetic acid (10 mL). Then water (2 mL) and acetone (2 mL) were added. The solution was cooled to 5° C. KMnO₄ (259 mg, 1.64 mmol) was added portionwise. The mixture was stirred at 5° C. for 3 hours. The solution was washed with water, and extracted with ethyl acetate (50 mL). The organic layer was dried over Na₂SO₄. The solvent was evaporated in vacuo to give the title compound (478 mg, yield 80%). LC-MS (ESI): m/z=731 (M+H)⁺.

Step 5: (2S,3S,5R)-3-((3,4-dihydroxybenzamido)methyl)-3-methyl-7-oxo-4-thia-1-azabicyclo[3.2.0]heptane-2-carboxylic acid 4,4-dioxide. (2S,3S,5R)-benzhydryl 3-((3,4-bis(benzyloxy)benzamido)methyl)-3-methyl-7-oxo-4-thia-1-azabicyclo[3.2.0]heptane-2-carboxylate 4,4-dioxide (478 mg, 0.65 mmol) was dissolved in THF (5 mL). The mixture was degassed with N₂ twice, Pd/C (10%, 150 mg) was added, then the flask was degassed with H₂ twice, and stirred at rt for 12 hours. The solution was filtered, and the filtrate was concentrated. Ethyl acetate (10 mL) was added, and stirred for 30 min. The slurry was filtered and the cake was washed with MTBE (20 mL) to give the title compound (100 mg, yield 40%). ¹H NMR (400 MHz, DMSO-d6) δ13.84 (br, 1H), 9.45 (s, 1H), 9.34 (s, 1H), 7.82 (br, 1H), 6.88 (d, 1H), 6.86 (s, 1H), 6.81 (d, 1H), 5.47 (d, 1H), 4.72 (s, 1H), 4.11 (d, 1H), 3.56 (d, 1H), 3.52 (dd, 1H), 2.67 (dd, 1H), 1.51 (s, 3H). LC-MS (ESI): m/z=385 (M+H)⁺.

Example 116

(2S,3S,5R)-3-(acetamidomethyl)-3-methyl-7-oxo-4-thia-1-azabicyclo[3.2.0]heptane-2-carboxylic acid 4,4-dioxide

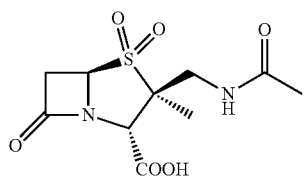 [SMILES: CC(=O)NC[C@@]1(C)[C@H](C(=O)O)N2C(=O)C[C@H]2S1(=O)=O]

The title compound was prepared using the similar procedure as described in EXAMPLE 115. $^1$H NMR (400 MHz, DMSO-d6) δ 12.84 (br, 1H), 5.47 (d, 1H), 4.72 (s, 1H), 4.11 (d, 1H), 3.56 (d, 1H), 3.52 (dd, 1H), 2.67 (dd, 1H), 2.25 (s, 3H), 1.51 (s, 3H). LC-MS (ESI): m/z=291 (M+H)$^+$.

Example 117

(2S,3S,5R)-3-(((3,4-dihydroxyphenyl)amino)methyl)-3-methyl-7-oxo-4-thia-1-azabicyclo[3.2.0]heptane-2-carboxylic acid 4,4-dioxide

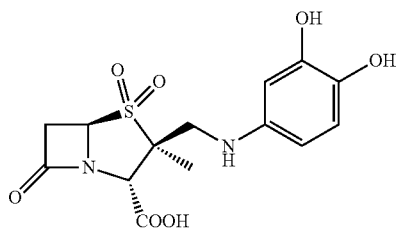 [SMILES: C[C@]1(CNc2ccc(O)c(O)c2)[C@H](C(=O)O)N2C(=O)C[C@H]2S1(=O)=O]

Figure 16:
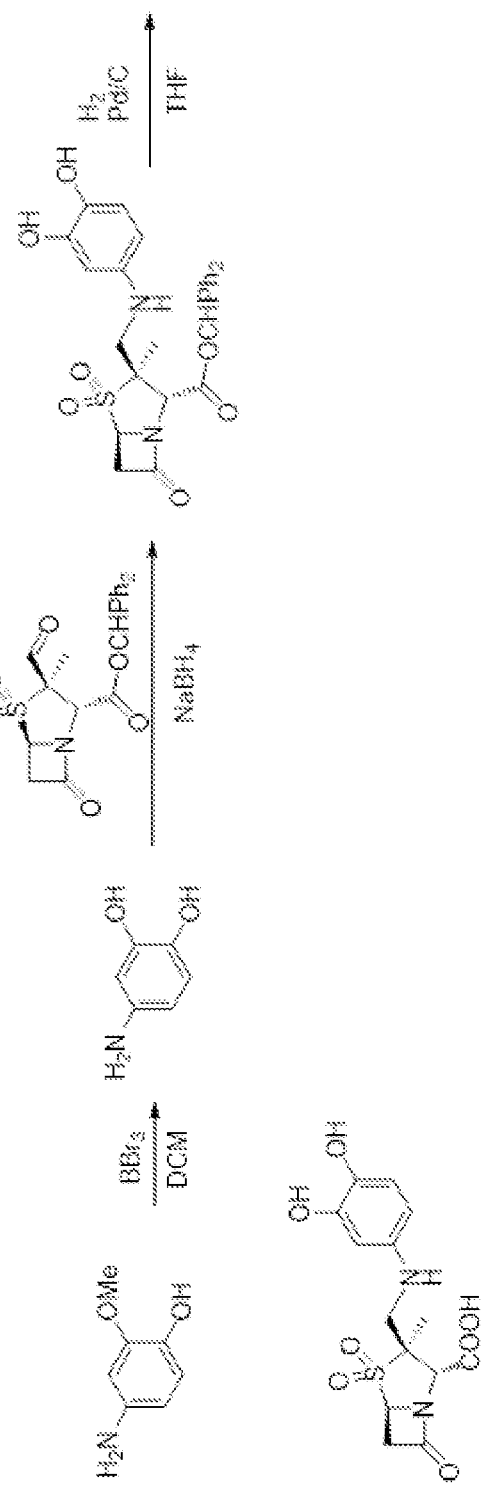

FIG. 16 shows a synthetic scheme for the preparation of this compound. Step 1. 4-aminobenzene-1,2-diol. To a solution of 4-amino-2-methoxyphenol (1000 mg, 7.19 mmol) in dichloromethane (20 mL) was added boron tribromide (2162 mg, 8.63 mmol). The reaction mixture was stirred at 0° C. for 2 hours. Then the crude was purified by column chromatography (silica gel) to afford the title compound (810 mg, yield 90%). LC-MS (ESI): m/z=247 (M+H)$^+$.

Step 2. (2S,3S,5R)-benzhydryl 3-(((3,4-dihydroxyphenyl)amino)methyl)-3-methyl-7-oxo-4-thia-1-azabicyclo[3.2.0]heptane-2-carboxylate 4,4-dioxide. To a solution of 4-aminobenzene-1,2-diol (30 mg, 0.24 mmol) in MeOH (2 mL) was added (2S,3R,5R)-benzhydryl 3-formyl-3-methyl-7-oxo-4-thia-1-azabicyclo[3.2.0]heptane-2-carboxylate 4,4-dioxide (100 mg, 0.24 mmol) and sodium borohydride (18 mg, 0.48 mmol). Then the crude was purified by column chromatography (silica gel) to afford the title compound (78 mg, yield 62%). LC-MS (ESI): m/z=523 (M+H)$^+$.

Step 3. (2S,3S,5R)-3-(((3,4-dihydroxyphenyl)amino)methyl)-3-methyl-7-oxo-4-thia-1-azabicyclo[3.2.0]heptane-2-carboxylic acid 4,4-dioxide. To a solution of 2S,3S,5R)-benzhydryl 3-(((3,4-dihydroxyphenyl)amino)methyl)-3-methyl-7-oxo-4-thia-1-azabicyclo[3.2.0]heptane-2-carboxylate 4,4-dioxide (78 mg, 0.15 mmol) in MeOH (2 mL) was as added Pd/C (10%, 30 mg). The reaction mixture was evacuated and inflated by hydrogen balloon. After stirring for 12 hours, 18 mg of the product was purified by flash chromatography in 33% yield. $^1$H NMR (400 MHz, DMSO-d6) δ 6.95 (d, 1H), 6.87 (d, 1H), 6.36 (d, 1H), 7.04 (d, 1H), 5.55 (s, 2H), 4.20 (s, 1H), 4.50 (s, 1H), 4.10 (s, 1H), 3.57 (m, 4H), 3.41 (m, 2H), 3.21 (m, 2H), 1.50 (s, 3H). LC-MS (ESI): m/z=357 (M+H)$^+$.

Example 118

(2S,3R,5R)-3-((E)-((2-(2-chloro-3,4-dihydroxybenzamido)ethoxy)imino)methyl)-3-methyl-7-oxo-4-thia-1-azabicyclo[3.2.0]heptane-2-carboxylic acid 4,4-dioxide

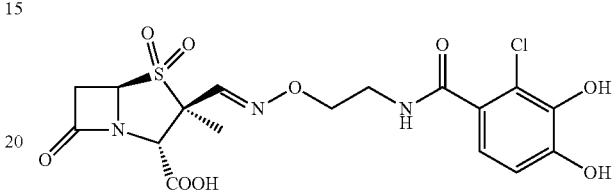

Figure 17:
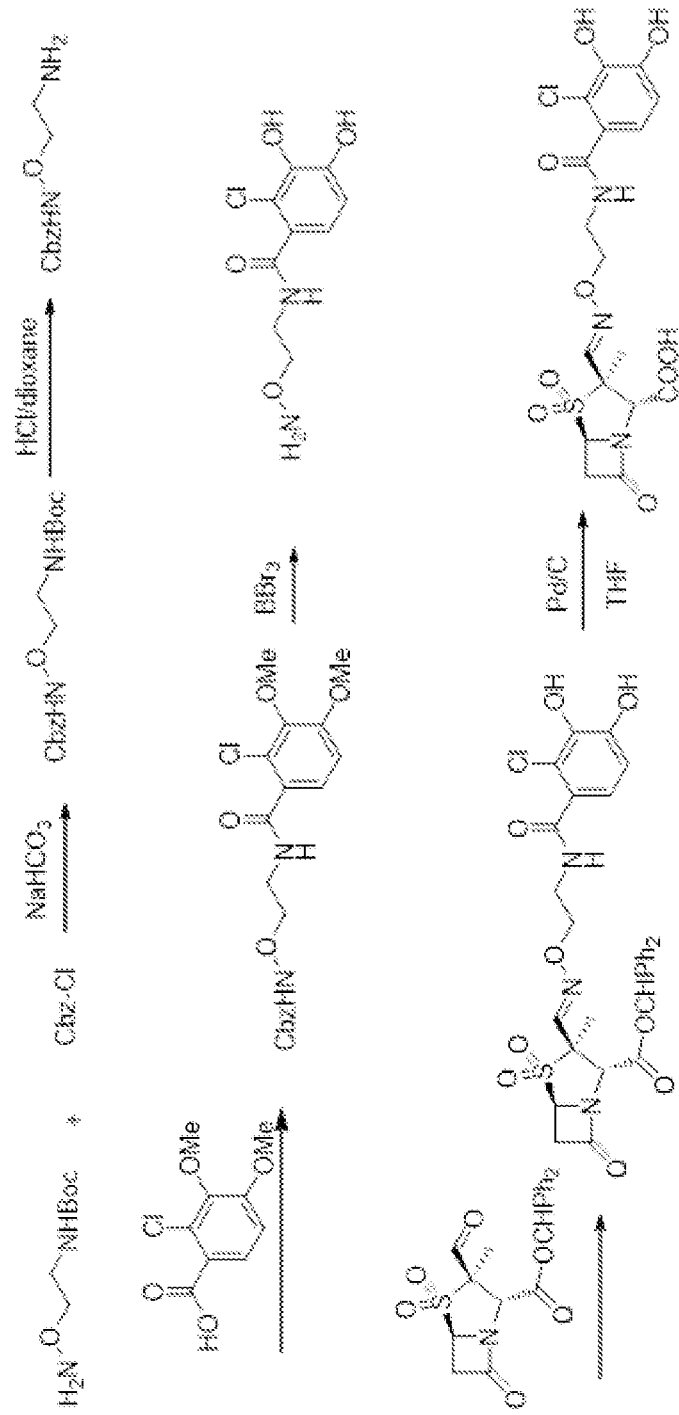

FIG. 17 shows a synthetic scheme for the preparation of this compound. Step 1. Benzyl [2-({[(2-methyl-2-propanyl)oxy]carbonyl}amino)ethoxy]carbamate. To a solution of tert-butyl (2-(aminooxy)ethyl)carbamate (1650 mg, 9.36 mmol) in THF (10 mL) was added NaHCO$_3$ (865 mg, 10.30 mmol) and Cbz-Cl (1597 mg, 9.36 mmol). The reaction mixture was stirred at room temperature for 4 hours and was purified by Flash Chromatagraphy to afford 2530 mg product in 87% yield. LC-MS (ESI): m/z=311 (M+H)$^+$.

Step 2. Benzyl 2-aminoethoxycarbamate. 3.2 mL of 4M HCl was added to a solution of Benzyl [2-({[(2-methyl-2-propanyl)oxy]carbonyl}amino)ethoxy]carbamate (1000 mg, 3.22 mmol) in ethyle acetate (5 mL). The reaction mixture was stirred at room temperature for 12 hours. After evaporation 630 mg of crude product was used for next step without further purification. LC-MS (ESI): m/z=211 (M+H)$^+$.

Step 3. Benzyl 2-(2-chloro-3,4-dimethoxybenzamido)ethoxycarbamate. N'-(Ethylkohlenstoffimidoyl)-N,N-dimethylpropan-1,3-diaminhydrochlorid (383 mg, 2.00 mmol) was added to a solution of benzyl 2-aminoethoxycarbamaten (210 mg, 1.00 mmol), 2-chloro-3,4-dimethoxybenzoic acid (217 mg, 1.00 mmol), 1-Hydroxybenzotriazole (135 mg, 1.00 mmol) and 4-Methylmorpholine (202 mg, 2.00 mmol) in N,N-Dimethylformamide (5 mL). The reaction mixture was stirred for 12 hours. 280 mg of product was afforded by Flash Chromatagraphy in 68% yield. LC-MS (ESI): m/z=409 (M+H)$^+$.

Step 4. N-(2-(aminooxy)ethyl)-2-chloro-3,4-dihydroxybenzamide. To a solution of benzyl 2-(2-chloro-3,4-dimethoxybenzamido)ethoxycarbamate e (250 mg, 0.61 mmol) in dichloromethane (3 mL) was added boron tribromide (613 mg, 2.44 mmol). The reaction mixture was stirred at 0° C. for 2 hours. 131 mg of product was afforded by Flash Chromatagraphy in 87% yield. LC-MS (ESI): m/z=247 (M+H)$^+$.

Step 5. (2S,3R,5R)-benzhydryl 3-((E)-((2-(2-chloro-3,4-dihydroxybenzamido)ethoxy)imino)methyl)-3-methyl-7-oxo-4-thia-1-azabicyclo[3.2.0]heptane-2-carboxylate 4,4-dioxide. To a solution of N-(2-(aminooxy)ethyl)-2-chloro-3,4-dihydroxybenzamide (107 mg, 0.44 mmol) in N,N-Dimethylformamide (2 mL) was added (2S,3R,5R)-benzhydryl 3-formyl-3-methyl-7-oxo-4-thia-1-azabicyclo[3.2.0]heptane-2-carboxylate 4,4-dioxide (180 mg, 0.44 mmol) and 0.1 mL 1M HCl. The reaction mixture was stirred for 12 hours and then poured into ice water. The product was filtrated to afford 70 mg white solid. LC-MS (ESI): m/z=643 (M+H)+.

Step 6. (2S,3R,5R)-3-((E)-((2-(2-chloro-3,4-dihydroxybenzamido)ethoxy)imino)methyl)-3-methyl-7-oxo-4-thia-1-azabicyclo[3.2.0]heptane-2-carboxylic acid 4,4-dioxide. To a solution of (2S,3R,5R)-benzhydryl 3-((E)-((2-(2-chloro-3,4-dihydroxybenzamido)ethoxy)imino)methyl)-3-methyl-7-oxo-4-thia-1-azabicyclo[3.2.0]heptane-2-carboxylate 4,4-dioxide (70 mg, 0.11 mmol) in tetrahydrofuran (2 mL) was added 10% Pd—C (50 mg). The reaction mixture was evacuated and inflated by hydrogen balloon. After stirring for 12 hours, 15 mg of the product was purified by flash chromatography in 29% yield. ¹H NMR (400 MHz, DMSO-d6) δ 8.03 (s, 1H), 7.50 (s, 1H), 7.36 (d, 1H), 7.04 (d, 1H), 5.35 (s, 2H), 4.70 (m, 1H), 4.50 (s, 1H), 3.83 (t, 2H), 3.46 (m, 4H), 3.30 (m, 2H), 3.21 (m, 2H), 1.45 (s, 3H). LC-MS (ESI): m/z=476 (M+H)+.

Example 119

(2S,3R,5R)-3-((E)-((4-(2-chloro-3,4-dihydroxybenzamido)phenoxy)imino)methyl)-3-methyl-7-oxo-4-thia-1-azabicyclo[3.2.0]heptane-2-carboxylic acid 4,4-dioxide

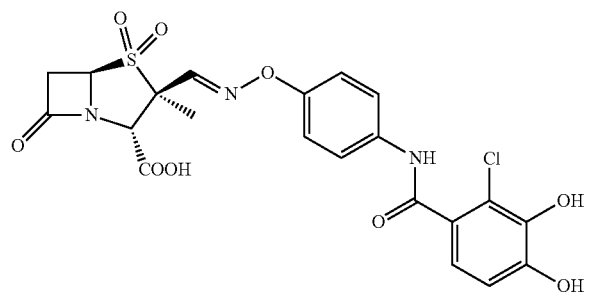 [SMILES: C[C@]1(/C=N/Oc2ccc(NC(=O)c3ccc(O)c(O)c3Cl)cc2)[C@H](C(=O)O)N2C(=O)C[C@H]2S1(=O)=O]

Figure 18:
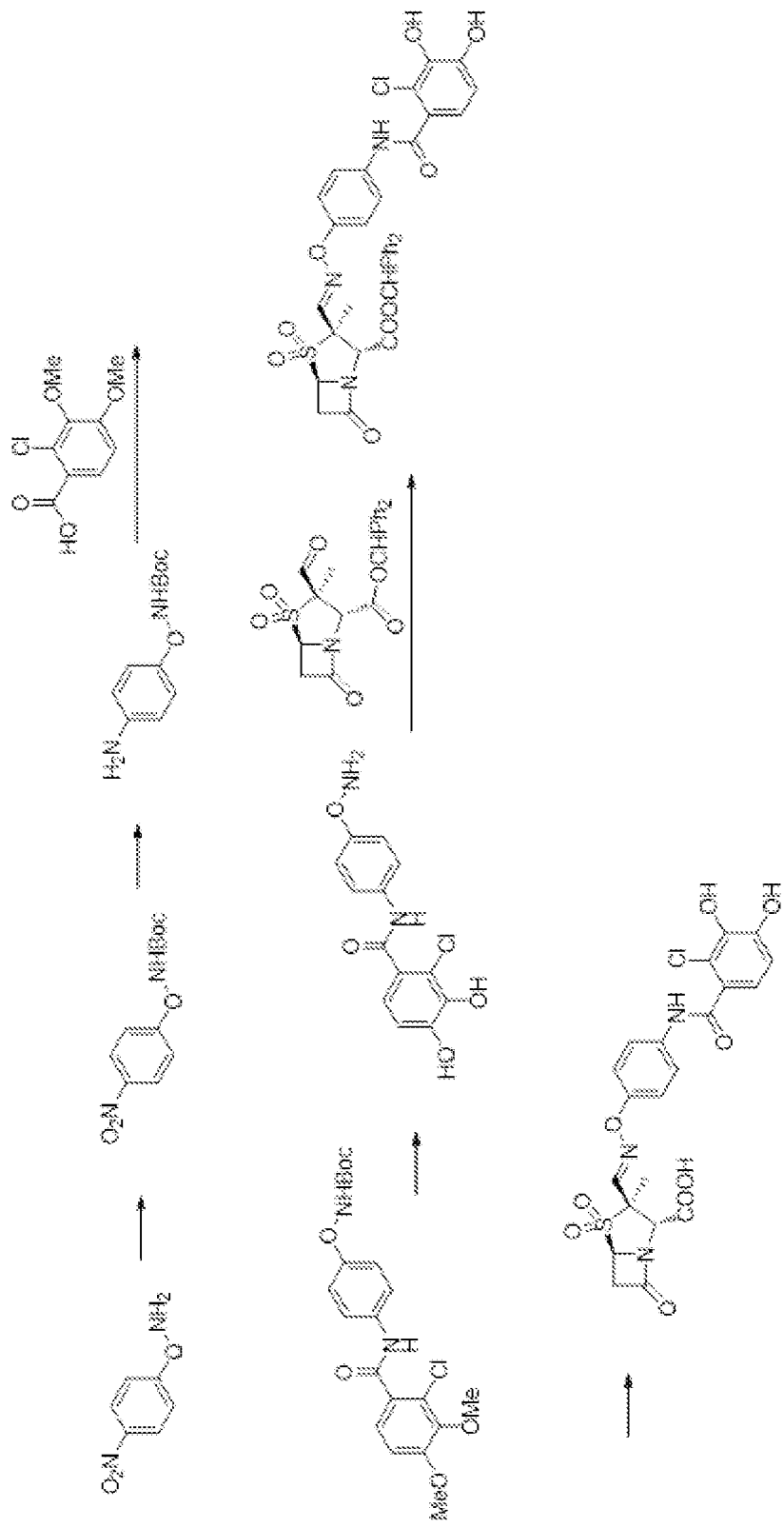

FIG. 18 shows a synthetic scheme for the preparation of this compound. Step 1. tert-butyl 4-nitrophenoxycarbamate. To a solution of O-(4-nitrophenyl)hydroxylamine (2500 mg, 12.22 mmol) in THF (50 mL) was added di-tert-butyl dicarbonate (2780 mg, 12.83 mmol) and triethylamine (3091 mg, 30.56 mmol). The reaction mixture was stirred for 12 hours. After evaporation 3550 mg of crude product was used for next step without further purification. LC-MS (ESI): m/z=255 (M+H)+.

Step 2. tert-butyl 4-aminophenoxycarbamate. To a solution of tert-butyl 4-nitrophenoxycarbamate (1000 mg, 3.73 mmol) was added Pd/C (10%, 100 mg). The reaction mixture was evacuated and inflated by hydrogen balloon. After stirring for 12 hours, 552 mg of the product was purified by flash Chromatography in 62% yield. LC-MS (ESI): m/z=239 (M+H)+.

Step 3. tert-butyl 4-(2-chloro-3,4-dimethoxybenzamido)phenoxycarbamate. To a solution of tert-butyl 4-(2-chloro-3,4-dimethoxybenzamido)phenoxycarbamate (500 mg, 2.10 mmol), 2-chloro-3,4-dimethoxybenzoic acid (455 mg, 2.10 mmol), 4-dimethylaminopyridine (26 mg, 0.21 mmol) was added N'-(Ethylkohlenstoffimidoyl)-N,N-dimethylpropan-1,3-diaminchlorid (483 mg, 2.52 mmol). The reaction mixture was stirred for 12 hours and then poured into ice water. The product was filtrated to afford 510 mg white solid. LC-MS (ESI): m/z=423 (M+H)+.

Step 4. N-(4-(aminooxy)phenyl)-2-chloro-3,4-dihydroxybenzamide. To a solution of tert-butyl 4-(2-chloro-3,4-dimethoxybenzamido)phenoxycarbamate (1000 mg, 2.32 mmol) in dichloromethane (3 mL) was added boron tribromide (1743 mg, 6.96 mmol). The reaction mixture was stirred at 0° C. for 2 hours. 400 mg of product was afforded by flash chromatography in 58% yield. LC-MS (ESI): m/z=247 (M+H)+.

Step 5. (2S,3R,5R)-benzhydryl 3-((E)-((4-(2-chloro-3,4-dihydroxybenzamido)phenoxy)imino)methyl)-3-methyl-7-oxo-4-thia-1-azabicyclo[3.2.0]heptane-2-carboxylate 4,4-dioxide. To a solution of N-(4-(aminooxy)phenyl)-2-chloro-3,4-dihydroxybenzamide (400 mg, 1.36 mmol) in N,N-Dimethylformamide (5 mL) was added (2S,3R,5R)-benzhydryl 3-formyl-3-methyl-7-oxo-4-thia-1-azabicyclo[3.2.0]heptane-2-carboxylate 4,4-dioxide (561 mg, 1.36 mmol) and 0.1 mL 1M HCl. The reaction mixture was stirred for 12 hours and then poured into ice water. The product was filtrated to afford 220 mg white solid. LC-MS (ESI): m/z=691 (M+H)+.

Step 6. (2S,3R,5R)-3-((E)-((4-(2-chloro-3,4-dihydroxybenzamido)phenoxy)imino)methyl)-3-methyl-7-oxo-4-thia-1-azabicyclo[3.2.0]heptane-2-carboxylic acid 4,4-dioxide. To a solution of (2S,3R,5R)-benzhydryl 3-((E)-((4-(2-chloro-3,4-dihydroxybenzamido)phenoxy)imino)methyl)-3-methyl-7-oxo-4-thia-1-azabicyclo[3.2.0]heptane-2-carboxylate 4,4-dioxide (50 mg, 0.07 mmol) in tetrahydrofuran (2 mL) was added Pd/C (10%, 50 mg). The reaction mixture was evacuated and inflated by hydrogen balloon. After stirring for 12 hours, 16 mg of the product was purified by flash chromatography in 43% yield. ¹H NMR (400 MHz, DMSO-d6) δ 9.10 (s, 1H), 7.84 (m, 1H), 7.51 (m, 1H), 7.45 (dd, 2H), 7.05 (dd, 2H), 5.37 (s, 2H), 4.76 (m, 1H), 4.55 (s, 1H), 3.50 (m, 2H), 3.25 (m, 2H), 1.45 (s, 3H). LC-MS (ESI): m/z=524 (M+H)+.

Example 120

(2S,3R,5R)-3-(5-(2-chloro-3,4-dihydroxybenzoyl)isoxazol-3-yl)-3-methyl-7-oxo-4-thia-1-azabicyclo[3.2.0]heptane-2-carboxylic acid 4,4-dioxide

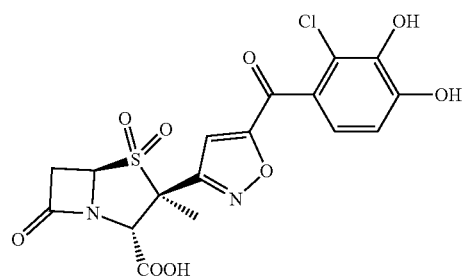

The title compound was prepared using the similar procedure as described in EXAMPLE 101 except 1-(2-chloro-3,4-bis((4-methoxybenzyl)oxy)phenyl)prop-2-yn-1-one was used in place of 4,4'-(((3-chloro-4-ethynyl-1,2-phenylene)bis(oxy))bis(methylene))bis(methoxybenzene). ¹H-NMR (400 MHz, DMSO) 7.52 (d, 2H), 7.01 (d, 1H), 5.52 (s, 1H), 5.32 (s, 1H), 3.78 (d, 1H), 3.67 (d, 1H), 1.92 (s, 3H). LC-MS (ESI): m/z=457 (M+H)+.

Example 121

(2S,3R,5R)-3-((E)-(2-(2-bromo-4,5-dihydroxyben-zoyl)hydrazono)methyl)-3-methyl-7-oxo-4-thia-1-azabicyclo[3.2.0]heptane-2-carboxylic acid 4,4-dioxide

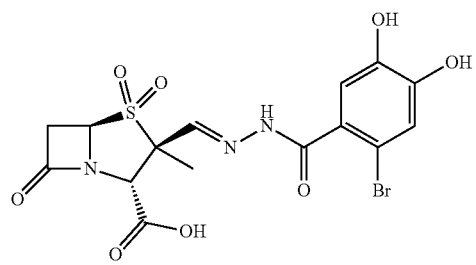 [SMILES: C[C@]1(/C=N/NC(=O)c2cc(O)c(O)cc2Br)[C@H](C(=O)O)N2C(=O)C[C@H]2S1(=O)=O]

The title compound was prepared using the similar procedure as described in EXAMPLE 1 except 2-bromo-4,5-dihydroxybenzohydrazide was used in place of 2-chloro-4,5-dihydroxybenzohydrazide. $^1$H NMR (400 MHz, DMSO-d6) δ 12.10 (s, H), 10.20 (s, 1H), 9.41 (s, 1H), 7.79 (s, 1H), 7.12 (s, 1H), 6.94 (d, 1H), 6.83 (d, 1H), 6.62 (s, 1H), 5.30 (d, 1H), 3.74 (t, 3H), 3.31 (m, 1H), 2.20 (s, 1H), 1.62 (s, 3H). LC-MS (ESI): m/z=475 (M+H)$^+$.

Example 122

(2S,3R,5R)-3-((E)-(2-(3-(3,4-dihydroxyphenyl)-5-methylisoxazole-4-carbonyl)hydrazono)methyl)-3-methyl-7-oxo-4-thia-1-azabicyclo[3.2.0]heptane-2-carboxylic acid 4,4-dioxide

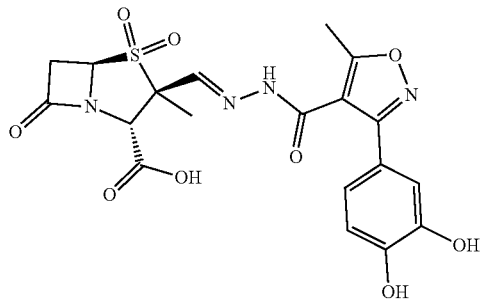 [SMILES: Cc1onc(-c2ccc(O)c(O)c2)c1C(=O)N/N=C/[C@@]1(C)[C@H](C(=O)O)N2C(=O)C[C@H]2S1(=O)=O]

The title compound was prepared using the similar procedure as described in EXAMPLE 1 except 3-(3,4-dihydroxyphenyl)-5-methylisoxazole-4-carbohydrazide was used in place of 2-chloro-4,5-dihydroxybenzohydrazide. $^1$H NMR (400 MHz, DMSO-d6) δ 12.3 (s, 1H), 12.1 (s, 1H), 7.50 (s, 3H), 7.07 (s, 1H), 6.99 (s, 1H), 6.83 (s, 1H), 5.41 (s, 1H), 4.70 (t, 1H), 4.22 (s, 1H), 3.66 (s, 1H), 3.46 (dd, 1H), 3.21 (dd, 1H), 2.38-2.34 (m, 3H), 1.56 (s, 3H). LC-MS (ESI): m/z=479 (M+H)$^+$.

Example 123

(2S,3R,5R)-3-((E)-(2-(3-(2-chloro-3,4-dihydroxyphenyl)isoxazole-5-carbonyl)hydrazono)methyl)-3-methyl-7-oxo-4-thia-1-azabicyclo[3.2.0]heptane-2-carboxylic acid 4,4-dioxide

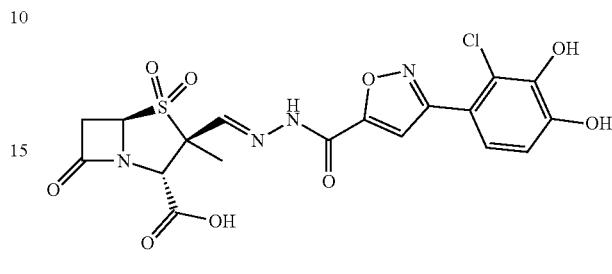

The title compound was prepared using the similar procedure as described in EXAMPLE 1 except 3-(2-chloro-3,4-dihydroxyphenyl)isoxazole-5-carbohydrazide was used in place of 2-chloro-4,5-dihydroxybenzohydrazide. $^1$H NMR (400 MHz, DMSO-d6) δ 12.2 (s, 1H), δ 7.56 (s, 1H), 7.50 (s, 1H), 7.03 (d, 1H), 6.69 (d, 1H), 5.12 (s, 1H), 4.70 (t, 1H), 4.50 (dd, 1H), 4.25 (dd, 1H), 3.71 (s, 1H), 1.78 (s, 3H). LC-MS (ESI): m/z=499 (M+H)$^+$.

Example 124

(2S,3R,5R)-3-((E)-(2-(3-(3,4-dihydroxyphenyl)isoxazole-5-carbonyl)hydrazono)methyl)-3-methyl-7-oxo-4-thia-1-azabicyclo[3.2.0]heptane-2-carboxylic acid 4,4-dioxide

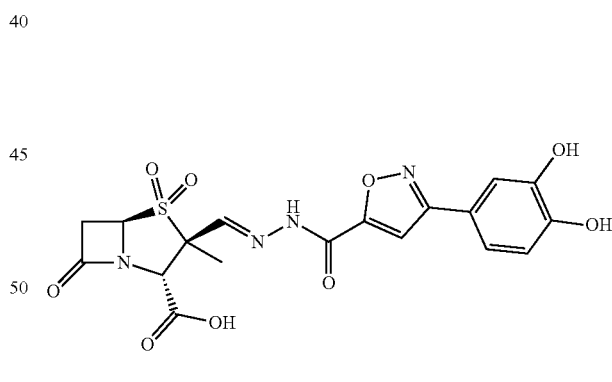

The title compound was prepared using the similar procedure as described in EXAMPLE 1 except 3-(3,4-dihydroxyphenyl)isoxazole-5-carbohydrazide was used in place of 2-chloro-4,5-dihydroxybenzohydrazide. $^1$H NMR (400 MHz, DMSO-d6) δ 12.2 (s, 1H), δ 7.56 (s, 1H), 7.50 (s, 1H), 7.10 (dd, 1H), 7.03 (d, 1H), 6.69 (d, 1H), 5.12 (s, 1H), 4.70 (t, 1H), 4.50 (dd, 1H), 4.25 (dd, 1H), 3.71 (s, 1H), 1.65 (s, 3H). LC-MS (ESI): m/z=465 (M+H)$^+$.

Example 125

(2S,3R,5R)-3-((E)-(2-((4S,5R)-2-(2,3-dihydroxyphenyl)-5-methyl-4,5-dihydrooxazole-4-carbonyl)hydrazono)methyl)-3-methyl-7-oxo-4-thia-1-azabicyclo[3.2.0]heptane-2-carboxylic acid 4,4-dioxide

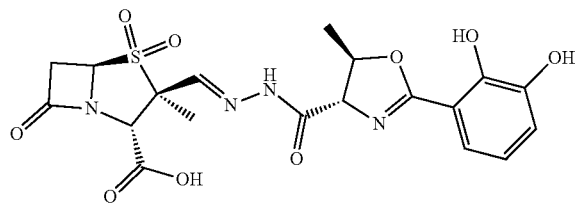 [SMILES: C[C@H]1OC(c2cccc(O)c2O)=N[C@@H]1C(=O)N/N=C/[C@@]1(C)[C@H](C(=O)O)N2C(=O)C[C@H]2S1(=O)=O]

The title compound was prepared using the similar procedure as described in EXAMPLE 1 except (4S,5R)-2-(2,3-dihydroxyphenyl)-5-methyl-4,5-dihydrooxazole-4-carbohydrazide was used in place of 2-chloro-4,5-dihydroxybenzohydrazide. $^1$H NMR (400 MHz, DMSO) δ 11.83 (d, J=40.2 Hz, 1H), 9.18 (d, J=62.8 Hz, 1H), 7.47 (dd, J=88.7, 55.2 Hz, 2H), 6.97 (d, J=7.7 Hz, 1H), 6.74 (t, J=7.8 Hz, 1H), 5.11 (s, 1H), 4.48-4.17 (m, 2H), 3.60 (d, J=15.5 Hz, 2H), 3.23-3.09 (m, 3H), 1.58 (d, J=7.4 Hz, 3H). LC-MS (ESI): m/z=481 (M+H)$^+$.

Example 126

(2S,3R,5R)-3-((E)-(2-((4S,5R)-2-(3,4-dihydroxyphenyl)-5-methyl-4,5-dihydrooxazole-4-carbonyl)hydrazono)methyl)-3-methyl-7-oxo-4-thia-1-azabicyclo[3.2.0]heptane-2-carboxylic acid 4,4-dioxide

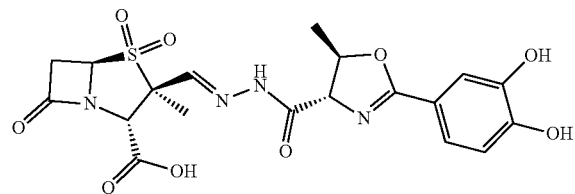 [SMILES: C[C@H]1OC(c2ccc(O)c(O)c2)=N[C@@H]1C(=O)N/N=C/[C@@]1(C)[C@H](C(=O)O)N2C(=O)C[C@H]2S1(=O)=O]

The title compound was prepared using the similar procedure as described in EXAMPLE 1 except (4S,5R)-2-(3,4-dihydroxyphenyl)-5-methyl-4,5-dihydrooxazole-4-carbohydrazide was used in place of 2-chloro-4,5-dihydroxybenzohydrazide. $^1$H NMR (400 MHz, DMSO) δ 12.18 (s, 1H), 7.99 (s, 1H), 7.30 (s, 1H), 6.89 (d, J=85.4 Hz, 2H), 5.34 (s, 1H), 4.98 (s, 1H), 3.76 (d, J=16.2 Hz, 2H), 3.45-3.26 (m, 3H), 1.66 (s, 3H). LC-MS (ESI): m/z=481 (M+H)$^+$.

Example 127

(2S,3R,5R)-3-(((2-(3-(2,3-dihydroxyphenyl)isoxazole-5-carbonyl)hydrazinecarbonyl)oxy)methyl)-3-methyl-7-oxo-4-thia-1-azabicyclo[3.2.0]heptane-2-carboxylic acid 4,4-dioxide

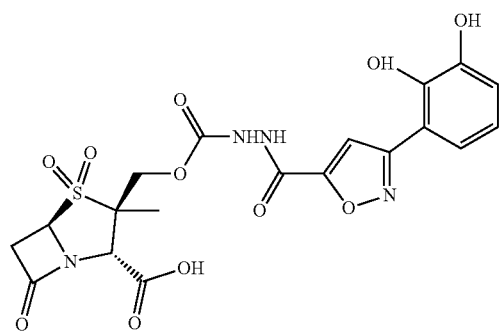

The title compound was prepared using the similar procedure as described in EXAMPLE 69 except 3-(2,3-dihydroxyphenyl)isoxazole-5-carbohydrazide was used in place of 3,4-dihydroxybenzohydrazide. $^1$H NMR (400 MHz, DMSO-d6) δ 14.02 (br, 1H), 11.00 (s, 1H), 9.88 (t, J=12 Hz, 1H), 9.65-9.19 (m, 2H), 7.26 (t, J=8 Hz, 1H), 6.97 (t, J=8 Hz, 1H), 6.83-6.76 (m, 1H), 5.78 (s, 1H), 5.17 (d, J=12 Hz, 1H), 4.74-4.49 (m, 3H), 3.71-3.68 (m, 1H), 3.24-3.17 (m, 2H), 1.49 (s, 3H). LC-MS (ESI): m/z=511 (M+H)$^+$.

Example 128

(2S,3R,5R)-3-(((2-(3-(2,3-dihydroxyphenyl)-4,5-dihydroisoxazole-5-carbonyl)hydrazinecarbonyl)oxy)methyl)-3-methyl-7-oxo-4-thia-1-azabicyclo[3.2.0]heptane-2-carboxylic acid 4,4-dioxide

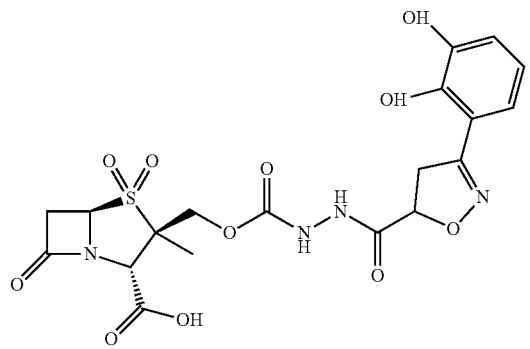 [SMILES: C[C@]1(COC(=O)NNC(=O)C2CC(c3cccc(O)c3O)=NO2)[C@H](C(=O)O)N2C(=O)C[C@H]2S1(=O)=O]

The title compound was prepared using the similar procedure as described in EXAMPLE 69 except 3-(2,3-dihydroxyphenyl)-4,5-dihydroisoxazole-5-carbohydrazide was used in place of 3,4-dihydroxybenzohydrazide. $^1$H NMR (400 MHz, DMSO-d6) δ 13.96 (br, 1H), 12.57 (s, 1H), 10.27 (s, 1H), 9.62 (s, 1H), 9.53 (s, 1H), 9.51 (s, 1H), 9.27 (s, 1H), 9.21 (s, 1H), 7.01 (t, J=8 Hz, 2H), 6.92 (t, J=8 Hz, 2H), 6.76 (t, J=8 Hz, 2H), 5.68 (t, J=8 Hz, 1H), 5.18-5.12 (m, 2H), 4.67 (d, J=12 Hz, 1H), 4.57 (s, 1H), 4.50 (dt, 12, 4 Hz, 1H), 3.89-3.65 (m, 6H), 3.28 (d, J=16 Hz, 1H), 1.50 (s, 3H). LC-MS (ESI): m/z=513 (M+H)$^+$.

Example 129

(2S,3R,5R)-3-(((4-(2-chloro-3,4-dihydroxybenzoyl)piperazine-1-carbonyl)oxy)methyl)-3-methyl-7-oxo-4-thia-1-azabicyclo[3.2.0]heptane-2-carboxylic acid 4,4-dioxide

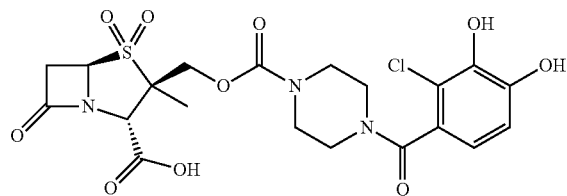 [SMILES: C[C@]1(COC(=O)N2CCN(C(=O)c3ccc(O)c(O)c3Cl)CC2)[C@H](C(=O)O)N2C(=O)C[C@H]2S1(=O)=O]

The title compound was prepared using the similar procedure as described in EXAMPLE 69 except (2-chloro-3,4-dihydroxyphenyl)(piperazin-1-yl)methanone was used in place of 3,4-dihydroxybenzohydrazide. $^1$H NMR (400 MHz, DMSO-d6) δ 13.96 (br, 1H), 10.04 (s, 1H), 9.40 (s, 1H), 6.81 (d, J=8 Hz, 1H), 6.64 (d, J=8 Hz, 1H), 5.17 (s, 1H), 4.61-4.50 (m, 3H), 3.71-3.65 (m, 3H), 3.49-3.26 (m, 8H), 3.18 (s, 2H), 1.50 (s, 3H). LC-MS (ESI): m/z=532 (M+H)$^+$.

Example 130

(2S,3R,5R)-3-(((3-(2-chloro-3,4-dihydroxybenzamido)azetidine-1-carbonyl)oxy)methyl)-3-methyl-7-oxo-4-thia-1-azabicyclo[3.2.0]heptane-2-carboxylic acid 4,4-dioxide

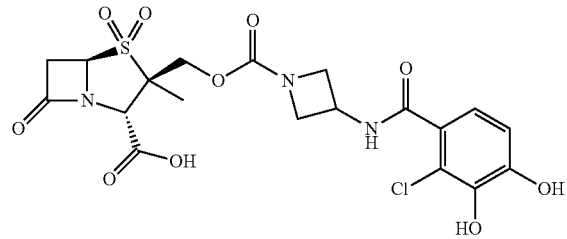 [SMILES: C[C@]1(COC(=O)N2CC(NC(=O)c3ccc(O)c(O)c3Cl)C2)[C@H](C(=O)O)N2C(=O)C[C@H]2S1(=O)=O]

The title compound was prepared using the similar procedure as described in EXAMPLE 69 except N-(azetidin-3-yl)-2-chloro-3,4-dihydroxybenzamide was used in place of 3,4-dihydroxybenzohydrazide. $^1$H NMR (400 MHz, DMSO-d6) δ 10.14 (s, 1H), 9.36 (s, 1H), 8.89 (s, 1H), 6.81 (dd, J=12, 8 Hz, 2H), 6.60 (dd, J=12, 8 Hz, 1H), 5.17 (s, 1H), 4.64-4.58 (m 2H), 4.51 (dd, J=48, 12 Hz, 2H), 4.24 (br, 1H), 3.91 (br, 1H), 3.70 (dd, J=16, 4 Hz, 2H), 3.31-3.27 (m, 2H), 2.25 (s, 1H), 1.51 (s, 3H). LC-MS (ESI): m/z=518 (M+H)$^+$.

Example 131

(2S,3R,5R)-3-(((2-(3-(2-chloro-3,4-dihydroxyphenyl)-4,5-dihydroisoxazole-5-carbonyl)hydrazine-1-carbonyl)oxy)methyl)-3-methyl-7-oxo-4-thia-1-azabicyclo[3.2.0]heptane-2-carboxylic acid 4,4-dioxide

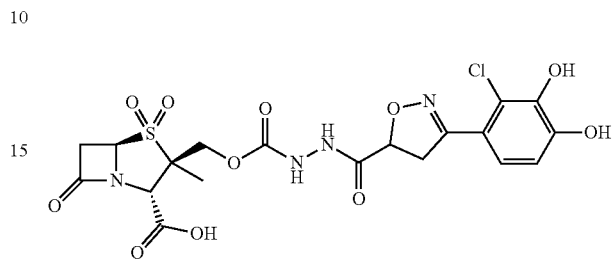

The title compound was prepared using the similar procedure as described in EXAMPLE 69 except 3-(2-chloro-3,4-dihydroxyphenyl)-4,5-dihydroisoxazole-5-carbohydrazide was used in place of 3,4-dihydroxybenzohydrazide. $^1$H NMR (400 MHz, DMSO-d6) δ 9.67 (s, 1H), 7.51 (s, 1H), 6.87 (d, J=7.5 Hz, 1H), 6.72 (d, J=7.5 Hz, 1H), 5.79 (s, 1H), 5.10 (t, J=4.6 Hz, 1H), 4.74-4.61 (m, 2H), 4.39 (t, J=6.2 Hz, 2H), 4.26 (s, 1H), 3.56 (s, 1H), 3.46 (dd, J=12.4, 8.2 Hz, 1H), 3.33 (dd, J=12.4, 4.5 Hz, 1H), 3.21 (dd, J=12.3, 8.2 Hz, 1H), 3.05 (dd, J=12.5, 4.6 Hz, 1H), 1.43 (s, 3H). LC-MS (ESI): m/z=547 (M+H)$^+$.

Example 132

(2S,3R,5R)-3-(((2-(3-(2-chloro-3,4-dihydroxyphenyl)-4,5-dihydroisoxazole-5-carbonyl)hydrazinecarbonyl)oxy)methyl)-3-methyl-7-oxo-4-thia-1-azabicyclo[3.2.0]heptane-2-carboxylic acid 4,4-dioxide

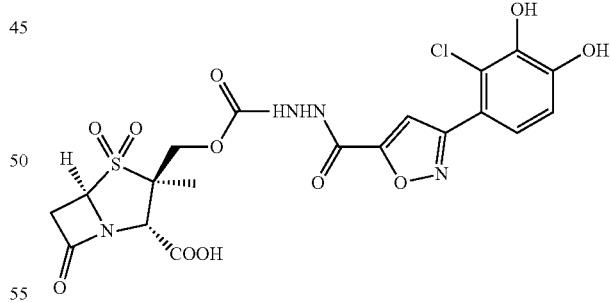

The title compound was prepared using the similar procedure as described in EXAMPLE 69 except 3-(2-chloro-3,4-dihydroxyphenyl)isoxazole-5-carbohydrazide was used in place of 3,4-dihydroxybenzohydrazide. $^1$H NMR (400 MHz, DMSO-d6) δ 14.02 (br, 1H), 10.99 (s, 1H), 10.38 (s, 1H), 9.84 (s, 1H), 9.56 (s, 1H), 7.52 (s, 1H), 7.07 (d, J=8.4 Hz, 1H), 6.90 (d, J=8.4 Hz, 1H), 5.20 (d, J=3.2 Hz, 1H), 4.72 (d, J=12.4 Hz, 1H), 4.62 (s, 1H), 4.56 (d, J=12.8 Hz, 1H), 3.70 (dd, J=16.4, 4.4 Hz, 1H), 3.30 (d, J=16.4 Hz, 1H), 1.53 (s, 3H). LC-MS (ESI): m/z=545 (M+H)$^+$.

Example 133

(2S,3R,5R)-3-(((2-((4S,5R)-2-(2,3-dihydroxyphenyl)-5-methyl-4,5-dihydrooxazole-4-carbonyl)hydrazinecarbonyl)oxy)methyl)-3-methyl-7-oxo-4-thia-1-azabicyclo[3.2.0]heptane-2-carboxylic acid 4,4-dioxide

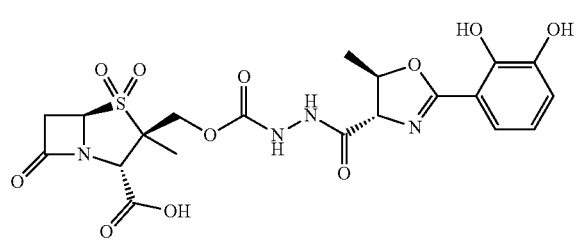 [SMILES: C[C@H]1OC(c2cccc(O)c2O)=N[C@@H]1C(=O)NNC(=O)OC[C@@]1(C)[C@H](C(=O)O)N2C(=O)C[C@H]2S1(=O)=O]

The title compound was prepared using the similar procedure as described in EXAMPLE 69 except (4S,5R)-2-(2,3-dihydroxyphenyl)-5-methyl-4,5-dihydrooxazole-4-carbohydrazide was used in place of 3,4-dihydroxybenzohydrazide. $^1$H NMR (400 MHz, DMSO-d6) δ 14.02 (br, 1H), 10.91 (s, 1H), 10.32 (s, 1H), 7.16 (t, J=7.5 Hz, 1H), 6.88-6.77 (m, 3H), 5.19 (dq, J=8.0, 5.7 Hz, 1H), 5.11 (s, 1H), 4.73-4.61 (m, 2H), 4.50 (dd, J=12.5, 6.0 Hz, 1H), 4.39 (t, J=6.2 Hz, 2H), 4.25 (dd, J=12.4, 6.1 Hz, 1H), 3.98 (d, J=8.1 Hz, 1H), 3.55 (s, 1H), 1.68 (d, J=5.7 Hz, 3H), 1.43 (s, 3H). LC-MS (ESI): m/z=527 (M+H)$^+$.

Example 134

(2S,3R,5R)-3-((((3,4-dihydroxyphenethyl)carbamoyl)oxy)methyl)-3-methyl-7-oxo-4-thia-1-azabicyclo[3.2.0]heptane-2-carboxylic acid 4,4-dioxide

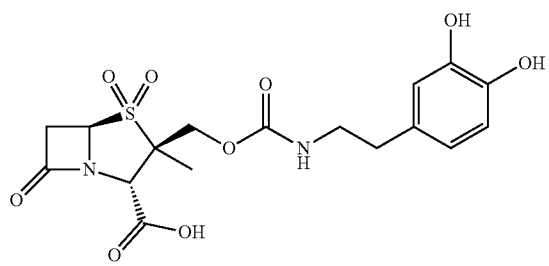 [SMILES: C[C@]1(COC(=O)NCCc2ccc(O)c(O)c2)[C@H](C(=O)O)N2C(=O)C[C@H]2S1(=O)=O]

The title compound was prepared using the similar procedure as described in EXAMPLE 69 except 4-(2-aminoethyl)benzene-1,2-diol was used in place of 3,4-dihydroxybenzohydrazide. $^1$H NMR (400 MHz, DMSO-d6) δ 14.01 (br, 1H), 10.59 (s, 1H), 10.32 (s, 1H), δ 6.64-6.44 (m, 3H), 4.74-4.61 (m, 2H), 4.48 (s, 1H), 4.39 (t, J=6.2 Hz, 2H), 3.59 (s, 1H), 3.50-3.34 (m, 3H), 3.21 (dd, J=12.5, 9.2 Hz, 1H), 2.87 (t, J=6.0 Hz, 2H), 1.43 (s, 3H). LC-MS (ESI): m/z=429 (M+H)$^+$.

Example 135

(2S,3R,5R)-3-(5-(3,4-dihydroxybenzoyl)isoxazol-3-yl)-3-methyl-7-oxo-4-thia-1-azabicyclo[3.2.0]heptane-2-carboxylic acid 4,4-dioxide

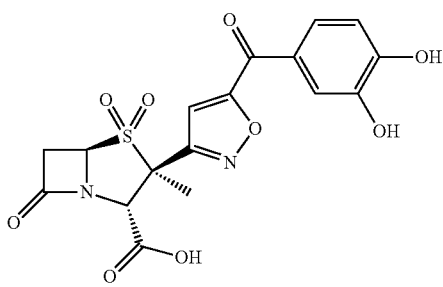 [SMILES: C[C@]1(c2cc(C(=O)c3ccc(O)c(O)c3)on2)[C@H](C(=O)O)N2C(=O)C[C@H]2S1(=O)=O]

The title compound was prepared using the similar procedure as described in EXAMPLE 101 except 1-(3,4-bis(benzyloxy)phenyl)prop-2-yn-1-one was used in place of 4,4'-(((3-chloro-4-ethynyl-1,2-phenylene)bis(oxy))bis(methylene))bis(methoxybenzene). $^1$H NMR (400 MHz, DMSO) δ 7.72 (s, 1H), 7.52 (dd, J=6.3, 2.0 Hz, 2H), 6.97 (d, J=8.9 Hz, 1H), 5.43 (s, 1H), 5.26 (s, 1H), 3.75 (dd, J=16.6, 4.6 Hz, 2H), 1.94 (s, 3H). LC-MS (ESI): m/z=423 (M+H)$^+$.

Example 136

(2S,3S,5R)-3-((4-((E)-(2-(2-chloro-3,4-dihydroxybenzoyl)hydrazono)methyl)-1H-imidazol-1-yl)methyl)-3-methyl-7-oxo-4-thia-1-azabicyclo[3.2.0]heptane-2-carboxylic acid 4,4-dioxide

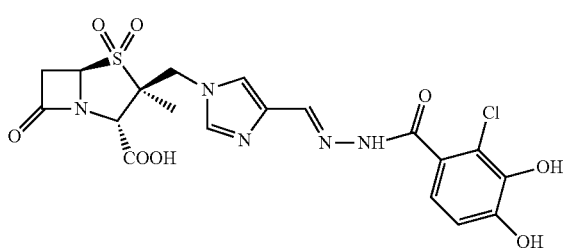 [SMILES: C[C@]1(Cn2cnc(/C=N/NC(=O)c3ccc(O)c(O)c3Cl)c2)[C@H](C(=O)O)N2C(=O)C[C@H]2S1(=O)=O]

Figure 19:
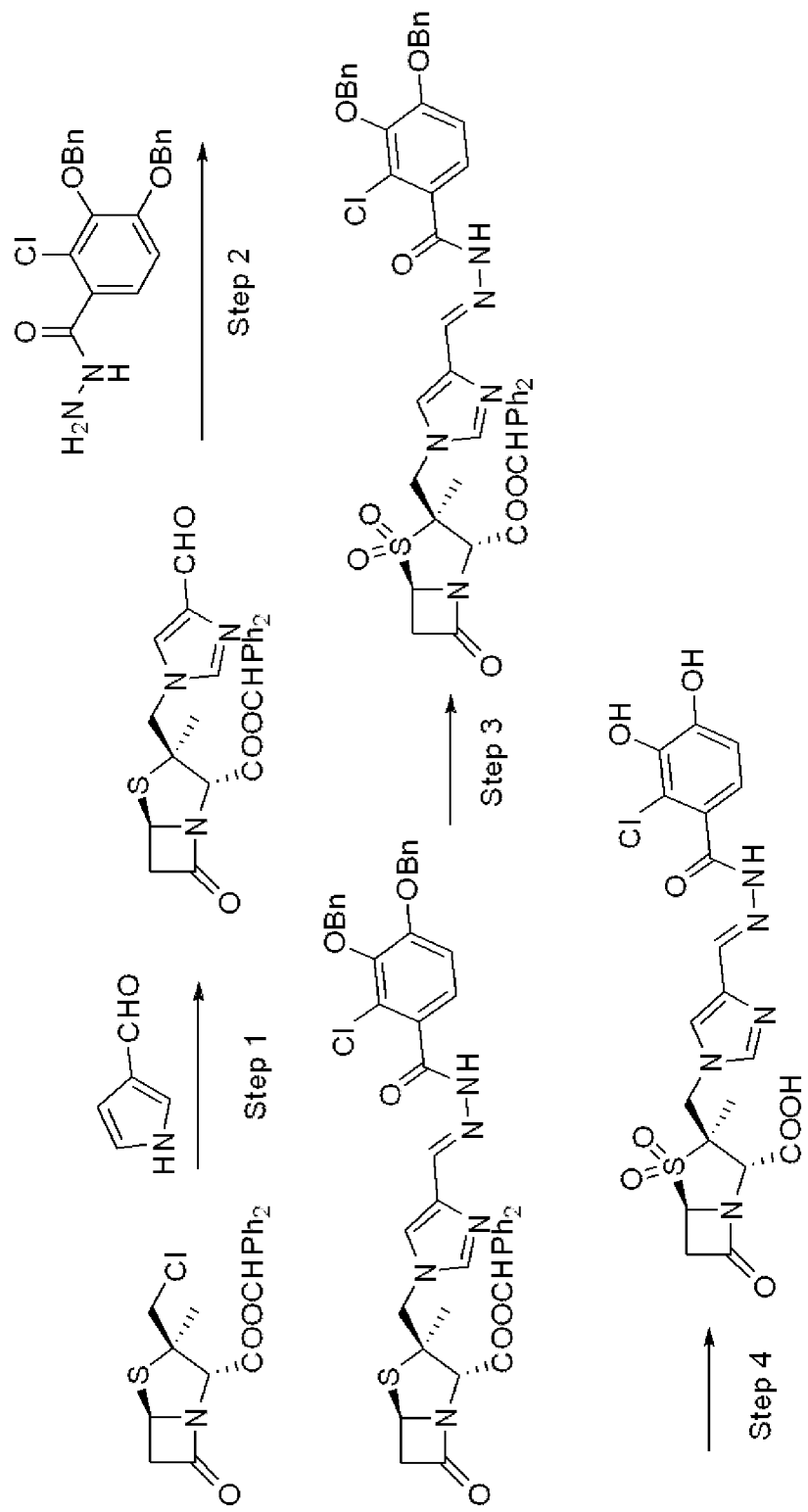

FIG. 19 shows a synthetic scheme for the preparation of this compound. Step 1, To a solution of benzhydryl (2S,3R,5R)-3-(chloromethyl)-3-methyl-7-oxo-4-thia-1-azabicyclo[3.2.0]heptane-2-carboxylate (1.5 g, 3.7 mmol) in acetonitrile (15 mL) and H$_2$O (5 mL) was added 1H-pyrrole-3-carbaldehyde (0.35 g, 3.7 mmol) and sodium bicarbonate (0.62 g, 7.4 mmol). The mixture was stirred at room temperature for 10 hours. Then the solvent was extracted by ethyl acetate, the residue was evaporated in vacuo to afford (2S,3S,5R)-benzhydryl 3-((4-formyl-1H-imidazol-1-yl)methyl)-3-methyl-7-oxo-4-thia-1-azabicyclo[3.2.0]heptane-2-carboxylate (1 g, yield 58.8%). LC-MS (ESI): m/z=462.

Step 2, To a solution of benzhydryl (2S,3S,5R)-3-((4-formyl-1H-imidazol-1-yl)methyl)-3-methyl-7-oxo-4-thia-1-azabicyclo[3.2.0]heptane-2-carboxylate (1 g, 2.2 mmol) in DCM (10 mL) and EtOH (10 mL) was added 3,4-bis(benzyloxy)-2-chlorobenzohydrazide (0.84 g, 2.2 mmol). The mixture was stirred at room temperature for 6 hours. Then the solvent was evaporated in vacuo, the residue was purified by flash chromatography (DCM:MeOH=20:1) to afforded benzhydryl (2S,3S,5R)-3-((4-((E)-(2-(3,4-bis(benzyloxy)-2-chlorobenzoyl)hydrazono)methyl)-1H-imidazol-1-yl)methyl)-3-methyl-7-oxo-4-thia-1-azabicyclo[3.2.0]heptane-2-carboxylate as white solid (0.85 g, yield 47.4%). LC-MS (ESI): m/z=826.

Step 3, To a solution of benzhydryl (2S,3S,5R)-3-((4-((E)-(2-(3,4-bis(benzyloxy)-2-chlorobenzoyl)hydrazono)methyl)-1H-imidazol-1-yl)methyl)-3-methyl-7-oxo-4-thia-1-azabicyclo[3.2.0]heptane-2-carboxylate (0.85 g, 1.0 mmol) in acetic acid (10 mL) acetone (2 mL) and H₂O (2 mL) was cooled to 0° C., then was slowly added potassium permanganate (0.32 g, 2.0 mmol). The mixture was stirred at room temperature for 2 hours. Then the reaction was quenched by adding sodium metabisulfite solution and was extracted by ethyl acetate. The solvent was evaporated in vacuo, the residue was purified by flash chromatography (DCM:MeOH=20:1) to afford Benzhydryl (2S,3S,5R)-3-((4-((E)-(2-(3,4-bis(benzyloxy)-2-chlorobenzoyl)hydrazono)methyl)-1H-imidazol-1-yl)methyl)-3-methyl-7-oxo-4-thia-1-azabicyclo[3.2.0]heptane-2-carboxylate 4,4-dioxide as white solid (0.3 g, yield 34.9%). LC-MS (ESI): m/z=858.

Step 4, Benzhydryl (2S,3S,5R)-3-((4-((E)-(2-(3,4-bis(benzyloxy)-2-chlorobenzoyl)hydrazono)methyl)-1H-imidazol-1-yl)methyl)-3-methyl-7-oxo-4-thia-1-azabicyclo[3.2.0]heptane-2-carboxylate 4,4-dioxide (0.3 g, 0.35 mmol) was dissolved into 10 mL of THF, Pd/C (10%, 100 mg) was added and the solution was stirred under charged hydrogen balloon for 8 hours. Filtration to remove the palladium, then the solvent was evaporated in vacuo, the residue was purified by column chromatography (silica gel, DCM:MeOH=20:1) to afford the title compound as white solid (85 mg, yield 47.5%). ¹H NMR (400 MHz, DMSO) δ 11.58 (s, 1H), 10.14 (s, 1H), 9.34 (s, 1H), 8.31 (s, 1H), 7.82 (s, 1H), 7.39 (s, 1H), 7.25 (dd, J=19.7, 7.0 Hz, 1H), 6.87 (d, J=8.2 Hz, 1H), 6.82-6.77 (m, 1H), 5.16 (d, J=3.2 Hz, 1H), 5.09 (d, J=15.4 Hz, 1H), 4.98 (d, J=15.5 Hz, 1H), 4.62 (s, 1H), 3.32 (s, 2H), 1.45 (s, 3H). LC-MS (ESI): m/z=512 (M+H)⁺.

Example 137

(2S,3R,5R)-3-((E)-(((1-(2-chloro-3,4-dihydroxybenzoyl)piperidin-4-yl)oxy)imino)methyl)-3-methyl-7-oxo-4-thia-1-azabicyclo[3.2.0]heptane-2-carboxylic acid 4,4-dioxide

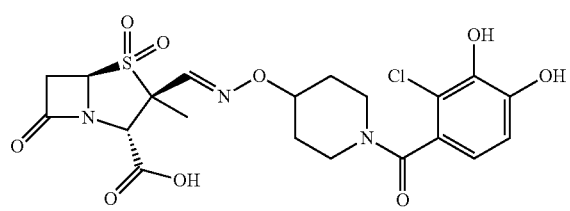 [SMILES: C[C@]1(/C=N/OC2CCN(C(=O)c3ccc(O)c(O)c3Cl)CC2)[C@H](C(=O)O)N2C(=O)C[C@H]2S1(=O)=O]

The title compound was prepared using the similar procedure as described in EXAMPLE 119 except (4-(aminooxy)piperidin-1-yl)(2-chloro-3,4-dihydroxyphenyl)methanone was used in place of N-(4-(aminooxy)phenyl)-2-chloro-3,4-dihydroxybenzamide. ¹H NMR (400 MHz, DMSO-d6) δ 14.01 (br, 1H), 10.58 (s, 1H), 10.32 (s, 1H), 7.48 (s, 1H), 7.16 (d, J=7.5 Hz, 1H), 6.65 (d, J=7.5 Hz, 1H), 6.06 (s, 1H), 4.70 (t, J=9.3 Hz, 1H), 4.56-4.47 (m, 1H), 3.66 (dt, J=12.4, 5.3 Hz, 2H), 3.50-3.35 (m, 3H), 3.21 (dd, J=12.4, 9.3 Hz, 1H), 2.39 (dqd, J=12.8, 5.4, 2.2 Hz, 2H), 1.82 (dqd, J=12.9, 5.4, 2.2 Hz, 2H), 1.56 (s, 3H). LC-MS (ESI): m/z=516 (M+H)⁺.

Example 138

(2S,3R,5R)-3-((E)-(((1-(2-chloro-3,4-dihydroxybenzoyl)azetidin-3-yl)oxy)imino)methyl)-3-methyl-7-oxo-4-thia-1-azabicyclo[3.2.0]heptane-2-carboxylic acid 4,4-dioxide

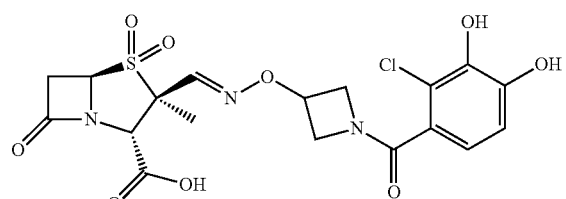

The title compound was prepared using the similar procedure as described in EXAMPLE 119 except (3-(aminooxy)azetidin-1-yl)(2-chloro-3,4-dihydroxyphenyl)methanone was used in place of N-(4-(aminooxy)phenyl)-2-chloro-3,4-dihydroxybenzamide. ¹H NMR (400 MHz, DMSO-d6) δ 14.01 (br, 1H), 10.58 (s, 1H), 10.32 (s, 1H), 7.49 (s, 1H), 7.27 (s, 1H), 6.66 (s, 1H), 5.41 (s, 1H), 4.70 (s, 1H), 4.59 (s, 1H), 4.20-4.04 (m, 2H), 3.95-3.80 (m, 2H), 3.46 (s, 1H), 3.21 (s, 1H), 1.58-1.54 (m, 3H). LC-MS (ESI): m/z=488 (M+H)⁺.

Example 139

BIOLOGICAL ACTIVITY

MIC Determination

Minimum inhibitory concentration (MIC) is determined by a broth microdilution method according to the recommendation of the Clinical and Laboratory Standards Institute (CLSI) with minor modification. In all MIC tests, iron-depleted cation-adjusted Mueller-Hinton broth (supplemented with 2,2-dipyridyl at 160 μM) was used to complex iron and thereby induce iron uptake systems. Strains of an ESKAPE panel (*E. faecium* ATCC 700221, *S. aureus* ATCC 29213, *K. pneumoniae* ATCC 43816, *A. baumannii* ATCC 19606, *P. aeruginosa* ATCC 27853 and *Escherichia coli* ATCC 25922) were obtained originally from the American Type Culture Collection (ATCC) and used for MIC determinations of compounds. The bacteria inoculum in the test is ~5×10⁵ CFU/well. MIC is defined as the minimum concentration after incubation at 37° C. for 18-20 hours in the presence of 5% CO₂ to prevent visible bacterial growth. The results are summarized in Table 2 and Table 3 below.

TABLE 2

MIC (µg/mL) of selected compounds and comparators against ESKAPE bacterial strain

| Compounds | E. faecium ATCC 700221 | S. aureus ATCC 29213 | K. pneumoniae ATCC 43816 | A. baumannii ATCC 19606 | P. aeruginosa ATCC 27853 | E. coli ATCC 25922 |
|---|---|---|---|---|---|---|
| Example 5 | >128 | 128 | 32 | 4 | >128 | 64 |
| Example 20 | >128 | 32 | >128 | 64 | >128 | >128 |
| Example 28 | >128 | >128 | >128 | >128 | >128 | >128 |
| Example 29 | >128 | >128 | >128 | >128 | >128 | >128 |
| Example 35 | >128 | 128 | >128 | >128 | >128 | >128 |
| Example 38 | >128 | 128 | 32 | 8 | >128 | >128 |
| Example 42 | >128 | 128 | >128 | 1 | >128 | >128 |
| Example 43 | NA | >128 | >128 | 8 | >128 | >128 |
| Example 60 | >128 | >128 | 16 | 2 | >128 | >128 |
| Example 62 | >128 | 128 | >128 | 4 | >128 | >128 |
| Example 64 | >128 | 64 | 128 | 8 | >128 | >128 |
| Example 67 | >128 | 128 | 128 | 4 | >128 | >128 |
| Example 70 | >128 | >128 | >128 | 1 | >128 | >128 |
| Example 76 | >128 | >128 | >128 | 1 | >128 | >128 |
| Example 77 | >128 | >128 | 16 | 0.25 | >128 | 64 |
| Example 80 | >128 | >128 | 16 | 0.25 | >128 | 64 |
| Example 112 | >64 | >64 | >64 | 32 | >64 | >64 |
| Example 114 | >128 | 16 | 2 | <0.06 | >128 | 8 |
| Example 117 | >128 | >128 | >128 | 4 | >128 | >128 |
| Example 118 | >128 | >128 | >128 | >128 | >128 | >128 |
| Meropenem | >128 | 0.125 | <0.06 | 1 | 0.5 | <0.06 |
| Imipenem | >128 | <0.06 | 0.5 | 0.25 | 1 | 0.25 |
| Sulbactam | >128 | >128 | 64 | 0.5 | >128 | 32 |

TABLE 3

MIC (µg/mL) of selected compounds alone and in combination with antibiotics against *A. baumannii* clinical isolates

| Cpds. | Compounds alone A.b TNP 4170 4 | Compounds alone A.b TNP 4170 8 | Compounds alone A.b TNP 4170 9 | Compounds + sulbactam (1:1) A.b TNP 4170 4 | Compounds + sulbactam (1:1) A.b TNP 4170 8 | Compounds + sulbactam (1:1) A.b TNP 4170 9 | Compounds + meropenem (1:1) A.b TNP 4170 4 | Compounds + meropenem (1:1) A.b TNP 4170 8 | Compounds + meropenem (1:1) A.b TNP 4170 9 | Compounds + Imipenem (1:1) A.b TNP 4170 4 | Compounds + Imipenem (1:1) A.b TNP 4170 8 | Compounds + Imipenem (1:1) A.b TNP 4170 9 |
|---|---|---|---|---|---|---|---|---|---|---|---|---|
| Ex. 28 | >128 | >128 | >128 | 4 | 8 | 8 | 8 | 8 | 4 | NT | NT | NT |
| Ex. 29 | >128 | >128 | >128 | 8 | 32 | 32 | 32 | 32 | 32 | NT | NT | NT |
| Ex. 5 | >128 | >128 | 32 | 4 | 8 | 4 | 4 | 4 | 2 | NT | NT | NT |
| Ex. 20 | >128 | >128 | >128 | 4 | 8 | 16 | 8 | 8 | 8 | NT | NT | NT |
| Ex. 64 | >128 | >128 | >128 | 4 | 8 | 4 | 2 | 4 | 2 | NT | NT | NT |
| Ex. 62 | >128 | >128 | >128 | 8 | 8 | 2 | 4 | 4 | 2 | NT | NT | NT |
| Ex. 38 | >128 | >128 | >128 | 4 | 8 | 8 | 4 | 4 | 2 | NT | NT | NT |
| Ex. 42 | >128 | >128 | >128 | 8 | 8 | 4 | 2 | 2 | 2 | NT | NT | NT |
| Ex. 43 | >128 | >128 | >128 | 4 | 8 | 4 | 4 | 4 | 4 | 8 | 8 | 4 |
| Ex. 70 | 8 | 16 | 8 | 4 | 8 | 4 | 8 | 8 | 4 | NT | NT | NT |
| Ex. 76 | >128 | >128 | >128 | 8 | 16 | 8 | 16 | 32 | 16 | NT | NT | NT |
| Ex. 80 | >128 | >128 | >128 | 4 | 32 | 8 | 16 | 64 | 32 | NT | NT | NT |
| Ex. 77 | >128 | >128 | >128 | 8 | 32 | 16 | 16 | 32 | 16 | NT | NT | NT |
| Ex. 60 | 64 | >128 | >128 | 1 | 8 | 8 | 2 | 2 | 2 | 2 | 2 | 1 |
| Ex. 67 | >128 | >128 | >128 | 1 | 8 | 8 | 4 | 2 | 4 | 4 | 4 | 8 |
| Ex. 117 | 64 | 128 | 64 | 4 | 4 | 4 | 8 | 8 | 8 | NT | NT | NT |
| Ex. 118 | >128 | >128 | >128 | 16 | >128 | >128 | 128 | >128 | >128 | NT | NT | NT |
| Ex. 35 | >128 | >128 | >128 | 4 | 16 | 4 | 32 | 1 | 32 | NT | NT | NT |
| Ex. 112 | >64 | >64 | >64 | 2 | 8 | 2 | 16 | 16 | 8 | NT | NT | NT |
| Ex. 114 | >128 | >128 | >128 | 8 | 32 | 16 | 64 | 64 | 64 | NT | NT | NT |
| Meropenem | 64 | 128 | 128 | NT | NT | NT | NT | NT | NT | NT | NT | NT |
| Imipenem | 16 | 32 | 32 | NT | NT | NT | NT | NT | NT | NT | NT | NT |
| Sulbactam | 8 | 32 | 32 | NT | NT | NT | NT | NT | NT | NT | NT | NT |

NT: No test

β-Lactamase Inhibitor Activity Determination

Hydrolytic inactivation of the β-lactam antibiotics by β-lactamases is the most widespread drug resistant mechanism and the most challenge clinically among Gram-negative bacterial pathogens. Based on the amino acid sequences, the β-lactamases are grouped into four classes (Ambler classification), of which A, C and D are serine hydrolases and B encompasses metallo-β-lactamases. The $IC_{50}$ of selected derivatives disclosed herein (identified with reference to example number) plus six reference β-lactam or β-lactamase inhibitors were determined against 7 representative β-lactamases of various classes in a standard spectrophotometric assay of nitrocefin hydrolysis. The results are summarized in Table 4 below. The assay is performed in 384-well plate. The seven recombinant β-lactamases AmpC_AB (from *A. baumannii*), AmpC_PA (from *P. aeruginosa*), KPC-2, NDM-1, IMP-1, VIM-1 and OXA 24/40) are expressed and purified. The reaction buffer for class A, C and D enzymes is 100 mM $Na_2HPO_4$—$KH_2PO_4$ (pH 7.1) plus 0.005% Tween-20, and for class B enzymes 10 μM $ZnSO_4$ is added. The control compounds include Clavulanate, Sulbactam, Tazobactam, Avibactam, Relebactam and Zidebactam. The 50 μL of reaction solution composed of 2 pM of β-lactamase, 200 μM of nitrocefin and series of 3-fold dilutions of test or control compounds are added by Cybio SELMA system into 384-plate and incubated in dark at 25° C. for 2 hours. The $OD_{490}$ is read in MC SpectraMax Plus384 plate reader. The % inhibition at each concentration is calculated by [1−(compound OD-no enzyme average OD)/(enzyme average OD-non-enzyme average OD)]× 100% and the $IC_{50}$ is calculated by XLfit. The $IC_{50}$ of Avibactam and Relebactam from the assay are consistent with historical data, therefore validates the assay method. The results demonstrate that the testing compounds have strong inhibitory activities against AmpC_AB, AmpC_PA of Class C β-lactamase and OXA24/40 of class D β-lactamases with $IC_{50}$ range of 409-65,160 nM. Except the example 70 showing weak activity against KPC-2 of class A and example 7 against VIM-1 of class B, other Examples show no detected activities against class A and B β-lactamases.

What is claimed is:

1. A compound having a formula of:

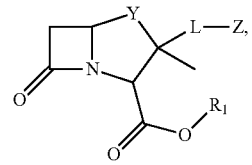

or a stereoisomer, pharmaceutically acceptable salt, solvate, prodrug, or deuterium-exchanged compound thereof, wherein $R_1$ is hydrogen, a pharmaceutically acceptable salt forming agent, or an ester residue;

Y is independently selected from —S—, —SO—, and —$SO_2$—;

L is one or a combination of groups selected from:
($C_1$-$C_8$)alkylene, ($C_3$-$C_8$)cycloalkylene containing one to three heteroatoms, arylene, heteroarylene, ($C_3$-$C_8$) heterocycloalkylene, —C(=O)—, —O—, —S(O)$_n$—, wherein n is 0, 1, or 2, —N($R_2$)—, —C($R_3$)=C($R_4$)—, and —C≡N—, wherein $R_2$, $R_3$ and $R_4$ are selected from hydrogen, ($C_1$-$C_8$)alkyl, ($C_3$-$C_8$)cycloalkyl, ($C_1$-$C_8$)alkyloxy, aryl, heteroaryl, and ($C_3$-$C_8$)heterocycloalkyl, or $R_3$ and $R_4$ join together to form a bond; and Z is an iron chelating moiety selected from

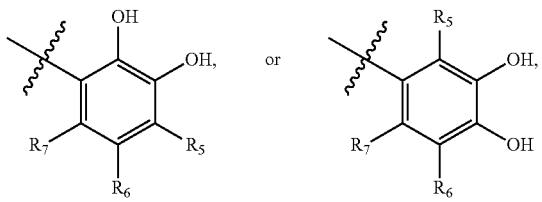

TABLE 4

| $IC_{50}$ (nM) of exemplary compounds against various β-lactamases | | | | | | | |
|---|---|---|---|---|---|---|---|
| Compounds | AmpC_AB | AmpC_PA | KPC-2 | OXA 24/40 | NDM-1 | IMP-1 | VIM-1 |
| Clavulanate | >200000 | >200000 | >200000 | >200000 | >200000 | >200000 | >200000 |
| Sulbactam | 10300.32 | 10316.82 | 53399.27 | >200000 | >200000 | >200000 | >200000 |
| Tazobactam | 23822.28 | 1175.87 | 90207.95 | 122597.83 | >200000 | >200000 | >200000 |
| Avibactam | 2607.27 | 873.46 | 296.22 | 99395.24 | >200000 | >200000 | >200000 |
| Relebactam | 891.79 | 372.21 | 457.52 | >200000 | >200000 | >200000 | >200000 |
| Zidebactam | 248.07 | 101.62 | 2361.77 | 50953.91 | >200000 | >200000 | >200000 |
| Example 3 | 720.18 | 2418.14 | >200000 | 2302.83 | >200000 | >200000 | >200000 |
| Example 5 | 1042.20 | 1716.43 | >200000 | 11570.94 | >200000 | >200000 | >200000 |
| Example 7 | 596.47 | 1519.72 | >200000 | 6029.71 | >200000 | >200000 | 58214.71 |
| Example 19 | 5758.21 | 3678.22 | >200000 | 2485.01 | >200000 | >200000 | >200000 |
| Example 23 | 717.51 | 2451.63 | >200000 | 3181.44 | >200000 | >200000 | >200000 |
| Example 38 | 7623.08 | 2375.29 | >200000 | 5931.10 | >200000 | >200000 | >200000 |
| Example 64 | 473.73 | 641.21 | >200000 | 5765.99 | >200000 | >200000 | >200000 |
| Example 69 | 3602.93 | 8596.88 | >200000 | 65160.24 | >200000 | >200000 | >200000 |
| Example 70 | 7179.35 | 9142.31 | 139922.06 | 29624.59 | >200000 | >200000 | >200000 | wherein $R_5$, $R_6$ and $R_7$ are independently hydrogen, hydroxyl, halogen, nitrile, nitro, amino, $CF_3$, $OCF_3$, alkyl, alkylamino, alkoxy, aryl, or heteroaryl, or wherein two of $R_5$, $R_6$ and $R_7$ join together to form a 5-8 membered ring.

2. The compound of claim 1, wherein L comprises carbon or nitrogen atoms further substituted by one to three substituents.

3. The compound of claim 1, wherein the 5-8 membered ring formed by two of $R_5$, $R_6$ and $R_7$ is further substituted.

4. The compound of claim 1, wherein Y is —$SO_2$—.

5. The compound of claim 1, wherein L is selected from

—CH=N—N($R_2$)—X—,
—$CH_2$OC(O)—N($R_2$)—X—, —CH=N—O—X—,
—$CH_2$OC(O)—X—, —$CH_2$N($R_2$)—X—,

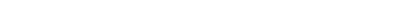, ,

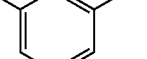, or 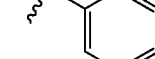, wherein X is one or a combination of two to five groups selected from ($C_1$-$C_8$)alkylene, ($C_3$-$C_8$)cycloalkylene, ($C_3$-$C_8$)heterocycloalkylene, arylene, heteroarylene, —O—, —N($R_2$)—, and —C(O)—, and wherein $R_2$ is hydrogen, ($C_1$-$C_8$)alkyl, ($C_3$-$C_8$)cycloalkyl, ($C_1$-$C_8$)alkyloxyl, aryl, heteroaryl, or ($C_3$-$C_8$)heterocycloalkyl.

6. The compound of claim 1, wherein L is ($C_3$-$C_8$) heterocycloalkylene and wherein the ($C_3$-$C_8$)heterocycloalkylene is unsaturated.

7. The compound of claim 1, wherein Z is selected from:

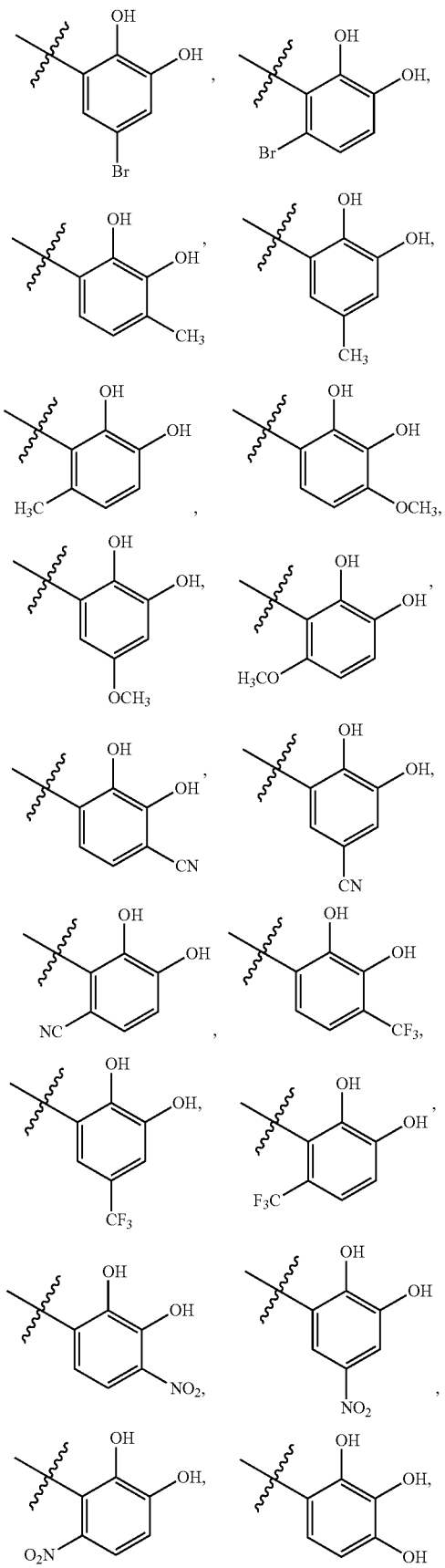

-continued

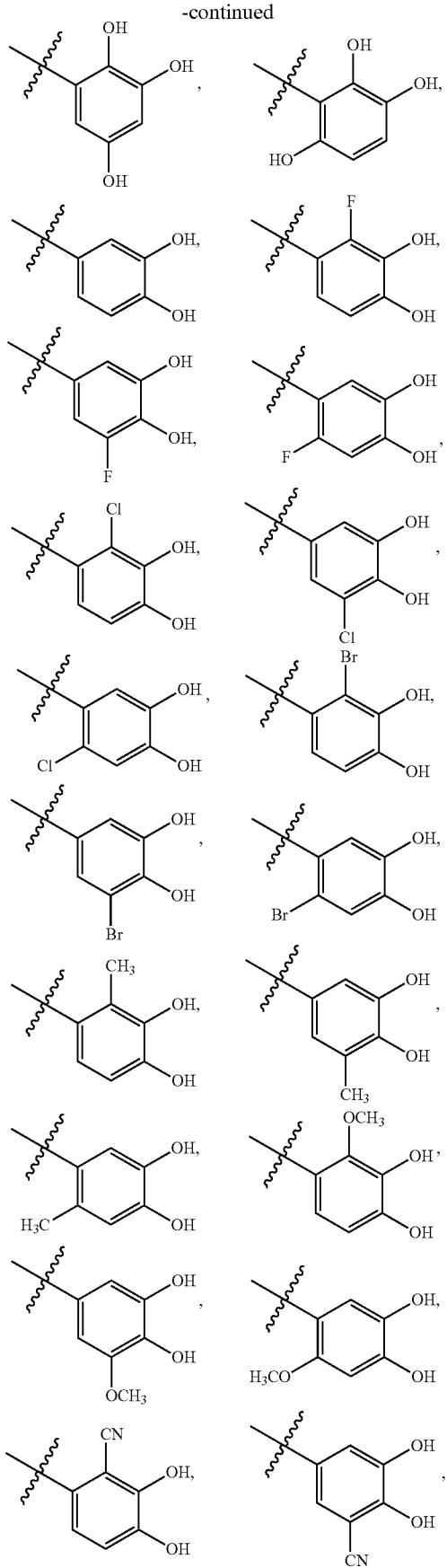

-continued

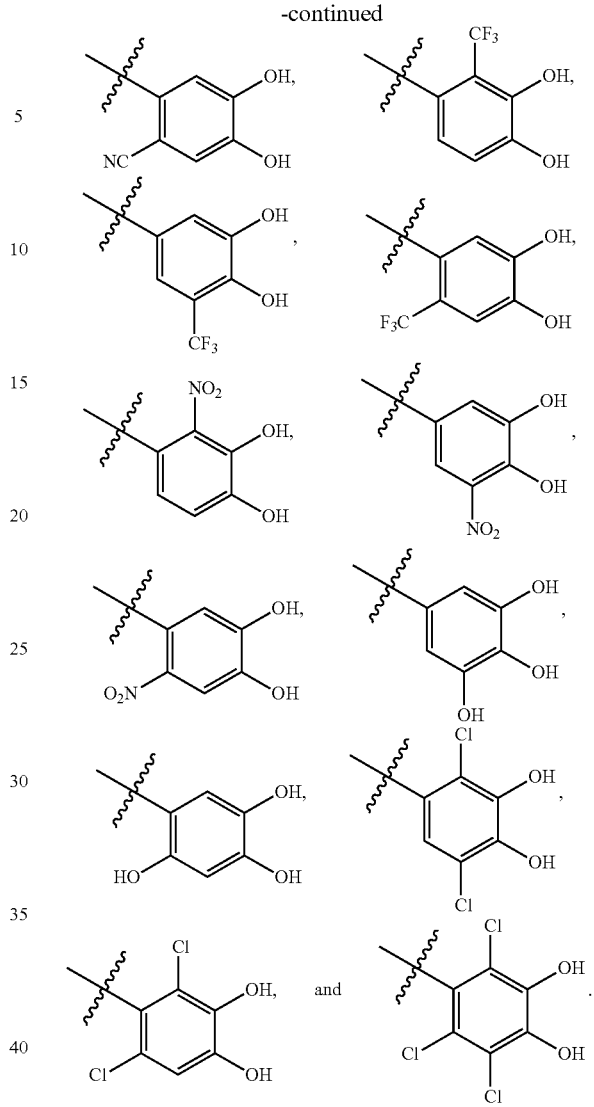

8. A pharmaceutical composition comprising a pharmaceutically effective amount of a compound of claim 1 in combination with a pharmaceutically acceptable carrier.

9. The pharmaceutical composition of claim 8, further comprising one or more additional antibacterial agents.

10. A method of treating or preventing a microbial infection in a subject in need of such treatment by administering the pharmaceutical composition of claim 8.

11. A compound selected from:
(2S,3R,5R)-3-((E)-(2-(2-chloro-4,5-dihydroxybenzoyl)hydrazono)methyl)-3-methyl-7-oxo-4-thia-1-azabicyclo[3.2.0]heptane-2-carboxylic acid 4,4-dioxide;
(2S,3R,5R)-3-methyl-7-oxo-3-((E)-(2-(2,3,4-trihydroxybenzoyl)hydrazono)methyl)-4-thia-1-azabicyclo[3.2.0]heptane-2-carboxylic acid 4,4-dioxide;
(2S,3R,5R)-3-((E)-(2-(2-chloro-3,4-dihydroxybenzoyl)-2-methylhydrazono)methyl)-3-methyl-7-oxo-4-thia-1-azabicyclo[3.2.0]heptane-2-carboxylic acid 4,4-dioxide;
(2S,3R,5R)-3-((E)-(2-(2,5-dichloro-3,4-dihydroxybenzoyl)hydrazono)methyl)-3-methyl-7-oxo-4-thia-1-azabicyclo[3.2.0]heptane-2-carboxylic acid 4,4-dioxide;

(2S,3R,5R)-3-((E)-(2-(3,4-dihydroxybenzoyl)hydrazono)
methyl)-3-methyl-7-oxo-4-thia-1-azabicyclo[3.2.0]
heptane-2-carboxylic acid 4,4-dioxide;

(2S,3R,5R)-3-methyl-7-oxo-3-((E)-(2-(3,4,5-trihydroxy-
benzoyl)hydrazono)methyl)-4-thia-1-azabicyclo[3.2.0]
heptane-2-carboxylic acid 4,4-dioxide;

(2S,3R,5R)-3-((E)-(2-(3,4-dihydroxybenzoyl)-2-methyl-
hydrazono)methyl)-3-methyl-7-oxo-4-thia-1-azabicy-
clo[3.2.0]heptane-2-carboxylic acid 4,4-dioxide;

(2S,3R,5R)-3-((E)-(2-(2-bromo-3,4-dihydroxybenzoyl)
hydrazono)methyl)-3-methyl-7-oxo-4-thia-1-azabicy-
clo[3.2.0]heptane-2-carboxylic acid 4,4-dioxide;

(2S,3R,5R)-3-methyl-7-oxo-3-((E)-(2-(2,3,6-trichloro-4,
5-dihydroxybenzoyl)hydrazono)methyl)-4-thia-1-
azabicyclo[3.2.0]heptane-2-carboxylic acid 4,4-diox-
ide;

(2S,3R,5R)-3-((E)-(2-(2,6-dichloro-3,4-dihydroxyben-
zoyl)hydrazono)methyl)-3-methyl-7-oxo-4-thia-1-
azabicyclo[3.2.0]heptane-2-carboxylic acid 4,4-diox-
ide;

(2S,3R,5R)-3-((E)-(2-(2-fluoro-3,4-dihydroxybenzoyl)
hydrazono)methyl)-3-methyl-7-oxo-4-thia-1-azabicy-
clo[3.2.0]heptane-2-carboxylic acid 4,4-dioxide;

(2S,3R,5R)-3-((E)-(2-(3,4-dihydroxy-2-methylbenzoyl)
hydrazono)methyl)-3-methyl-7-oxo-4-thia-1-azabicy-
clo[3.2.0]heptane-2-carboxylic acid 4,4-dioxide;

(2S,3R,5R)-3-((E)-(2-(2-(3,4-dihydroxyphenyl)acetyl)
hydrazono)methyl)-3-methyl-7-oxo-4-thia-1-azabicy-
clo[3.2.0]heptane-2-carboxylic acid 4,4-dioxide;

(2S,3R,5R)-3-((E)-(2-((R)-2-((tert-butoxycarbonyl)
amino)-3-(3,4-dihydroxyphenyl)propanoyl)hydra-
zono)methyl)-3-methyl-7-oxo-4-thia-1-azabicyclo
[3.2.0]heptane-2-carboxylic acid 4,4-dioxide;

(2S,3R,5R)-3-((E)-(2-(3-chloro-4,5-dihydroxybenzoyl)
hydrazono)methyl)-3-methyl-7-oxo-4-thia-1-azabicy-
clo[3.2.0]heptane-2-carboxylic acid 4,4-dioxide;

(2S,3R,5R)-3-((E)-(2-(2-chloro-3,4-dihydroxybenzoyl)
hydrazono)methyl)-3-methyl-7-oxo-4-thia-1-azabicy-
clo[3.2.0]heptane-2-carboxylic acid 4,4-dioxide;

(2S,3R,5R)-3-((E)-(2-(3-(3,4-dihydroxyphenyl)pro-
panoyl)hydrazono)methyl)-3-methyl-7-oxo-4-thia-1-
azabicyclo[3.2.0]heptane-2-carboxylic acid 4,4-diox-
ide;

(2S,3R,5R)-3-((E)-(2-(2,5-dihydroxy-3,6-dimethylben-
zoyl)hydrazono)methyl)-3-methyl-7-oxo-4-thia-1-
azabicyclo[3.2.0]heptane-2-carboxylic acid 4,4-diox-
ide;

(2S,3R,5R)-3-((E)-(2-(2,3-dihydroxybenzoyl)hydrazono)
methyl)-3-methyl-7-oxo-4-thia-1-azabicyclo[3.2.0]
heptane-2-carboxylic acid 4,4-dioxide;

(2S,3R,5R)-3-((E)-(2-(1-(2-chloro-3,4-dihydroxyben-
zoyl)pyrrolidine-3-carbonyl)hydrazono)methyl)-3-
methyl-7-oxo-4-thia-1-azabicyclo[3.2.0]heptane-2-
carboxylic acid 4,4-dioxide;

(2S,3R,5R)-3-((E)-(2-(1-(2-chloro-3,4-dihydroxyben-
zoyl)azetidine-3-carbonyl)hydrazono)methyl)-3-
methyl-7-oxo-4-thia-1-azabicyclo[3.2.0]heptane-2-
carboxylic acid 4,4-dioxide;

(2S,3R,5R)-3-((E)-(2-(1-(2-chloro-3,4-dihydroxyben-
zoyl)pyrrolidine-2-carbonyl)hydrazono)methyl)-3-
methyl-7-oxo-4-thia-1-azabicyclo[3.2.0]heptane-2-
carboxylic acid 4,4-dioxide;

(2S,3R,5R)-3-((E)-(2-(5-(3,4-dihydroxybenzamido)pi-
colinoyl)hydrazono)methyl)-3-methyl-7-oxo-4-thia-1-
azabicyclo[3.2.0]heptane-2-carboxylic acid 4,4-diox-
ide;

(2S,3R,5R)-3-((E)-(2-(1-(2-chloro-3,4-dihydroxyben-
zoyl)piperidine-4-carbonyl)hydrazono)methyl)-3-
methyl-7-oxo-4-thia-1-azabicyclo[3.2.0]heptane-2-
carboxylic acid 4,4-dioxide;

(2S,3R,5R)-3-((E)-(2-(2-(2-chloro-3,4-dihydroxyben-
zamido)-3-hydroxypropanoyl)hydrazono)methyl)-3-
methyl-7-oxo-4-thia-1-azabicyclo[3.2.0]heptane-2-
carboxylic acid 4,4-dioxide;

(2S,3R,5R)-3-((E)-(2-(2-(2-chloro-3,4-dihydroxyben-
zamido)-3-phenylpropanoyl)hydrazono)methyl)-3-
methyl-7-oxo-4-thia-1-azabicyclo[3.2.0]heptane-2-
carboxylic acid 4,4-dioxide;

(2S,3R,5R)-3-((E)-(2-(4-((2-chloro-3,4-dihydroxyben-
zamido)methyl)benzoyl)hydrazono)methyl)-3-methyl-
7-oxo-4-thia-1-azabicyclo[3.2.0]heptane-2-carboxylic
acid 4,4-dioxide;

(2S,3R,5R)-3-((E)-(2-(4-((3,4-dihydroxybenzamido)
methyl)benzoyl)hydrazono)methyl)-3-methyl-7-oxo-
4-thia-1-azabicyclo[3.2.0]heptane-2-carboxylic acid
4,4-dioxide;

((2S,3R,5R)-3-((E)-(2-(2-(3,4-dihydroxybenzamido)-3-
methylbutanoyl)hydrazono)methyl)-3-methyl-7-oxo-
4-thia-1-azabicyclo[3.2.0]heptane-2-carboxylic acid
4,4-dioxide;

(2S,3R,5R)-3-((E)-(2-(2-(2-chloro-3,4-dihydroxyben-
zamido)-3-methylbutanoyl)hydrazono)methyl)-3-
methyl-7-oxo-4-thia-1-azabicyclo[3.2.0]heptane-2-
carboxylic acid 4,4-dioxide;

(2S,3R,5R)-3-((E)-(2-(1-(2-chloro-3,4-dihydroxyben-
zoyl)piperidine-3-carbonyl)hydrazono)methyl)-3-
methyl-7-oxo-4-thia-1-azabicyclo[3.2.0]heptane-2-
carboxylic acid 4,4-dioxide;

(2S,3R,5R)-3-((E)-(2-(2-(3,4-dihydroxybenzamido)-3-
hydroxypropanoyl)hydrazono)methyl)-3-methyl-7-
oxo-4-thia-1-azabicyclo[3.2.0]heptane-2-carboxylic
acid 4,4-dioxide;

(2S,3R,5R)-3-((E)-(2-(2-(3,4-dihydroxybenzamido)-3-
phenylpropanoyl)hydrazono)methyl)-3-methyl-7-oxo-
4-thia-1-azabicyclo[3.2.0]heptane-2-carboxylic acid
4,4-dioxide;

(2S,3R,5R)-3-((E)-(2-(1-(3,4-dihydroxybenzamido)cy-
clopropanecarbonyl)hydrazono)methyl)-3-methyl-7-
oxo-4-thia-1-azabicyclo[3.2.0]heptane-2-carboxylic
acid 4,4-dioxide;

(2S,3R,5R)-3-((E)-(2-(1-(2-chloro-3,4-dihydroxyben-
zamido)cyclopropanecarbonyl)hydrazono)methyl)-3-
methyl-7-oxo-4-thia-1-azabicyclo[3.2.0]heptane-2-
carboxylic acid 4,4-dioxide;

(2S,3R,5R)-3-((E)-(2-(4-((3,4-dihydroxybenzoyl)oxy)
benzoyl)hydrazono)methyl)-3-methyl-7-oxo-4-thia-1-
azabicyclo[3.2.0]heptane-2-carboxylic acid 4,4-diox-
ide;

(2S,3R,5R)-3-((E)-(2-(2-((tert-butoxycarbonyl)amino)-3-
((2-chloro-3,4-dihydroxybenzoyl)oxy)propanoyl)hy-
drazono)methyl)-3-methyl-7-oxo-4-thia-1-azabicyclo
[3.2.0]heptane-2-carboxylic acid 4,4-dioxide;

(2S,3R,5R)-3-((E)-(2-(3',4'-dihydroxy-[1,1'-biphenyl]-4-
carbonyl)hydrazono)methyl)-3-methyl-7-oxo-4-thia-1-
azabicyclo[3.2.0]heptane-2-carboxylic acid 4,4-diox-
ide;

(2S,3R,5R)-3-((E)-(2-(4-((2-chloro-3,4-dihydroxyben-
zoyl)oxy)benzoyl)hydrazono)methyl)-3-methyl-7-oxo-
4-thia-1-azabicyclo[3.2.0]heptane-2-carboxylic acid
4,4-dioxide;

(2S,3R,5R)-3-((E)-(2-(5-(2-chloro-3,4-dihydroxybenzamido)picolinoyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-(2-(2-chloro-3,4-dihydroxybenzamido)acetyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-(3-(2-chloro-3,4-dihydroxybenzamido)propanoyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-(6-(2-chloro-3,4-dihydroxybenzamido)hexanoyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-((S)-2-(2-chloro-3,4-dihydroxybenzamido)propanoyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-(4-(2-chloro-3,4-dihydroxybenzamido)butanoyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-(2-(3,4-dihydroxybenzamido)acetyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-((S)-2-(3,4-dihydroxybenzamido)propanoyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-(4-(3,4-dihydroxybenzamido)butanoyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-(3-(3,4-dihydroxybenzamido)propanoyl)hydrazono)methyl)-3-methyl-7-oxo-4-thia-1-azabicyclo[3.2.0]heptane-2-carboxylic acid 4,4-dioxide;
(2S,3R,5R)-3-((E)-(2-(6-(3,4-dihydroxybenzamido)hexanoyl)hydrazono)methyl)-3-methyl-7-oxo-4-thia-1-azabicyclo[3.2.0]heptane-2-carboxylic acid 4,4-dioxide;
(2S,3R,5R)-3-(((2-(3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(2-chloro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(2-(3,4-dihydroxyphenyl)-2-oxoethyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(2,3-dihydroxybenzoyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-methyl-7-oxo-3-(((2-(3,4,5-trihydroxybenzoyl)hydrazinecarbonyl)oxy)methyl)-4-thia-1-azabicyclo[3.2.0]heptane-2-carboxylic acid 4,4-dioxide;
(2S,3R,5R)-3-(((2-(3,4-dihydroxybenzoyl)-1-methylhydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(2-chloro-4,5-dihydroxybenzoyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(2-chloro-3,4-dihydroxybenzoyl)-1-methylhydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(3,4-dihydroxybenzoyl)-2-methylhydrazinecarbonyl)oxy)methyl)-3-methyl-7-oxo-4-thia-1-azabicyclo[3.2.0]heptane-2-carboxylic acid 4,4-dioxide;
(2S,3R,5R)-3-methyl-7-oxo-3-(((2-(2,3,4-trihydroxybenzoyl)hydrazinecarbonyl)oxy)methyl)-4-thia-1-azabicyclo[3.2.0]heptane-2-carboxylic acid 4,4-dioxide;
(2S,3R,5R)-3-(((2-(2,6-dichloro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(2,5-dichloro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(2-fluoro-3,4-dihydroxybenzoyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(3-(3,4-dihydroxyphenyl)-3-oxopropyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(2-chloro-4,5-dihydroxybenzoyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-((((E)-2-(3,4-dihydroxybenzylidene)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(3-chloro-4,5-dihydroxybenzoyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((2-(2-(3,4-dihydroxybenzamido)acetyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-(((3-(3,4-dihydroxybenzamido)pyrrolidine-1-carbonyl)oxy)methyl)-3-methyl-7-oxo-4-thia-1-azabicyclo[3.2.0]heptane-2-carboxylic acid 4,4-dioxide;
(2S,3R,5R)-3-(((4-(3,4-dihydroxybenzoyl)piperazine-1-carbonyl)oxy)methyl)-3-methyl-7-oxo-4-thia-1-azabicyclo[3.2.0]heptane-2-carboxylic acid 4,4-dioxide;
(2S,3R,5R)-3-(((2-(2-(2-chloro-3,4-dihydroxybenzamido)acetyl)hydrazinecarbonyl)oxy)methyl)-3-methyl-7-oxo-4-thia-1-azabicyclo[3.2.0]heptane-2-carboxylic acid 4,4-dioxide;
(2S,3R,5R)-3-((((2-(2-chloro-3,4-dihydroxybenzamido)ethyl)carbamoyl)oxy)methyl)-3-methyl-7-oxo-4-thia-1-azabicyclo[3.2.0]heptane-2-carboxylic acid 4,4-dioxide;
(2S,3R,5R)-3-(((4-(3,4-dihydroxybenzamido)piperidine-1-carbonyl)oxy)methyl)-3-methyl-7-oxo-4-thia-1-azabicyclo[3.2.0]heptane-2-carboxylic acid 4,4-dioxide;

(2S,3R,5R)-3-((((1-(3,4-dihydroxybenzoyl)pyrrolidin-3-yl)carbamoyl)oxy)methyl)-3-methyl-7-oxo-4-thia-1-azabicyclo[3.2.0]heptane-2-carboxylic acid 4,4-dioxide;

(2S,3R,5R)-3-(((3-(3,4-dihydroxybenzamido)azetidine-1-carbonyl)oxy)methyl)-3-methyl-7-oxo-4-thia-1-azabicyclo[3.2.0]heptane-2-carboxylic acid 4,4-dioxide;

(2S,3R,5R)-3-(5-(2-(2-chloro-3,4-dihydroxyphenyl)-2-oxoethyl)isoxazol-3-yl)-3-methyl-7-oxo-4-thia-1-azabicyclo[3.2.0]heptane-2-carboxylic acid 4,4-dioxide;

(2S,3R,5R)-3-(5-(2-(3,4-dihydroxyphenyl)-2-oxoethyl)isoxazol-3-yl)-3-methyl-7-oxo-4-thia-1-azabicyclo[3.2.0]heptane-2-carboxylic acid 4,4-dioxide;

(2S,3R,5R)-3-(5-(2-chloro-3,4-dihydroxyphenyl)isoxazol-3-yl)-3-methyl-7-oxo-4-thia-1-azabicyclo[3.2.0]heptane-2-carboxylic acid 4,4-dioxide;

(2S,3R,5R)-3-(5-(2-(2,5-dichloro-3,4-dihydroxyphenyl)-2-oxoethyl)isoxazol-3-yl)-3-methyl-7-oxo-4-thia-1-azabicyclo[3.2.0]heptane-2-carboxylic acid 4,4-dioxide;

(2S,3R,5R)-3-(5-(3,4-dihydroxyphenyl)isoxazol-3-yl)-3-methyl-7-oxo-4-thia-1-azabicyclo[3.2.0]heptane-2-carboxylic acid 4,4-dioxide;

(2S,3R,5R)-3-(5-(2-((2-chloro-3,4-dihydroxybenzoyl)oxy)ethyl)isoxazol-3-yl)-3-methyl-7-oxo-4-thia-1-azabicyclo[3.2.0]heptane-2-carboxylic acid 4,4-dioxide;

(2S,3R,5R)-3-(5-(2,5-dichloro-3,4-dihydroxyphenyl)isoxazol-3-yl)-3-methyl-7-oxo-4-thia-1-azabicyclo[3.2.0]heptane-2-carboxylic acid 4,4-dioxide;

(2S,3R,5R)-3-(5-(2-((3,4-dihydroxybenzoyl)oxy)ethyl)isoxazol-3-yl)-3-methyl-7-oxo-4-thia-1-azabicyclo[3.2.0]heptane-2-carboxylic acid 4,4-dioxide;

(2S,3R,5R)-3-(5-(2-((2-chloro-3,4-dihydroxybenzoyl)oxy)ethyl)-4,5-dihydroisoxazol-3-yl)-3-methyl-7-oxo-4-thia-1-azabicyclo[3.2.0]heptane-2-carboxylic acid 4,4-dioxide;

(2S,3R,5R)-3-(5-(2-chloro-3,4-dihydroxyphenyl)-4,5-dihydroisoxazol-3-yl)-3-methyl-7-oxo-4-thia-1-azabicyclo[3.2.0]heptane-2-carboxylic acid 4,4-dioxide;

(2S,3R,5R)-3-(5-((2,5-dichloro-3,4-dihydroxybenzamido)methyl)-4,5-dihydroisoxazol-3-yl)-3-methyl-7-oxo-4-thia-1-azabicyclo[3.2.0]heptane-2-carboxylic acid 4,4-dioxide;

(2S,3R,5R)-3-(5-(2-((3,4-dihydroxybenzoyl)oxy)ethyl)-4,5-dihydroisoxazol-3-yl)-3-methyl-7-oxo-4-thia-1-azabicyclo[3.2.0]heptane-2-carboxylic acid 4,4-dioxide;

(2S,3R,5R)-3-(5-((2-chloro-3,4-dihydroxybenzamido)methyl)-4,5-dihydroisoxazol-3-yl)-3-methyl-7-oxo-4-thia-1-azabicyclo[3.2.0]heptane-2-carboxylic acid 4,4-dioxide;

(2S,3R,5R)-3-(5-(3,4-dihydroxybenzoyl)isoxazol-3-yl)-3-methyl-7-oxo-4-thia-1-azabicyclo[3.2.0]heptane-2-carboxylic acid 4,4-dioxide;

(2S,3R,5R)-3-(((3,4-dihydroxybenzoyl)oxy)methyl)-3-methyl-7-oxo-4-thia-1-azabicyclo[3.2.0]heptane-2-carboxylic acid 4,4-dioxide;

(2S,3R,5R)-3-(((2-chloro-3,4-dihydroxybenzoyl)oxy)methyl)-3-methyl-7-oxo-4-thia-1-azabicyclo[3.2.0]heptane-2-carboxylic acid 4,4-dioxide;

(2S,3S,5R)-3-(((3,4-dihydroxyphenyl)amino)methyl)-3-methyl-7-oxo-4-thia-1-azabicyclo[3.2.0]heptane-2-carboxylic acid 4,4-dioxide;

(2S,3R,5R)-3-((E)-((2-(2-chloro-3,4-dihydroxybenzamido)ethoxy)imino)methyl)-3-methyl-7-oxo-4-thia-1-azabicyclo[3.2.0]heptane-2-carboxylic acid 4,4-dioxide;

(2S,3R,5R)-3-((E)-((4-(2-chloro-3,4-dihydroxybenzamido)phenoxy)imino)methyl)-3-methyl-7-oxo-4-thia-1-azabicyclo[3.2.0]heptane-2-carboxylic acid 4,4-dioxide;

(2S,3R,5R)-3-(5-(2-chloro-3,4-dihydroxybenzoyl)isoxazol-3-yl)-3-methyl-7-oxo-4-thia-1-azabicyclo[3.2.0]heptane-2-carboxylic acid 4,4-dioxide;

(2S,3R,5R)-3-((E)-(2-(2-bromo-4,5-dihydroxybenzoyl)hydrazono)methyl)-3-methyl-7-oxo-4-thia-1-azabicyclo[3.2.0]heptane-2-carboxylic acid 4,4-dioxide;

(2S,3R,5R)-3-((E)-(2-(3-(3,4-dihydroxyphenyl)-5-methylisoxazole-4-carbonyl)hydrazono)methyl)-3-methyl-7-oxo-4-thia-1-azabicyclo[3.2.0]heptane-2-carboxylic acid 4,4-dioxide;

(2S,3R,5R)-3-((E)-(2-(3-(2-chloro-3,4-dihydroxyphenyl)isoxazole-5-carbonyl)hydrazono)methyl)-3-methyl-7-oxo-4-thia-1-azabicyclo[3.2.0]heptane-2-carboxylic acid 4,4-dioxide;

(2S,3R,5R)-3-((E)-(2-(3-(3,4-dihydroxyphenyl)isoxazole-5-carbonyl)hydrazono)methyl)-3-methyl-7-oxo-4-thia-1-azabicyclo[3.2.0]heptane-2-carboxylic acid 4,4-dioxide;

(2S,3R,5R)-3-((E)-(2-((4S,5R)-2-(2,3-dihydroxyphenyl)-5-methyl-4,5-dihydrooxazole-4-carbonyl)hydrazono)methyl)-3-methyl-7-oxo-4-thia-1-azabicyclo[3.2.0]heptane-2-carboxylic acid 4,4-dioxide;

(2S,3R,5R)-3-((E)-(2-((4S,5R)-2-(3,4-dihydroxyphenyl)-5-methyl-4,5-dihydrooxazole-4-carbonyl)hydrazono)methyl)-3-methyl-7-oxo-4-thia-1-azabicyclo[3.2.0]heptane-2-carboxylic acid 4,4-dioxide;

(2S,3R,5R)-3-(((2-(3-(2,3-dihydroxyphenyl)isoxazole-5-carbonyl)hydrazinecarbonyl)oxy)methyl)-3-methyl-7-oxo-4-thia-1-azabicyclo[3.2.0]heptane-2-carboxylic acid 4,4-dioxide;

(2S,3R,5R)-3-(((2-(3-(2,3-dihydroxyphenyl)-4,5-dihydroisoxazole-5-carbonyl)hydrazinecarbonyl)oxy)methyl)-3-methyl-7-oxo-4-thia-1-azabicyclo[3.2.0]heptane-2-carboxylic acid 4,4-dioxide;

(2S,3R,5R)-3-(((4-(2-chloro-3,4-dihydroxybenzoyl)piperazine-1-carbonyl)oxy)methyl)-3-methyl-7-oxo-4-thia-1-azabicyclo[3.2.0]heptane-2-carboxylic acid 4,4-dioxide;

(2S,3R,5R)-3-(((3-(2-chloro-3,4-dihydroxybenzamido)azetidine-1-carbonyl)oxy)methyl)-3-methyl-7-oxo-4-thia-1-azabicyclo[3.2.0]heptane-2-carboxylic acid 4,4-dioxide;

(2S,3R,5R)-3-(((2-(3-(2-chloro-3,4-dihydroxyphenyl)-4,5-dihydroisoxazole-5-carbonyl)hydrazine-1-carbonyl)oxy)methyl)-3-methyl-7-oxo-4-thia-1-azabicyclo[3.2.0]heptane-2-carboxylic acid 4,4-dioxide;

(2S,3R,5R)-3-(((2-(3-(2-chloro-3,4-dihydroxyphenyl)-4,5-dihydroisoxazole-5-carbonyl)hydrazinecarbonyl)oxy)methyl)-3-methyl-7-oxo-4-thia-1-azabicyclo[3.2.0]heptane-2-carboxylic acid 4,4-dioxide;

(2S,3R,5R)-3-(((2-((4S,5R)-2-(2,3-dihydroxyphenyl)-5-methyl-4,5-dihydrooxazole-4-carbonyl)hydrazinecarbonyl)oxy)methyl)-3-methyl-7-oxo-4-thia-1-azabicyclo[3.2.0]heptane-2-carboxylic acid 4,4-dioxide;

(2S,3R,5R)-3-((((3,4-dihydroxyphenethyl)carbamoyl)oxy)methyl)-3-methyl-7-oxo-4-thia-1-azabicyclo[3.2.0]heptane-2-carboxylic acid 4,4-dioxide;

(2S,3R,5R)-3-(5-(3,4-dihydroxybenzoyl)isoxazol-3-yl)-3-methyl-7-oxo-4-thia-1-azabicyclo[3.2.0]heptane-2-carboxylic acid 4,4-dioxide;

(2S,3S,5R)-3-((4-((E)-(2-(2-chloro-3,4-dihydroxybenzoyl)hydrazono)methyl)-1H-imidazol-1-yl)methyl)-3-methyl-7-oxo-4-thia-1-azabicyclo[3.2.0]heptane-2-carboxylic acid 4,4-dioxide;

(2S,3R,5R)-3-((E)-(((1-(2-chloro-3,4-dihydroxybenzoyl)piperidin-4-yl)oxy)imino)methyl)-3-methyl-7-oxo-4-thia-1-azabicyclo[3.2.0]heptane-2-carboxylic acid 4,4-dioxide; and (2S,3R,5R)-3-((E)-(((1-(2-chloro-3,4-dihydroxybenzoyl)azetidin-3-yl)oxy)imino)methyl)-3-methyl-7-oxo-4-thia-1-azabicyclo[3.2.0]heptane-2-carboxylic acid 4,4-dioxide.

12. A pharmaceutical composition comprising a pharmaceutically effective amount of a compound of claim 11 in combination with a pharmaceutically acceptable carrier.

13. The pharmaceutical composition of claim 12, further comprising one or more additional antibacterial agents.

14. A method of treating or preventing a microbial infection in a subject in need of such treatment by administering the pharmaceutical composition of claim 12.

\* \* \* \* \*